US010287638B2

(12) United States Patent
Loneragan et al.

(10) Patent No.: US 10,287,638 B2
(45) Date of Patent: May 14, 2019

(54) **MOLECULAR DISCRIMINATION OF REGULATED AND NON-REGULATED *SALMONELLA* SEROTYPES**

(71) Applicant: Texas Tech University System, Lubbock, TX (US)

(72) Inventors: Guy Loneragan, Wolfforth, TX (US); Mindy M. Brashears, Wolfforth, TX (US); Kendra Nightingale, Lubbock, TX (US); Marie Bugarel, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 31 days.

(21) Appl. No.: 15/129,108

(22) PCT Filed: Mar. 26, 2015

(86) PCT No.: PCT/US2015/022704
§ 371 (c)(1),
(2) Date: Jun. 8, 2017

(87) PCT Pub. No.: WO2015/148785
PCT Pub. Date: Oct. 1, 2015

(65) Prior Publication Data
US 2017/0268044 A1   Sep. 21, 2017

Related U.S. Application Data

(60) Provisional application No. 61/970,535, filed on Mar. 26, 2014.

(51) Int. Cl.
*C07H 21/04*   (2006.01)
*C12Q 1/689*   (2018.01)
*G01N 33/02*   (2006.01)

(52) U.S. Cl.
CPC ............ *C12Q 1/689* (2013.01); *G01N 33/02* (2013.01); *C12Q 2600/16* (2013.01); *Y02A 50/451* (2018.01)

(58) Field of Classification Search
None
See application file for complete search history.

(56) References Cited

U.S. PATENT DOCUMENTS

| | | | |
|---|---|---|---|
| 5,824,795 | A | 10/1998 | Popoff et al. |
| 6,080,545 | A | 6/2000 | Popoff et al. |
| 7,326,779 | B2 | 2/2008 | Nakano et al. |
| 8,268,984 | B2 | 9/2012 | Tourniaire |
| 2009/0298076 | A1 | 12/2009 | Tourniaire |
| 2013/0280714 | A1 | 10/2013 | Fields et al. |

FOREIGN PATENT DOCUMENTS

EP   1739193 A2   1/2007

OTHER PUBLICATIONS

NCBI, GenBank accession No. CP005995.1 (Dec. 18, 2013).
NCBI, GenBank accession No. CP006631.1 (Dec. 11, 2013).
NCBI, GenBank accession No. HF937208.1 (Nov. 14, 2013).
International Search Report and Written Opinion—PCT/US2015/022704 [KIPO] dated May 29, 2015.

*Primary Examiner* — Jennifer E Graser
(74) *Attorney, Agent, or Firm* — Edwin S. Flores; Daniel J. Chalker; Chalker Flores, LLP

(57) ABSTRACT

The present invention provides a set of oligonucleotides to screen for the presence of targeted *Salmonella* serotypes in an enrichment or to characterize presumptive colonies. The set of oligonucleotides includes at least one set of primers and probe for the detection of *Salmonella* serotype selected from *typhimurium, enteritidis, newport, heidelberg, infantis, virchow* and *Hadar*. The set of oligonucleotides may include up to 5 different primer sets and the corresponding probes.

5 Claims, 72 Drawing Sheets
Specification includes a Sequence Listing.

Figure 1A

```
SEQ ID NO: 16    TGATGGATAACCTTCTTCTGCCCCCGAGGATCAGAGAGCCGGttttttGTGCATCCTGG   60
                ||||||||||||||||||||||||||||||||||||||||||    ||||||||||||
SEQ ID NO: 29    TGATGGATAACCTTCTTCTGCCCCCGAGGATCAGAGAGCCGGTTTTTTGTGCATCCTGG   1478179

Query     61     AAAATTCACGTGAAGGAACCGGCTCTCAACCAGAGAAGAAGAGGCGtttttTCGATACA    120
                 ||||||||||||||||||||||||||||||||||||||||||||     |||||||||
Sbjct     1478180 AAAATTCACGTGAAGGAACCGGCTCTCAACCAGAGAAGAAGAGGCGTTTTTTCGATACA    1478239

Query     121    ACTATCGTAATTACTCCGTTGGTGGTGCTGGCACGTAAAGTGTGGATAGTGCGTTTATGA   180
                 ||||||||||||||||||||||||||||||||||||||||||||||||||||||||||
Sbjct     1478240 ACTATCGTAATTACTCCGTTGGTGGTGCTGGCACGTAAAGTGTGGATAGTGCGTTTATGA   1478299

Query     181    TGAGTGCATGATGTATATCCTGATACAGCATCCGGTTTGTGGGGCGGAGAAGCCCCGAT    240
                 |||||||||||||||||||||||||||||||||||||||||||||||||||||||||
Sbjct     1478300 TGAGTGCATGATGTATATCCTGATACAGCATCCGGTTTGTGGGGCGGAGAAGCCCCGAT    1478359

Query     241    GGACTCAGTGCCACAATTTTTTATTGCATTCAGATAGCGTACTGTGAATCGGATAAATGA   300
                 ||||||||||||||||||||||||||||||||||||||||||||||||||||||||||
Sbjct     1478360 GGACTCAGTGCCACAATTTTTTATTGCATTCAGATAGCGTACTGTGAATCGGATAAATGA   1478419

Query     301    GAATGTCAGTGTGTTGGTAATGCGGGGTTCTCAGTGCGCTATCTGAATGCAGTGAAATCT   360
                 ||||||||||||||||||||||||||||||||||||||||||||||||||||||||||
Sbjct     1478420 GAATGTCAGTGTGTTGGTAATGCGGGGTTCTCAGTGCGCTATCTGAATGCAGTGAAATCT   1478479

Query     361    GCTCTGAGCAGAGCTAAACAGCATTGTCTGCGTTTGATCAATTTGTAGCGGGTCATAGTG   420
                 ||||||||||||||||||||||||||||||||||||||||||||||||||||||||||
Sbjct     1478480 GCTCTGAGCAGAGCTAAACAGCATTGTCTGCGTTTGATCAATTTGTAGCGGGTCATAGTG   1478539

Query     421    GCTGACTAAAGACTCTCCGGGGCATCCCGGCACTGCATTTATTACTAAAAATCTTCATAT   480
                 ||||||||||||||||||||||||||||||||||||||||||||||||||||||||||
Sbjct     1478540 GCTGACTAAAGACTCTCCGGGGCATCCCGGCACTGCATTTATTACTAAAAATCTTCATAT   1478599

Query     481    CACAGAGGCAGAACATACGGAAAATTCTTGTCAATACAACACCTGACACAGCAATATTTT   540
                 ||||||||||||||||||||||||||||||||||||||||||||||||||||||||||
Sbjct     1478600 CACAGAGGCAGAACATACGGAAAATTCTTGTCAATACAACACCTGACACAGCAATATTTT   1478659

Query     541    TCGGGAGTCCCCGGCGCCTCAGGTTTTTTATCGCCATCAATAAAACTATAATAATAACTC   600
                 ||||||||||||||||||||||||||||||||||||||||||||||||||||||||||
Sbjct     1478660 TCGGGAGTCCCCGGCGCCTCAGGTTTTTTATCGCCATCAATAAAACTATAATAATAACTC   1478719

Query     601    CATGTTATGATTACCACCTCTCTCTCATGAGGTGGttttttATTCCCGCAAATTGCAGA   660
                 |||||||||||||||||||||||||||||||||||    ||||||||||||||||||
Sbjct     1478720 CATGTTATGATTACCACCTCTCTCTCATGAGGTGGTTTTTTATTCCCGCAAATTGCAGA   1478779

Query     661    AATAAGATGGAGTCATCAGAATATGCCCTGATTGTATTTTGTCTTTTTTGAATTAATGCA   720
                 ||||||||||||||||||||||||||||||||||||||||||||||||||||||||||
Sbjct     1478780 AATAAGATGGAGTCATCAGAATATGCCCTGATTGTATTTTGTCTTTTTTGAATTAATGCA   1478839

Query     721    AAACATTTGGAATAAATAAACATCTAATGATAAATTTACATTTCTTGACGCGACTGCTTG   780
                 ||||||||||||||||||||||||||||||||||||||||||||||||||||||||||
Sbjct     1478840 AAACATTTGGAATAAATAAACATCTAATGATAAATTTACATTTCTTGACGCGACTGCTTG   1478899

Query     781    TTGAAATGAAATTTTTATGATTTATTATTGTCGACAGTTTGGCGGAGGTGACTGGCAGAT   840
                 ||||||||||||||||||||||||||||||||||||||||||||||||||||||||||
Sbjct     1478900 TTGAAATGAAATTTTTATGATTTATTATTGTCGACAGTTTGGCGGAGGTGACTGGCAGAT   1478959

Query     841    TTCTCCACTCCGTCGAATAAGAGAGTTGATTCTTTATACCTCCTGAGTCGTCTGATTAAA   900
                 ||||||||||||||||||||||||||||||||||||||||||||||||||||||||||
Sbjct     1478960 TTCTCCACTCCGTCGAATAAGAGAGTTGATTCTTTATACCTCCTGAGTCGTCTGATTAAA   1479019

Query     901    GAATCATCACTCGATTTGGCATTAAGGTGAAATTAAGATTCCATTGATATAGGTATCGTT   960
                 ||||||||||||||||||||||||||||||||||||||||||||||||||||||||||
Sbjct     1479020 GAATCATCACTCGATTTGGCATTAAGGTGAAATTAAGATTCCATTGATATAGGTATCGTT   1479079

Query     961    CTTACTCTTTGTGGTGCAGGCATATGGATATGGGTGGTACATTAATGTTCCTTTAATT   1020
                 |||||||||||||||||||||||||||||||||||||||||||||||||||||||||
Sbjct     1479080 CTTACTCTTTGTGGTGCAGGCATATGGATATGGGTGGTACATTAATGTTCCTTTAATT   1479139

Query     1021   TAACCTCCTGATAGTGAATCAGGCACCGCAAttttttACTGCATTCAGATGGCGTACTG   1080
                 |||||||||||||||||||||||||||||    |||||||||||||||||||||||||
```

Figure 1A (continued)

```
Sbjct  1479140  TAACCTCCTGATAGTGAATCAGGCACCGCAATTTTTTTACTGCATTCAGATGGCGTACTG  1479199

Query  1081    CaaaaaaaCGGTCATTGCTTGCGCCACTGTCTGATGCTCTTGTAACACATACGGGATTTG  1140
               ||||||||||||||||||||||||||||||||||||||||||||||||||||||||||||
Sbjct  1479200  CAAAAAAACGGTCATTGCTTGCGCCACTGTCTGATGCTCTTGTAACACATACGGGATTTG  1479259

Query  1141    TGGTACGCCATCTGAATGCAGTGAAACCCACATAAAGTGGGGCATAAACAGGATATGAGG  1200
               ||||||||||||||||||||||||||||||||||||||||||||||||||||||||||||
Sbjct  1479260  TGGTACGCCATCTGAATGCAGTGAAACCCACATAAAGTGGGGCATAAACAGGATATGAGG  1479319

Query  1201    TGCGTTTATTTTCGTCTGCGGGTCATGGTGACTGACCAACGGCCCTCCGGAGATAATTCC  1260
               ||||||||||||||||||||||||||||||||||||||||||||||||||||||||||||
Sbjct  1479320  TGCGTTTATTTTCGTCTGCGGGTCATGGTGACTGACCAACGGCCCTCCGGAGATAATTCC  1479379

Query  1261    GGCACTGCATTATTTATTGAGGTGTTCCCCAGTGCGGGGGTGACCGGGAAAAATGTTCTG  1320
               ||||||||||||||||||||||||||||||||||||||||||||||||||||||||||||
Sbjct  1479380  GGCACTGCATTATTTATTGAGGTGTTCCCCAGTGCGGGGGTGACCGGGAAAAATGTTCTG  1479439

Query  1321    CCGATGGTCACAGACACATACCGGGCTAATATGTGTTTTCGGGAGGCACCCGACACCTCT  1380
               ||||||||||||||||||||||||||||||||||||||||||||||||||||||||||||
Sbjct  1479440  CCGATGGTCACAGACACATACCGGGCTAATATGTGTTTTCGGGAGGCACCCGACACCTCT  1479499

Query  1381    ACTGTTTTTCCAGTCGATAACTATAAAACATGCTTCAGATATTGAGCACCGCCTCCCGTG  1440
               ||||||||||||||||||||||||||||||||||||||||||||||||||||||||||||
Sbjct  1479500  ACTGTTTTTCCAGTCGATAACTATAAAACATGCTTCAGATATTGAGCACCGCCTCCCGTG  1479559

Query  1441    AGGCGGttttttttATTCCGGGAAAAGTTCTGCCCGCCATATAATAAAGTTAACGTTTT  1500
               ||||||||||||||||||||||||||||||||||||||||||||||||||||||||||||
Sbjct  1479560  AGGCGGTTTTTTTTATTCCGGGAAAAGTTCTGCCCGCCATATAATAAAGTTAACGTTTT  1479619

Query  1501    CAGACCAGGGTGCGGGAAGTATCCGGGGCGGGAAATAATGAATTAAAAAGAAGCGCGGC  1560
               ||||||||||||||||||||||||||||||||||||||||||||||||||||||||||||
Sbjct  1479620  CAGACCAGGGTGCGGGAAGTATCCGGGGCGGGAAATAATGAATTAAAAAGAAGCGCGGC  1479679

Query  1561    TGTCGGATTTAAGCCGCGGGACAATGTCCGTGATAGATAGTTGAAAAATTTCAGGCTATC  1620
               ||||||||||||||||||||||||||||||||||||||||||||||||||||||||||||
Sbjct  1479680  TGTCGGATTTAAGCCGCGGGACAATGTCCGTGATAGATAGTTGAAAAATTTCAGGCTATC  1479739

Query  1621    CCTTTCGGGAGGTCGCCATTATTTTACTCATAACAAAATAAGACCGGAACCCCGGAAACA  1680
               ||||||||||||||||||||||||||||||||||||||||||||||||||||||||||||
Sbjct  1479740  CCTTTCGGGAGGTCGCCATTATTTTACTCATAACAAAATAAGACCGGAACCCCGGAAACA  1479799
```

SEQ ID NO:17
GTGGGGCATAAACAGGATATGAGGTGCGTTTATTTTCGTCTGCGGGTCATGGTGACTGACCAACGGCCCTCCGGAGATAATTCCGGCAC
TGCATTATTTATTGAGGTGTTCCCCAGTGCGGGGGTGACCGGGAAAAATGTTCTGCCGATGGTCACAGACACATACCGGGCTAATATGT
GTTTTCGGGAGGCACCCGACACCTCTACTGTTTTTCCAGTCGATAACTATAAAACATGCTTCAGATATTGA

Figure 1B

```
SEQ ID NO: 13   1  CTGGCCTCGTTCCTGTCCCGCCTTGCTGACTACAACGGTAAACCGCTGGATGCGCTGTGT   60
                   ||||||||||||||||||||||||||||||||||||||||||||||||||||||||||||
SEQ ID NO: 30      CTGGCCTCGTTCCTGTCCCGCCTTGCTGACTACAACGGTAAACCGCTGGATGCGCTGTGT   1480353

Query          61  GCAGTGGTGATGTCGGTGCTGTCAGTGAAATTTCTGACCTTCATTCATGACCAGGACATT   120
                   ||||||||||||||||||||||||||||||||||||||||||||||||||||||||||||
Sbjct     1480354  GCAGTGGTGATGTCGGTGCTGTCAGTGAAATTTCTGACCTTCATTCATGACCAGGACATT   1480413

Query         121  TCATCGCTGACCGGGGTTTTTTCACGGATGCGGGGAGGAGGGAGTGGTCATGGAAAGTAA   180
                   ||||||||||||||||||||||||||||||||||||||||||||||||||||||||||||
Sbjct     1480414  TCATCGCTGACCGGGGTTTTTTCACGGATGCGGGGAGGAGGGAGTGGTCATGGAAAGTAA   1480473

Query         181  TCTGACCGGCACACTGAATGCGGGCCTGTGCCTGGTGACAGTGCTGGCCCTTTTTCTCTA   240
                   ||||||||||||||||||||||||||||||||||||||||||||||||||||||||||||
Sbjct     1480474  TCTGACCGGCACACTGAATGCGGGCCTGTGCCTGGTGACAGTGCTGGCCCTTTTTCTCTA   1480533

Query         241  CCGCCGGAACGGCGCCAGATACAAACCGGGAATAGCCTGGCTGTCGTACCTGCTGATGCT   300
                   ||||||||||||||||||||||||||||||||||||||||||||||||||||||||||||
Sbjct     1480534  CCGCCGGAACGGCGCCAGATACAAACCGGGAATAGCCTGGCTGTCGTACCTGCTGATGCT   1480593

Query         301  GGGCTATGCGCTGGTTCCGTTCCGTTTTCTGGCCGGACATTACCCGTCTTCATCCTGGCC   360
                   ||||||||||||||||||||||||||||||||||||||||||||||||||||||||||||
Sbjct     1480594  GGGCTATGCGCTGGTTCCGTTCCGTTTTCTGGCCGGACATTACCCGTCTTCATCCTGGCC   1480653

Query         361  TGTGGTGCTGATGAACGCGCTGTTCTGCGGGCTGGTGCTGTGGGCGCGGGGTAATGTGTC   420
                   ||||||||||||||||||||||||||||||||||||||||||||||||||||||||||||
Sbjct     1480654  TGTGGTGCTGATGAACGCGCTGTTCTGCGGGCTGGTGCTGTGGGCGCGGGGTAATGTGTC   1480713

Query         421  GAAAATACTTTCACTGCTGAGGCTGCGATGAAACCGAAGGACGAAATTTTTGATGAAATT   480
                   ||||||||||||||||||||||||||||||||||||||||||||||||||||||||||||
Sbjct     1480714  GAAAATACTTTCACTGCTGAGGCTGCGATGAAACCGAAGGACGAAATTTTTGATGAAATT   1480773

Query         481  CTGGGTAAGGAAGGCGGCTACGTCAACCATCCGGACGATAAAGGCGGGCCGACAAAATGG   540
                   ||||||||||||||||||||||||||||||||||||||||||||||||||||||||||||
Sbjct     1480774  CTGGGTAAGGAAGGCGGCTACGTCAACCATCCGGACGATAAAGGCGGGCCGACAAAATGG   1480833

Query         541  GGTATTACGGAAAAAGTTGCCCGCGCCCACGGATACCGTGGTGATATGCGCAATTTAACC   600
                   ||||||||||||||||||||||||||||||||||||||||||||||||||||||||||||
Sbjct     1480834  GGTATTACGGAAAAAGTTGCCCGCGCCCACGGATACCGTGGTGATATGCGCAATTTAACC   1480893

Query         601  CGTGGACAGGCGCTGGAAATTCTGGAGACCGACTACTGGTACGGTCCCCGCTTTGACCGG   660
                   ||||||||||||||||||||||||||||||||||||||||||||||||||||||||||||
Sbjct     1480894  CGTGGACAGGCGCTGGAAATTCTGGAGACCGACTACTGGTACGGTCCCCGCTTTGACCGG   1480953

Query         661  GTGGCGAAGGCCTCGCCGGATGTTGCTGCCGAACTGTGTGACACGGGCGTGAACATGGGG   720
                   ||||||||||||||||||||||||||||||||||||||||||||||||||||||||||||
Sbjct     1480954  GTGGCGAAGGCCTCGCCGGATGTTGCTGCCGAACTGTGTGACACGGGCGTGAACATGGGG   1481013

Query         721  CCGTCGGTGGCAGCGAAAATGTTGCAGCGCTGGCTGAACGTGTTCAACCAGGGCGGGAGG   780
                   ||||||||||||||||||||||||||||||||||||||||||||||||||||||||||||
Sbjct     1481014  CCGTCGGTGGCAGCGAAAATGTTGCAGCGCTGGCTGAACGTGTTCAACCAGGGCGGGAGG   1481073

Query         781  CTGTATCCGGATATGGATACGGACGGGCGCATCGGGCCGCGAACCCTTAACGCGTTACGT   840
                   ||||||||||||||||||||||||||||||||||||||||||||||||||||||||||||
Sbjct     1481074  CTGTATCCGGATATGGATACGGACGGGCGCATCGGGCCGCGAACCCTTAACGCGTTACGT   1481133

Query         841  GTTTATCTGGAAAAGCGCGGTAAGGATGGCGAGCGTGTACTGCTGGTGGCGCTGAACTGC   900
                   ||||||||||||||||||||||||||||||||||||||||||||||||||||||||||||
Sbjct     1481134  GTTTATCTGGAAAAGCGCGGTAAGGATGGCGAGCGTGTACTGCTGGTGGCGCTGAACTGC   1481193

Query         901  ACGCAGGGGAGCGCTATCTGGAGCTGGCGGAAAAGCGGGAGGCTGACGAGTCGTTTGTC   960
                   ||||||||||||||||||||||||||||||||||||||||||||||||||||||||||||
Sbjct     1481194  ACGCAGGGGAGCGCTATCTGGAGCTGGCGGAAAAGCGGGAGGCTGACGAGTCGTTTGTC   1481253

Query         961  TATGGCTGGATGAAAGAGCGCGTATTGAT   989
                   |||||||||||||||||||||||||||||
Sbjct     1481254  TATGGCTGGATGAAAGAGCGCGTATTGAT   1481282
```

Figure 1B (Continued)

SEQ ID NO:14
CTGGCCTCGTTCCTGTCCCGCCTTGCTGACTACAACGGTAAACCGCTGGATGCGCTGTGTGCAGTGGTGA

SEQ ID NO:15
TGGTCATGGAAAGTAATCTGACCGGCACACTGAATGCGGGCCTGTGCCTGGTGACAGTGCTGGCCCTTTTTCTCTACCGCCGGAACGGC
GCCAGATACAAACCGGGAATAGCCTGGCTGTCGTACCTGCTGATGCTGGGCTATGCGCTGGTTCCGTTCCGTTTTCTGGCCGGACATTA
CCCGTCTTCATCCTGGCCTGTGGTGCTGATGAACGCGCTGTTCTGCGGGCTGGTGCTGTGGGCGCGGGGTAATGTGTCGAAAATACTTT
CACTGCTGAGGCTGCGATGAAACCGAAGGACGAAATTTTTGATGAAATTCTGGGTAAGGAAGGCGGCTACGTCAACCATCCGGACGATA
AAGGCGGGCCGACAAAATGGGGTATTACGGAAAAAGTTGCCCGCGCCCACGGATACCGTGGTGATATGCGCAATTTAACCCGTGGACAG
GCGCTGGAAATTCTGGAGACCGACTACTGGTACGGTCCCCGCTTTGACCGGGTGGCGAAGGCCTCGCCGGATGTTGCTGCCGAACTGTG
TGACACGGGCGTGAACATGGGGCCGTCGGTGGCAGCGAAAATGTTGCAGCGCTGGCTGAACGTGTTCAACCAGGGCGGGAGGCTGTATC
CGGATATGGATACGGACGGGCGCATCGGGCCGCGAACCCTTAACGCGTTACGTGTTTATCTGGAAAAGCGCGGTAAGGATGGCGAGCGT
GTACTGCTGGTGGCGCTGAACTGCACGCAGGGGGAGCGCTATCTGGAGCTGGCGGAAAAGCGGGAGGCTGACGAGTCGTTTGTCTATGG
CTGGATGAAAGAGCGCGTATTGAT

Figure 1C

```
SEQ ID NO: 18        GCTGCCGGGCAGAGTCGTAGTGAACGTCTTTTGGGCCTGAAAAGTAAATCCCCAGTTGTT    60
                     ||||||||||||||||||||||||||||||||||||||||||||||||||||||||||||
SEQ ID NO: 25        GCTGCCGGGCAGAGTCGTAGTGAACGTCTTTTGGGCCTGAAAAGTAAATCCCCAGTTGTT    1481468

Query       61       GCTGACAACTGGGGATTTTTATAACAGCATATAAATCGTAAAGGAAATTGTCATATGCCA    120
                     ||||||||||||||||||||||||||||||||||||||||||||||||||||||||||||
Sbjct       1481469   GCTGACAACTGGGGATTTTTATAACAGCATATAAATCGTAAAGGAAATTGTCATATGCCA    1481528

Query       121      TATTCAAGAACGTGCTGAGGTTGAGAAGTTTTGGAATTTTTCGGTggcaaaaatggggc     180
                     ||||||||||||||||||||||||||||||||||||||||||||||||||||||||||||
Sbjct       1481529   TATTCAAGAACGTGCTGAGGTTGAGAAGTTTTGGAATTTTTCGGTGGCAAAAATGGGGC    1481588

Query       181      aaaatgctgtaaaaggggcaaaaatggggcaacaaaaGAGTGGATTATCGTAGCTTATTG    240
                     ||||||||||||||||||||||||||||||||||||||||||||||||||||||||||||
Sbjct       1481589   AAAATGCTGTAAAAGGGGCAAAAATGGGGCAACAAAAGAGTGGATTATCGTAGCTTATTG    1481648

Query       241      TTGTTGCTGATAATGCTTAACGCATTGAAAAATAAATAAAACTATTATGCATCAGATGGT    300
                     ||||||||||||||||||||||||||||||||||||||||||||||||||||||||||||
Sbjct       1481649   TTGTTGCTGATAATGCTTAACGCATTGAAAAATAAATAAAACTATTATGCATCAGATGGT    1481708

Query       301      TGTGATTTTTGCCCTT    316
                     ||||||||||||||||
Sbjct       1481709   TGTGATTTTTGCCCTT    1481724
```

SEQ ID NO:19
GCTGCCGGGCAGAGTCGTAGTGAACGTCTTTTGGGCCTGAAAAGTAAATCCCCAGTTGTTGCTGACAACTGGGGATTTTTATAA

FIGURE 2

```
SEQ ID NO 20      1    AAAGGAAACGTCCCTTTAAGGGACGTTTCCGGGCGATTACTCAAGGTCAGCGTGTCTCTT    60
AMBX01000015  106934    ............................................................  106993
AMBV01000052   48638    ............................................................   48697
AMBU01000072  107521    ............................................................  107580
AJHA01000079   13919    ............................................................   13978
AJGZ01000001  231824    ............................................................  231883
AJGX01000034  231651    ............................................................  231710
AJGW01000056   42142    ............................................................   42201
ABEL01000005  221404    ............................................................  221463
AMBW01000028   21312    ............................................................   21253
AJGY01000001   32188    ............................................................   32129

Query            61    AAACATCGTGTCGCTGGTTTCACCGAGTTGGGCCATCAGCTCAAGCACGATAGCGTCATA   120
AMBX01000015  106994    ............................................................  107053
AMBV01000052   48698    ............................................................   48757
AMBU01000072  107581    ............................................................  107640
AJHA01000079   13979    ............................................................   14038
AJGZ01000001  231884    ............................................................  231943
AJGX01000034  231711    ............................................................  231770
AJGW01000056   42202    ............................................................   42261
ABEL01000005  221464    ............................................................  221523
AMBW01000028   21252    ............................................................   21193
AJGY01000001   32128    ............................................................   32069

Query           121    GGTGATAAAGCAGAGTTGCTCAAAAGCCGATCCCATAGGCTGCGAAAAAGCACCTTCTTC   180
AMBX01000015  107054    ............................................................  107113
AMBV01000052   48758    ............................................................   48817
AMBU01000072  107641    ............................................................  107700
AJHA01000079   14039    ............................................................   14098
AJGZ01000001  231944    ............................................................  232003
AJGX01000034  231771    ............................................................  231830
AJGW01000056   42262    ............................................................   42321
ABEL01000005  221524    ............................................................  221583
AMBW01000028   21192    ............................................................   21133
AJGY01000001   32068    ............................................................   32009

Query           181    GCGATCGTTGTCTTCTTTCACAGTTCCAGGCAATACAAGAGTACTTTTGGCCAGTTTGCC   240
AMBX01000015  107114    ............................................................  107173
AMBV01000052   48818    ............................................................   48877
AMBU01000072  107701    ............................................................  107760
AJHA01000079   14099    ............................................................   14158
AJGZ01000001  232004    ............................................................  232063
AJGX01000034  231831    ............................................................  231890
AJGW01000056   42322    ............................................................   42381
ABEL01000005  221584    ............................................................  221643
AMBW01000028   21132    ............................................................   21073
AJGY01000001   32008    ............................................................   31949

Query           241    GATTGTGGACTCCGCTTTCATTGTGACAAGCGCCACATCCACGCCACAGGCTACGGCCTT   300
AMBX01000015  107174    ............................................................  107233
AMBV01000052   48878    ............................................................   48937
AMBU01000072  107761    ............................................................  107820
AJHA01000079   14159    ............................................................   14218
AJGZ01000001  232064    ............................................................  232123
AJGX01000034  231891    ............................................................  231950
AJGW01000056   42382    ............................................................   42441
ABEL01000005  221644    ............................................................  221703
AMBW01000028   21072    ............................................................   21013
AJGY01000001   31948    ............................................................   31889

Query           301    CTGCGCCAGGCTCACCAGACTGCCGGTCTCACCGCTACCGGAGCCAATAATGACCAGGTC   360
AMBX01000015  107234    ............................................................  107293
AMBV01000052   48938    ............................................................   48997
AMBU01000072  107821    ............................................................  107880
AJHA01000079   14219    ............................................................   14278
AJGZ01000001  232124    ............................................................  232183
AJGX01000034  231951    ............................................................  232010
AJGW01000056   42442    ............................................................   42501
ABEL01000005  221704    ............................................................  221763
AMBW01000028   21012    ............................................................   20953
AJGY01000001   31888    ............................................................   31829

Query           361    GCCCGGTTTCGTATGAGGAGAAGAAATTTCGCCCACTACGCTTACTGAAAAACCGAGGTG   420
AMBX01000015  107294    ............................................................  107353
AMBV01000052   48998    ............................................................   49057
AMBU01000072  107881    ............................................................  107940
AJHA01000079   14279    ............................................................   14338
AJGZ01000001  232184    ............................................................  232243
AJGX01000034  232011    ............................................................  232070
```

Figure 2 (Continued)

```
AJGW01000056   42902   ............................................................   42961
ABEL01000005   221764  ............................................................   221823
AMBW01000028   20952   ............................................................   20893
AJGY01000001   31828   ............................................................   31769

Query          421     GAGAAGGCGGTTTGCAAAGCCGCGGATGGCGATGCCGCTACGACCCGCGCCCTGCAGAAA   480
AMBX01000015   107354  ............................................................   107413
AMBV01000052   49058   ............................................................   49117
AMBU01000072   107941  ............................................................   108000
AJHA01000079   14339   ............................................................   14398
AJGZ01000001   232244  ............................................................   232303
AJGX01000034   232071  ............................................................   232130
AJGW01000056   42562   ............................................................   42621
ABEL01000005   221824  ............................................................   221883
AMBW01000028   20892   ............................................................   20833
AJGY01000001   31768   ............................................................   31709

Query          481     GATATGTTTGGCATTCTTAATCTGTGCGACGAATTGGGCAGCCTGGGCATCATCAATCTT   540
AMBX01000015   107414  ............................................................   107473
AMBV01000052   49118   ............................................................   49177
AMBU01000072   108001  ............................................................   108060
AJHA01000079   14399   ............................................................   14458
AJGZ01000001   232304  ............................................................   232363
AJGX01000034   232131  ............................................................   232190
AJGW01000056   42622   ............................................................   42681
ABEL01000005   221884  ............................................................   221943
AMBW01000028   20832   ............................................................   20773
AJGY01000001   31708   ............................................................   31649

Query          541     CATCGCATTTTGCTGCAACTCGCTCAGGATATTTAAAGTATTTTGTTGAACGCTCATGTG   600
AMBX01000015   107474  ............................................................   107533
AMBV01000052   49178   ............................................................   49237
AMBU01000072   108061  ............................................................   108120
AJHA01000079   14459   ............................................................   14518
AJGZ01000001   232364  ............................................................   232423
AJGX01000034   232191  ............................................................   232250
AJGW01000056   42682   ............................................................   42741
ABEL01000005   221944  ............................................................   222003
AMBW01000028   20772   ............................................................   20713
AJGY01000001   31648   ............................................................   31589

Query          601     ATTCCCTCCCTTTAAGCGATGGTACGACCACCATCCATCAGAATGGTTTGCCCCTGGATG   660
AMBX01000015   107534  ............................................................   107593
AMBV01000052   49238   ............................................................   49297
AMBU01000072   108121  ............................................................   108180
AJHA01000079   14519   ............................................................   14578
AJGZ01000001   232424  ............................................................   232483
AJGX01000034   232251  ............................................................   232310
AJGW01000056   42742   ............................................................   42801
ABEL01000005   222004  ............................................................   222063
AMBW01000028   20712   ............................................................   20653
AJGY01000001   31588   ............................................................   31529

Query          661     TACGAGTTGTCTTTATCAGCCAAAAAGATTGCAAGGTTTGCTACATCGTCAATGGTTCCA   720
AMBX01000015   107594  ............................................................   107653
AMBV01000052   49298   ............................................................   49357
AMBU01000072   108181  ............................................................   108240
AJHA01000079   14579   ............................................................   14638
AJGZ01000001   232484  ............................................................   232543
AJGX01000034   232311  ............................................................   232370
AJGW01000056   42802   ............................................................   42861
ABEL01000005   222064  ............................................................   222123
AMBW01000028   20652   ............................................................   20593
AJGY01000001   31528   ............................................................   31469

Query          721     AGGCGGCGCACTGGAATTTTTTCCAGAACGGCATCAAGATCGGCCTGGGTAGGATAATTG   780
AMBX01000015   107654  ............................................................   107713
AMBV01000052   49358   ............................................................   49417
AMBU01000072   108241  ............................................................   108300
AJHA01000079   14639   ............................................................   14698
AJGZ01000001   232544  ............................................................   232603
AJGX01000034   232371  ............................................................   232430
AJGW01000056   42862   ............................................................   42921
ABEL01000005   222124  ............................................................   222183
AMBW01000028   20592   ............................................................   20533
AJGY01000001   31468   ............................................................   31409

Query          781     ACGCGCATCATTTCACCGGTATCAATCAGGCGTGGAGCGATAGCATTAACATTGACACCC   840
AMBX01000015   107714  ............................................................   107773
AMBV01000052   49418   ............................................................   49477
AMBU01000072   108301  ............................................................   108360
```

Figure 2 (Continued)

```
AJHA01000079    14699   ............................................................   14758
AJGZ01000001    232604  ............................................................   232663
AJGX01000034    232431  ............................................................   232490
AJGW01000056    42922   ............................................................   42981
ABEL01000005    222184  ............................................................   222243
AMBW01000028    20532   ............................................................   20473
AJGY01000001    31408   ............................................................   31349

Query           841     TTAGGTCCCAGTTCTTTTGCCAGACCACGAATCAATCCTTCACCGCCAGCTTTACTGGCC   900
AMBX01000015    107774  ............................................................   107833
AMBV01000052    49478   ............................................................   49537
AMBU01000072    108361  ............................................................   108420
AJHA01000079    14759   ............................................................   14818
AJGZ01000001    232664  ............................................................   232723
AJGX01000034    232491  ............................................................   232550
AJGW01000056    42982   ............................................................   43041
ABEL01000005    222244  ............................................................   222303
AMBW01000028    20472   ............................................................   20413
AJGY01000001    31348   ............................................................   31289

Query           901     GGGTAACTCACGCCACCGCCAGTACCGGAAAGCGCCGAGCCGGATGAGATATAAACGATA   960
AMBX01000015    107834  ............................................................   107893
AMBV01000052    49538   ............................................................   49597
AMBU01000072    108421  ............................................................   108480
AJHA01000079    14819   ............................................................   14878
AJGZ01000001    232724  ............................................................   232783
AJGX01000034    232551  ............................................................   232610
AJGW01000056    43042   ............................................................   43101
ABEL01000005    222304  ............................................................   222363
AMBW01000028    20412   ............................................................   20353
AJGY01000001    31288   ............................................................   31229

Query           961     GATCCATGGTTAGTAGTGAAGTCGTCGTAGAATGCTTTAACGGTGTTAAACAGGCCAGTA   1020
AMBX01000015    107894  ............................................................   107953
AMBV01000052    49598   ............................................................   49657
AMBU01000072    108481  ............................................................   108540
AJHA01000079    14879   ............................................................   14938
AJGZ01000001    232784  ............................................................   232843
AJGX01000034    232611  ............................................................   232670
AJGW01000056    43102   ............................................................   43161
ABEL01000005    222364  ............................................................   222423
AMBW01000028    20352   ............................................................   20293
AJGY01000001    31228   ............................................................   31169

Query           1021    AGGTTAATTGCAATCGTCTTATTCCACTCTTCAAAAGTGATGTTATTAACCTTATTAGCA   1080
AMBX01000015    107954  ............................................................   108013
AMBV01000052    49658   ............................................................   49717
AMBU01000072    108541  ............................................................   108600
AJHA01000079    14939   ............................................................   14998
AJGZ01000001    232844  ............................................................   232903
AJGX01000034    232671  ............................................................   232730
AJGW01000056    43162   ............................................................   43221
ABEL01000005    222424  ............................................................   222483
AMBW01000028    20292   ............................................................   20233
AJGY01000001    31168   ............................................................   31109

Query           1081    AACGCCACGCCAGCGTTTAATACCAAAATATCAATACGTCCGAAGGTTTGAAAAACCTGC   1140
AMBX01000015    108014  ............................................................   108073
AMBV01000052    49718   ............................................................   49777
AMBU01000072    108601  ............................................................   108660
AJHA01000079    14999   ............................................................   15058
AJGZ01000001    232904  ............................................................   232963
AJGX01000034    232731  ............................................................   232790
AJGW01000056    43222   ............................................................   43281
ABEL01000005    222484  ............................................................   222543
AMBW01000028    20232   ............................................................   20173
AJGY01000001    31108   ............................................................   31049

Query           1141    TCACGAACGTTTTCCAGAGCTTTCGGATCGGATACATCGGTTTTAACGAATAAGGATTTA   1200
AMBX01000015    108074  ............................................................   108133
AMBV01000052    49778   ............................................................   49837
AMBU01000072    108661  ............................................................   108720
AJHA01000079    15059   ............................................................   15118
AJGZ01000001    232964  ............................................................   233023
AJGX01000034    232791  ............................................................   232850
AJGW01000056    43282   ............................................................   43341
ABEL01000005    222544  ............................................................   222603
AMBW01000028    20172   ............................................................   20113
AJGY01000001    31048   ............................................................   30989

Query           1201    ACATTACCGAAAGTTAACTCTTCGGCCGTCTTTTTACCATTTTCTTCGTTATAATCGACA   1260
```

Figure 2 (Continued)

```
AMBX01000015  108134  ............................................................  108193
AMBV01000052  49838   ............................................................  49897
AMBU01000072  108721  ............................................................  108780
AJHA01000079  15119   ............................................................  15178
AJGZ01000001  233024  ............................................................  233083
AJGX01000034  232851  ............................................................  232910
AJGW01000056  43342   ............................................................  43401
ABEL01000005  222604  ............................................................  222663
AMBW01000028  20112   ............................................................  20053
AJGY01000001  30988   ............................................................  30929

Query         1261    ATGACAGTATGAGCCCCACGGTCTGCGAATTGCTTAGCAATTCCTTTACCGATTCCATGT  1320
AMBX01000015  108194  ............................................................  108253
AMBV01000052  49898   ............................................................  49957
AMBU01000072  108781  ............................................................  108840
AJHA01000079  15179   ............................................................  15238
AJGZ01000001  233084  ............................................................  233143
AJGX01000034  232911  ............................................................  232970
AJGW01000056  43402   ............................................................  43461
ABEL01000005  222664  ............................................................  222723
AMBW01000028  20052   ............................................................  19993
AJGY01000001  30928   ............................................................  30869

Query         1321    GCCCCACCGGTTACTAGCGCGACTTTACCTTCAAATTTACTCATTTCACTATACTCCTCA  1380
AMBX01000015  108254  ............................................................  108313
AMBV01000052  49958   ............................................................  50017
AMBU01000072  108841  ............................................................  108900
AJHA01000079  15239   ............................................................  15298
AJGZ01000001  233144  ............................................................  233203
AJGX01000034  232971  ............................................................  233030
AJGW01000056  43462   ............................................................  43521
ABEL01000005  222724  ............................................................  222783
AMBW01000028  19992   ............................................................  19933
AJGY01000001  30868   ............................................................  30809

Query         1381    AAATCTCATGACAAAGGGGAGGACAACTCCCCTTTCAGGTAATTGGTGATTTAATGAATG  1440
AMBX01000015  108314  ............................................................  108373
AMBV01000052  50018   ............................................................  50077
AMBU01000072  108901  ............................................................  108960
AJHA01000079  15299   ............................................................  15358
AJGZ01000001  233204  ............................................................  233263
AJGX01000034  233031  ............................................................  233090
AJGW01000056  43522   ............................................................  43581
ABEL01000005  222784  ............................................................  222843
AMBW01000028  19932   ............................................................  19873
AJGY01000001  30808   ............................................................  30749

Query         1441    CCAATAATAGCGTCCAGGGTTACTGGGTTTATTTGGTACCGAACTGCTATTGGATCGCTG  1500
AMBX01000015  108374  ............................................................  108433
AMBV01000052  50078   ............................................................  50137
AMBU01000072  108961  ............................................................  109020
AJHA01000079  15359   ............................................................  15418
AJGZ01000001  233264  ............................................................  233323
AJGX01000034  233091  ............................................................  233150
AJGW01000056  43582   ............................................................  43641
ABEL01000005  222844  ............................................................  222903
AMBW01000028  19872   ............................................................  19813
AJGY01000001  30748   ............................................................  30689

Query         1501    CCCTTAATTTCTGATAGCTTTCTCTCGGTGCATCATTAAATAACGCGCCACCAACAACAA  1560
AMBX01000015  108434  ............................................................  108493
AMBV01000052  50138   ............................................................  50197
AMBU01000072  109021  ............................................................  109080
AJHA01000079  15419   ............................................................  15478
AJGZ01000001  233324  ............................................................  233383
AJGX01000034  233151  ............................................................  233210
AJGW01000056  43642   ............................................................  43701
ABEL01000005  222904  ............................................................  222963
AMBW01000028  19812   ............................................................  19753
AJGY01000001  30688   ............................................................  30629

Query         1561    TTAAATCAGCACCCGCTTCTTTTACCTTTTTAGCAATTTCAGCATTAACGCGGCCATCAA  1620
AMBX01000015  108494  ............................................................  108553
AMBV01000052  50198   ............................................................  50257
AMBU01000072  109081  ............................................................  109140
AJHA01000079  15479   ............................................................  15538
AJGZ01000001  233384  ............................................................  233443
AJGX01000034  233211  ............................................................  233270
AJGW01000056  43702   ............................................................  43761
ABEL01000005  222964  ............................................................  223023
AMBW01000028  19752   ............................................................  19693
```

Figure 2 (Continued)

```
AJGY01000001   30628   ..............................................................   30569

Query          1621    CCTCAATCTGAATATTACGTCCGGCAACCATCTTTTTAGTATTCCTGATTTTCTCCAGAC   1680
AMBX01000015   108554  ..............................................................   108613
AMBV01000052   50258   ..............................................................   50317
AMBU01000072   109141  ..............................................................   109200
AJHA01000079   15539   ..............................................................   15598
AJGZ01000001   233444  ..............................................................   233503
AJGX01000034   233271  ..............................................................   233330
AJGW01000056   43762   ..............................................................   43821
ABEL01000005   223024  ..............................................................   223083
AMBW01000028   19692   ..............................................................   19633
AJGY01000001   30568   ..............................................................   30509

Query          1681    TTTTTTCAATAAATGTCTGACCAGGCTGACCTGGGTTGATGGTCATAATCAAAACATAAT   1740
AMBX01000015   108614  ..............................................................   108673
AMBV01000052   50318   ..............................................................   50377
AMBU01000072   109201  ..............................................................   109260
AJHA01000079   15599   ..............................................................   15658
AJGZ01000001   233504  ..............................................................   233563
AJGX01000034   233331  ..............................................................   233390
AJGW01000056   43822   ..............................................................   43881
ABEL01000005   223084  ..............................................................   223143
AMBW01000028   19632   ..............................................................   19573
AJGY01000001   30508   ..............................................................   30449

Query          1741    CAATATCATCCAGGAGGTATTCAATTACATGTTCCGGCGTCCCCGGATTGAGTACCACAC   1800
AMBX01000015   108674  ..............................................................   108733
AMBV01000052   50378   ..............................................................   50437
AMBU01000072   109261  ..............................................................   109320
AJHA01000079   15659   ..............................................................   15718
AJGZ01000001   233564  ..............................................................   233623
AJGX01000034   233391  ..............................................................   233450
AJGW01000056   43882   ..............................................................   43941
ABEL01000005   223144  ..............................................................   223203
AMBW01000028   19572   ..............................................................   19513
AJGY01000001   30448   ..............................................................   30389

Query          1801    CGGCTTTGCGCCCGGCTTTCTTGATCTTCTGGATAATATAATGAACGTGCGGCGTTGATT   1860
AMBX01000015   108734  ..............................................................   108793
AMBV01000052   50438   ..............................................................   50497
AMBU01000072   109321  ..............................................................   109380
AJHA01000079   15719   ..............................................................   15778
AJGZ01000001   233624  ..............................................................   233683
AJGX01000034   233451  ..............................................................   233510
AJGW01000056   43942   ..............................................................   44001
ABEL01000005   223204  ..............................................................   223263
AMBW01000028   19512   ..............................................................   19453
AJGY01000001   30388   ..............................................................   30329

Query          1861    CATAATGAACCGAGATCATTTCCGCTCCGGTTTTAATAACATCATCGATATGTCTTTCCG   1920
AMBX01000015   108794  ..............................................................   108853
AMBV01000052   50498   ..............................................................   50557
AMBU01000072   109381  ..............................................................   109440
AJHA01000079   15779   ..............................................................   15838
AJGZ01000001   233684  ..............................................................   233743
AJGX01000034   233511  ..............................................................   233570
AJGW01000056   44002   ..............................................................   44061
ABEL01000005   223264  ..............................................................   223323
AMBW01000028   19452   ..............................................................   19393
AJGY01000001   30328   ..............................................................   30269

Query          1921    GGTTTGCCAGCATCATATGCACATCAAATGTCATTGAACTGGCTTTTTCATTGCCGCAA   1980
AMBX01000015   108854  ..............................................................   108913
AMBV01000052   50558   ..............................................................   50617
AMBU01000072   109441  ..............................................................   109500
AJHA01000079   15839   ..............................................................   15898
AJGZ01000001   233744  ..............................................................   233803
AJGX01000034   233571  ..............................................................   233630
AJGW01000056   44062   ..............................................................   44121
ABEL01000005   223324  ..............................................................   223383
AMBW01000028   19392   ..............................................................   19333
AJGY01000001   30268   ..............................................................   30209

Query          1981    TTTGGTTAGGACCGAAAGCTATATTGCTTACATAAGTACCATCCATTAAATCAACATGCA   2040
AMBX01000015   108914  ..............................................................   108973
AMBV01000052   50618   ..............................................................   50677
AMBU01000072   109501  ..............................................................   109560
AJHA01000079   15899   ..............................................................   15958
AJGZ01000001   233804  ..............................................................   233863
AJGX01000034   233631  ..............................................................   233690
```

Figure 2 (Continued)

```
AJGW01000056   44122   .................................................... 44181
ABEL01000005  223384   .................................................... 223443
AMBW01000028   19332   .................................................... 19273
AJGY01000001   30208   .................................................... 30149

Query           2041   GAATTCTGTTTTTTCTGTTTCCAGAAACTGAATTTCTTCCTGCAAACGTAATATGTTTG 2100
AMBX01000015  108974   .................................................... 109033
AMBV01000052   50678   .................................................... 50737
AMBU01000072  109561   .................................................... 109620
AJHA01000079   15959   .................................................... 16018
AJGZ01000001  233864   .................................................... 233923
AJGX01000034  233691   .................................................... 233750
AJGW01000056   44182   .................................................... 44241
ABEL01000005  223444   .................................................... 223503
AMBW01000028   19272   .................................................... 19213
AJGY01000001   30148   .................................................... 30089

Query           2101   CACCAAATACTGATGGTAAAATTTGTGCCATTTTAGTCAACTCCAGAAATTAATGCGTAA 2160
AMBX01000015  109034   .................................................... 109093
AMBV01000052   50738   .................................................... 50797
AMBU01000072  109621   .................................................... 109680
AJHA01000079   16019   .................................................... 16078
AJGZ01000001  233924   .................................................... 233983
AJGX01000034  233751   .................................................... 233810
AJGW01000056   44242   .................................................... 44301
ABEL01000005  223504   .................................................... 223563
AMBW01000028   19212   .................................................... 19153
AJGY01000001   30088   .................................................... 30029

Query           2161   CTGTGCTCAACCAGTAGGTCAGAATCTCCCATGGGCCGGTTAATACGAAGTCCGTGCCCT 2220
AMBX01000015  109094   .................................................... 109153
AMBV01000052   50798   .................................................... 50857
AMBU01000072  109681   .................................................... 109740
AJHA01000079   16079   .................................................... 16138
AJGZ01000001  233984   .................................................... 234043
AJGX01000034  233811   .................................................... 233870
AJGW01000056   44302   .................................................... 44361
ABEL01000005  223564   .................................................... 223623
AMBW01000028   19152   .................................................... 19093
AJGY01000001   30028   .................................................... 29969

Query           2221   GGCCATTAAGGCCGACGCCAGCACCGTTCAGGAACTCAGTTGCACCGGGCGCGACATAcc 2280
AMBX01000015  109154   .................................................... 109213
AMBV01000052   50858   .................................................... 50917
AMBU01000072  109741   .................................................... 109800
AJHA01000079   16139   .................................................... 16198
AJGZ01000001  234044   .................................................... 234103
AJGX01000034  233871   .................................................... 233930
AJGW01000056   44362   .................................................... 44421
ABEL01000005  223624   .................................................... 223683
AMBW01000028   19092   .................................................... 19033
AJGY01000001   29968   .................................................... 29909

Query           2281   cccccAGATACATAACCACTACACAGAACAGTAAGGTTGAGATAATCGAGCGAATAACGT 2340
AMBX01000015  109214   .................................................... 109273
AMBV01000052   50918   .................................................... 50977
AMBU01000072  109801   .................................................... 109860
AJHA01000079   16199   .................................................... 16258
AJGZ01000001  234104   .................................................... 234163
AJGX01000034  233931   .................................................... 233990
AJGW01000056   44422   .................................................... 44481
ABEL01000005  223684   .................................................... 223743
AMBW01000028   19032   .................................................... 18973
AJGY01000001   29908   .................................................... 29849

Query           2341   TGCCGTTACTGACCATGACTGTCATGGTCGTCATGTAGATAATTGACATCAGCACGCCGA 2400
AMBX01000015  109274   .................................................... 109333
AMBV01000052   50978   .................................................... 51037
AMBU01000072  109861   .................................................... 109920
AJHA01000079   16259   .................................................... 16318
AJGZ01000001  234164   .................................................... 234223
AJGX01000034  233991   .................................................... 234050
AJGW01000056   44482   .................................................... 44541
ABEL01000005  223744   .................................................... 223803
AMBW01000028   18972   .................................................... 18913
AJGY01000001   29848   .................................................... 29789

Query           2401   TTGGGAATATCTGAATACCCGGTAAAACCAGCGCACAAAGCATTGTCAGAGGGATGGTAA 2460
AMBX01000015  109334   .................................................... 109393
AMBV01000052   51038   .................................................... 51097
AMBU01000072  109921   .................................................... 109980
```

Figure 2 (Continued)

```
AJHA01000079  16319  ..............................................................  16378
AJGZ01000001  234224 ..............................................................  234283
AJGX01000034  234051 ..............................................................  234110
AJGW01000056  44542  ..............................................................  44601
ABEL01000005  223804 ..............................................................  223863
AMBW01000028  18912  ..............................................................  18853
AJGY01000001  29788  ..............................................................  29729

Query         2461   TAACGGTGACAGTAACCGTTGCTGGGTCGCCAAGCGCAAGGGCACAGTCCATCCCGATAT  2520
AMBX01000015  109394 ..............................................................  109453
AMBV01000052  51098  ..............................................................  51157
AMBU01000072  109981 ..............................................................  110040
AJHA01000079  16379  ..............................................................  16438
AJGZ01000001  234284 ..............................................................  234343
AJGX01000034  234111 ..............................................................  234170
AJGW01000056  44602  ..............................................................  44661
ABEL01000005  223864 ..............................................................  223923
AMBW01000028  18852  ..............................................................  18793
AJGY01000001  29728  ..............................................................  29669

Query         2521   TCAGCTCCGCATCTTTACCCATCTGCTTTTGCATGATTTCTTTAGCACTCTTACCTATCG  2580
AMBX01000015  109454 ..............................................................  109513
AMBV01000052  51158  ..............................................................  51217
AMBU01000072  110041 ..............................................................  110100
AJHA01000079  16439  ..............................................................  16498
AJGZ01000001  234344 ..............................................................  234403
AJGX01000034  234171 ..............................................................  234230
AJGW01000056  44662  ..............................................................  44721
ABEL01000005  223924 ..............................................................  223983
AMBW01000028  18792  ..............................................................  18733
AJGY01000001  29668  ..............................................................  29609

Query         2581   GGTTAAGCCCTTCCATAAGGACCCCAACCACTTTTGGCAACAGCACCATGACGCCAGCCA  2640
AMBX01000015  109514 ..............................................................  109573
AMBV01000052  51218  ..............................................................  51277
AMBU01000072  110101 ..............................................................  110160
AJHA01000079  16499  ..............................................................  16558
AJGZ01000001  234404 ..............................................................  234463
AJGX01000034  234231 ..............................................................  234290
AJGW01000056  44722  ..............................................................  44781
ABEL01000005  223984 ..............................................................  224043
AMBW01000028  18732  ..............................................................  18673
AJGY01000001  29608  ..............................................................  29549

Query         2641   CGCCCATCGCCATTGGCACGATGGTTGTAATGGGTTGTTTGGTTAACAATCCCAGGAGAC  2700
AMBX01000015  109574 ..............................................................  109633
AMBV01000052  51278  ..............................................................  51337
AMBU01000072  110161 ..............................................................  110220
AJHA01000079  16559  ..............................................................  16618
AJGZ01000001  234464 ..............................................................  234523
AJGX01000034  234291 ..............................................................  234350
AJGW01000056  44782  ..............................................................  44841
ABEL01000005  224044 ..............................................................  224103
AMBW01000028  18672  ..............................................................  18613
AJGY01000001  29548  ..............................................................  29489

Query         2701   AACCGACAATCACGCCGATGATTGCGGGTTCACCGAATACACCCAGTCGTTTCTGAACGC  2760
AMBX01000015  109634 ..............................................................  109693
AMBV01000052  51338  ..............................................................  51397
AMBU01000072  110221 ..............................................................  110280
AJHA01000079  16619  ..............................................................  16678
AJGZ01000001  234524 ..............................................................  234583
AJGX01000034  234351 ..............................................................  234410
AJGW01000056  44842  ..............................................................  44901
ABEL01000005  224104 ..............................................................  224163
AMBW01000028  18612  ..............................................................  18553
AJGY01000001  29488  ..............................................................  29429

Query         2761   TCTCTAAATCCACATCCAGCTTGTTAAACCCGGAATGAAATCGATAATTTTGTTAACAA   2820
AMBX01000015  109694 ..............................................................  109753
AMBV01000052  51398  ..............................................................  51457
AMBU01000072  110281 ..............................................................  110340
AJHA01000079  16679  ..............................................................  16738
AJGZ01000001  234584 ..............................................................  234643
AJGX01000034  234411 ..............................................................  234470
AJGW01000056  44902  ..............................................................  44961
ABEL01000005  224164 ..............................................................  224223
AMBW01000028  18552  ..............................................................  18493
AJGY01000001  29428  ..............................................................  29369

Query         2821   CCCATGCAAATGGAAGTGTCCATCCGATGTGGATCATCGTGGTACAGGTCGTCCCCTCGA  2880
```

Figure 2 (Continued)

```
AMBX01000015  109754  ............................................................  109813
AMBV01000052   51458  ............................................................   51517
AMBU01000072  110341  ............................................................  110400
AJHA01000079   16739  ............................................................   16798
AJGZ01000001  234644  ............................................................  234703
AJGX01000034  234471  ............................................................  234530
AJGW01000056   44962  ............................................................   45021
ABEL01000005  224224  ............................................................  224283
AMBW01000028   18492  ............................................................   18433
AJGY01000001   29368  ............................................................   29309

Query           2881  GGCCGTAGTATTTCTGCCATCTTGGCGCAATAAGATCGCCAATAAACAGTGCGGCTACGC  2940
AMBX01000015  109814  ............................................................  109873
AMBV01000052   51518  ............................................................   51577
AMBU01000072  110401  ............................................................  110460
AJHA01000079   16799  ............................................................   16858
AJGZ01000001  234704  ............................................................  234763
AJGX01000034  234531  ............................................................  234590
AJGW01000056   45022  ............................................................   45081
ABEL01000005  224284  ............................................................  224343
AMBW01000028   18432  ............................................................   18373
AJGY01000001   29308  ............................................................   29249

Query           2941  TCAGAGCCACGGCGACACCCAACCCAAGGAAAAAGCTGTCAAAGACGAAATACGCAAGAG  3000
AMBX01000015  109874  ............................................................  109933
AMBV01000052   51578  ............................................................   51637
AMBU01000072  110461  ............................................................  110520
AJHA01000079   16859  ............................................................   16918
AJGZ01000001  234764  ............................................................  234823
AJGX01000034  234591  ............................................................  234650
AJGW01000056   45082  ............................................................   45141
ABEL01000005  224344  ............................................................  224403
AMBW01000028   18372  ............................................................   18313
AJGY01000001   29248  ............................................................   29189

Query           3001  CCCCCGGAACCAGGAAATGCATGTAGTTCCAGATGTCCACATTAAGAGTTTTGGTAAGCT  3060
AMBX01000015  109934  ............................................................  109993
AMBV01000052   51638  ............................................................   51697
AMBU01000072  110521  ............................................................  110580
AJHA01000079   16919  ............................................................   16978
AJGZ01000001  234824  ............................................................  234883
AJGX01000034  234651  ............................................................  234710
AJGW01000056   45142  ............................................................   45201
ABEL01000005  224404  ............................................................  224463
AMBW01000028   18312  ............................................................   18253
AJGY01000001   29188  ............................................................   29129

Query           3061  TCAGACGAACCAGGATCAGGTTCAGGATAATGCCAATAGGAATAACCATTGCGGCAAACG  3120
AMBX01000015  109994  ............................................................  110053
AMBV01000052   51698  ............................................................   51757
AMBU01000072  110581  ............................................................  110640
AJHA01000079   16979  ............................................................   17038
AJGZ01000001  234884  ............................................................  234943
AJGX01000034  234711  ............................................................  234770
AJGW01000056   45202  ............................................................   45261
ABEL01000005  224464  ............................................................  224523
AMBW01000028   18252  ............................................................   18193
AJGY01000001   29128  ............................................................   29069

Query           3121  GGGCAACCCACGCAGCTGCGCCAACGGCAGGCCATCCAATATCAGCCACGGTGAACCCGC  3180
AMBX01000015  110054  ............................................................  110113
AMBV01000052   51758  ............................................................   51817
AMBU01000072  110641  ............................................................  110700
AJHA01000079   17039  ............................................................   17098
AJGZ01000001  234944  ............................................................  235003
AJGX01000034  234771  ............................................................  234830
AJGW01000056   45262  ............................................................   45321
ABEL01000005  224524  ............................................................  224583
AMBW01000028   18192  ............................................................   18133
AJGY01000001   29068  ............................................................   29009

Query           3181  TGCCAATTTTTGAGTAATACGTAATTGCTGGCTGCAGGGCTGTGTTTAGCAGCCCAACAA  3240
AMBX01000015  110114  ............................................................  110173
AMBV01000052   51818  ............................................................   51877
AMBU01000072  110701  ............................................................  110760
AJHA01000079   17099  ............................................................   17158
AJGZ01000001  235004  ............................................................  235063
AJGX01000034  234831  ............................................................  234890
AJGW01000056   45322  ............................................................   45381
ABEL01000005  224584  ............................................................  224643
AMBW01000028   18132  ............................................................   18073
```

Figure 2 (Continued)

```
AJGY01000001   29008   ..................................................   28949

Query          3241   CCAGTCCCAGACCGATGAAACCGATACCTACAGTGATGCCAGATTTAATAGCGGCACCCA   3300
AMBX01000015   110174  ..................................................   110233
AMBV01000052   51878   ..................................................   51937
AMBU01000072   110761  ..................................................   110820
AJHA01000079   17159   ..................................................   17218
AJGZ01000001   235064  ..................................................   235123
AJGX01000034   234891  ..................................................   234950
AJGW01000056   45382   ..................................................   45441
ABEL01000005   224644  ..................................................   224703
AMBW01000028   18072   ..................................................   18013
AJGY01000001   28948   ..................................................   28889

Query          3301   CTTTCATTCGAAAAACCAGACCTAAAAGGAAAATAACAAGCGGCAATATTGCTGTAGCGC   3360
AMBX01000015   110234  ..................................................   110293
AMBV01000052   51938   ..................................................   51997
AMBU01000072   110821  ..................................................   110880
AJHA01000079   17219   ..................................................   17278
AJGZ01000001   235124  ..................................................   235183
AJGX01000034   234951  ..................................................   235010
AJGW01000056   45442   ..................................................   45501
ABEL01000005   224704  ..................................................   224763
AMBW01000028   18012   ..................................................   17953
AJGY01000001   28888   ..................................................   28829

Query          3361   CCATGCTTGTAATAGTAAACATGATGCTTTTTAACATTTCCATTTAACCATCCCCGTCT   3420
AMBX01000015   110294  ..................................................   110353
AMBV01000052   51998   ..................................................   52057
AMBU01000072   110881  ..................................................   110940
AJHA01000079   17279   ..................................................   17338
AJGZ01000001   235184  ..................................................   235243
AJGX01000034   235011  ..................................................   235070
AJGW01000056   45502   ..................................................   45561
ABEL01000005   224764  ..................................................   224823
AMBW01000028   17952   ..................................................   17893
AJGY01000001   28828   ..................................................   28769

Query          3421   TTTTTAGACTTTAGCCTTTGGAAATTTCGCTTAACAGTTCACCTAATTTTTTACGCAGTG   3480
AMBX01000015   110354  ..................................................   110413
AMBV01000052   52058   ..................................................   52117
AMBU01000072   110941  ..................................................   111000
AJHA01000079   17339   ..................................................   17398
AJGZ01000001   235244  ..................................................   235303
AJGX01000034   235071  ..................................................   235130
AJGW01000056   45562   ..................................................   45621
ABEL01000005   224824  ..................................................   224883
AMBW01000028   17892   ..................................................   17833
AJGY01000001   28768   ..................................................   28709

Query          3481   CGGCTTCGTTAATACCGGTAATAAAACCTGCGACGCTCATGTGCGGCTTACCAATATCAC   3540
AMBX01000015   110414  ..................................................   110473
AMBV01000052   52118   ..................................................   52177
AMBU01000072   111001  ..................................................   111060
AJHA01000079   17399   ..................................................   17458
AJGZ01000001   235304  ..................................................   235363
AJGX01000034   235131  ..................................................   235190
AJGW01000056   45622   ..................................................   45681
ABEL01000005   224884  ..................................................   224943
AMBW01000028   17832   ..................................................   17773
AJGY01000001   28708   ..................................................   28649

Query          3541   CTTTATAATTATTCGTCGTCAGGACCACATCAGCGCTTTGCATTTCAGAGGCCAGCTCGG   3600
AMBX01000015   110474  ..................................................   110533
AMBV01000052   52178   ..................................................   52237
AMBU01000072   111061  ..................................................   111120
AJHA01000079   17459   ..................................................   17518
AJGZ01000001   235364  ..................................................   235423
AJGX01000034   235191  ..................................................   235250
AJGW01000056   45682   ..................................................   45741
ABEL01000005   224944  ..................................................   225003
AMBW01000028   17772   ..................................................   17713
AJGY01000001   28648   ..................................................   28589

Query          3601   ACATGCTGCATTTATTAATCTTAAAGTTGGCAATTCCGTATTCAGCACAAACCGATTTAA   3660
AMBX01000015   110534  ..................................................   110593
AMBV01000052   52238   ..................................................   52297
AMBU01000072   111121  ..................................................   111180
AJHA01000079   17519   ..................................................   17578
AJGZ01000001   235424  ..................................................   235483
AJGX01000034   235251  ..................................................   235310
```

Figure 2 (Continued)

```
AJGW01000056   45742    ..............................................................   45801
ABEL01000005   225004   ..............................................................   225063
AMBW01000028   17712    ..............................................................   17653
AJGY01000001   28588    ..............................................................   28529

Query          3661     CTTCATCAGCGGCTAGTGTGGAGGTTGCGACACCGCTTCCGCAGGCTACGAGGATAGTAA    3720
AMBX01000015   110594   ..............................................................   110653
AMBV01000052   52298    ..............................................................   52357
AMBU01000072   111181   ..............................................................   111240
AJHA01000079   17579    ..............................................................   17638
AJGZ01000001   235484   ..............................................................   235543
AJGX01000034   235311   ..............................................................   235370
AJGW01000056   45802    ..............................................................   45861
ABEL01000005   225064   ..............................................................   225123
AMBW01000028   17652    ..............................................................   17593
AJGY01000001   28528    ..............................................................   28469

Query          3721     TCATGGTAAAATCTCCGGGTAATTGTTATTTAATTATCGTGTTAATAAACAATGCCTTTG    3780
AMBX01000015   110654   ..............................................................   110713
AMBV01000052   52358    ..............................................................   52417
AMBU01000072   111241   ..............................................................   111300
AJHA01000079   17639    ..............................................................   17698
AJGZ01000001   235544   ..............................................................   235603
AJGX01000034   235371   ..............................................................   235430
AJGW01000056   45862    ..............................................................   45921
ABEL01000005   225124   ..............................................................   225183
AMBW01000028   17592    ..............................................................   17533
AJGY01000001   28468    ..............................................................   28409

Query          3781     CTTCTTCAGCAGGAAGCTCCAGCATCTGGTGGTAAAAATCAGCTAACTGAAGATGGTTAA    3840
AMBX01000015   110714   ..............................................................   110773
AMBV01000052   52418    ..............................................................   52477
AMBU01000072   111301   ..............................................................   111360
AJHA01000079   17699    ..............................................................   17758
AJGZ01000001   235604   ..............................................................   235663
AJGX01000034   235431   ..............................................................   235490
AJGW01000056   45922    ..............................................................   45981
ABEL01000005   225184   ..............................................................   225243
AMBW01000028   17532    ..............................................................   17473
AJGY01000001   28408    ..............................................................   28349

Query          3841     ACAGCGCCTTCAACAACTGCAATTGATCTGCAGGTTGGGTAACAACCAGGTTGACAACCA    3900
AMBX01000015   110774   ..............................................................   110833
AMBV01000052   52478    ..............................................................   52537
AMBU01000072   111361   ..............................................................   111420
AJHA01000079   17759    ..............................................................   17818
AJGZ01000001   235664   ..............................................................   235723
AJGX01000034   235491   ..............................................................   235550
AJGW01000056   45982    ..............................................................   46041
ABEL01000005   225244   ..............................................................   225303
AMBW01000028   17472    ..............................................................   17413
AJGY01000001   28348    ..............................................................   28289

Query          3901     GGCGGACCCACAGTTTTTCATCGCCATCTGCCTGATTAACTTCTATTTCCTGTGGCAAAC    3960
AMBX01000015   110834   ..............................................................   110893
AMBV01000052   52538    ..............................................................   52597
AMBU01000072   111421   ..............................................................   111480
AJHA01000079   17819    ..............................................................   17878
AJGZ01000001   235724   ..............................................................   235783
AJGX01000034   235551   ..............................................................   235610
AJGW01000056   46042    ..............................................................   46101
ABEL01000005   225304   ..............................................................   225363
AMBW01000028   17412    ..............................................................   17353
AJGY01000001   28288    ..............................................................   28229

Query          3961     GAATGATATAAATCGCCGGGCTGACGGCGTGCTGGCTATCGCAATGGGGGATGGCGACAG    4020
AMBX01000015   110894   ..............................................................   110953
AMBV01000052   52598    ..............................................................   52657
AMBU01000072   111481   ..............................................................   111540
AJHA01000079   17879    ..............................................................   17938
AJGZ01000001   235784   ..............................................................   235843
AJGX01000034   235611   ..............................................................   235670
AJGW01000056   46102    ..............................................................   46161
ABEL01000005   225364   ..............................................................   225423
AMBW01000028   17352    ..............................................................   17293
AJGY01000001   28228    ..............................................................   28169

Query          4021     CATAGCCGTCAAGTAAAATTCCAGTTGGATAGTCGGCTTCACGTTCACGCAGCGCCTGGA    4080
AMBX01000015   110954   ..............................................................   111013
AMBV01000052   52658    ..............................................................   52717
AMBU01000072   111541   ..............................................................   111600
```

Figure 2 (Continued)

```
AJHA01000079    17939   ..............................................................  17998
AJGZ01000001   235844   ..............................................................  235903
AJGX01000034   235671   ..............................................................  235730
AJGW01000056    46162   ..............................................................  46221
ABEL01000005   225424   ..............................................................  225483
AMBW01000028    17292   ..............................................................  17233
AJGY01000001    28168   ..............................................................  28109

Query            4081   GGTAAGTCTCTCTTACAATCCCATCGGCCAGATGTTTCTGGTGAATATGCTCCAGCACTT   4140
AMBX01000015   111014   ..............................................................  111073
AMBV01000052    52718   ..............................................................  52777
AMBU01000072   111601   ..............................................................  111660
AJHA01000079    17999   ..............................................................  18058
AJGZ01000001   235904   ..............................................................  235963
AJGX01000034   235731   ..............................................................  235790
AJGW01000056    46222   ..............................................................  46281
ABEL01000005   225484   ..............................................................  225543
AMBW01000028    17232   ..............................................................  17173
AJGY01000001    28108   ..............................................................  28049

Query            4141   CATCATAATTTTTGAATGCCGCCCCATCCGCGACATTGATAGAAATTGCACCCACTTTCT   4200
AMBX01000015   111074   ..............................................................  111133
AMBV01000052    52778   ..............................................................  52837
AMBU01000072   111661   ..............................................................  111720
AJHA01000079    18059   ..............................................................  18118
AJGZ01000001   235964   ..............................................................  236023
AJGX01000034   235791   ..............................................................  235850
AJGW01000056    46282   ..............................................................  46341
ABEL01000005   225544   ..............................................................  225603
AMBW01000028    17172   ..............................................................  17113
AJGY01000001    28048   ..............................................................  27989

Query            4201   TCTCCTCACCTAACAACTCGCTCATGTGAGCATAAATCCAATCACATGAGCAGTTATAGC   4260
AMBX01000015   111134   ..............................................................  111193
AMBV01000052    52838   ..............................................................  52897
AMBU01000072   111721   ..............................................................  111780
AJHA01000079    18119   ..............................................................  18178
AJGZ01000001   236024   ..............................................................  236083
AJGX01000034   235851   ..............................................................  235910
AJGW01000056    46342   ..............................................................  46401
ABEL01000005   225604   ..............................................................  225663
AMBW01000028    17112   ..............................................................  17053
AJGY01000001    27988   ..............................................................  27929

Query            4261   ACATCAGTGAATTGCTGAAATAGGGAGCTTGCAAAAGTTATATCTTGATCACACAAAATC   4320
AMBX01000015   111194   ..............................................................  111253
AMBV01000052    52898   ..............................................................  52957
AMBU01000072   111781   ..............................................................  111840
AJHA01000079    18179   ..............................................................  18238
AJGZ01000001   236084   ..............................................................  236143
AJGX01000034   235911   ..............................................................  235970
AJGW01000056    46402   ..............................................................  46461
ABEL01000005   225664   ..............................................................  225723
AMBW01000028    17052   ..............................................................  16993
AJGY01000001    27928   ..............................................................  27869

Query            4321   ACATACGCGCAATCATTAAAATGCTCACATGAGCAAACATGCCGATTGCTCAATGCACCA   4380
AMBX01000015   111254   ..............................................................  111313
AMBV01000052    52958   ..............................................................  53017
AMBU01000072   111841   ..............................................................  111900
AJHA01000079    18239   ..............................................................  18298
AJGZ01000001   236144   ..............................................................  236203
AJGX01000034   235971   ..............................................................  236030
AJGW01000056    46462   ..............................................................  46521
ABEL01000005   225724   ..............................................................  225783
AMBW01000028    16992   ..............................................................  16933
AJGY01000001    27868   ..............................................................  27809

Query            4381   CAAATGCTTATACCATTGAATTTTAATTAATTTAATTGAATTGGCTTACTTTGGGGATTT   4440
AMBX01000015   111314   ..............................................................  111373
AMBV01000052    53018   ..............................................................  53077
AMBU01000072   111901   ..............................................................  111960
AJHA01000079    18299   ..............................................................  18358
AJGZ01000001   236204   ..............................................................  236263
AJGX01000034   236031   ..............................................................  236090
AJGW01000056    46522   ..............................................................  46581
ABEL01000005   225784   ..............................................................  225843
AMBW01000028    16932   ..............................................................  16873
AJGY01000001    27808   ..............................................................  27749

Query            4441   TTACGTTGGTAATAATTCAAACGCTCTTATGAGCATGGCGTTCTGATAGTGTGGTTTCT   4500
```

Figure 2 (Continued)

```
AMBX01000015    111374    ..........................................................    111433
AMBV01000052     53078    ..........................................................     53137
AMBU01000072    111961    ..........................................................    112020
AJHA01000079     18359    ..........................................................     18418
AJGZ01000001    236264    ..........................................................    236323
AJGX01000034    236091    ..........................................................    236150
AJGW01000056     46582    ..........................................................     46641
ABEL01000005    225844    ..........................................................    225903
AMBW01000028     16872    ..........................................................     16813
AJGY01000001     27748    ..........................................................     27689

Query             4501    GCAGGACAACGGCACATGAAATGTACCGTTATTGAATTTAGAATCAACAGGTTATCACTG    4560
AMBX01000015    111434    ............................................................    111493
AMBV01000052     53138    ............................................................     53197
AMBU01000072    112021    ............................................................    112080
AJHA01000079     18419    ............................................................     18478
AJGZ01000001    236324    ............................................................    236383
AJGX01000034    236151    ............................................................    236210
AJGW01000056     46642    ............................................................     46701
ABEL01000005    225904    ............................................................    225963
AMBW01000028     16812    ............................................................     16753
AJGY01000001     27688    ............................................................     27629

Query             4561    TTGTATGTTTCGCAACTTCGGCAATACCGTCTTTATCAGCAATATCATTAGTGATCAGTG    4620
AMBX01000015    111494    ............................................................    111553
AMBV01000052     53198    ............................................................     53257
AMBU01000072    112081    ............................................................    112140
AJHA01000079     18479    ............................................................     18538
AJGZ01000001    236384    ............................................................    236443
AJGX01000034    236211    ............................................................    236270
AJGW01000056     46702    ............................................................     46761
ABEL01000005    225964    ............................................................    226023
AMBW01000028     16752    ............................................................     16693
AJGY01000001     27628    ............................................................     27569

Query             4621    CGGTAATCTCAGACCAGTCGCAGATCTTAAATAAGCTGCTGCGCTGGAACTTAGTGTAAT    4680
AMBX01000015    111554    ............................................................    111613
AMBV01000052     53258    ............................................................     53317
AMBU01000072    112141    ............................................................    112200
AJHA01000079     18539    ............................................................     18598
AJGZ01000001    236444    ............................................................    236503
AJGX01000034    236271    ............................................................    236330
AJGW01000056     46762    ............................................................     46821
ABEL01000005    226024    ............................................................    226083
AMBW01000028     16692    ............................................................     16633
AJGY01000001     27568    ............................................................     27509

Query             4681    CGCCCAGGATATATTTCTTCTCGGAATGGGCAATGATCGTTCGATCCAAAAAGGCATCTG    4740
AMBX01000015    111614    ............................................................    111673
AMBV01000052     53318    ............................................................     53377
AMBU01000072    112201    ............................................................    112260
AJHA01000079     18599    ............................................................     18658
AJGZ01000001    236504    ............................................................    236563
AJGX01000034    236331    ............................................................    236390
AJGW01000056     46822    ............................................................     46881
ABEL01000005    226084    ............................................................    226143
AMBW01000028     16632    ............................................................     16573
AJGY01000001     27508    ............................................................     27449

Query             4741    AGGAGGACGGAGTGGACGGGCCCGTCATATTGTTGAAACCATCAGTGCCGATAAAGCATA    4800
AMBX01000015    111674    ............................................................    111733
AMBV01000052     53378    ............................................................     53437
AMBU01000072    112261    ............................................................    112320
AJHA01000079     18659    ............................................................     18718
AJGZ01000001    236564    ............................................................    236623
AJGX01000034    236391    ............................................................    236450
AJGW01000056     46882    ............................................................     46941
ABEL01000005    226144    ............................................................    226203
AMBW01000028     16572    ............................................................     16513
AJGY01000001     27448    ............................................................     27389

Query             4801    GATCAACGTTAATATCATTAATCATTGACACAGCCCACCCACCAAAGACAGAAGAGCttt    4860
AMBX01000015    111734    ............................................................    111793
AMBV01000052     53438    ............................................................     53497
AMBU01000072    112321    ............................................................    112380
AJHA01000079     18719    ............................................................     18778
AJGZ01000001    236624    ............................................................    236683
AJGX01000034    236451    ............................................................    236510
AJGW01000056     46942    ............................................................     47001
ABEL01000005    226204    ............................................................    226263
AMBW01000028     16512    ............................................................     16453
```

Figure 2 (Continued)

```
AJGY01000001   27388   ............................................................   27329

Query          4861    ttttCCTCAGTTCTCCGCCGAACAAAAAGACCTGGTTATCTGACTCGATCAGCACACTGG   4920
AMBX01000015   111794  ............................................................   111853
AMBV01000052   53498   ............................................................   53557
AMBU01000072   112381  ............................................................   112440
AJHA01000079   18779   ............................................................   18838
AJGZ01000001   236684  ............................................................   236743
AJGX01000034   236511  ............................................................   236570
AJGW01000056   47002   ............................................................   47061
ABEL01000005   226264  ............................................................   226323
AMBW01000028   16452   ............................................................   16393
AJGY01000001   27328   ............................................................   27269

Query          4921    CCACCGGCAAAGAATCGGTAAAAATTTTAAAGCCAGATTTCATGCACAACAGATTAGCCA   4980
AMBX01000015   111854  ............................................................   111913
AMBV01000052   53558   ............................................................   53617
AMBU01000072   112441  ............................................................   112500
AJHA01000079   18839   ............................................................   18898
AJGZ01000001   236744  ............................................................   236803
AJGX01000034   236571  ............................................................   236630
AJGW01000056   47062   ............................................................   47121
ABEL01000005   226324  ............................................................   226383
AMBW01000028   16392   ............................................................   16333
AJGY01000001   27268   ............................................................   27209

Query          4981    GTTCATAGTTAGAACTCCCGGTACCAATAATCATTGAGCTATTggggggATAAAATCCA    5040
AMBX01000015   111914  ............................................................   111973
AMBV01000052   53618   ............................................................   53677
AMBU01000072   112501  ............................................................   112560
AJHA01000079   18899   ............................................................   18958
AJGZ01000001   236804  ............................................................   236863
AJGX01000034   236631  ............................................................   236690
AJGW01000056   47122   ............................................................   47181
ABEL01000005   226384  ............................................................   226443
AMBW01000028   16332   ............................................................   16273
AJGY01000001   27208   ............................................................   27149

Query          5041    GCCCTTTTCTGGCTATAGCTTGTTTGAAAGTACTGTTTCTTTTTCCCTGACCTGGAAAG    5100
AMBX01000015   111974  ............................................................   112033
AMBV01000052   53678   ............................................................   53737
AMBU01000072   112561  ............................................................   112620
AJHA01000079   18959   ............................................................   19018
AJGZ01000001   236864  ............................................................   236923
AJGX01000034   236691  ............................................................   236750
AJGW01000056   47182   ............................................................   47241
ABEL01000005   226444  ............................................................   226503
AMBW01000028   16272   ............................................................   16213
AJGY01000001   27148   ............................................................   27089

Query          5101    GATGTTCGACCGCCCCCTGCTTTAAGGTTGCACCTCCATGGCTTTTAACCAGCAGCCCtt   5160
AMBX01000015   112034  ............................................................   112093
AMBV01000052   53738   ............................................................   53797
AMBU01000072   112621  ............................................................   112680
AJHA01000079   19019   ............................................................   19078
AJGZ01000001   236924  ............................................................   236983
AJGX01000034   236751  ............................................................   236810
AJGW01000056   47242   ............................................................   47301
ABEL01000005   226504  ............................................................   226563
AMBW01000028   16212   ............................................................   16153
AJGY01000001   27088   ............................................................   27029

Query          5161    tttttCAAGATGGGTGAGATCTTTGCGGATGGTTTCATAAGTGACCTCATACTTTTTAG   5220
AMBX01000015   112094  ............................................................   112153
AMBV01000052   53798   ............................................................   53857
AMBU01000072   112681  ............................................................   112740
AJHA01000079   19079   ............................................................   19138
AJGZ01000001   236984  ............................................................   237043
AJGX01000034   236811  ............................................................   236870
AJGW01000056   47302   ............................................................   47361
ABEL01000005   226564  ............................................................   226623
AMBW01000028   16152   ............................................................   16093
AJGY01000001   27028   ............................................................   26969

Query          5221    CAAGATCGCTAACGTACACGGTACCCGCCGAAATAATCTCTTCAAGGATCAATTTTCTCC   5280
AMBX01000015   112154  ............................................................   112213
AMBV01000052   53858   ............................................................   53917
AMBU01000072   112741  ............................................................   112800
AJHA01000079   19139   ............................................................   19198
AJGZ01000001   237044  ............................................................   237103
AJGX01000034   236871  ............................................................   236930
```

Figure 2 (Continued)

```
AJGW01000056   47362   ..............................................................   47421
ABEL01000005   226624  ..............................................................   226683
AMBW01000028   16092   ..............................................................   16033
AJGY01000001   26968   ..............................................................   26909

Query          5281    TTTCTTCAACCAGGTACATCCTTCCCCCCTATAACCATTCAACTCAATGCCATGAAGCGA    5340
AMBX01000015   112214  ..............................................................   112273
AMBV01000052   53918   ..............................................................   53977
AMBU01000072   112801  ..............................................................   112860
AJHA01000079   19199   ..............................................................   19258
AJGZ01000001   237104  ..............................................................   237163
AJGX01000034   236931  ..............................................................   236990
AJGW01000056   47422   ..............................................................   47481
ABEL01000005   226684  ..............................................................   226743
AMBW01000028   16032   ..............................................................   15973
AJGY01000001   26908   ..............................................................   26849

Query          5341    ATCATAGCACACAAGATGCAAACAAAAACAAACTCAAGGAGAAGACAAGTTGCCATCGGC    5400
AMBX01000015   112274  ..............................................................   112333
AMBV01000052   53978   ..............................................................   54037
AMBU01000072   112861  ..............................................................   112920
AJHA01000079   19259   ..............................................................   19318
AJGZ01000001   237164  ..............................................................   237223
AJGX01000034   236991  ..............................................................   237050
AJGW01000056   47482   ..............................................................   47541
ABEL01000005   226744  ..............................................................   226803
AMBW01000028   15972   ..............................................................   15913
AJGY01000001   26848   ..............................................................   26789

Query          5401    CTGTGAGCAGTCATTCGCGAAAGTAACAGTCGaaaaaaaaTAAAATATTTTTAAATCAAT    5460
AMBX01000015   112334  ..............................................................   112393
AMBV01000052   54038   ..............................................................   54097
AMBU01000072   112921  ..............................................................   112980
AJHA01000079   19319   ..............................................................   19378
AJGZ01000001   237224  ..............................................................   237283
AJGX01000034   237051  ..............................................................   237110
AJGW01000056   47542   ..............................................................   47601
ABEL01000005   226804  ..............................................................   226863
AMBW01000028   15912   ..............................................................   15853
AJGY01000001   26788   .............................................................-   26730

Query          5461    ACATTAAATGCGTTAAATCGAGTTTATTGTCTACAGCCTATAAATCCTTTTTCCCTGAAT    5520
AMBX01000015   112394  ..............................................................   112453
AMBV01000052   54098   ..............................................................   54157
AMBU01000072   112981  ..............................................................   113040
AJHA01000079   19379   ..............................................................   19438
AJGZ01000001   237284  ..............................................................   237343
AJGX01000034   237111  ..............................................................   237170
AJGW01000056   47602   ..............................................................   47661
ABEL01000005   226864  ..............................................................   226923
AMBW01000028   15852   ..............................................................   15793
AJGY01000001   26729   ..............................................................   26670

Query          5521    GGCACAACACAATTGGTATAAATTAGttttatttgtttttattggttttaatttaaat    5580
AMBX01000015   112454  ..............................................................   112513
AMBV01000052   54158   ..............................................................   54217
AMBU01000072   113041  ..............................................................   113100
AJHA01000079   19439   ..............................................................   19498
AJGZ01000001   237344  ..............................................................   237403
AJGX01000034   237171  ..............................................................   237230
AJGW01000056   47662   ..............................................................   47721
ABEL01000005   226924  ..............................................................   226983
AMBW01000028   15792   ..............................................................   15733
AJGY01000001   26669   ..............................................................   26610

Query          5581    aaaatcaataagttatgaattttgtgattttgATCTCAGTTGACAACCAATATTTACCAA    5640
AMBX01000015   112514  ..............................................................   112573
AMBV01000052   54218   ..............................................................   54277
AMBU01000072   113101  ..............................................................   113160
AJHA01000079   19499   ..............................................................   19558
AJGZ01000001   237404  ..............................................................   237463
AJGX01000034   237231  ..............................................................   237290
AJGW01000056   47722   ..............................................................   47761
ABEL01000005   226984  ..............................................................   227043
AMBW01000028   15732   ..............................................................   15673
AJGY01000001   26609   ..............................................................   26550

Query          5641    CAGCATACTTGGCTTAAGTTCTTTATGACAGGTTAGTTGAGATGAAAACGAAAATTGCAA    5700
AMBX01000015   112574  ..............................................................   112633
AMBV01000052   54278   ..............................................................   54337
AMBU01000072   113161  ..............................................................   113220
```

Figure 2 (Continued)

```
AJHA01000079    19559   ..............................................................  19618
AJGZ01000001    237464  ..............................................................  237523
AJGX01000034    237291  ..............................................................  237350
AJGW01000056    47782   ..............................................................  47841
ABEL01000005    227044  ..............................................................  227103
AMBW01000028    15672   ..............................................................  15613
AJGY01000001    26549   ..............................................................  26490

Query           5701    TCGCATGTGATGATGTAGGGTTTGATCGTAAGGAGGAGATTAAAAAGTACCTTGAAGAAG    5760
AMBX01000015    112634  ..............................................................  112693
AMBV01000052    54338   ..............................................................  54397
AMBU01000072    113221  ..............................................................  113280
AJHA01000079    19619   ..............................................................  19678
AJGZ01000001    237524  ..............................................................  237583
AJGX01000034    237351  ..............................................................  237410
AJGW01000056    47842   ..............................................................  47901
ABEL01000005    227104  ..............................................................  227163
AMBW01000028    15612   ..............................................................  15553
AJGY01000001    26489   ..............................................................  26430

Query           5761    AGAAAAATGCAGATGTCGTGTACGATCCCGTAAAACGAAAAGAAGACGGTTTCAACAACT    5820
AMBX01000015    112694  ..............................................................  112753
AMBV01000052    54398   ..............................................................  54457
AMBU01000072    113281  ..............................................................  113340
AJHA01000079    19679   ..............................................................  19738
AJGZ01000001    237584  ..............................................................  237643
AJGX01000034    237411  ..............................................................  237470
AJGW01000056    47902   ..............................................................  47961
ABEL01000005    227164  ..............................................................  227223
AMBW01000028    15552   ..............................................................  15493
AJGY01000001    26429   ..............................................................  26370

Query           5821    TCGCTCGTCTGGCGGATGAAATGGCAGGTGTTATTCAGCGGGATGAATGCCGCCTCGGTA    5880
AMBX01000015    112754  ..............................................................  112813
AMBV01000052    54458   ..............................................................  54517
AMBU01000072    113341  ..............................................................  113400
AJHA01000079    19739   ..............................................................  19798
AJGZ01000001    237644  ..............................................................  237703
AJGX01000034    237471  ..............................................................  237530
AJGW01000056    47962   ..............................................................  48021
ABEL01000005    227224  ..............................................................  227283
AMBW01000028    15492   ..............................................................  15433
AJGY01000001    26369   ..............................................................  26310

Query           5881    TCTACATCTGTGGAACCGGAATTGGCTTTACTTGCCAGATAAATAAGCACTGGGGGATCC    5940
AMBX01000015    112814  ..............................................................  112873
AMBV01000052    54518   ..............................................................  54577
AMBU01000072    113401  ..............................................................  113460
AJHA01000079    19799   ..............................................................  19858
AJGZ01000001    237704  ..............................................................  237763
AJGX01000034    237531  ..............................................................  237590
AJGW01000056    48022   ..............................................................  48081
ABEL01000005    227284  ..............................................................  227343
AMBW01000028    15432   ..............................................................  15373
AJGY01000001    26309   ..............................................................  26250

Query           5941    GTGCAGTCGCCGTCACCAACCCCTACTCAGCCAAGCGAGCAAGACTCAGTAACAATGCTC    6000
AMBX01000015    112874  ..............................................................  112933
AMBV01000052    54578   ..............................................................  54637
AMBU01000072    113461  ..............................................................  113520
AJHA01000079    19859   ..............................................................  19918
AJGZ01000001    237764  ..............................................................  237823
AJGX01000034    237591  ..............................................................  237650
AJGW01000056    48082   ..............................................................  48141
ABEL01000005    227344  ..............................................................  227403
AMBW01000028    15372   ..............................................................  15313
AJGY01000001    26249   ..............................................................  26190

Query           6001    AGGTGATTGGTCTTGGCTGCAGAGTTAATGATCTTGAATACACAAAAATGATCGTTGATG    6060
AMBX01000015    112934  ..............................................................  112993
AMBV01000052    54638   ..............................................................  54697
AMBU01000072    113521  ..............................................................  113580
AJHA01000079    19919   ..............................................................  19978
AJGZ01000001    237824  ..............................................................  237883
AJGX01000034    237651  ..............................................................  237710
AJGW01000056    48142   ..............................................................  48201
ABEL01000005    227404  ..............................................................  227463
AMBW01000028    15312   ..............................................................  15253
AJGY01000001    26189   ..............................................................  26130

Query           6061    CCTGGTATGACAATGCGTTCGACTTTGCCACTGCAAGGGAAAATTCCAAAAAGAATCTAC    6120
```

Figure 2 (Continued)

```
AMBX01000015   112994  ..............................................................  113053
AMBV01000052    54698  ..............................................................   54757
AMBU01000072   113581  ..............................................................  113640
AJHA01000079    19979  ..............................................................   20038
AJGZ01000001   237884  ..............................................................  237943
AJGX01000034   237711  ..............................................................  237770
AJGW01000056    48202  ..............................................................   48261
ABEL01000005   227464  ..............................................................  227523
AMBW01000028    15252  ..............................................................   15193
AJGY01000001    26129  ..............................................................   26070

Query            6121  TCGAAGCAGAACGCAGCGACAACGCATTGCTGACGAAACCTGAAGATGTGCGATGGAATA   6180
AMBX01000015   113054  ..............................................................  113113
AMBV01000052    54758  ..............................................................   54817
AMBU01000072   113641  ..............................................................  113700
AJHA01000079    20039  ..............................................................   20098
AJGZ01000001   237944  ..............................................................  238003
AJGX01000034   237771  ..............................................................  237830
AJGW01000056    48262  ..............................................................   48321
ABEL01000005   227524  ..............................................................  227583
AMBW01000028    15192  ..............................................................   15133
AJGY01000001    26069  ..............................................................   26010

Query            6181  TGGGTTTCAGACCAGATGATGAGAAATCTGAGGGCTAATAAATGGAACTGATCACACAGT   6240
AMBX01000015   113114  ..............................................................  113173
AMBV01000052    54818  ..............................................................   54877
AMBU01000072   113701  ..............................................................  113760
AJHA01000079    20099  ..............................................................   20158
AJGZ01000001   238004  ..............................................................  238063
AJGX01000034   237831  ..............................................................  237890
AJGW01000056    48322  ..............................................................   48381
ABEL01000005   227584  ..............................................................  227643
AMBW01000028    15132  ..............................................................   15073
AJGY01000001    26009  ..............................................................   25950

Query            6241  TTATCAATGACCTGGGTAACTTTATTTTTATACCGGTCATTTTCCTTGTACTGATGAAAC   6300
AMBX01000015   113174  ..............................................................  113233
AMBV01000052    54878  ..............................................................   54937
AMBU01000072   113761  ..............................................................  113820
AJHA01000079    20159  ..............................................................   20218
AJGZ01000001   238064  ..............................................................  238123
AJGX01000034   237891  ..............................................................  237950
AJGW01000056    48382  ..............................................................   48441
ABEL01000005   227644  ..............................................................  227703
AMBW01000028    15072  ..............................................................   15014
AJGY01000001    25949  ..............................................................   25890

Query            6301  TTCTGGGGCGTCCGCTGTCGGAGTGTATTTCATCAGCCATTAAAGTCGGCATCGGTTTTA   6360
AMBX01000015   113234  ..............................................................  113293
AMBV01000052    54938  ..............................................................   54997
AMBU01000072   113821  ..............................................................  113880
AJHA01000079    20219  ..............................................................   20278
AJGZ01000001   238124  ..............................................................  238183
AJGX01000034   237951  ..............................................................  238010
AJGW01000056    48442  ..............................................................   48501
ABEL01000005   227704  ..............................................................  227763
AMBW01000028    15013  ..............................................................   14954
AJGY01000001    25889  ..............................................................   25830

Query            6361  TTGCATTAACCATGACCATCAAGCTGATGCTTGAAAAAATGCAGCCAGCGGTGACAGGGC   6420
AMBX01000015   113294  ..............................................................  113353
AMBV01000052    54998  ..............................................................   55057
AMBU01000072   113881  ..............................................................  113940
AJHA01000079    20279  ..............................................................   20338
AJGZ01000001   238184  ..............................................................  238243
AJGX01000034   238011  ..............................................................  238070
AJGW01000056    48502  ..............................................................   48561
ABEL01000005   227764  ..............................................................  227823
AMBW01000028    14953  ..............................................................   14894
AJGY01000001    25829  ..............................................................   25770

Query            6421  TTGCTGAGGCCACCGGCTCCTCACTGAGCGCCATTGATGTTGGTGGCGCAGCCACAGCAG   6480
AMBX01000015   113354  ..............................................................  113413
AMBV01000052    55058  ..............................................................   55117
AMBU01000072   113941  ..............................................................  114000
AJHA01000079    20339  ..............................................................   20398
AJGZ01000001   238244  ..............................................................  238303
AJGX01000034   238071  ..............................................................  238130
AJGW01000056    48562  ..............................................................   48621
ABEL01000005   227824  ..............................................................  227883
AMBW01000028    14893  ..............................................................   14834
```

Figure 2 (Continued)

```
AJGY01000001   25769   ..............................................................   25710

Query          6481    TTATGGGTTTTGGCTCAAGCATGGGGCGATAATTATTCCACTGTGCGTTGCCGTGAATA     6540
AMBX01000015   113414  ..............................................................   113473
AMBV01000052   55118   ..............................................................   55177
AMBU01000072   114001  ..............................................................   114060
AJHA01000079   20399   ..............................................................   20458
AJGZ01000001   238304  ..............................................................   238363
AJGX01000034   238131  ..............................................................   238190
AJGW01000056   48622   ..............................................................   48681
ABEL01000005   227884  ..............................................................   227943
AMBW01000028   14833   ..............................................................   14774
AJGY01000001   25709   ..............................................................   25650

Query          6541    TTGCCATGCTGGTGGCCCGTTTGACGGACTGCGTAAACGTTGACGTATTTAACCTTCACC    6600
AMBX01000015   113474  ..............................................................   113533
AMBV01000052   55178   ..............................................................   55237
AMBU01000072   114061  ..............................................................   114120
AJHA01000079   20459   ..............................................................   20518
AJGZ01000001   238364  ..............................................................   238423
AJGX01000034   238191  ..............................................................   238250
AJGW01000056   48682   ..............................................................   48741
ABEL01000005   227944  ..............................................................   228003
AMBW01000028   14773   ..............................................................   14714
AJGY01000001   25649   ..............................................................   25590

Query          6601    AAAATGCCTCAATGGGAGCAATCGTTGGAGTTTACTCCGGCAGCTTCCTTTACGGTGTTC    6660
AMBX01000015   113534  ..............................................................   113593
AMBV01000052   55238   ..............................................................   55297
AMBU01000072   114121  ..............................................................   114180
AJHA01000079   20519   ..............................................................   20578
AJGZ01000001   238424  ..............................................................   238483
AJGX01000034   238251  ..............................................................   238310
AJGW01000056   48742   ..............................................................   48801
ABEL01000005   228004  ..............................................................   228063
AMBW01000028   14713   ..............................................................   14654
AJGY01000001   25589   ..............................................................   25530

Query          6661    TTACGGCTGCATTGTTCCATGTCTGGGCGCTTATTGCGGCTGACCTGGGTGCGAAAAACA    6720
AMBX01000015   113594  ..............................................................   113653
AMBV01000052   55298   ..............................................................   55357
AMBU01000072   114181  ..............................................................   114240
AJHA01000079   20579   ..............................................................   20638
AJGZ01000001   238484  ..............................................................   238543
AJGX01000034   238311  ..............................................................   238370
AJGW01000056   48802   ..............................................................   48861
ABEL01000005   228064  ..............................................................   228123
AMBW01000028   14653   ..............................................................   14594
AJGY01000001   25529   ..............................................................   25470

Query          6721    ACGAAAAATTCTTCAACCTGCCAAAAGGCGTTGCCATCTCCCACCCGGTTGCAAACACCT    6780
AMBX01000015   113654  ..............................................................   113713
AMBV01000052   55358   ..............................................................   55417
AMBU01000072   114241  ..............................................................   114300
AJHA01000079   20639   ..............................................................   20698
AJGZ01000001   238544  ..............................................................   238603
AJGX01000034   238371  ..............................................................   238430
AJGW01000056   48862   ..............................................................   48921
ABEL01000005   228124  ..............................................................   228183
AMBW01000028   14593   ..............................................................   14534
AJGY01000001   25469   ..............................................................   25410

Query          6781    ATTTGCTGTTCGCTTATCCGTTTAACTGGATATACGATCGCATCCCTGGATTCCGTAATC    6840
AMBX01000015   113714  ..............................................................   113773
AMBV01000052   55418   ..............................................................   55477
AMBU01000072   114301  ..............................................................   114360
AJHA01000079   20699   ..............................................................   20758
AJGZ01000001   238604  ..............................................................   238663
AJGX01000034   238431  ..............................................................   238490
AJGW01000056   48922   ..............................................................   48981
ABEL01000005   228184  ..............................................................   228243
AMBW01000028   14533   ..............................................................   14474
AJGY01000001   25409   ..............................................................   25350

Query          6841    TGAACGTTACGGCGGAAAGCATTCAGAAACGCTTTGGTATCCTTGGCGATCCGACCATGG    6900
AMBX01000015   113774  ..............................................................   113833
AMBV01000052   55478   ..............................................................   55537
AMBU01000072   114361  ..............................................................   114420
AJHA01000079   20759   ..............................................................   20818
AJGZ01000001   238664  ..............................................................   238723
AJGX01000034   238491  ..............................................................   238550
```

Figure 2 (Continued)

```
AJGW01000056    48982   ............................................................    49041
ABEL01000005    228244  ............................................................    228303
AMBW01000028    14473   ............................................................    14414
AJGY01000001    25349   ............................................................    25290

Query           6901    TTGGTTTCATTATTGGTATTCTTCTTGGCTTCTGTGGTTATGGTTGGGAATCTCCGTATC    6960
AMBX01000015    113834  ............................................................    113893
AMBV01000052    55538   ............................................................    55597
AMBU01000072    114421  ............................................................    114480
AJHA01000079    20819   ............................................................    20878
AJGZ01000001    238724  ............................................................    238783
AJGX01000034    238551  ............................................................    238610
AJGW01000056    49042   ............................................................    49101
ABEL01000005    228304  ............................................................    228363
AMBW01000028    14413   ............................................................    14354
AJGY01000001    25289   ............................................................    25230

Query           6961    ACACCATTATCGCCAGCCTGCAGTTGGGTATGTACCTTGCCGCCGTGATGCTCCTGCTGC    7020
AMBX01000015    113894  ............................................................    113953
AMBV01000052    55598   ............................................................    55657
AMBU01000072    114481  ............................................................    114540
AJHA01000079    20879   ............................................................    20938
AJGZ01000001    238784  ............................................................    238843
AJGX01000034    238611  ............................................................    238670
AJGW01000056    49102   ............................................................    49161
ABEL01000005    228364  ............................................................    228423
AMBW01000028    14353   ............................................................    14294
AJGY01000001    25229   ............................................................    25170

Query           7021    CGCGCATGACCTCAATCATGATGGAAGGTCTGGTTCCGCTCTCCAACGTGGCACGTAAGA    7080
AMBX01000015    113954  ............................................................    114013
AMBV01000052    55658   ............................................................    55717
AMBU01000072    114541  ............................................................    114600
AJHA01000079    20939   ............................................................    20998
AJGZ01000001    238844  ............................................................    238903
AJGX01000034    238671  ............................................................    238730
AJGW01000056    49162   ............................................................    49221
ABEL01000005    228424  ............................................................    228483
AMBW01000028    14293   ............................................................    14234
AJGY01000001    25169   ............................................................    25110

Query           7081    AACTGGTTAAACGTTTCCCGGATCGTGAGATCACTGTCGGGATGGATACCGCACTGATAG    7140
AMBX01000015    114014  ............................................................    114073
AMBV01000052    55718   ............................................................    55777
AMBU01000072    114601  ............................................................    114660
AJHA01000079    20999   ............................................................    21058
AJGZ01000001    238904  ............................................................    238963
AJGX01000034    238731  ............................................................    238790
AJGW01000056    49222   ............................................................    49281
ABEL01000005    228484  ............................................................    228543
AMBW01000028    14233   ............................................................    14174
AJGY01000001    25109   ............................................................    25050

Query           7141    TTGGTCATCCGTCCGTTATCGCGCCTGCACTGCTGCTGATCCCGGTCATTGTTATCCTCG    7200
AMBX01000015    114074  ............................................................    114133
AMBV01000052    55778   ............................................................    55837
AMBU01000072    114661  ............................................................    114720
AJHA01000079    21059   ............................................................    21118
AJGZ01000001    238964  ............................................................    239023
AJGX01000034    238791  ............................................................    238850
AJGW01000056    49282   ............................................................    49341
ABEL01000005    228544  ............................................................    228603
AMBW01000028    14173   ............................................................    14114
AJGY01000001    25049   ............................................................    24990

Query           7201    CCGTTGTCCTTCCCGGCAACCGAGTGATGCCGCTGGGGGACCTCTCACAGTTCGTATTCT    7260
AMBX01000015    114134  ............................................................    114193
AMBV01000052    55838   ............................................................    55897
AMBU01000072    114721  ............................................................    114780
AJHA01000079    21119   ............................................................    21178
AJGZ01000001    239024  ............................................................    239083
AJGX01000034    238851  ............................................................    238910
AJGW01000056    49342   ............................................................    49401
ABEL01000005    228604  ............................................................    228663
AMBW01000028    14113   ............................................................    14054
AJGY01000001    24989   ............................................................    24930

Query           7261    TTATTGCGTGCATGGTACCGGTTTTAATGGCAACATTATTCGTACCTGGGTGACTTCCA    7320
AMBX01000015    114194  ............................................................    114253
AMBV01000052    55898   ............................................................    55957
AMBU01000072    114781  ............................................................    114840
```

Figure 2 (Continued)

```
AJHA01000079    21179   ............................................................   21238
AJGZ01000001   239084   ............................................................  239143
AJGX01000034   238911   ............................................................  238970
AJGW01000056    49402   ............................................................   49461
ABEL01000005   228664   ............................................................  228723
AMBW01000028    14053   ............................................................   13994
AJGY01000001    24929   ............................................................   24870

Query            7321   TCATCCTTTTTGGCGGCGGCTTATACATCGCATCCTGGATGGCTCCAGCAACAAATGAAG    7380
AMBX01000015   114254   ............................................................  114313
AMBV01000052    55958   ............................................................   56017
AMBU01000072   114841   ............................................................  114900
AJHA01000079    21239   ............................................................   21298
AJGZ01000001   239144   ............................................................  239203
AJGX01000034   238971   ............................................................  239030
AJGW01000056    49462   ............................................................   49521
ABEL01000005   228724   ............................................................  228783
AMBW01000028    13993   ............................................................   13934
AJGY01000001    24869   ............................................................   24810

Query            7381   TGTTTCAGAAATTCGGCACTAATCCTGATGCCAGCGTGATGTACTCATCGCTTAACCCTT    7440
AMBX01000015   114314   ............................................................  114373
AMBV01000052    56018   ............................................................   56077
AMBU01000072   114901   ............................................................  114960
AJHA01000079    21299   ............................................................   21358
AJGZ01000001   239204   ............................................................  239263
AJGX01000034   239031   ............................................................  239090
AJGW01000056    49522   ............................................................   49581
ABEL01000005   228784   ............................................................  228843
AMBW01000028    13933   ............................................................   13874
AJGY01000001    24809   ............................................................   24750

Query            7441   CAGCTAACCCGTTCACCGGACTCTTTGCTGGACTCAGCCATGTTGGCATCGCAGGTTATG    7500
AMBX01000015   114374   ............................................................  114433
AMBV01000052    56078   ............................................................   56137
AMBU01000072   114961   ............................................................  115020
AJHA01000079    21359   ............................................................   21418
AJGZ01000001   239264   ............................................................  239323
AJGX01000034   239091   ............................................................  239150
AJGW01000056    49582   ............................................................   49641
ABEL01000005   228844   ............................................................  228903
AMBW01000028    13873   ............................................................   13814
AJGY01000001    24749   ............................................................   24690

Query            7501   CTCTCGCCGCTGTGTGGCTGTTGTCCGTAGGCTATTTACTCAAACAGAAAGCACGCCGTC    7560
AMBX01000015   114434   ............................................................  114493
AMBV01000052    56138   ............................................................   56197
AMBU01000072   115021   ............................................................  115080
AJHA01000079    21419   ............................................................   21478
AJGZ01000001   239324   ............................................................  239383
AJGX01000034   239151   ............................................................  239210
AJGW01000056    49642   ............................................................   49701
ABEL01000005   228904   ............................................................  228963
AMBW01000028    13813   ............................................................   13754
AJGY01000001    24689   ............................................................   24630

Query            7561   AGTTGAAAACTGAGGCAGAAAAAACGGCTTAAAACTTCATAAGGTGATTGAAAATGAAAA    7620
AMBX01000015   114494   ............................................................  114553
AMBV01000052    56198   ............................................................   56257
AMBU01000072   115081   ............................................................  115140
AJHA01000079    21479   ............................................................   21538
AJGZ01000001   239384   ............................................................  239443
AJGX01000034   239211   ............................................................  239270
AJGW01000056    49702   ............................................................   49761
ABEL01000005   228964   ............................................................  229023
AMBW01000028    13753   ............................................................   13694
AJGY01000001    24629   ............................................................   24570

Query            7621   AGATTTTAGTTGTATGCGGAAACGGCATAGCCTCCTCTTCCATCATGGTTTCTGTCCTGC    7680
AMBX01000015   114554   ............................................................  114613
AMBV01000052    56258   ............................................................   56317
AMBU01000072   115141   ............................................................  115200
AJHA01000079    21539   ............................................................   21598
AJGZ01000001   239444   ............................................................  239503
AJGX01000034   239271   ............................................................  239330
AJGW01000056    49762   ............................................................   49821
ABEL01000005   229024   ............................................................  229083
AMBW01000028    13693   ............................................................   13634
AJGY01000001    24569   ............................................................   24510

Query            7681   AGGACTACCTGAAAGAACAGAATATCGAAGCGCAGGTAGATAAATCCTCATTGATGGCTT    7740
```

Figure 2 (Continued)

```
AMBX01000015  114614  ............................................................  114673
AMBV01000052   56318  ............................................................   56377
AMBU01000072  115201  ............................................................  115260
AJHA01000079   21599  ............................................................   21658
AJGZ01000001  239504  ............................................................  239563
AJGX01000034  239331  ............................................................  239390
AJGW01000056   49822  ............................................................   49881
ABEL01000005  229084  ............................................................  229143
AMBW01000028   13633  ............................................................   13574
AJGY01000001   24509  ............................................................   24450

Query           7741  GCACCACGGACACATTTAACAGCTATGACCTGATTGTTTCTTCAACCAAGCTGGATAACC    7800
AMBX01000015  114674  ............................................................  114733
AMBV01000052   56378  ............................................................   56437
AMBU01000072  115261  ............................................................  115320
AJHA01000079   21659  ............................................................   21718
AJGZ01000001  239564  ............................................................  239623
AJGX01000034  239391  ............................................................  239450
AJGW01000056   49882  ............................................................   49941
ABEL01000005  229144  ............................................................  229203
AMBW01000028   13573  ............................................................   13514
AJGY01000001   24449  ............................................................   24390

Query           7801  CAGGCATCACTACTCGTGTGATTGTCGGAGCGGGCCTGTTAACGGGATTGGGCGAAGATG    7860
AMBX01000015  114734  ............................................................  114793
AMBV01000052   56438  ............................................................   56497
AMBU01000072  115321  ............................................................  115380
AJHA01000079   21719  ............................................................   21778
AJGZ01000001  239624  ............................................................  239683
AJGX01000034  239451  ............................................................  239510
AJGW01000056   49942  ............................................................   50001
ABEL01000005  229204  ............................................................  229263
AMBW01000028   13513  ............................................................   13454
AJGY01000001   24389  ............................................................   24330

Query           7861  AGATTTTTGATGCTGTTAAAGAAGAAATGCTTAAGTAGGTGAATGATGAAGCTTGAGATT    7920
AMBX01000015  114794  ............................................................  114853
AMBV01000052   56498  ............................................................   56557
AMBU01000072  115381  ............................................................  115440
AJHA01000079   21779  ............................................................   21838
AJGZ01000001  239684  ............................................................  239743
AJGX01000034  239511  ............................................................  239570
AJGW01000056   50002  ............................................................   50061
ABEL01000005  229264  ............................................................  229323
AMBW01000028   13453  ............................................................   13394
AJGY01000001   24329  ............................................................   24270

Query           7921  CTGGTAAATGACGTTGAGGGTACGATCGCTGACTGGCATGCAGCAATTGAGTTTGCCGGC    7980
AMBX01000015  114854  ............................................................  114913
AMBV01000052   56558  ............................................................   56617
AMBU01000072  115441  ............................................................  115500
AJHA01000079   21839  ............................................................   21898
AJGZ01000001  239744  ............................................................  239803
AJGX01000034  239571  ............................................................  239630
AJGW01000056   50062  ............................................................   50121
ABEL01000005  229324  ............................................................  229383
AMBW01000028   13393  ............................................................   13334
AJGY01000001   24269  ............................................................   24210

Query           7981  CAGAAGCTTTTGGAGAAAGGCTATATCACTCCCGAGTATATTCAGGCCTGCCTGGAGCGT    8040
AMBX01000015  114914  ............................................................  114973
AMBV01000052   56618  ............................................................   56677
AMBU01000072  115501  ............................................................  115560
AJHA01000079   21899  ............................................................   21958
AJGZ01000001  239804  ............................................................  239863
AJGX01000034  239631  ............................................................  239690
AJGW01000056   50122  ............................................................   50181
ABEL01000005  229384  ............................................................  229443
AMBW01000028   13333  ............................................................   13274
AJGY01000001   24209  ............................................................   24150

Query           8041  GAAAAGACTTATCCAACGGGTTTATTGATGGCGAACGGTCAGGGCATTGCCATCCCGCAT    8100
AMBX01000015  114974  ............................................................  115033
AMBV01000052   56678  ............................................................   56737
AMBU01000072  115561  ............................................................  115620
AJHA01000079   21959  ............................................................   22018
AJGZ01000001  239864  ............................................................  239923
AJGX01000034  239691  ............................................................  239750
AJGW01000056   50182  ............................................................   50241
ABEL01000005  229444  ............................................................  229503
AMBW01000028   13273  ............................................................   13214
```

Figure 2 (Continued)

```
AJGY01000001  24149   ............................................................  24090

Query         8101    GCAGACTATACGCTGGTAAAAACCAACAGCATAAGCATTGTGCGTTTTGATAAAGGAGTC  8160
AMBX01000015  115034  ............................................................  115093
AMBV01000052  56738   ............................................................  56797
AMBU01000072  115621  ............................................................  115680
AJHA01000079  22019   ............................................................  22078
AJGZ01000001  239924  ............................................................  239983
AJGX01000034  239751  ............................................................  239810
AJGW01000056  50242   ............................................................  50301
ABEL01000005  229504  ............................................................  229563
AMBW01000028  13213   ............................................................  13154
AJGY01000001  24089   ............................................................  24030

Query         8161    GTGTTTGGTCAGATGGAAGATGCTGACCTAACAGTTGAATGCAGCATTATGTTTAATCTC  8220
AMBX01000015  115094  ............................................................  115153
AMBV01000052  56798   ............................................................  56857
AMBU01000072  115681  ............................................................  115740
AJHA01000079  22079   ............................................................  22138
AJGZ01000001  239984  ............................................................  240043
AJGX01000034  239811  ............................................................  239870
AJGW01000056  50302   ............................................................  50361
ABEL01000005  229564  ............................................................  229623
AMBW01000028  13153   ............................................................  13094
AJGY01000001  24029   ............................................................  23970

Query         8221    GCATTCGCAACCAGCGACCAGCATATGTCTGTGCTGCGTCGCCTTTTTACGCTCTTCCAG  8280
AMBX01000015  115154  ............................................................  115213
AMBV01000052  56858   ............................................................  56917
AMBU01000072  115741  ............................................................  115800
AJHA01000079  22139   ............................................................  22198
AJGZ01000001  240044  ............................................................  240103
AJGX01000034  239871  ............................................................  239930
AJGW01000056  50362   ............................................................  50421
ABEL01000005  229624  ............................................................  229683
AMBW01000028  13093   ............................................................  13034
AJGY01000001  23969   ............................................................  23910

Query         8281    GATATTTCATTCATCGAGTCGTGCCGTAATCTCAAAACGCACGAAGTCGGGAAATATGTT  8340
AMBX01000015  115214  ............................................................  115273
AMBV01000052  56918   ............................................................  56977
AMBU01000072  115801  ............................................................  115860
AJHA01000079  22199   ............................................................  22258
AJGZ01000001  240104  ............................................................  240163
AJGX01000034  239931  ............................................................  239990
AJGW01000056  50422   ............................................................  50481
ABEL01000005  229684  ............................................................  229743
AMBW01000028  13033   ............................................................  12974
AJGY01000001  23909   ............................................................  23850

Query         8341    GAAGAGATGCTTGCCGCATCCTGATAGCGTGTTTCCTTCTGGAACTGTCTGGCGGCATAC  8400
AMBX01000015  115274  ............................................................  115333
AMBV01000052  56978   ............................................................  57037
AMBU01000072  115861  ............................................................  115920
AJHA01000079  22259   ............................................................  22318
AJGZ01000001  240164  ............................................................  240223
AJGX01000034  239991  ............................................................  240050
AJGW01000056  50482   ............................................................  50541
ABEL01000005  229744  ............................................................  229803
AMBW01000028  12973   ............................................................  12914
AJGY01000001  23849   ............................................................  23790

Query         8401    GGCGTCATCCGTCTGAGGCAGATACCTCCGTATCTGCCTCAGATTTCTGACAAAGTGCAT  8460
AMBX01000015  115334  ............................................................  115393
AMBV01000052  57038   ............................................................  57097
AMBU01000072  115921  ............................................................  115980
AJHA01000079  22319   ............................................................  22378
AJGZ01000001  240224  ............................................................  240283
AJGX01000034  240051  ............................................................  240110
AJGW01000056  50542   ............................................................  50601
ABEL01000005  229804  ............................................................  229863
AMBW01000028  12913   ............................................................  12854
AJGY01000001  23789   ............................................................  23730

Query         8461    ACCTGTTGGAATTGCCCAGGTTTGTCATCAGTCACCACTGCAGGCTGTGTAACGACCAAT  8520
AMBX01000015  115394  ............................................................  115453
AMBV01000052  57098   ............................................................  57157
AMBU01000072  115981  ............................................................  116040
AJHA01000079  22379   ............................................................  22438
AJGZ01000001  240284  ............................................................  240343
AJGX01000034  240111  ............................................................  240170
```

Figure 2 (Continued)

```
AJGW01000056   50602   ..............................................................   50661
ABEL01000005   229864  ..............................................................   229923
AMBW01000028   12853   ..............................................................   12794
AJGY01000001   23729   ..............................................................   23670

Query          8521    GAAAATGAAAACGGCTATTAATCCAGCAGTTTAATAGCCGTATCAAAGTCAGTGATCAGC   8580
AMBX01000015   115454  ..............................................................   115513
AMBV01000052   57158   ..............................................................   57217
AMBU01000072   116041  ..............................................................   116100
AJHA01000079   22439   ..............................................................   22498
AJGZ01000001   240344  ..............................................................   240403
AJGX01000034   240171  ..............................................................   240230
AJGW01000056   50662   ..............................................................   50721
ABEL01000005   229924  ..............................................................   229983
AMBW01000028   12793   ..............................................................   12734
AJGY01000001   23669   ..............................................................   23610

Query          8581    ACATTCAGAAGACCTGATTTGAGAGAGGCAACTATACCTTCATATTTTTCGTCCCCTCCA   8640
AMBX01000015   115514  ..............................................................   115573
AMBV01000052   57218   ..............................................................   57277
AMBU01000072   116101  ..............................................................   116160
AJHA01000079   22499   ..............................................................   22558
AJGZ01000001   240404  ..............................................................   240463
AJGX01000034   240231  ..............................................................   240290
AJGW01000056   50722   ..............................................................   50781
ABEL01000005   229984  ..............................................................   230043
AMBW01000028   12733   ..............................................................   12674
AJGY01000001   23609   ..............................................................   23550

Query          8641    GCCACACCAATCAGTTTCTTTGTGGCACGCAATTGATCTGTCGTAATGCCGAAACCCAGG   8700
AMBX01000015   115574  ..............................................................   115633
AMBV01000052   57278   ..............................................................   57337
AMBU01000072   116161  ..............................................................   116220
AJHA01000079   22559   ..............................................................   22618
AJGZ01000001   240464  ..............................................................   240523
AJGX01000034   240291  ..............................................................   240350
AJGW01000056   50782   ..............................................................   50841
ABEL01000005   230044  ..............................................................   230103
AMBW01000028   12673   ..............................................................   12614
AJGY01000001   23549   ..............................................................   23490

Query          8701    CGGTTCAGCGGACTATCCAGAATTTCCCCTTTGCTATTTACCAGTGTTACGCATACATCA   8760
AMBX01000015   115634  ..............................................................   115693
AMBV01000052   57338   ..............................................................   57397
AMBU01000072   116221  ..............................................................   116280
AJHA01000079   22619   ..............................................................   22678
AJGZ01000001   240524  ..............................................................   240583
AJGX01000034   240351  ..............................................................   240410
AJGW01000056   50842   ..............................................................   50901
ABEL01000005   230104  ..............................................................   230163
AMBW01000028   12613   ..............................................................   12554
AJGY01000001   23489   ..............................................................   23430

Query          8761    GCAGTAATGTCCTGGCTTATTAAAGCCTCACGCCACGCTTCAGGGAATATATCGCATAGA   8820
AMBX01000015   115694  ..............................................................   115753
AMBV01000052   57398   ..............................................................   57457
AMBU01000072   116281  ..............................................................   116340
AJHA01000079   22679   ..............................................................   22738
AJGZ01000001   240584  ..............................................................   240643
AJGX01000034   240411  ..............................................................   240470
AJGW01000056   50902   ..............................................................   50961
ABEL01000005   230164  ..............................................................   230223
AMBW01000028   12553   ..............................................................   12494
AJGY01000001   23429   ..............................................................   23370

Query          8821    CTGGAAGAGCCTGTTTTCCAGGCCCCAATCCCTGTAATTACGACATCCATATTTGAGTAA   8880
AMBX01000015   115754  ..............................................................   115813
AMBV01000052   57458   ..............................................................   57517
AMBU01000072   116341  ..............................................................   116400
AJHA01000079   22739   ..............................................................   22798
AJGZ01000001   240644  ..............................................................   240703
AJGX01000034   240471  ..............................................................   240530
AJGW01000056   50962   ..............................................................   51021
ABEL01000005   230224  ..............................................................   230283
AMBW01000028   12493   ..............................................................   12434
AJGY01000001   23369   ..............................................................   23310

Query          8881    AATTTTTGCGTATCCTGAACAGCCTGATCGTCAGCGAGTTTCTGGGCTAAACTTTCGTCA   8940
AMBX01000015   115814  ..............................................................   115873
AMBV01000052   57518   ..............................................................   57577
AMBU01000072   116401  ..............................................................   116460
```

Figure 2 (Continued)

```
AJHA01000079    22799   ..............................................................    22858
AJGZ01000001   240704   ..............................................................   240763
AJGX01000034   240531   ..............................................................   240590
AJGW01000056    51022   ..............................................................    51081
ABEL01000005   230284   ..............................................................   230343
AMBW01000028    12433   ..............................................................    12374
AJGY01000001    23309   ..............................................................    23250

Query            8941   TCCACCCACATGGGTACATACATCGGGTGCGCTCTTCCGTGGGAAATTGCGGCAACTTTG    9000
AMBX01000015   115874   ..............................................................   115933
AMBV01000052    57578   ..............................................................    57637
AMBU01000072   116461   ..............................................................   116520
AJHA01000079    22859   ..............................................................    22918
AJGZ01000001   240764   ..............................................................   240823
AJGX01000034   240591   ..............................................................   240650
AJGW01000056    51082   ..............................................................    51141
ABEL01000005   230344   ..............................................................   230403
AMBW01000028    12373   ..............................................................    12314
AJGY01000001    23249   ..............................................................    23190

Query            9001   TGTATTAGATCAATCGGTCCCTGACTAAATTCAATACCAGGATGAACGCCAGAAAGCTGA    9060
AMBX01000015   115934   ..............................................................   115993
AMBV01000052    57638   ..............................................................    57697
AMBU01000072   116521   ..............................................................   116580
AJHA01000079    22919   ..............................................................    22978
AJGZ01000001   240824   ..............................................................   240883
AJGX01000034   240651   ..............................................................   240710
AJGW01000056    51142   ..............................................................    51201
ABEL01000005   230404   ..............................................................   230463
AMBW01000028    12313   ..............................................................    12254
AJGY01000001    23189   ..............................................................    23130

Query            9061   ACCACATCCAGAACAGGTAATGTCGTCAGTTGACTCACCGTACTTGAAAGAACCCGCCCC    9120
AMBX01000015   115994   ..............................................................   116053
AMBV01000052    57698   ..............................................................    57757
AMBU01000072   116581   ..............................................................   116640
AJHA01000079    22979   ..............................................................    23038
AJGZ01000001   240884   ..............................................................   240943
AJGX01000034   240711   ..............................................................   240770
AJGW01000056    51202   ..............................................................    51261
ABEL01000005   230464   ..............................................................   230523
AMBW01000028    12253   ..............................................................    12194
AJGY01000001    23129   ..............................................................    23070

Query            9121   CAGGCCAGACCAAACTTCATACCCTCTTTAAGAATCTCACTCAAGTAGGTCGCCGTTATC    9180
AMBX01000015   116054   ..............................................................   116113
AMBV01000052    57758   ..............................................................    57817
AMBU01000072   116641   ..............................................................   116700
AJHA01000079    23039   ..............................................................    23098
AJGZ01000001   240944   ..............................................................   241003
AJGX01000034   240771   ..............................................................   240830
AJGW01000056    51262   ..............................................................    51321
ABEL01000005   230524   ..............................................................   230583
AMBW01000028    12193   ..............................................................    12134
AJGY01000001    23069   ..............................................................    23010

Query            9181   CCTCCCAGCTTGACGTTTAATTGTTCCTGGGAAGACCAGGACTCGGAAACGGAGAGCACA    9240
AMBX01000015   116114   ..............................................................   116173
AMBV01000052    57818   ..............................................................    57877
AMBU01000072   116701   ..............................................................   116760
AJHA01000079    23099   ..............................................................    23158
AJGZ01000001   241004   ..............................................................   241063
AJGX01000034   240831   ..............................................................   240890
AJGW01000056    51322   ..............................................................    51381
ABEL01000005   230584   ..............................................................   230643
AMBW01000028    12133   ..............................................................    12074
AJGY01000001    23009   ..............................................................    22950

Query            9241   ACTGCATCCTGCAATCCGTATTCTTACAGAGATTTTGCGCTATTTCCTCGTCCAGAGCT    9300
AMBX01000015   116174   ..............................................................   116233
AMBV01000052    57878   ..............................................................    57937
AMBU01000072   116761   ..............................................................   116820
AJHA01000079    23159   ..............................................................    23218
AJGZ01000001   241064   ..............................................................   241123
AJGX01000034   240891   ..............................................................   240950
AJGW01000056    51382   ..............................................................    51441
ABEL01000005   230644   ..............................................................   230703
AMBW01000028    12073   ..............................................................    12014
AJGY01000001    22949   ..............................................................    22890

Query            9301   TGCTGTTTAGGGAAGGTAAATTTTACATACTCTTGCGCAATGGCTTCATCAATCAGGCGT    9360
```

Figure 2 (Continued)

```
AMBX01000015   116234  ............................................................  116293
AMBV01000052    57938  ............................................................   57997
AMBU01000072   116821  ............................................................  116880
AJHA01000079    23219  ............................................................   23278
AJGZ01000001   241124  ............................................................  241183
AJGX01000034   240951  ............................................................  241010
AJGW01000056    51442  ............................................................   51501
ABEL01000005   230704  ............................................................  230763
AMBW01000028    12013  ............................................................   11954
AJGY01000001    22889  ............................................................   22830

Query            9361  GCAACTTTGAAGCGAGACAGACCGAGCTCCTCTGCAATTTCTACCTTCGTCTTCATCTCA   9420
AMBX01000015   116294  ............................................................  116353
AMBV01000052    57998  ............................................................   58057
AMBU01000072   116881  ............................................................  116940
AJHA01000079    23279  ............................................................   23338
AJGZ01000001   241184  ............................................................  241243
AJGX01000034   241011  ............................................................  241070
AJGW01000056    51502  ............................................................   51561
ABEL01000005   230764  ............................................................  230823
AMBW01000028    11953  ............................................................   11894
AJGY01000001    22829  ............................................................   22770

Query            9421  GAGAAATAACGCTTAACAACAAGAGAGTAGATAAAACGAGGATCGTAGTTGCGCAGCTTC   9480
AMBX01000015   116354  ............................................................  116413
AMBV01000052    58058  ............................................................   58117
AMBU01000072   116941  ............................................................  117000
AJHA01000079    23339  ............................................................   23398
AJGZ01000001   241244  ............................................................  241303
AJGX01000034   241071  ............................................................  241130
AJGW01000056    51562  ............................................................   51621
ABEL01000005   230824  ............................................................  230883
AMBW01000028    11893  ............................................................   11834
AJGY01000001    22769  ............................................................   22710

Query            9481  GGATTTTTGTTCTCTTTTGGC   9501
AMBX01000015   116414  .....................   116434
AMBV01000052    58118  .....................    58138
AMBU01000072   117001  .....................   117021
AJHA01000079    23399  .....................    23419
AJGZ01000001   241304  .....................   241324
AJGX01000034   241131  .....................   241151
AJGW01000056    51622  .....................    51642
ABEL01000005   230884  .....................   230904
AMBW01000028    11833  .....................    11813
AJGY01000001    22709  .....................    22689
```

SEQ ID NO: 21
TTACTCAAGGTCAGCGTGTCTCTTAAACATCGTGTCGCTGGTTTCACCGAGTTGGGCCATCAGCTCAAGCACGATAGC
GTCATAGGTGATAAAGCAGAGTTGCTCAAAAGCCGATCCCATAGGCTGCGAAAAGCCACCTTCTTCGCGATCGTTGTC
TTCTTTCACAGTTCCAGGCAATACAAGAGTACTTTTGGCCAGTTTGCCGATTGTGGACTCCGCTTTCATTGTGACAAG
CGCCACATCCACGCCACAGGCTACGGCCTTCTGCGCCAGGCTCACCAGACTGCCGGTCTCACCGCTACCGGAGCCAAT
AATGACCAGGTCGCCCGGTTTCGTATGAGGAGAAGAAATTTCGCCCACTACGCTTACTGAAAAACCGAGGTGGAGAAG
GCGGTTTGCAAAGCCGCGGATGGCGATGCCGCTACGACCCGCGCCCTGCAGAAAGATATGTTTGGCATTCTTAATCTG
TGCGACGAATTGGGCAGCCTGGGCATCATCAATCTTCATCGCATTTTGCTGCAACTCGCTCAGGATATTTAAAGTATT
TTGTTGAACGCTCAT

SEQ ID NO: 22
TTAAGCGATGGTACGACCACCATCCATCAGAATGGTTTGCCCCTGGATGTACGAGTTGTCTTTATCAGCCAAAAAGAT
TGCAAGGTTTGCTACATCGTCAATGGTTCCAAGGCGGCGCACTGGAATTTTTTCCAGAACGGCATCAAGATCGGCCTG
GGTAGGATAATTGACGCGCATCATTTCACCGGTATCAATCAGGCGTGGAGCGATAGCATTAACATTGACACCCTTAGG
TCCCAGTTCTTTTGCCAGACCACGAATCAATCCTTCACCGCCAGCTTTACTGGCCGGGTAACTCACGCCACCGCCAGT
ACCGGAAAGCGCCGAGCCGGATGAGATATAAACGATAGATCCATGGTTAGTAGTGAAGTCGTCGTAGAATGCTTTAAC
GGTGTTAAACAGGCCAGTAAGGTTAATTGCAATCGTCTTATTCCACTCTTCAAAAGTGATGTTATTAACCTTATTAGC
AAACGCCACGCCAGCGTTTAATACCAAAATATCAATACGTCCGAAGGTTTGAAAAACCTGCTCACGAACGTTTTCCAG
AGCTTTCGGATCGGATACATCGGTTTTAACGAATAAGGATTTAACATTACCGAAAGTTAACTCTTCGGCCGTCTTTTT
ACCATTTTCTTCGTTATAATCGACAATGACAGTATGAGCCCCACCGGTCTGCGAATTGCTTAGCAATTCCTTTACCGAT
TCCATGTGCCCCACCGGTTACTAGCGCGACTTTACCTTCAAATTTACTCAT

SEQ ID NO: 27
TTACTCAAGGTCAGCGTGTCTCTTAAACATCGTGTCGCTGGTTTCACCGAGTTGGGCCATCAGCTCAAGCACGATAGCGT
CATAGGTGATAAAGCAGAGTTGCTCAAAAGCCGATCCCATAGGCTGCGAAAAGCCACCTTCTTCGCGATCGTTGTCTTCT
TTCACAGTTCCAGGCAATACAAGAGTACTTTTGGCCAGTTTGCCGATTGTGGACTCCGCTTTCATTGTGACAAGCGCCAC

Figure 2 (Continued)

```
ATCCACGCCACAGGCTACGGCCTTCTGCGCCAGGCTCACCAGACTGCCGGTCTCACCGCTACCGGAGCCAATAATGACCA
GGTCGCCCGGTTTCGTATGAGGAGAAGAAATTTCGCCCACTACGCTTACTGAAAAACCGAGGTGGAGAAGGCGGTTTGCA
AAGCCGCGGATGGCGATGCCGCTACGACCCGCGCCCTGCAGAAAGATATGTTTGGCATTCTTAATCTGTGCGACGAATTG
GGCAGCCTGGGCATCATCAATCTTCATCGCATTTTGCTGCAACTCGCTCAGGATATTTAAAGTATTTTGTTGAACGCTCA
TGTGATTCCCTCCCTTTAAGCGATGGTACGACCACCATCCATCAGAATGGTTTGCCCCTGGATGTACGAGTTGTCTTTAT
CAGCCAAAAAGATTGCAAGGTTTGCTACATCGTCAATGGTTCCAAGGCGGCGCACTGGAATTTTTTCCAGAACGGCATCA
AGATCGGCCTGGGTAGGATAATTGACGCGCATCATTTCACCGGTATCAATCAGGCGTGGAGCGATAGCATTAACATTGAC
ACCCTTAGGTCCCAGTTCTTTTGCCAGACCACGAATCAATCCTTCACCGCCAGCTTTACTGGCCGGGTAACTCACGCCAC
CGCCAGTACCGGAAAGCGCCGAGCCGGATGAGATATAAACGATAGATCCATGGTTAGTAGTGAAGTCGTCGTAGAATGCT
TTAACGGTGTTAAACAGGCCAGTAAGGTTAATTGCAATCGTCTTATTCCACTCTTCAAAAGTGATGTTATTAACCTTATT
AGCAAACGCCACGCCAGCGTTTAATACCAAAATATCAATACGTCCGAAGGTTTGAAAAACCTGCTCACGAACGTTTTCCA
GAGCTTTCGGATCGGATACATCGGTTTTAACGAATAAGGATTTAACATTACCGAAAGTTAACTCTTCGGCCGTCTTTTTA
CCATTTTCTTCGTTATAATCGACAATGACAGTATGAGCCCCACGGTCTGCGAATTGCTTAGCAATTCCTTTACCGATTCC
ATGTGCCCCACCGGTTACTAGCGCGACTTTACCTTCAAATTTACTCAT
```

FIGURE 3A

```
Kottbus-F1            CGGAAACATAACACTAAAAGGATGGTACTTATCTACAGTAACTTTCTATTTTACTGACTT  SEQ ID NO: 32
Kottbus-R1cc          CGGAAACATAACACTAAAAGGATGGTACTTATCTACAGTAACTTTCTATTTTACTGACTT  SEQ ID NO: 33
Bovismorbificans-F1   CGGAAACATAACACTAAAAGGATGGTACTTATCTACAGTAACTTTCTATTTTACTGACTT  SEQ ID NO: 34
Bovismorbificans-R1cc CGGAAACATAACACTAAAAGGATGGTACTTATCTACAGTAACTTTCTATTTTACTGACTT  SEQ ID NO: 35
Bardo-F1              CGGAAACATAACACTAAAAGGATGGTACTTATCTACAGTAACTTTCTATTTTACTGACTT  SEQ ID NO: 36
Bardo-R1cc            CGGAAACATAACACTAAAAGGATGGTACTTATCTACAGTAACTTTCTATTTTACTGACTT  SEQ ID NO: 37
Blockley-F1           CGGAAACATAACACTAAAAGGATGGTACTTATCTACAGTAACTTTCTATTTTACTGACTT  SEQ ID NO: 38
Blockley-R1cc         CGGAAACATAACACTAAAAGGATGGTACTTATCTACAGTAACTTTCTATTTTACTGACTT  SEQ ID NO: 39
Newport1-F1           CGGAAACATAACACTAAAAGGATGGTACTTATCTACAGTAACTTTCTATTTTACTGACTT  SEQ ID NO: 40
Newport1-R1cc         CGGAAACATAACACTAAAAGGATGGTACTTATCTACAGTAACTTTCTATTTTACTGACTT  SEQ ID NO: 41
Newport2-F1           CGGAAACATAACACTAAAAGGATGGTACTTATCTACAGTAACTTTCTATTTTACTGACTT  SEQ ID NO: 42
Newport2-R1cc         CGGAAACATAACACTAAAAGGATGGTACTTATCTACAGTAACTTTCTATTTTACTGACTT  SEQ ID NO: 43
Newport3-F1           CGGAAACATAACACTAAAAGGATGGTACTTATCTACAGTAACTTTCTATTTTACTGACTT  SEQ ID NO: 44
Newport3-R1cc         CGGAAACATAACACTAAAAGGATGGTACTTATCTACAGTAACTTTCTATTTTACTGACTT  SEQ ID NO: 45
Newport4-F1           CGGAAACATAACACTAAAAGGATGGTACTTATCTACAGTAACTTTCTATTTTACTGACTT  SEQ ID NO: 46
Newport4-R1cc         CGGAAACATAACACTAAAAGGATGGTACTTATCTACAGTAACTTTCTATTTTACTGACTT  SEQ ID NO: 47
Newport5-F1           CGGAAACATAACACTAAAAGGATGGTACTTATCTACAGTAACTTTCTATTTTACTGACTT  SEQ ID NO: 48
Newport5-R1cc         CGGAAACATAACACTAAAAGGATGGTACTTATCTACAGTAACTTTCTATTTTACTGACTT  SEQ ID NO: 49
                      ************************************************************

Kottbus-F1            AGTCTGGTTTGCTCTTGCTATAAAGCTTTTTGGTTATTCTGAATGGATAACATACGTTAT
Kottbus-R1cc          AGTCTGGTTTGCTCTTGCTATAAAGCTTTTTGGTTATTCTGAATGGATAACATACGTTAT
Bovismorbificans-F1   AGTCTGGTTTGCTCTTGCTATAAAGCTTTTTGGTTATTCTGAATGGATAACATACGTTAT
Bovismorbificans-R1cc AGTCTGGTTTGCTCTTGCTATAAAGCTTTTTGGTTATTCTGAATGGATAACATACGTTAT
Bardo-F1              AGTCTGGTTTGCTCTTGCTATAAAGCTTTTTGGTTATTCTGAATGGATAACATACGTTAT
Bardo-R1cc            AGTCTGGTTTGCTCTTGCTATAAAGCTTTTTGGTTATTCTGAATGGATAACATACGTTAT
Blockley-F1           AGTCTGGTTTGCTCTTGCTATAAAGCTTTTTGGTTATTCTGAATGGATAACATACGTTAT
Blockley-R1cc         AGTCTGGTTTGCTCTTGCTATAAAGCTTTTTGGTTATTCTGAATGGATAACATACGTTAT
Newport1-F1           AGTCTGGTTTGCTCTTGCTATAAAGCTTTTTGGTTATTCTGAATGGATAACATACGTTAT
Newport1-R1cc         AGTCTGGTTTGCTCTTGCTATAAAGCTTTTTGGTTATTCTGAATGGATAACATACGTTAT
Newport2-F1           AGTCTGGTTTGCTCTTGCTATAAAGCTTTTTGGTTATTCTGAATGGATAACATACGTTAT
Newport2-R1cc         AGTCTGGTTTGCTCTTGCTATAAAGCTTTTTGGTTATTCTGAATGGATAACATACGTTAT
Newport3-F1           AGTCTGGTTTGCTCTTGCTATAAAGCTTTTTGGTTATTCTGAATGGATAACATACGTTAT
Newport3-R1cc         AGTCTGGTTTGCTCTTGCTATAAAGCTTTTTGGTTATTCTGAATGGATAACATACGTTAT
Newport4-F1           AGTCTGGTTTGCTCTTGCTATAAAGCTTTTTGGTTATTCTGAATGGATAACATACGTTAT
Newport4-R1cc         AGTCTGGTTTGCTCTTGCTATAAAGCTTTTTGGTTATTCTGAATGGATAACATACGTTAT
Newport5-F1           AGTCTGGTTTGCTCTTGCTATAAAGCTTTTTGGTTATTCTGAATGGATAACATACGTTAT
Newport5-R1cc         AGTCTGGTTTGCTCTTGCTATAAAGCTTTTTGGTTATTCTGAATGGATAACATACGTTAT
                      ************************************************************

Kottbus-F1            ACCTGGATTAATGGCTGGTAGCCTGTTCGCTTCATGCTATGCACTGGGAACAATTTCTGG
Kottbus-R1cc          ACCTGGATTAATGGCTGGTAGCCTGTTCGCTTCATGCTATGCACTGGGAACAATTTCTGG
Bovismorbificans-F1   ACCTGGATTAATGGCTGGTAGCCTGTTCGCTTCATGCTATGCACTGGGAACAATTTCTGG
Bovismorbificans-R1cc ACCTGGATTAATGGCTGGTAGCCTGTTCGCTTCATGCTATGCACTGGGAACAATTTCTGG
Bardo-F1              ACCTGGATTAATGGCTGGTAGCCTGTTCGCTTCATGCTATGCACTGGGAACAATTTCTGG
Bardo-R1cc            ACCTGGATTAATGGCTGGTAGCCTGTTCGCTTCATGCTATGCACTGGGAACAATTTCTGG
Blockley-F1           ACCTGGATTAATGGCTGGTAGCCTGTTCGCTTCATGCTATGCACTGGGAACAATTTCTGG
Blockley-R1cc         ACCTGGATTAATGGCTGGTAGCCTGTTCGCTTCATGCTATGCACTGGGAACAATTTCTGG
Newport1-F1           ACCTGGATTAATGGCTGGTAGCCTGTTCGCTTCATGCTATGCACTGGGAACAATTTCTGG
Newport1-R1cc         ACCTGGATTAATGGCTGGTAGCCTGTTCGCTTCATGCTATGCACTGGGAACAATTTCTGG
Newport2-F1           ACCTGGATTAATGGCTGGTAGCCTGTTCGCTTCATGCTATGCACTGGGAACAATTTCTGG
Newport2-R1cc         ACCTGGATTAATGGCTGGTAGCCTGTTCGCTTCATGCTATGCACTGGGAACAATTTCTGG
Newport3-F1           ACCTGGATTAATGGCTGGTAGCCTGTTCGCTTCATGCTATGCACTGGGAACAATTTCTGG
Newport3-R1cc         ACCTGGATTAATGGCTGGTAGCCTGTTCGCTTCATGCTATGCACTGGGAACAATTTCTGG
Newport4-F1           ACCTGGATTAATGGCTGGTAGCCTGTTCGCTTCATGCTATGCACTGGGAACAATTTCTGG
Newport4-R1cc         ACCTGGATTAATGGCTGGTAGCCTGTTCGCTTCATGCTATGCACTGGGAACAATTTCTGG
Newport5-F1           ACCTGGATTAATGGCTGGTAGCCTGTTCGCTTCATGCTATGCACTGGGAACAATTTCTGG
Newport5-R1cc         ACCTGGATTAATGGCTGGTAGCCTGTTCGCTTCATGCTATGCACTGGGAACAATTTCTGG
                      ************************************************************
```

Figure 3A (Continued)

```
Kottbus-F1              CTACAAAAAAGCATGGGCTTTGCTACTGTTCCTTGCTTTCCCTGGTGCTGCTGTCAGTTA
Kottbus-R1cc            CTACAAAAAAGCATGGGCTTTGCTACTGTTCCTTGCTTTCCCTGGTGCTGCTGTCAGTTA
Bovismorbificans-F1     CTACAAAAAAGCATGGGCTTTGCTACTGTTCCTTGCTTTCCCTGGTGCTGCTGTCAGTTA
Bovismorbificans-R1cc   CTACAAAAAAGCATGGGCTTTGCTACTGTTCCTTGCTTTCCCTGGTGCTGCTGTCAGTTA
Bardo-F1                CTACAAAAAAGCATGGGCTTTGCTACTGTTCCTTGCTTTCCCTGGTGCTGCTGTCAGTTA
Bardo-R1cc              CTACAAAAAAGCATGGGCTTTGCTACTGTTCCTTGCTTTCCCTGGTGCTGCTGTCAGTTA
Blockley-F1             CTACAAAAAAGCATGGGCTTTGCTACTGTTCCTTGCTTTCCCTGGTGCTGCTGTCAGTTA
Blockley-R1cc           CTACAAAAAAGCATGGGCTTTGCTACTGTTCCTTGCTTTCCCTGGTGCTGCTGTCAGTTA
Newport1-F1             CTACAAAAAAGCATGGGCTTTGCTACTGTTCCTTGCTTTCCCTGGTGCTGCTGTCAGTTA
Newport1-R1cc           CTACAAAAAAGCATGGGCTTTGCTACTGTTCCTTGCTTTCCCTGGTGCTGCTGTCAGTTA
Newport2-F1             CTACAAAAAAGCATGGGCTTTGCTACTGTTCCTTGCTTTCCCTGGTGCTGCTGTCAGTTA
Newport2-R1cc           CTACAAAAAAGCATGGGCTTTGCTACTGTTCCTTGCTTTCCCTGGTGCTGCTGTCAGTTA
Newport3-F1             CTACAAAAAAGCATGGGCTTTGCTACTGTTCCTTGCTTTCCCTGGTGCTGCTGTCAGTTA
Newport3-R1cc           CTACAAAAAAGCATGGGCTTTGCTACTGTTCCTTGCTTTCCCTGGTGCTGCTGTCAGTTA
Newport4-F1             CTACAAAAAAGCATGGGCTTTGCTACTGTTCCTTGCTTTCCCTGGTGCTGCTGTCAGTTA
Newport4-R1cc           CTACAAAAAAGCATGGGCTTTGCTACTGTTCCTTGCTTTCCCTGGTGCTGCTGTCAGTTA
Newport5-F1             CTACAAAAAAGCATGGGCTTTGCTACTGTTCCTTGCTTTCCCTGGTGCTGCTGTCAGTTA
Newport5-R1cc           CTACAAAAAAGCATGGGCTTTGCTACTGTTCCTTGCTTTCCCTGGTGCTGCTGTCAGTTA
                        ************************************************************

Kottbus-F1              CATGCTTTCTGTAGCGATAATCCATGTCCCTACATATACTTATATCGTTGTTTCATATAT
Kottbus-R1cc            CATGCTTTCTGTAGCGATAATCCATGTCCCTACATATACTTATATCGTTGTTTCATATAT
Bovismorbificans-F1     CATGCTTTCTGTAGCGATAATCCATGTCCCTACATATACTTATATCGTTGTTTCATATAT
Bovismorbificans-R1cc   CATGCTTTCTGTAGCGATAATCCATGTCCCTACATATACTTATATCGTTGTTTCATATAT
Bardo-F1                CATGCTTTCTGTAGCGATAATCCATGTCCCTACATATACTTATATCGTTATTTCATATAT
Bardo-R1cc              CATGCTTTCTGTAGCGATAATCCATGTCCCTACATATACTTATATCGTTATTTCATATAT
Blockley-F1             CATGCTTTCTGTAGCGATAATCCATGTCCCTACATATACTTATATCGTTGTTTCATATAT
Blockley-R1cc           CATGCTTTCTGTAGCGATAATCCATGTCCCTACATATACTTATATCGTTGTTTCATATAT
Newport1-F1             CATGCTTTCTGTAGCGATAATCCATGTCCCTACATATACTTATATCGTTGTTTCATATAT
Newport1-R1cc           CATGCTTTCTGTAGCGATAATCCATGTCCCTACATATACTTATATCGTTGTTTCATATAT
Newport2-F1             CATGCTTTCTGTAGCGATAATCCATGTCCCTACATATACTTATATCGTTATTTCATATAT
Newport2-R1cc           CATGCTTTCTGTAGCGATAATCCATGTCCCTACATATACTTATATCGTTATTTCATATAT
Newport3-F1             CATGCTTTCTGTAGCGATAATCCATGTCCCTACATATACTTATATCGTTATTTCATATAT
Newport3-R1cc           CATGCTTTCTGTAGCGATAATCCATGTCCCTACATATACTTATATCGTTATTTCATATAT
Newport4-F1             CATGCTTTCTGTAGCGATAATCCATGTCCCTACATATACTTATATCGTTGTTTCATATAT
Newport4-R1cc           CATGCTTTCTGTAGCGATAATCCATGTCCCTACATATACTTATATCGTTGTTTCATATAT
Newport5-F1             CATGCTTTCTGTAGCGATAATCCATGTCCCTACATATACTTATATCGTTGTTTCATATAT
Newport5-R1cc           CATGCTTTCTGTAGCGATAATCCATGTCCCTACATATACTTATATCGTTGTTTCATATAT
                        *********************************************** **********

Kottbus-F1              ATTAATTGATTTTTATTGTCGCAGAAGAAATAGATTATATTTATTTCTATCATCAATAAT
Kottbus-R1cc            ATTAATTGATTTTTATTGTCGCAGAAGAAATAGATTATATTTATTTCTATCATCAATAAT
Bovismorbificans-F1     ATTAATTGATTTTTATTGTCGCAGAAGAAATAGATTATATTTATTTCTATCATCAATAAT
Bovismorbificans-R1cc   ATTAATTGATTTTTATTGTCGCAGAAGAAATAGATTATATTTATTTCTATCATCAATAAT
Bardo-F1                ATTAATTGATTTTTATTGTCGCAGAAGAAATAGATTATATTTATTTCTATCATCAATAAT
Bardo-R1cc              ATTAATTGATTTTTATTGTCGCAGAAGAAATAGATTATATTTATTTCTATCATCAATAAT
Blockley-F1             ATTAATTGATTTTTATTGTCGCAGAAGAAATAGATTATATTTATTTCTATCATCAATAAT
Blockley-R1cc           ATTAATTGATTTTTATTGTCGCAGAAGAAATAGATTATATTTATTTCTATCATCAATAAT
Newport1-F1             ATTAATTGATTTTTATTGTCGCAGAAGAAATAGATTATATTTATTTCTATCATCAATAAT
Newport1-R1cc           ATTAATTGATTTTTATTGTCGCAGAAGAAATAGATTATATTTATTTCTATCATCAATAAT
Newport2-F1             ATTAATTGATTTTTATTGTCGCAGAAGAAATAGATTATATTTATTTCTATCATCAATAAT
Newport2-R1cc           ATTAATTGATTTTTATTGTCGCAGAAGAAATAGATTATATTTATTTCTATCATCAATAAT
Newport3-F1             ATTAATTGATTTTTATTGTCGCAGAAGAAATAGATTATATTTATTTCTATCATCAATAAT
Newport3-R1cc           ATTAATTGATTTTTATTGTCGCAGAAGAAATAGATTATATTTATTTCTATCATCAATAAT
Newport4-F1             ATTAATTGATTTTTATTGTCGCAGAAGAAATAGATTATATTTATTTCTATCATCAATAAT
Newport4-R1cc           ATTAATTGATTTTTATTGTCGCAGAAGAAATAGATTATATTTATTTCTATCATCAATAAT
Newport5-F1             ATTAATTGATTTTTATTGTCGCAGAAGAAATAGATTATATTTATTTCTATCATCAATAAT
Newport5-R1cc           ATTAATTGATTTTTATTGTCGCAGAAGAAATAGATTATATTTATTTCTATCATCAATAAT
                        ************************************************************
```

Figure 3A (Continued)

```
Kottbus-F1              CGCATCTTTAACGATATTTAGCGATGATATAACAATATATTTATTTTTTTTGCCAATTGC
Kottbus-R1cc            CGCATCTTTAACGATATTTAGCGATGATATAACAATATATTTATTTTTTTTGCCAATTGC
Bovismorbificans-F1     CGCATCTTTAACGATATTTAGCGATGATATAACAATATATTTATTTTTTTTGCCAATTGC
Bovismorbificans-R1cc   CGCATCTTTAACGATATTTAGCGATGATATAACAATATATTTATTTTTTTTGCCAATTGC
Bardo-F1                CGCATCTTTAACGATATTTAGCGATGATATAACAATATATTTATTTTTTTTGCCAATTGC
Bardo-R1cc              CGCATCTTTAACGATATTTAGCGATGATATAACAATATATTTATTTTTTTTGCCAATTGC
Blockley-F1             CGCATCTTTAACGATATTTAGCGATGATATAACAATATATTTATTTTTTTTGCCAATTGC
Blockley-R1cc           CGCATCTTTAACGATATTTAGCGATGATATAACAATATATTTATTTTTTTTGCCAATTGC
Newport1-F1             CGCATCTTTAACGATATTTAGCGATGATATAACAATATATTTATTTTTTTTGCCAATTGC
Newport1-R1cc           CGCATCTTTAACGATATTTAGCGATGATATAACAATATATTTATTTTTTTTGCCAATTGC
Newport2-F1             CGCATCTTTAACGATATTTAGCGATGATATAACAATATATTTATTTTTTTTGCCAATTGC
Newport2-R1cc           CGCATCTTTAACGATATTTAGCGATGATATAACAATATATTTATTTTTTTTGCCAATTGC
Newport3-F1             CGCATCTTTAACGATATTTAGCGATGATATAACAATATATTTATTTTTTTTGCCAATTGC
Newport3-R1cc           CGCATCTTTAACGATATTTAGCGATGATATAACAATATATTTATTTTTTTTGCCAATTGC
Newport4-F1             CGCATCTTTAACGATATTTAGCGATGATATAACAATATATTTATTTTTTTTGCCAATTGC
Newport4-R1cc           CGCATCTTTAACGATATTTAGCGATGATATAACAATATATTTATTTTTTTTGCCAATTGC
Newport5-F1             CGCATCTTTAACGATATTTAGCGATGATATAACAATATATTTATTTTTTTTGCCAATTGC
Newport5-R1cc           CGCATCTTTAACGATATTTAGCGATGATATAACAATATATTTATTTTTTTTGCCAATTGC
                        ************************************************************

Kottbus-F1              ATTGAGCTGTTTTATAGCCAATGAAAATGCAAAAGATAAATTTGTAATATTTTCGTCTTT
Kottbus-R1cc            ATTGAGCTGTTTTATAGCCAATGAAAATGCAAAAGATAAATTTGTAATATTTTCGTCTTT
Bovismorbificans-F1     ATTGAGCTGTTTTATAGCCAATGAAAATGCAAAAGATAAATTTGTAATATTTTCGTCTTT
Bovismorbificans-R1cc   ATTGAGCTGTTTTATAGCCAATGAAAATGCAAAAGATAAATTTGTAATATTTTCGTCTTT
Bardo-F1                ATTGAGCTGTTTTATAGCCAATGAAAATGCAAAAGATAAATTTGTAATATTTTCGTCTTT
Bardo-R1cc              ATTGAGCTGTTTTATAGCCAATGAAAATGCAAAAGATAAATTTGTAATATTTTCGTCTTT
Blockley-F1             ATTGAGCTGTTTTATAGCCAATGAAAATGCAAAAGATAAATTTGTAATATTTTCGTCTTT
Blockley-R1cc           ATTGAGCTGTTTTATAGCCAATGAAAATGCAAAAGATAAATTTGTAATATTTTCGTCTTT
Newport1-F1             ATTGAGCTGTTTTATAGCCAATGAAAATGCAAAAGATAAATTTGTAATATTTTCGTCTTT
Newport1-R1cc           ATTGAGCTGTTTTATAGCCAATGAAAATGCAAAAGATAAATTTGTAATATTTTCGTCTTT
Newport2-F1             ATTGAGCTGTTTTATAGCCAATGAAAATGCAAAAGATAAATTTGTAATATTTTCGTCTTT
Newport2-R1cc           ATTGAGCTGTTTTATAGCCAATGAAAATGCAAAAGATAAATTTGTAATATTTTCGTCTTT
Newport3-F1             ATTGAGCTGTTTTATAGCCAATGAAAATGCAAAAGATAAATTTGTAATATTTTCGTCTTT
Newport3-R1cc           ATTGAGCTGTTTTATAGCCAATGAAAATGCAAAAGATAAATTTGTAATATTTTCGTCTTT
Newport4-F1             ATTGAGCTGTTTTATAGCCAATGAAAATGCAAAAGATAAATTTGTAATATTTTCGTCTTT
Newport4-R1cc           ATTGAGCTGTTTTATAGCCAATGAAAATGCAAAAGATAAATTTGTAATATTTTCGTCTTT
Newport5-F1             ATTGAGCTGTTTTATAGCCAATGAAAATGCAAAAGATAAATTTGTAATATTTTCGTCTTT
Newport5-R1cc           ATTGAGCTGTTTTATAGCCAATGAAAATGCAAAAGATAAATTTGTAATATTTTCGTCTTT
                        ************************************************************

Kottbus-F1              GGTTTTTTCGTATTTTTTATTCAAGTTAATCTTACATTTTACTAACTCGGCTGATTTTTT
Kottbus-R1cc            GGTTTTTTCGTATTTTTTATTCAAGTTAATCTTACATTTTACTAACTCGGCTGATTTTTT
Bovismorbificans-F1     GGTTTTTTCGTATTTTTTATTCAAGTTAATCTTACATTTTACTAACTCGGCTGATTTTTT
Bovismorbificans-R1cc   GGTTTTTTCGTATTTTTTATTCAAGTTAATCTTACATTTTACTAACTCGGCTGATTTTTT
Bardo-F1                GGTTTTTTCGTATTTTTTATTCAAGTTAATCTTACATTTTACTAACTCGGCTGATTTTTT
Bardo-R1cc              GGTTTTTTCGTATTTTTTATTCAAGTTAATCTTACATTTTACTAACTCGGCTGATTTTTT
Blockley-F1             GGTTTTTTCGTATTTTTTATTCAAGTTAATCTTACATTTTACTAACTCGGCTGATTTTTT
Blockley-R1cc           GGTTTTTTCGTATTTTTTATTCAAGTTAATCTTACATTTTACTAACTCGGCTGATTTTTT
Newport1-F1             GGTTTTTTCGTATTTTTTATTCAAGTTAATCTTACATTTTACTAACTCGGCTGATTTTTT
Newport1-R1cc           GGTTTTTTCGTATTTTTTATTCAAGTTAATCTTACATTTTACTAACTCGGCTGATTTTTT
Newport2-F1             GGTTTTTTCGTATTTTTTATTCAAGTTAATCTTACATTTTACTAACTCGGCTGATTTTTT
Newport2-R1cc           GGTTTTTTCGTATTTTTTATTCAAGTTAATCTTACATTTTACTAACTCGGCTGATTTTTT
Newport3-F1             GGTTTTTTCGTATTTTTTATTCAAGTTAATCTTACATTTTACTAACTCGGCTGATTTTTT
Newport3-R1cc           GGTTTTTTCGTATTTTTTATTCAAGTTAATCTTACATTTTACTAACTCGGCTGATTTTTT
Newport4-F1             GGTTTTTTCGTATTTTTTATTCAAGTTAATCTTACATTTTACTAACTCGGCTGATTTTTT
Newport4-R1cc           GGTTTTTTCGTATTTTTTATTCAAGTTAATCTTACATTTTACTAACTCGGCTGATTTTTT
Newport5-F1             GGTTTTTTCGTATTTTTTATTCAAGTTAATCTTACATTTTACTAACTCGGCTGATTTTTT
Newport5-R1cc           GGTTTTTTCGTATTTTTTATTCAAGTTAATCTTACATTTTACTAACTCGGCTGATTTTTT
                        ************************************************************

Kottbus-F1              TTATTTGCCAGGGGTTGGTTCGCCTACATTTGTTAGTTATG
Kottbus-R1cc            TTATTTGCCAGGGGTTGGTTCGCCTACATTTGTTAGTTATG
Bovismorbificans-F1     TTATTTGCCAGGGGTTGGTTCGCCTACATTTGTTAGTTATG
Bovismorbificans-R1cc   TTATTTGCCAGGGGTTGGTTCGCCTACATTTGTTAGTTATG
Bardo-F1                TTATTTGCCAGGGGTTGGTTCGCCTACATTTGTTAGTTATG
Bardo-R1cc              TTATTTGCCAGGGGTTGGTTCGCCTACATTTGTTAGTTATG
Blockley-F1             TTATTTGCCAGGGGTTGGTTCGCCTACATTTGTTAGTTATG
Blockley-R1cc           TTATTTGCCAGGGGTTGGTTCGCCTACATTTGTTAGTTATG
Newport1-F1             TTATTTGCCAGGGGTTGGTTCGCCTACATTTGTTAGTTATG
Newport1-R1cc           TTATTTGCCAGGGGTTGGTTCGCCTACATTTGTTAGTTATG
Newport2-F1             TTATTTGCCAGGGGTTGGTTCGCCTACATTTGTTAGTTATG
Newport2-R1cc           TTATTTGCCAGGGGTTGGTTCGCCTACATTTGTTAGTTATG
Newport3-F1             TTATTTGCCAGGGGTTGGTTCGCCTACATTTGTTAGTTATG
Newport3-R1cc           TTATTTGCCAGGGGTTGGTTCGCCTACATTTGTTAGTTATG
Newport4-F1             TTATTTGCCAGGGGTTGGTTCGCCTACATTTGTTAGTTATG
Newport4-R1cc           TTATTTGCCAGGGGTTGGTTCGCCTACATTTGTTAGTTATG
Newport5-F1             TTATTTGCCAGGGGTTGGTTCGCCTACATTTGTTAGTTATG
Newport5-R1cc           TTATTTGCCAGGGGTTGGTTCGCCTACATTTGTTAGTTATG
                        *****************************************
```

FIGURE 3B

```
Bovismorbificans-F2    ATTCCTGTCATTATTTTTGGTTCAATTTTCTTATGTCGAAATGCGAATGTACCAAAGATA  SEQ ID NO 50
Bovismorbificans-R2cc  ATTCCTGTCATTATTTTTGGTTCAATTTTCTTATGTCGAAATGCGAATGTACCAAAGATA  SEQ ID NO 51
Bardo-F2               ATTCCTGTCATTATTTTTGGTTCAATTTTCTTATGTCGAAATGCGAATGTACCAAAGATA  SEQ ID NO 52
Bardo-R2cc             ATTCCTGTCATTATTTTTGGTTCAATTTTCTTATGTCGAAATGCGAATGTACCAAAGATA  SEQ ID NO 53
Blockley-F2            ATTCCTGTCATTATTTTTGGTTCAATTTTCTTATGTCGAAATGCGAATGTACCAAAGATA  SEQ ID NO 54
Blockley-R2cc          ATTCCTGTCATTATTTTTGGTTCAATTTTCTTATGTCGAAATGCGAATGTACCAAAGATA  SEQ ID NO 55
Newport1-F2            ATTCCTGTCATTATTTTTGGTTCAATTTTCTTATGTCGAAATGCGAATGTACCAAAGATA  SEQ ID NO 56
Newport1-R2cc          ATTCCTGTCATTATTTTTGGTTCAATTTTCTTATGTCGAAATGCGAATGTACCAAAGATA  SEQ ID NO 57
Newport2-F2            ATTCCTGTCATTATTTTTGGTTCAATTTTCTTATGTCGAAATGCGAATGTACCAAAGATA  SEQ ID NO 58
Newport2-R2cc          ATTCCTGTCATTATTTTTGGTTCAATTTTCTTATGTCGAAATGCGAATGTACCAAAGATA  SEQ ID NO 59
Newport3-F2            ATTCCTGTCATTATTTTTGGTTCAATTTTCTTATGTCGAAATGCGAATGTACCAAAGATA  SEQ ID NO 60
Newport3-R2cc          ATTCCTGTCATTATTTTTGGTTCAATTTTCTTATGTCGAAATGCGAATGTACCAAAGATA  SEQ ID NO 61
Newport4-F2            ATTCCTGTCATTATTTTTGGTTCAATTTTCTTATGTCGAAATGCGAATGTACCAAAGATA  SEQ ID NO 62
Newport4-R2cc          ATTCCTGTCATTATTTTTGGTTCAATTTTCTTATGTCGAAATGCGAATGTACCAAAGATA  SEQ ID NO 63
                       ************************************************************

Bovismorbificans-F2    TCAAATATAGTTTTATGGTTTTTTTCAATTTCAATTTCTGCTTATTCATTAATATATGTA
Bovismorbificans-R2cc  TCAAATATAGTTTTATGGTTTTTTTCAATTTCAATTTCTGCTTATTCATTAATATATGTA
Bardo-F2               TCAAATATAGTTTTATGGTTTTTTTCAATTTCAATTTCTGCTTATTCATTAATATATGTA
Bardo-R2cc             TCAAATATAGTTTTATGGTTTTTTTCAATTTCAATTTCTGCTTATTCATTAATATATGTA
Blockley-F2            TCAAATATAGTTTTATGGTTTTTTTCAATTTCAATTTCTGCTTATTCATTAATATATGTA
Blockley-R2cc          TCAAATATAGTTTTATGGTTTTTTTCAATTTCAATTTCTGCTTATTCATTAATATATGTA
Newport1-F2            TCAAATATAGTTTTATGGTTTTTTTCAATTTCAATTTCTGCTTATTCATTAATATATGTA
Newport1-R2cc          TCAAATATAGTTTTATGGTTTTTTTCAATTTCAATTTCTGCTTATTCATTAATATATGTA
Newport2-F2            TCAAATATAGTTTTATGGTTTTTTTCAATTTCAATTTCTGCTTATTCATTAATATATGTA
Newport2-R2cc          TCAAATATAGTTTTATGGTTTTTTTCAATTTCAATTTCTGCTTATTCATTAATATATGTA
Newport3-F2            TCAAATATAGTTTTATGGTTTTTTTCAATTTCAATTTCTGCTTATTCATTAATATATGTA
Newport3-R2cc          TCAAATATAGTTTTATGGTTTTTTTCAATTTCAATTTCTGCTTATTCATTAATATATGTA
Newport4-F2            TCAAATATAGTTTTATGGTTTTTTTCAATTTCAATTTCTGCTTATTCATTAATATATGTA
Newport4-R2cc          TCAAATATAGTTTTATGGTTTTTTTCAATTTCAATTTCTGCTTATTCATTAATATATGTA
                       ************************************************************

Bovismorbificans-F2    AATCAGCCTGATTTCTTATTTCGCAATGACAGAACCACATCAAAATATAGGCTTATATCT
Bovismorbificans-R2cc  AATCAGCCTGATTTCTTATTTCGCAATGACAGAACCACATCAAAATATAGGCTTATATCT
Bardo-F2               AATCAGCCTGATTTCTTATTTCGCAATGACAGAACCACATCAAAATATAGGCTTATATCT
Bardo-R2cc             AATCAGCCTGATTTCTTATTTCGCAATGACAGAACCACATCAAAATATAGGCTTATATCT
Blockley-F2            AATCAGCCTGATTTCTTATTTCGCAATGACAGAACCACATCAAAATATAGGCTTATATCT
Blockley-R2cc          AATCAGCCTGATTTCTTATTTCGCAATGACAGAACCACATCAAAATATAGGCTTATATCT
Newport1-F2            AATCAGCCTGATTTCTTATTTCGCAATGACAGAACCACATCAAAATATAGGCTTATATCT
Newport1-R2cc          AATCAGCCTGATTTCTTATTTCGCAATGACAGAACCACATCAAAATATAGGCTTATATCT
Newport2-F2            AATCAGCCTGATTTCTTATTTCGCAATGACAGAACCACATCAAAATATAGGCTTATATCT
Newport2-R2cc          AATCAGCCTGATTTCTTATTTCGCAATGACAGAACCACATCAAAATATAGGCTTATATCT
Newport3-F2            AATCAGCCTGATTTCTTATTTCGCAATGACAGAACCACATCAAAATATAGGCTTATATCT
Newport3-R2cc          AATCAGCCTGATTTCTTATTTCGCAATGACAGAACCACATCAAAATATAGGCTTATATCT
Newport4-F2            AATCAGCCTGATTTCTTATTTCGCAATGACAGAACCACATCAAAATATAGGCTTATATCT
Newport4-R2cc          AATCAGCCTGATTTCTTATTTCGCAATGACAGAACCACATCAAAATATAGGCTTATATCT
                       ************************************************************

Bovismorbificans-F2    AATTTTTTGACTCAACACAACTTATCTAATGGATATGCAACATTCTGGAATGCGGCAGCG
Bovismorbificans-R2cc  AATTTTTTGACTCAACACAACTTATCTAATGGATATGCAACATTCTGGAATGCGGCAGCG
Bardo-F2               AATTTTTTGACTCAACACAACTTATCTAATGGATATGCAACATTCTGGAATGCGGCAGCG
Bardo-R2cc             AATTTTTTGACTCAACACAACTTATCTAATGGATATGCAACATTCTGGAATGCGGCAGCG
Blockley-F2            AATTTTTTGACTCAACACAACTTATCTAATGGATATGCAACATTCTGGAATGCGGCAGCG
Blockley-R2cc          AATTTTTTGACTCAACACAACTTATCTAATGGATATGCAACATTCTGGAATGCGGCAGCG
Newport1-F2            AATTTTTTGACTCAACACAACTTATCTAATGGATATGCAACATTCTGGAATGCGGCAGCG
Newport1-R2cc          AATTTTTTGACTCAACACAACTTATCTAATGGATATGCAACATTCTGGAATGCGGCAGCG
Newport2-F2            AATTTTTTGACTCAACACAACTTATCTAATGGATATGCAACATTCTGGAATGCGGCAGCG
Newport2-R2cc          AATTTTTTGACTCAACACAACTTATCTAATGGATATGCAACATTCTGGAATGCGGCAGCG
Newport3-F2            AATTTTTTGACTCAACACAACTTATCTAATGGATATGCAACATTCTGGAATGCGGCAGCG
Newport3-R2cc          AATTTTTTGACTCAACACAACTTATCTAATGGATATGCAACATTCTGGAATGCGGCAGCG
Newport4-F2            AATTTTTTGACTCAACACAACTTATCTAATGGATATGCAACATTCTGGAATGCGGCAGCG
Newport4-R2cc          AATTTTTTGACTCAACACAACTTATCTAATGGATATGCAACATTCTGGAATGCGGCAGCG
                       ************************************************************

Bovismorbificans-F2    GTGAGTGTGGAAAAGAAATTCAATATAGCCCCTGTTAACATCGACATAGAAAATAAAAAA
Bovismorbificans-R2cc  GTGAGTGTGGAAAAGAAATTCAATATAGCCCCTGTTAACATCGACATAGAAAATAAAAAA
Bardo-F2               GTGAGTGTGGAAAAGAAATTCAATATAGCCCCTGTTAACATCGACATAGAAAATAAAAAA
Bardo-R2cc             GTGAGTGTGGAAAAGAAATTCAATATAGCCCCTGTTAACATCGACATAGAAAATAAAAAA
Blockley-F2            GTGAGTGTGGAAAAGAAATTCAATATAGCCCCTGTTAACATCGACATAGAAAATAAAAAA
Blockley-R2cc          GTGAGTGTGGAAAAGAAATTCAATATAGCCCCTGTTAACATCGACATAGAAAATAAAAAA
Newport1-F2            GTGAGTGTGGAAAAGAAATTCAATATAGCCCCTGTTAACATCGACATAGAAAATAAAAAA
Newport1-R2cc          GTGAGTGTGGAAAAGAAATTCAATATAGCCCCTGTTAACATCGACATAGAAAATAAAAAA
Newport2-F2            GTGAGTGTGGAAAAGAAATTCAATATAGCCCCTGTTAACATCGACATAGAAAATAAAAAA
Newport2-R2cc          GTGAGTGTGGAAAAGAAATTCAATATAGCCCCTGTTAACATCGACATAGAAAATAAAAAA
Newport3-F2            GTGAGTGTGGAAAAGAAATTCAATATAGCCCCTGTTAACATCGACATAGAAAATAAAAAA
Newport3-R2cc          GTGAGTGTGGAAAAGAAATTCAATATAGCCCCTGTTAACATCGACATAGAAAATAAAAAA
Newport4-F2            GTGAGTGTGGAAAAGAAATTCAATATAGCCCCTGTTAACATCGACATAGAAAATAAAAAA
Newport4-R2cc          GTGAGTGTGGAAAAGAAATTCAATATAGCCCCTGTTAACATCGACATAGAAAATAAAAAA
                       ************************************************************
```

Figure 3B (Continued)

```
Bovismorbificans-F2    GTTTTGCCATCTTTTTGGTTAACAAAAATATCATATTTTAACAATGGAAATAACTTTTTC
Bovismorbificans-R2cc  GTTTTGCCATCTTTTTGGTTAACAAAAATATCATATTTTAACAATGGAAATAACTTTTTC
Bardo-F2               GTTTTGCCATCTTTTTGGTTAACAAAAATATCATATTTAACAATGGAAATAACTTTTTC
Bardo-R2cc             GTTTTGCCATCTTTTTGGTTAACAAAAATATCATATTTAACAATGGAAATAACTTTTTC
Blockley-F2            GTTTTGCCATCTTTTTGGTTAACAAAAATATCATATTTTAACAATGGAAATAACTTTTTC
Blockley-R2cc          GTTTTGCCATCTTTTTGGTTAACAAAAATATCATATTTAACAATGGAAATAACTTTTTC
Newport1-F2            GTTTTGCCATCTTTTTGGTTAACAAAAATATCATATTTAACAATGGAAATAACTTTTTC
Newport1-R2cc          GTTTTGCCATCTTTTTGGTTAACAAAAATATCATATTTAACAATGGAAATAACTTTTTC
Newport2-F2            GTTTTGCCATCTTTTTGGTTAACAAAAATATCATATTTAACAATGGAAATAACTTTTTC
Newport2-R2cc          GTTTTGCCATCTTTTTGGTTAACAAAAATATCATATTTAACAATGGAAATAACTTTTTC
Newport3-F2            GTTTTGCCATCTTTTTGGTTAACAAAAATATCATATTTAACAATGGAAATAACTTTTTC
Newport3-R2cc          GTTTTGCCATCTTTTTGGTTAACAAAAATATCATATTTAACAATGGAAATAACTTTTTC
Newport4-F2            GTTTTGCCATCTTTTTGGTTAACAAAAATATCATATTTAACAATGGAAATAACTTTTTC
Newport4-R2cc          GTTTTGCCATCTTTTTGGTTAACAAAAATATCATATTTTAACAATGGAAATAACTTTTTC
                       ************************************************************

Bovismorbificans-F2    ATTGTTGATAATGACCAACAAAAAAAAGTCATAGAAGAATTATATGGCAAACCAGAATTA
Bovismorbificans-R2cc  ATTGTTGATAATGACCAACAAAAAAAAGTCATAGAAGAATTATATGGCAAACCAGAATTA
Bardo-F2               ATTGTTGATAATGACCAACAAAAAAAAGTCATAGAAGAATTATATGGCAAACCAGAATTA
Bardo-R2cc             ATTGTTGATAATGACCAACAAAAAAAAGTCATAGAAGAATTATATGGCAAACCAGAATTA
Blockley-F2            ATTGTTGATAATGACCAACAAAAAAAAGTCATAGAAGAATTATATGGCAAACCAGAATTA
Blockley-R2cc          ATTGTTGATAATGACCAACAAAAAAAAGTCATAGAAGAATTATATGGCAAACCAGAATTA
Newport1-F2            ATTGTTGATAATGACCAACAAAAAAAAGTCATAGAAGAATTATATGGCAAACCAGAATTA
Newport1-R2cc          ATTGTTGATAATGACCAACAAAAAAAAGTCATAGAAGAATTATATGGCAAACCAGAATTA
Newport2-F2            ATTGTTGATAATGACCAACAAAAAAAAGTCATAGAAGAATTATATGGCAAACCAGAATTA
Newport2-R2cc          ATTGTTGATAATGACCAACAAAAAAAAGTCATAGAAGAATTATATGGCAAACCAGAATTA
Newport3-F2            ATTGTTGATAATGACCAACAAAAAAAAGTCATAGAAGAATTATATGGCAAACCAGAATTA
Newport3-R2cc          ATTGTTGATAATGACCAACAAAAAAAAGTCATAGAAGAATTATATGGCAAACCAGAATTA
Newport4-F2            ATTGTTGATAATGACCAACAAAAAAAAGTCATAGAAGAATTATATGGCAAACCAGAATTA
Newport4-R2cc          ATTGTTGATAATGACCAACAAAAAAAAGTCATAGAAGAATTATATGGCAAACCAGAATTA
                       ************************************************************
```

Figure 3B (Continued)

```
Bovismorbificans-F2    ACATATATGGTGTGGGATTCCCCCATCCTGGTTTACAGTCATTCTATTAATATTTATGAT
Bovismorbificans-R2cc  ACATATATGGTGTGGGATTCCCCCATCCTGGTTTACAGTCATTCTATTAATATTTATGAT
Bardo-F2               ACATATATGGTGTGGGATTCCCCCATCCTGGTTTACAGTCATTCTATTAATATTTATGAT
Bardo-R2cc             ACATATATGGTGTGGGATTCCCCCATCCTGGTTTACAGTCATTCTATTAATATTTATGAT
Blockley-F2            ACATATATGGTGTGGGATTCCCCCATCCTGGTTTACAGTCATTCTATTAATATTTATGAT
Blockley-R2cc          ACATATATGGTGTGGGATTCCCCCATCCTGGTTTACAGTCATTCTATTAATATTTAGGAT
Newport1-F2            ACATATATGGTGTGGGATTCCCCCATCCTGGTTTACAGTCATTCTATTAATATTTATGAT
Newport1-R2cc          ACATATATGGTGTGGGATTCCCCCATCCTGGTTTACAGTCATTCTATTAATATTTATGAT
Newport2-F2            ACATATATGGTGTGGGATTCCCCCATCCTGGTTTACAGTCATTCTATTAATATTTATGAT
Newport2-R2cc          ACATATATGGTGTGGGATTCCCCCATCCTGGTTTACAGTCATTCTATTAATATTTATGAT
Newport3-F2            ACATATATGGTGTGGGATTCCCCCATCCTGGTTTACAGTCATTCTATTAATATTTATGAT
Newport3-R2cc          ACATATATGGTGTGGGATTCCCCCATCCTGGTTTACAGTCATTCTATTAATATTTATGAT
Newport4-F2            ACATATATGGTGTGGGATTCCCCCATCCTGGTTTACAGTCATTCTATTAATATTTATGAT
Newport4-R2cc          ACATATATGGTGTGGGATTCCCCCATCCTGGTTTACAGTCATTCTATTAATATTTATGAT
                       ********************************************************  ***

Bovismorbificans-F2    GGCGATATAGAAGGAAGTGCCAATGTAGTAAAAAG
Bovismorbificans-R2cc  GGCGATATAGAAGGAAGTGCCAATGTAGTAAAAAG
Bardo-F2               GGCGATATAGAAGGAAGTGCCAATGTAGTAAAAAG
Bardo-R2cc             GGCGATATAGAAGGAAGTGCCAATGTAGTAAAAAG
Blockley-F2            GGCGATATAGAAGGAAGTGCCAATGTAGTAAAAAG
Blockley-R2cc          GGCGATATAGAAGGAAGTGCCAATGTAGTAAAAAG
Newport1-F2            GGCGATATAGAAGGAAGTGCCAATGTAGTAAAAAG
Newport1-R2cc          GGCGATATAGAAGGAAGTGCCAATGTAGTAAAAAG
Newport2-F2            GGCGATATAGAAGGAAGTGCCAATGTAGTAAAAAG
Newport2-R2cc          GGCGATATAGAAGGAAGTGCCAATGTAGTAAAAAG
Newport3-F2            GGCGATATAGAAGGAAGTGCCAATGTAGTAAAAAG
Newport3-R2cc          GGCGATATAGAAGGAAGTGCCAATGTAGTAAAAAG
Newport4-F2            GGCGATATAGAAGGAAGTGCCAATGTAGTAAAAAG
Newport4-R2cc          GGCGATATAGAAGGAAGTGCCAATGTAGTAAAAAG
                       ***********************************
```

FIGURE 3C

```
Newport1          AAATTAATGCACATGGCGATCAGTATGAAGCATTAATTTTTTCTTATATAACAGGAAAAA  SEQ ID NO 64
Newport2          AAATTAATGCACATGGCGATCAGTATGAAGCATTAATTTTTTCTTATATAACAGGAAAAA  SEQ ID NO 65
Newport3          AAATTAATGCACATGGCGATCAGTATGAAGCATTAATTTTTTCTTATATAACAGGAAAAA  SEQ ID NO 66
Newport4          AAATTAATGCACATGGCGATCAGTATGAAGCATTAATTTTTTCTTATATAACAGGAAAAA  SEQ ID NO 67
Newport5          -------ATGCACATGGCGATCAGTATGAAGCATTAATTTTTTCTTATATAACAGGAAAAA  SEQ ID NO 68
Bardo             ----------------GGCGATCAGTATGAAGCATTAATTTTTTCTTATATAACAGGAAAAA  SEQ ID NO 69
Bovismorbificans  -------ATGCACATGGCGATCAGTATGAAGCATTAATTTTTTCTTATATAACAGGAAAAA  SEQ ID NO 70
Blockley          ----------------GGCGATCAGTATGAAGCATTAATTTTTTCTTATATAACAGGAAAAA  SEQ ID NO 71
Kottbus           -------ATGCACATGGCGATCAGTATGAAGCATTAATTTTTTCTTATATAACAGGAAAAA  SEQ ID NO 72
                                 ************************************************

Newport1          AAATCAAGATGTCTGAGAATAAATATAAAAATGGTTCTTATATTTTCGAAATAAACGAAG
Newport2          AAATCAAGATGTCTGAGAATAAATATAAAAATGGTTCTTATATTTTCGAAATAAACGAAG
Newport3          AAATCAAGATGTCTGAGAATAAATATAAAAATGGTTCTTATATTTTCGAAATAAACGAAG
Newport4          AAATCAAGATGTCTGAGAATAAATATAAAAATGGTTCTTATATTTTCGAAATAAACGAAG
Newport5          AAATCAAGATGTCTGAGAATAAATATAAAAATGGTTCTTATATTTTCGAAATAAACGAAG
Bardo             AAATCAAGATGTCTGAGAATAAATATAAAAATGGTTCTTATATTTTCGAAATAAACGAAG
Bovismorbificans  AAATCAAGATGTCTGAGAATAAATATAAAAATGGTTCTTATATTTTCGAAATAAACGAAG
Blockley          AAATCAAGATGTCTGAGAATAAATATAAAAATGGTTCTTATATTTTCGAAATAAACGAAG
Kottbus           AAATCAAGATGTCTGAGAATAAATATAAAAATGGTTCTTATATTTTCGAAATAAACGAAG
                  ************************************************************

Newport1          ATATGCCATCTGCAGAAATACAGTTATTCGCTCAAAAAGATTCAAATGTATGTTTTGAGT
Newport2          ATATGCCATCTGCAGAAATACAGTTATTCGCTCAAAAAGATTCAAATGTATGTTTTGAGT
Newport3          ATATGCCATCTGCAGAAATACAGTTATTCGCTCAAAAAGATTCAAATGTATGTTTTGAGT
Newport4          ATATGCCATCTGCAGAAATACAGTTATTCGCTCAAAAAGATTCAAATGTATGTTTTGAGT
Newport5          ATATGCCATCTGCAGAAATACAGTTATTCGCTCAAAAAGATTCAAATGTATGTTTTGAGT
Bardo             ATATGCCATCTGCAGAAATACAGTTATTCGCTCAAAAAGATTCAAATGTATGTTTTGAGT
Bovismorbificans  ATATGCCATCTGCAGAAATACAGTTATTCGCTCAAAAAGATTCAAATGTATGTTTTGAGT
Blockley          ATATGCCATCTGCAGAAATACAGTTATTCGCTCAAAAAGATTCAAATGTATGTTTTGAGT
Kottbus           ATATGCCATCTGCAGAAATACAGTTATTCGCTCAAAAAGATTCAAATGTATGTTTTGAGT
                  ************************************************************
```

Figure 3C (Continued)

```
Newport1          CATACTCACTTCAGCATATAAAATAATAAAGTCATGGAAAAGCGTCAGTAACTAATACAG
Newport2          CATACTCACTTCAGCATATAAAATAATAAAGTCATGGAAAAGCGTCAGTAACTAATACAG
Newport3          CATACTCACTTCAGCATATAAAATAATAAAGTCATGGAAAAGCGTCAGTAACTAATACAG
Newport4          CATACTCACTTCAGCATATAAAATAATAAAGTCATGGAAAAGCGTCAGTAACTAATACAG
Newport5          CATACTCACTTCAGCATATAAAATAATAAAGTCATGGAAAAGCGTCAGTAACTAATACAG
Bardo             CATACTCACTTCAGCATATAAAATAATAAAGTCATGGAAAAGCGTCAGTAACTAATACAG
Bovismorbificans  CATACTCACTTCAGCATATAAAATAATAAAGTCATGGAAAAGCGTCAGTAACTAATACAG
Blockley          CATACTCACTTCAGCATATAAAATAATAAAGTCATGGAAAAGCGTCAGTAACTAATACAG
Kottbus           CATACTCACTTCAGCATATAAAATAATTAAGTCATGGAAAAGCGTCAGTAACTAATACAG
                  *****************************:******************************

Newport1          GCGCTTTTTGTCTATAGAAAACTCATGCTGTTAAGCGGGTTTTGGTTGAAATGTTCCGAA
Newport2          GCGCTTTTTGTCTATAGAAAACTCATGCTGTTAAGCGGGTTTTGGTTGAAATGTTCCGAA
Newport3          GCGCTTTTTGTCTATAGAAAACTCATGCTGTTAAGCGGGTTTTGGTTGAAATGTTCCGAA
Newport4          GCGCTTTTTGTCTATAGAAAACTCATGCTGTTAAGCGGGTTTTGGTTGAAATGTTCCGAA
Newport5          GCGCTTTTTGTCTATAGAAAACTCATGCTGTTAAGCGGGTTTTGGTTGAAATGTTCCGAA
Bardo             GCGCTTTTTGTCTATAGAAAACTCATGCTGTTAAGCGGGTTTTGGTTGAAATGTTCCGAA
Bovismorbificans  GCGCTTTTTGTCTATAGAAAACTCATGCTGTTAAGCGGGTTTTGGTTGAAATGTTCCGAA
Blockley          GCGCTTTTTGTCTATAGAAAACTCATGCTGTTAAGCGGGTTTTGGTTGAAATGTTCCGAA
Kottbus           GCGCTTTTTGTCTATAGAAAACTCATGCTGTTAAGCGGGTTTTGGTTGAAATGTTCCGAA
                  ************************************************************

Newport1          AATCGGAATAGTTATTCCACACCAGCGCTATGAATTAGATGGCGAAGAGCATGCTGTAAC
Newport2          AATCGGAATAGTTATTCCACACCAGCGCTATGAATTAGATGGCGAAGAGCATGCTGTAAC
Newport3          AATCGGAATAGTTATTCCACACCAGCGCTATGAATTAGATGGCGAAGAGCATGCTGTAAC
Newport4          AATCGGAATAGTTATTCCACACCAGCGCTATGAATTAGATGGCGAAGAGCATGCTGTAAC
Newport5          AATCGGAATAGTTATTCCACACCAGCGCTATGAATTAGATGGCGAAGAGCATGCTGTAAC
Bardo             AATCGGAATAGTTATTCCACACCAGCGCTATGAATTAGATGGCGAAGAGCATGCTGTAAC
Bovismorbificans  AATCGGAATAGTTATTCCACACCAGCGCTATGAATTAGATGGCGAAGAGCATGCTGTAAC
Blockley          AATCGGAATAGTTATTCCACACCAGCGCTATGAATTAGATGGCGAAGAGCATGCTGTAAC
Kottbus           AATCGGAATAGTTATTCCACACCAGCGCTATGAATTAGATGGCGAAGAGCATGCTGTAAC
                  ************************************************************

Newport1          CCCTACTATAGTAGCACCTTCAGATTGAACATACATGGTACCAATCTTATATAATTGCC
Newport2          CCCTACTATAGTAGCACCTTCAGATTGAACATACATGGTACCAATCTTATATAATTGCC
Newport3          CCCTACTATAGTAGCACCTTCAGATTGAACATACATGGTACCAATCTTATATAATTGCC
Newport4          CCCTACTATAGTAGCACCTTCAGATTGAACATACATGGTACCAATCTTATATAATTGCC
Newport5          CCCTACTATAGTAGCACCTTCAGATTGAACATACATGGTACCAATCTTATATAATTGCC
Bardo             CCCTACTATAGTAGCACCTTCAGATTGAACATACATGGTACCAATCTTATATAATTGCC
Bovismorbificans  CCCTACTATAGTAGCACCTTCAGATTGAACATACATGGTACCAATCTTATATAATTGCC
Blockley          CCCTACTATAGTAGCACCTTCAGATTGAACATACATGGTACCAATCTTATATAATTGCC
Kottbus           CCCTACTATAGTAGCACCTTCAGATTGAACATACATGGTACCAATCTTATATAATTGCC
                  ************************************************************

Newport1          TGGCGTCGAACGCCCCGAGAAGTACCGTACCAGTAGTTGCCGTCGATTATGTCTGGCGAG
Newport2          TGGCGTCGAACGCCCCGAGAAGTACCGTACCAGTAGTTGCCGTCGATTATGTCTGGCGAG
Newport3          TGGCGTCGAACGCCCCGAGAAGTACCGTACCAGTAGTTGCCGTCGATTATGTCTGGCGAG
Newport4          TGGCGTCGAACGCCCCGAGAAGTACCGTACCAGTAGTTGCCGTCGATTATGTCTGGCGAG
Newport5          TGGCGTCGAACGCCCCGAGAAGTACCGTACCAGTAGTTGCCGTCGATTATGTCTGGCGAG
Bardo             TGGCGTCGAACGCCCCGAGAAGTACCGTACCAGTAGTTGCCGTCGATTATGTCTGGCGAG
Bovismorbificans  TGGCGTCGAACGCCCCGAGAAGTACCGTACCAGTAGTTGCCGTCGATTATGTCTGGCGAG
Blockley          TGGCGTCGAACGCCCCGAGAAGTACCGTACCAGTAGTTGCCGTCGATTATGTCTGGCGAG
Kottbus           TGGCGTCGAACGCCCCGAGAAGTACCGTACCAGTAGTTGCCGTCGATTATGTCTGGCGAG
                  ************************************************************

Newport1          CGCCGATAACTTTCATGCCGCCTACTGAACAAGATGTTACCACATTAAGAGAGGAGACCA
Newport2          CGCCGATAACTTTCATGCCGCCTACTGAACAAGATGTTACCACATTAAGAGAGGAGACCA
Newport3          CGCCGATAACTTTCATGCCGCCTACTGAACAAGATGTTACCACATTAAGAGAGGAGACCA
Newport4          CGCCGATAACTTTCATGCCGCCTACTGAACAAGATGTTACCACATTAAGAGAGGAGACCA
Newport5          CGCCGATAACTTTCATGCCGCCTACTGAACAAGATGTTACCACATTAAGAGAGGAGACCA
Bardo             CGCCGATAACTTTCATGCCGCCTACTGAACAAGATGTTACCACATTAAGAGAGGAGACCA
Bovismorbificans  CGCCGATAACTTTCATGCCGCCTACTGAACAAGATGTTACCACATTAAGAGAGGAGACCA
Blockley          CGCCGATAACTTTCATGCCGCCTACTGAACAAGATGTTACCACATTAAGAGAGGAGACCA
Kottbus           CGCCGATAACTTTCATGCCGCCTACTGAACAAGATGTTACCACATTAAGAGAGGAGACCA
                  ************************************************************

Newport1          GCGATTACGATATTGCATCTGTTTTCGACACGTAGTCGTTCTCAATAGAAGAGGCGAAAA
Newport2          GCGATTACGATATTGCATCTGTTTTCGACACGTAGTCGTTCTCAATAGAAGAGGCGAAAA
Newport3          GCGATTACGATATTGCATCTGTTTTCGACACGTAGTCGTTCTCAATAGAAGAGGCGAAAA
Newport4          GCGATTACGATATTGCATCTGTTTTCGACACGTAGTCGTTCTCAATAGAAGAGGCGAAAA
Newport5          GCGATTACGATATTGCATCTGTTTTCGACACGTAGTCGTTCTCAATAGAAGAGGCGAAAA
Bardo             GCGATTACGATATTGCATCTGTTTTCGACACGTAGTCGTTCTCAATAGAAGAGGCGAAAA
Bovismorbificans  GCGATTACGATATTGCATCTGTTTTCGACACGTAGTCGTTCTCAATAGAAGAGGCGAAAA
Blockley          GCGATTACGATATTGCATCTGTTTTCGACACGTAGTCGTTCTCAATAGAAGAGGCGAAAA
Kottbus           GCGATTACGATATTGCATCTGTTTTCGACACGTAGTCGTTCTCAATAGAAGAGGCGAAAA
                  ************************************************************

Newport1          AACACCAAGCCACTTGATGGCGTTTTTTATTAGAGGCAATAAATGTCGGCTT
Newport2          AACACCAAGCCACTTGATGGCGTTTTTTATTAGAGGCAATAAATGTCGGCTT
Newport3          AACACCAAGCCACTTGATGGCGTTTTTTATTAGAGGCAATAAATGTCGGCTT
Newport4          AACACCAAGCCACTTGATGGCGTTTTTTATTAGAGGCAATAAATGTCGGCTT
```

Figure 3C (Continued)

```
Newport5          AACACCAAGCCACTTGATGGCGTTTTTTATTAGAGGCAATAAATGTCGGCTT
Bardo             AACACCAAGCCACTTGATGGCGTTTTTTATTAGAGGCAATAAATGTCGGCTT
Bovismorbificans  AACACCAAGCCACTTGATGGCGTTTTTTATTAGAGGCAATAAATGTCGGCTT
Blockley          AACACCAAGCCACTTGATGGCGTTTTTTATTAGAGGCAATAAATGTCGGCTT
Kottbus           AACACCAAGCCACTTGATGGCGTTTTTTATTAGAGGCAATAAATGTCGGCTT
                  ****************************************************
```

FIGURE 3D

```
Newport1          CAGCAGGCTTCCGCAGATGTGTCTGGCTTGTTCAGCAGTCTCCAGAATCAGGGATACATC SEQ ID NO 73
Newport2          -------CTTCCGCAGATGTGTCTGGCTTGTTCAGCAGTCTCCAGAATCAGGGATACATC SEQ ID NO 74
Newport3          ------------------------GTTCAGCAGTCTCCAGAATCAGGGATACATC SEQ ID NO 75
Newport4          ----------------------GTCTGGCTTGTTCAGCAGTCTCCAGAATCAGGGATACATC SEQ ID NO 76
Newport5          ----------------------GTCTGGCTTGTTCAGCAGTCTCCAGAATCAGGGATACATC SEQ ID NO 77
Bardo             CAGCAGGCTTCCGCAGATGTGTCTGGCTTGTTCAGCAGTCTCCAGAATCAGGGATACATC SEQ ID NO 78
Bovismorbificans  ------------------GTGTCTGGCTTGTTCAGCAGTCTCCAGAATCAGGGATACATC SEQ ID NO 79
Blockley          CAGCAGGCTTCCGCAGATGTGTCTGGCTTGTTCAGCAGTCTCCAGAATCAGGGATACATC SEQ ID NO 80
Kottbus           ----------------------GTCTGGCTTGTTCAGCAGTCTCCAGAATCAGGGATACATC SEQ ID NO 81
                                        ******************************

Newport1          CGAAAAACGTCAAAATGAGTTCCGGAATTCAAAGATGCCCTCAGTAAATCGGACTCCCTC
Newport2          CGAAAAACGTCAAAATGAGTTCCGGAATTCAAAGATGCCCTCAGTAAATCGGACTCCCTC
Newport3          CGAAAAACGTCAAAATGAGTTCCGGAATTCAAAGATGCCCTCAGTAAATCGGACTCCCTC
Newport4          CGAAAAACGTCAAAATGAGTTCCGGAATTCAAAGATGCCCTCAGTAAATCGGACTCCCTC
Newport5          CGAAAAACGTCAAAATGAGTTCCGGAATTCAAAGATGCCCTCAGTAAATCGGACTCCCTC
Bardo             CGAAAAACGTCAAAATGAGTTCCGGAATTCAAAGATGCCCTCAGTAAATCGGACTCCCTC
Bovismorbificans  CGAAAAACGTCAAAATGAGTTCCGGAATTCAAAGATGCCCTCAGTAAATCGGACTCCCTC
Blockley          CGAAAAACGTCAAAATGAGTTCCGGAATTCAAAGATGCCCTCAGTAAATCGGACTCCCTC
Kottbus           CGAAAAACGTCAAAATGAGTTCCGGAATTCAAAGATGCCCTCAGTAAATCGGACTCCCTC
                  ************************************************************

Newport1          GTTGCGCTGTTAAAGTCTGAAATGGAGACACGCAGGAATGTAGCACCAACAACTCGCTAG
Newport2          GTTGCGCTGTTAAAGTCTGAAATGGAGACACGCAGGAATGTAGCACCAACAACTCGCTAG
Newport3          GTTGCGCTGTTAAAGTCTGAAATGGAGACACGCAGGAATGTAGCACCAACAACTCGCTAG
Newport4          GTTGCGCTGTTAAAGTCTGAAATGGAGACACGCAGGAATGTAGCACCAACAACTCGCTAG
Newport5          GTTGCGCTGTTAAAGTCTGAAATGGAGACACGCAGGAATGTAGCACCAACAACTCGCTAG
Bardo             GTTGCGCTGTTAAAGTCTGAAATGGAGACACGCAGGAATGTAGCACCAACAACTCGCTAG
Bovismorbificans  GTTGCGCTGTTAAAGTCTGAAATGGAGACACGCAGGAATGTAGCACCAACAACTCGCTAG
Blockley          GTTGCGCTGTTAAAGTCTGAAATGGAGACACGCAGGAATGTAGCACCAACAACTCGCTAG
Kottbus           GTTGCGCTGTTAAAGTCTGAAATGGAGACACGCAGGAATGTAGCACCAACAACTCGCTAG
                  ************************************************************

Newport1          AGAATCAAAAAGCTGAGCCAGATGCCCCCGGAATCACACAGCCTCACACTTGATGATGCC
Newport2          AGAATCAAAAAGCTGAGCCAGATGCCCCCGGAATCACACAGCCTCACACTTGATGATGCC
Newport3          AGAATCAAAAAGCTGAGCCAGATGCCCCCGGAATCACACAGCCTCACACTTGATGATGCC
Newport4          AGAATCAAAAAGCTGAGCCAGATGCCCCCGGAATCACACAGCCTCACACTTGATGATGCC
Newport5          AGAATCAAAAAGCTGAGCCAGATGCCCCCGGAATCACACAGCCTCACACTTGATGATGCC
Bardo             AGAATCAAAAAGCTGAGCCAGATGCCCCCGGAATCACACAGCCTCACACTTGATGATGCC
Bovismorbificans  AGAATCAAAAAGCTGAGCCAGATGCCCCCGGAATCACACAGCCTCACACTTGATGATGCC
Blockley          AGAATCAAAAAGCTGAGCCAGATGCCCCCGGAATCACACAGCCTCACACTTGATGATGCC
Kottbus           AGAATCAAAAAGCTGAGCCAGATGCCCCCGGAATCACACAGCCTCACACTTGATGATGCC
                  ************************************************************

Newport1          TGTGTATTTCTTCAAGTTACCAAACCTATCGCTACTAACTGGATTCACACAGGCTGTCTG
Newport2          TGTGTATTTCTTCAAGTTACCAAACCTATCGCTACTAACTGGATTCACACAGGCTGTCTG
Newport3          TGTGTATTTCTTCAAGTTACCAAACCTATCGCTACTAACTGGATTCACACAGGCTGTCTG
Newport4          TGTGTATTTCTTCAAGTTACCAAACCTATCGCTACTAACTGGATTCACACAGGCTGTCTG
Newport5          TGTGTATTTCTTCAAGTTACCAAACCTATCGCTACTAACTGGATTCACACAGGCTGTCTG
Bardo             TGTGTATTTCTTCAAGTTACCAAACCTATCGCTACTAACTGGATTCACACAGGCTGTCTG
Bovismorbificans  TGTGTATTTCTTCAAGTTACCAAACCTATCGCTACTAACTGGATTCACACAGGCTGTCTG
Blockley          TGTGTATTTCTTCAAGTTACCAAACCTATCGCTACTAACTGGATTCACACAGGCTGTCTG
Kottbus           TGTGTATTTCTTCAAGTTACCAAACCTATCGCTACTAACTGGATTCACACAGGCTGTCTG
                  ************************************************************

Newport1          TAAACATCATGTAAAGATTCCGCCAAGTCAGTCAATAGGTATGCATAAATTTAACCGAAC
Newport2          TAAACATCATGTAAAGATTCCGCCAAGTCAGTCAATAGGTATGCATAAATTTAACCGAAC
Newport3          TAAACATCATGTAAAGATTCCGCCAAGTCAGTCAATAGGTATGCATAAATTTAACCGAAC
Newport4          TAAACATCATGTAAAGATTCCGCCAAGTCAGTCAATAGGTATGCATAAATTTAACCGAAC
Newport5          TAAACATCATGTAAAGATTCCGCCAAGTCAGTCAATAGGTATGCATAAATTTAACCGAAC
Bardo             TAAACATCATGTAAAGATTCCGCCAAGTCAGTCAATAGGTATGCATAAATTTAACCGAAC
Bovismorbificans  TAAACATCATGTAAAGATTCCGCCAAGTCAGTCAATAGGTATGCATAAATTTAACCGAAC
Blockley          TAAACATCATGTAAAGATTCCGCCAAGTCAGTCAATAGGTATGCATAAATTTAACCGAAC
Kottbus           TAAACATCATGTAAAGATTCCGCCAAGTCAGTCAATAGGTATGCATAAATTTAACCGAAC
                  ************************************************************
```

FIGURE 4

SEQ ID NO 26
TTAAATAATCTCCGGTGCATTGCCGGTAATGGCTTTCACATCCGCCAGCAGATCGCCAAACTTACCGTAGTTAACCTTAA
CGCCGTCGTCGAGATCAATACTGATTCTCATATCAGCATAGTGGCGCAGGCGATCGTCGAAGCTGCGCAGTTCGTTGAAT
TTTTTGCTCAGGCTATCACGCTCACGTTTCAGACGGGTGGCTTCGCCGCCTGAGGCTCCATCGACCTGTTCGTTCAGGCG
ATCGATATTGGCCTGATAGCGCGCCAGCAGCGGCACTACATATTCGGTACGCATTCTCGCCAGCGTCGCATCGTTGTAGC
GATGCAGATAGACCAGGCACTCAAACGCTTTCTCTTTACCGGAGCTGAACAGCCAGTATATCGGACGCTTTTTATACATC
TTCATATGATCTTTCCAGAACTGAGTGGAAAGATAGCGGCGGATGGTATCCAGCGCAGATTCGCCTTTTTTGGTTTTAT
CGCGTATAAACAGAGGCTTTCGGCGATAAATTCGAGATTTTCCTGCAAGTGTTCTTCGCCCAAACGGTGCGAACAAACT
CTTTGACGCGAGAGGTAACGTCATCGTCAAACCACTCGTCATCCATCAGCGGCAGGATACCGTCATTGTCAGCCGGGAAG
GTTTTGTACGCGTCTTCAGCGACCAGTTCGGCAAAGCCTTTATTGCCTTCATGGGCATAGACCAGTCCTTCGCGATCGAG
GGAGTAGCGGCCCATCATGCAGCCGATGATGTAGCTTAAGATATC<ins>TATAGTGATATCAGTGTAATACTTATTGGTTAGAT
CGGTATGATCTTGAATATTTTTATATCGATAGTTTGGATTACATAGTAGAGTTATTTCACTTTGCAATACAGCTTTAATT
ATAGTTTTGTCAAGTTGTAATTTATCTATAAAAATATTATTTATAGTATTTTCTATTAGGAGAAGTGTTTCGACTAACTT
GATATTTGTATTGATTTTTTGTTTGTAGATATTCCGTAGCAATTGAGTTGAATTGTGTTCAAGCAATGGTGAACAAACAT
AATCCCATGATTGCTCTTGAGAGTCCCAGTCATTTTTAGCTATTTCAATAGCATTGGTGACTAATTCGATAATTTCATCT
TCAATTTCTGGATATGGTACTGAGGCTAATTCACCACTAGTAAAGCTAAGTGTGGGGCTAGTATTGATAAATAATGGTT
TACAACCGGAGTGCACATTAATCCCGCAGCGTAAAGCAACTCATTTTTGTTATTTGAAAAGCCGCAACGGCCTGTATCAT
CAAAAACAAACCCTTTTGGACGATATCTCACGCAAAAATTACCTTGGCTTATTTTTGACCATGTTATGCCTTCTCTAAAG
TAATACTCATCATTTCTTACGGCAGAGCGAGTTTTGCCATTCTCAAATTTAAAATTTCGTATTTCGTAACCATTATTTTC
CCAATTTACAACTATTTCGTTATTACCATACCACTTTCGATATTCACCTCCACTACTACAAGGAAACCATTTGATATTAT
GAATGTCGATTTTTGTATTTGATTCTTTATTTGTGATAAGGGTTTTTTTTATTGAAACCTCGTACCAATATCTTTGAAAT
TTAATATTGTCACCGGTGGACATGCCTGCTTTTAATGCTATTTTTTCTCCAAGTTTTTTATGGTGGCGAAAAGATAATAG
ACTCGGTAAGTCTATCCAATATGCTATTGGCATTCCTGGTATGTTTTTAAAATCATGCTGTGTAAATTTATCAAATATAT
TTTTCCTTAGAAGTAGATCGCTTTTCTTTACTTCTTCCCTACCATCTATAAGTCTAAAAAATACAGGTTGGTAACGTTCG
GAGTGT</ins>TGGTTTTTAATCACCCAGGCAGTTGTCTGTACAACCTCTCCAGAAATTTGCCCAAAAGCCCGAGCTCCCAAATG
TGCCATCGTAATAAATGTTTTATTGTCCAATAACCAGTTACGTAGTGCTTCATAACTTGACAAAAACATCCATGATTGCA
TATTGACTTGAGCATTAAACCCATTTTCTTTAAGCAAAGAAAATGCATTCTGCATAAACATTGCAAACAAATCAGCTTTA
CTATCCGGGAAGTTATTTTTGGCAAACTCTTTCAGCTCACTATTCATTCCCTTGCCACCCATATACGGCGGATTCGCCAC
TACCGCATCATACCGCTGCGCCAGGATCCACGCCTGCTGAATATACGGAATAAACGCTTTCGCCGCTGCCTTCTGCTGGA
AATCGCCTTCCTGCTCCATGCGATATAGCGCTTCGAGAAACGCCTTCAGTTCCGCCTCTTCTTCCTGTGGCACCTGGATC
AGCGAGCCCAGCGTTTTGGCGTTCACAAAGCGCTTCAGCGTGCGCATCAGCAGCTGATATTCTGCGCTGTCGGTATGGGC
TAATGCTGTATTTTCGGCAAACATATCCCCCATGCTACCAGTCTGGTTCTGCTGGTGGAAGTTCAGCTGCTGCCACAGCT
TAGCAATATCCAGATGCAGGCTCTCCTGCAGGGAGACAATATTCAGACGCACGTCGCGGGTGAATATCCGGCGGTCATCC
TGACGGGCCATCATTAATAAGGCAAAGCCGGAAAGCTGGGCAGCACGGTCGTCAATGTCGAGACCAAAAATATTATTTTC
CAGAATTAGCTGTGGAATATCGCGGGCGCGATAGCCGCGCTCTTCATAGATATTTTTCAGCACATTATAGACTTCAATCA
GAATATGCCCGGAGCCGCAGGCCGGGTCGAGTACTTTGATGCTTTCCGGTTCAATACTGGCAGGTGTAATGGCGGCCAGC
TGCGCCTGCACTTCTGGCGTCTGTTCGGCTGGCTCAATGTAGTAGTCCATTTTGCCTTTCAGCGGCGAATCGGGTAGGT
CTGCAACCACTGGCGGCCGACGGAGTTCTGTACCAGATACTGCACAATCCAGTTTGGGGTAAACAGCTGGGTGGCGGCAG
GAATATCTTCGCTCTTCACCACCTTACCGATAACCGCATCTTTTTTCTCAGAGATATAGAACTGATACAGCCAGCCGATA
ACCTCAACTTCTTGCCAGTCTTCTTCCGGAATACCGTCCACCAGACCGCGTAGAATGGAGTCGGTGCGGGTCAGGTTATC
CGGCAGCAGTAGTTCAGCTTCATCGTCCACAGCTTCAAACAGGAACGGCATCGCGCGGTGCAGGGCGTGGCACTGGGCCA
GCAGCAGTTCACGGTAGATGGCTTCGTCCTGGTTGCCGGAAAGCTTCATCTCGACCAGCTGCGCCTTTTTCTCTGGTAGT
AATGCTTCCGCGACTTCCGGTACGTGGTCCAGCACCTTCAAAGCCTGTCGGGTTATCCGGTGCGAGAGCATGTGGAAGCC
GTGGTCAAGATAACCGTGGATTTCCATATAACGAATGGCGCACAGGCGGTTGAACCAGGTGTAGGCACAGTGCTCAACCA
GCACGTCAAAGCCCTGCTCGCGGGCGCGTTTTACCAGACGATCGCGGCGGGTGAGGGTGGATTTGGGGTAGTCGAACTGA
CCATAGCGCATGGTTTCGCCGACGAGCTCGGCATCCGCAATTTGCAGATTGCCTTTTTTATCAGCGGAAATCCCCAGCGT
GGTTAGCTTTTGGATCACCGCATCGCGGAACTGGTTACGGGCCTGTGGAGCGTATTTTTTGATGTTATTGGTATTCATAG
AAAATCCTGCAAAGGG SEQ ID NO 28
<ins>TATAGTGATATCAGTGTAATACTTATTGGTTAGATCGGTATGATCTTGAATATTTTTATATCGATAGTTTGGATTACATA
GTAGAGTTATTTCACTTTGCAATACAGCTTTAATTATAGTTTTGTCAAGTTGTAATTTATCTATAAAAATATTATTTATA
GTATTTTCTATTAGGAGAAGTGTTTCGACTAACTTGATATTTGTATTGATTTTTTGTTTGTAGATATTCCGTAGCAATTG
AGTTGAATTGTGTTCAAGCAATGGTGAACAAACATAATCCCATGATTGCTCTTGAGAGTCCCAGTCATTTTTAGCTATTT
CAATAGCATTGGTGACTAATTCGATAATTTCATCTTCAATTTCTGGATATGGTACTGAGGCTAATTCACCACTAGTAAAG
CTAAGTGTGGGGCTAGTATTGATAAATAATGGTTTACAACCGGAGTGCACATTAATCCCGCAGCGTAAAGCAACTCATT
TTTGTTATTTGAAAAGCCGCAACGGCCTGTATCATCAAAAACAAACCCTTTTGGACGATATCTCACGCAAAAATTACCTT
GGCTTATTTTTGACCATGTTATGCCTTCTCTAAAGTAATACTCATCATTTCTTACGGCAGAGCGAGTTTTGCCATTCTCA
AATTTAAAATTTCGTATTTCGTAACCATTATTTTCCCAATTTACAACTATTTCGTTATTACCATACCACTTTCGATATTC
ACCTCCACTACTACAAGGAAACCATTTGATATTATGAATGTCGATTTTTGTATTTGATTCTTTATTTGTGATAAGGGTTT
TTTTTATTGAAACCTCGTACCAATATCTTTGAAATTTAATATTGTCACCGGTGGACATGCCTGCTTTTAATGCTATTTTT
TCTCCAAGTTTTTTATGGTGGCGAAAAGATAATAGACTCGGTAAGTCTATCCAATATGCTATTGGCATTCCTGGTATGTT
TTTAAAATCATGCTGTGTAAATTTATCAAATATATTTTTCCTTAGAAGTAGATCGCTTTTCTTTACTTCTTCCCTACCAT</ins>

Figure 4 (Continued)

CTATAAGTCTAAAAAATACAGGTTGGTAACGTTCGGAGTGT

FIGURE 5A

| Strain ID | Serotype | STM2 | Ent4 | Heid2 | Newp2 |
|---|---|---|---|---|---|
| T1-293 | Aarhus | - | - | - | - |
| T1-273 | Aberdeen | - | 36.18/1500 | - | - |
| T1-456 | Abony | - | 38.69/1000 | - | - |
| 1391.10 | Adelaide | - | - | - | - |
| 10214.07 | Agbeni | - | - | - | - |
| 1546.10 | Agona | - | - | - | - |
| 2122.10 | Agona | - | - | - | - |
| T1-204 | Agona | - | - | - | - |
| T1-223 | Agona | - | - | - | - |
| T1-236 | Agona | - | - | - | - |
| 6504.92 | Alachua | - | - | 38.45/1500 | - |
| 1382.10 | Albany | - | - | - | - |
| T1-340 | Amager | - | - | - | - |
| 585 | Anatum | - | 38.20/1500 | - | - |
| 1398.10 | Anatum | - | - | - | - |
| C-001 | Anatum | - | - | - | - |
| C-113 | Anatum | - | - | - | - |
| T1-280 | Anatum var 15+ | - | - | - | - |
| T1-421 | Apapa | - | - | - | - |
| T1-458 | Arechavaleta | - | - | - | - |
| T1-263 | Baildon | - | 39.39/1100 | - | - |
| 9816.04 | Bardo | - | 37.05/1500 | - | 19.23/7500 |
| 2019.10 | Bareilly | - | 35.74/1500 | - | - |
| 8677.10 | Bareilly | - | 37.14/1500 | - | - |
| 9001.10 | Bareilly | - | - | - | - |
| T1-228 | Bareilly | - | - | - | - |
| T1-342 | Bareilly | - | - | - | - |
| T1-316 | Barranquilla | - | - | - | - |
| T1-216 | Berta | - | 39.99/1000 | - | - |
| Blockley IP | Blockley | - | 39.31/1100 | - | 21.96/7000 |
| 2296.03 | Bovismorbificans | - | - | - | 28.53/2000 |
| 1390.10 | Braenderup | - | - | - | - |
| 1813 | Braenderup | - | - | - | - |
| 1849 | Braenderup | - | - | - | - |
| T1-347 | Braenderup | - | - | - | - |
| T1-350 | Braenderup | - | - | - | - |
| 1795 | Brandenburg | - | - | - | - |
| 1932.10 | Brandenburg | - | - | - | - |
| 1838 | Brandenburg | - | - | - | - |

FIGURE 5B

| 1789 | Bredeney | - | - | - | - |
|---|---|---|---|---|---|
| 1808 | Bredeney | - | - | - | - |
| 1859 | Bredeney | - | - | - | - |
| 2336.03 | Bredeney | - | - | - | - |
| 9236.06 | Carrau | - | - | - | - |

Figure 5B (Continued)

| | | | | | |
|---|---|---|---|---|---|
| 25RV | Cerro | - | - | - | - |
| 39TT | Cerro | - | - | - | 39.52/1000 |
| 586 | Cerro | - | - | - | - |
| 324RV | Cerro | - | - | - | 39.25/1000 |
| 592 | Cerro | - | - | - | - |
| 6490.02 | Chester | - | - | - | - |
| T1-448 | Cholerasuis | - | - | - | 37.5/1500 |
| T1-439 | Colindale | - | - | - | - |
| T1-304 | Concord | - | - | - | - |
| T1-202 | Copenhagen | 22.09/11000 | - | - | - |
| 1457.10 | Corvallis | - | - | - | - |
| T1-310 | Cotham | - | - | - | - |
| 1975.03 | Cubana | - | - | 37.93/1500 | - |
| 9047.10 | Derby | - | - | - | - |
| 9056.10 | Derby | - | - | - | - |
| 151TT | Derby | - | - | - | - |
| 9127.10 | Dublin | - | - | - | - |
| T1-281 | Dublin | - | - | - | - |
| T1-313 | Dublin | - | - | - | - |
| T1-405 | Durban | - | - | - | - |
| 2010.10 | Ealing | - | - | - | - |
| 13 | Enteritidis | - | 27.90/3000 | - | - |
| 3982.08 | Enteritidis | - | 22.20/3500 | - | - |
| 9157.10 | Enteritidis | - | 26.50/2800 | - | - |
| ATCC 13076 | Enteritidis | - | 26.93/2500 | - | - |
| ATCC 31194 | Enteritidis | - | 26.33/3000 | - | - |
| C2-060 | Enteritidis | - | 23.26/5000 | - | - |
| C2-061 | Enteritidis | - | 22.86/5000 | - | - |
| C2-062 | Enteritidis | - | 26.49/2750 | - | - |
| C2-063 | Enteritidis | - | 25.59/3000 | - | - |
| C2-064 | Enteritidis | - | 26.34/2750 | - | - |
| C2-065 | Enteritidis | - | 25.33/2500 | - | - |
| IV | Enteritidis | - | 25.41/3250 | - | - |
| SE* | Enteritidis | - | 28.13/2750 | - | - |
| T1-493 | Enteritidis | - | * | 39.92/1000 | - |

FIGURE 5C

| | | | | | |
|---|---|---|---|---|---|
| T1-494 | Enteritidis | - | 27.19/3000 | - | - |
| T1-495 | Enteritidis | - | 21.35/3500 | - | - |
| T1-496 | Enteritidis | - | 23.65/3750 | - | - |
| T1-497 | Enteritidis | - | 24.44/3500 | - | - |
| T1-498 | Enteritidis | - | 21.93/3500 | - | - |
| T1-499 | Enteritidis | - | 24.6/3250 | - | - |
| T1-500 | Enteritidis | - | 24.49/3500 | - | - |
| T1-501 | Enteritidis | - | 24.47/3500 | - | - |
| T1-502 | Enteritidis | - | 27.09/3000 | - | - |
| T1-503 | Enteritidis | - | 28.61/3000 | - | - |

Figure 5C (Continued)

| T1-504 | Enteritidis | - | 25.67.3000 | - | - |
|---|---|---|---|---|---|
| T1-505 | Enteritidis | - | 25.93/3000 | - | - |
| T1-452 | Florida | - | - | - | - |
| T1-210 | Gaminara | - | - | - | - |
| 1833 | Give | - | - | - | - |
| 7285.03 | Give | - | - | - | - |
| Mes20x1 | Give | - | - | - | - |
| T1-428 | Give var.15+ | - | - | - | - |
| T1-355 | Glostrup | - | - | - | 24.79/2500 |
| 1900.10 | Grumpensis | - | - | - | - |
| 3049.10 | Hadar | - | 37.68/1400 | - | 21.15/3000 |
| 3296.10 | Hadar | - | 39.88/1000 | - | 25.38/5250 |
| T1-213 | Hadar | - | - | - | 20.26/7500 |
| T1.231 | Hadar | - | - | - | 19.60/4100 |
| T1-235 | Hadar | - | 39.21/1000 | - | 23.13/3500 |
| T1-248 | Hadar | - | - | - | * |
| T1-267 | Hadar | - | - | - | 19.1/4000 |
| T1-289 | Hadar | - | - | - | 19.81/4000 |
| T1-314 | Hadar | - | 39.14/1100 | - | 24.04/3250 |
| T1-332 | Hadar | - | - | - | 19.81/4000 |
| T1-357 | Hadar | - | - | - | 22.81/3500 |
| T1-358 | Hadar | - | - | - | 23.59/3500 |
| T1-359 | Hadar | - | - | - | 23.68/4000 |
| T1-361 | Hadar | - | 37.93/1200 | - | 22.83/4500 |
| T1-362 | Hadar | - | 38.72/1000 | - | 22.46/4500 |
| T1-363 | Hadar | - | - | - | 21.03/5000 |
| T1-364 | Hadar | - | 39.56/1000 | - | 22.73/3250 |
| T1-366 | Hadar | - | - | - | 21.43/4250 |
| T1-373 | Hadar | - | 38.27/1200 | - | 22.20/4000 |
| T1-374 | Hadar | - | 39.32/1100 | - | 21.81/4000 |

FIGURE 5D

| T1-378 | Hadar | - | 37.94/1400 | - | 21.43/4500 |
|---|---|---|---|---|---|
| T1-379 | Hadar | - | 38.45/1200 | - | 22.08/4000 |
| T1-382 | Hadar | - | 37.64/1200 | - | 21.84/5000 |
| T1-387 | Hadar | - | 38.99/1100 | - | 22.34/5000 |
| T1-391 | Hadar | - | - | - | * |
| 3468.07 | Hartford | - | 38.84/1100 | - | - |
| 2135.10 | Havana | - | - | - | - |
| 2161.10 | Havana | - | - | - | - |
| 3527.08 | Heidelberg | - | - | 22.98/8500 | - |
| 4660.09 | Heidelberg | - | - | 21.95/6000 | - |
| T1-480 | Heidelberg | - | 38.92/1000 | 23.56/5000 | - |
| T1-481 | Heidelberg | - | 37.75/1250 | 23.59/5000 | - |
| T1-482 | Heidelberg | - | 38.13/1250 | 23.87/5000 | - |
| T1-483 | Heidelberg | - | 38.94/1000 | 25.89/5000 | - |
| T1-484 | Heidelberg | - | 39.17/1000 | 26.19/4750 | - |

Figure 5D (Continued)

| | | | | | |
|---|---|---|---|---|---|
| T1-485 | Heidelberg | - | 38.70/1000 | 24.55/5000 | - |
| T1-486 | Heidelberg | - | 36.79/1750 | 26.23/4500 | - |
| T1-487 | Heidelberg | 20.88/15000 | 35.82/2000 | * | - |
| T1-488 | Heidelberg | - | 38.72/1000 | 24.06/5000 | - |
| T1-489 | Heidelberg | - | 39.58/1000 | 23.39/6000 | - |
| T1-490 | Heidelberg | - | 39.26/1000 | 25.42/4000 | - |
| T1-491 | Heidelberg | - | - | 23.86/5500 | - |
| T1-492 | Heidelberg | - | 38.00/1250 | 24.27/5000 | - |
| T1-510 | Heidelberg | - | - | 24.11/3500 | - |
| T1-511 | Heidelberg | - | 39.91/1000 | 26.29/3500 | - |
| T1-512 | Heidelberg | - | 37.15/1500 | 27.12/3000 | - |
| T1-513 | Heidelberg | - | 33.65/2500 | 25.83/3500 | - |
| T1-514 | Heidelberg | - | - | 26.67/2750 | - |
| T1-515 | Heidelberg | - | - | 24.17/3750 | - |
| T1-516 | Heidelberg | - | - | 28.49/3000 | - |
| T1-518 | Heidelberg | - | 32.57/2500 | 27.61/3500 | - |
| T1-519 | Heidelberg | - | - | 26.22/3500 | - |
| T1-520 | Heidelberg | 38.06/1750 | 39.46/1000 | 23.45/4000 | 39.81/1000 |
| T1-521 | Heidelberg | - | - | 26.47/2500 | - |
| T1-522 | Heidelberg | - | - | 25.79/3500 | - |
| T1-377 | Hindmarsh | - | - | - | - |
| T1-224 | Holcomb | - | - | - | - |
| 1544.10 | Hvittingfoss | - | - | - | - |
| 2607.06 | Ibadan | - | - | - | - |
| 1404.10 | Indiana | - | - | - | - |

FIGURE 5E

| | | | | | |
|---|---|---|---|---|---|
| 1367 | Infantis | - | - | 23.92/5500 | - |
| 12TT | Infantis | - | - | 20.92/8000 | - |
| 21TT | Infantis | - | - | 20.22/8000 | - |
| 26TT | Infantis | - | 39.59/1100 | 19.06/9000 | - |
| 281TT | Infantis | - | - | 19.47/9500 | - |
| 282TT | Infantis | - | - | 19.00/9250 | - |
| 284TT | Infantis | - | - | 20.26/9000 | - |
| 294TT | Infantis | - | - | 18.73/9250 | - |
| 29TT | Infantis | - | - | 19.99/8000 | - |
| 307TT | Infantis | - | - | 22.68/8000 | - |
| 40TT | Infantis | - | - | 19.09/9500 | - |
| C-043 | Infantis | - | - | 26.41/6000 | - |
| T1-388 | Inverness | - | - | - | - |
| T1-432 | Istanbul | - | - | - | 23.74/3250 |
| 4311.99 | Itami | - | - | - | - |
| 2802.10 | Javiana | - | - | - | - |
| T1-211 | Javiana | 39.87/1000 | - | - | - |
| T1-230 | Javiana | - | - | - | - |
| T1-234 | Javiana | - | - | - | - |
| T1-301 | Javiana | - | - | - | - |

Figure 5E (Continued)

| | | | | | |
|---|---|---|---|---|---|
| 10713.01 | Johannesburg | - | - | - | - |
| 1780 | Kentucky | - | - | - | - |
| 1794 | Kentucky | - | - | - | - |
| 1845 | Kentucky | - | - | - | - |
| 28TT | Kentucky | - | - | - | - |
| 79TT | Kentucky | - | - | - | - |
| C-127 | Kentucky | - | - | - | - |
| Fec06 | Kentucky | - | - | - | - |
| Fec11 | Kentucky | - | - | - | - |
| Mes05x2 | Kentucky | 39.64/1000 | - | - | - |
| SubLN06 | Kentucky | - | - | - | - |
| SubLN18 | Kentucky | - | - | - | - |
| SubLN19 | Kentucky | - | - | - | - |
| 1543.10 | Kiambu | - | - | - | - |
| T1-455 | Kintambo | - | 39.75/1000 | 25.76/4000 | - |
| 1409.10 | Kottbus | - | 39.21/1100 | - | 22.15/3000 |
| T1-447 | Kuzendorf (Choleraesuis var.) | - | 37.91/1200 | - | - |
| T1-375 | Lexington | - | - | - | - |
| 14TT | Lille | - | - | - | - |
| 15TT | Lille | - | - | - | - |

FIGURE 5F

| | | | | | |
|---|---|---|---|---|---|
| 16TT | Lille | - | - | - | - |
| 67TT | Lille | - | - | - | - |
| 2214.03 | Litchfield | - | - | - | 20.81/3500 |
| T1-440 | Liverpool | - | - | - | - |
| T1-392 | Livingstone | - | - | - | - |
| 1999.09 | London | - | - | - | - |
| T1-381 | Luciana | - | - | - | - |
| 5784.06 | Madelia | - | - | - | - |
| 1866.10 | Manhattan | - | 38.30/1100 | - | 20.06/4000 |
| 75TT | Manhattan | - | - | - | 20.28/3500 |
| 1811 | Mbandaka | - | - | - | - |
| 1864 | Mbandaka | - | - | - | - |
| 1865 | Mbandaka | - | - | - | - |
| 173TT | Mbandaka | - | - | - | - |
| 223TT | Mbandaka | - | - | - | - |
| 27TT | Mbandaka | - | - | - | - |
| 471 | Meleagridis | - | - | - | - |
| 488 | Meleagridis | - | - | - | - |
| 532 | Meleagridis | - | - | - | - |
| 118TT | Meleagridis | - | - | - | - |
| 143TT | Meleagridis | - | - | - | - |
| 9848.06 | Miami | - | - | - | - |
| T1-265 | Mikawasima | - | 32.58/1750 | - | - |
| 2385.10 | Minnesota | - | - | - | - |
| T1-218 | Mississippi | - | 37.40/1400 | - | - |

Figure 5F (Continued)

| | | | | | |
|---|---|---|---|---|---|
| T1-325 | Mississippi | - | - | - | - |
| T1-339 | Mississippi | - | - | - | - |
| T1-343 | Mississippi | - | - | - | - |
| T1-360 | Mississippi | - | - | - | - |
| 11221.07 | Monschaui | - | - | - | - |
| 272 | Montevideo | - | - | - | - |
| 304 | Montevideo | - | - | - | - |
| 542 | Montevideo | - | - | - | - |
| 1600 | Montevideo | - | - | - | - |
| 150TT | Montevideo | - | - | - | - |
| 31TT | Montevideo | - | - | - | - |
| 5TT | Montevideo | - | - | - | - |
| 64TT | Montevideo | - | - | - | - |
| 81TT | Montevideo | - | - | - | - |
| C-004 | Montevideo | - | - | - | - |

FIGURE 5G

| | | | | | |
|---|---|---|---|---|---|
| C-040 | Montevideo | - | - | - | - |
| 2452.10 | Muenchen | - | 34.47/2000 | - | - |
| 3090.10 | Muenchen | - | 38.12/1100 | - | 20.59/4000 |
| 1011TT | Muenchen | - | - | - | 20.02/3400 |
| 272TT | Muenchen | - | - | - | 18.53/4000 |
| 296TT | Muenchen | - | 37.24/1400 | - | - |
| 565TT | Muenchen | - | - | - | - |
| 568TT | Muenchen | - | - | - | - |
| 611TT | Muenchen | - | - | - | - |
| 618TT | Muenchen | - | - | - | - |
| C-148 | Muenster | - | - | - | 39.68/1000 |
| 1489.10 | Muenster | - | - | - | - |
| 1552.10 | Napoli | - | - | - | - |
| 597 | Newport | - | - | - | 23.96/4000 |
| R1-023 | Newport | - | - | - | 20.10/3000 |
| R1-024 | Newport | - | 39.38/1000 | - | 19.00/3200 |
| R1-025 | Newport | - | - | - | 20.63/3500 |
| R1-026 | Newport | - | - | - | 25.86/2500 |
| R1-027 | Newport | - | 38.58/1100 | - | 22.30/3000 |
| R1-028 | Newport | - | - | - | 21.48/3000 |
| R1-029 | Newport | - | - | - | 19.89/3500 |
| R1-030 | Newport | - | - | - | 20.54/3250 |
| R1-031 | Newport | - | - | - | 20.74/3000 |
| R1-032 | Newport | - | - | - | 21.85/3000 |
| R1-033 | Newport | - | - | - | 20.17/3000 |
| R1-034 | Newport | - | 36.15/1500 | - | 20.28/4000 |
| R1-035 | Newport | - | - | - | 24.56/3000 |
| R1-036 | Newport | - | - | - | 21.40/3000 |
| R1-037 | Newport | - | - | - | 19.98/4000 |
| R1-038 | Newport | - | - | - | 21.79/3750 |

Figure 5G (Continued)

| R1-039 | Newport | - | - | - | 22.90/3000 |
|---|---|---|---|---|---|
| R1-040 | Newport | - | - | - | 23.44/3000 |
| R1-041 | Newport | - | - | - | 22.08/3000 |
| R1-042 | Newport | - | - | - | 18.50/4750 |
| T1-470 | Newport-A | - | - | - | 20.54/7500 |
| T1-471 | Newport-A | - | 39.80/1000 | - | 24.64/6500 |
| T1-472 | Newport-B | - | - | - | 26.36/5000 |
| T1-473 | Newport-A | - | - | - | 21.09/7500 |
| T1-474 | Newport-B | - | - | - | 20.93/7000 |
| T1-475 | Newport-B | - | - | - | 21.26/7000 |

FIGURE 5H

| T1-476 | Newport-A | - | - | - | 20.42/6000 |
|---|---|---|---|---|---|
| T1-477 | Newport-B | - | - | - | 21.55/6500 |
| T1-478 | Newport-B | - | - | - | 21.29/6000 |
| T1-422 | Norwich | - | - | - | - |
| 1886.10 | Ohio | - | - | - | - |
| 1890 | Ohio | - | - | - | - |
| 2131.10 | Oranienburg | - | - | - | - |
| T1-275 | Oranienburg | - | - | - | - |
| T1-276 | Oranienburg | - | - | - | - |
| T1-277 | Oranienburg | - | - | - | - |
| T1-278 | Oranienburg | - | - | - | 37.5/1600 |
| T1-341 | Orion | - | - | - | - |
| 2571.10 | Panama | - | - | - | - |
| 1853 | Panama | - | - | - | - |
| 2598.10 | ParatyphiB | - | - | 38.76/1250 | - |
| T1-321 | ParatyphiB | - | - | - | 37.77/1500 |
| T1-335 | ParatyphiB | - | - | - | - |
| T1-372 | ParatyphiB | - | - | - | - |
| T1-380 | ParatyphiB | - | - | - | - |
| T1-271 | Pomona | - | - | - | - |
| 8941.10 | Poona | - | - | - | - |
| 3534.07 | Potsdam | - | - | - | - |
| T1-214 | Putten | - | - | - | - |
| 680 | Reading | - | 39.21/1000 | - | - |
| C-039 | Reading | - | - | - | - |
| Fec08 | Reading | - | 38.87/1000 | - | - |
| Hid06 | Reading | - | - | - | - |
| ManLN01 | Reading | - | - | - | - |
| ManLN17 | Reading | - | - | - | - |
| MesLN01 | Reading | - | - | - | - |
| MesLN04 | Reading | - | - | - | - |
| MesLN08 | Reading | - | - | - | - |
| SubLN15 | Reading | - | 39.19/1000 | - | - |
| SubLN20 | Reading | - | - | - | - |
| T1-215 | Richmond | - | - | - | - |

Figure 5H (Continued)

| | | | | | |
|---|---|---|---|---|---|
| 1458.10 | Rissen | - | - | - | - |
| T1-424 | Roodeport | - | - | - | - |
| 334.05 | Rubislaw | - | - | - | - |
| T1-396 | S.I 1,4,[5],12:-:1,2 | 22.31/14000 | 37.25/1500 | - | - |
| 498.04 | S.I 1,4,[5],12:i:- | 21.77/8000 | - | - | - |

FIGURE 5I

| | | | | | |
|---|---|---|---|---|---|
| 9588.07 | S.I 1,4,[5],12:i:- | 21.99/8000 | 36.27/1500 | - | - |
| R1-142 | S.I 1,4,[5],12:i:- | 21.01/7000 | 36.79/1500 | - | - |
| R1-143 | S.I 1,4,[5],12:i:- | 21.07/10000 | 37.19/1250 | - | - |
| R1-144 | S.I 1,4,[5],12:i:- | 25.48/7500 | - | - | - |
| R1-145 | S.I 1,4,[5],12:i:- | 21.19/6000 | - | - | - |
| R1-146 | S.I 1,4,[5],12:i:- | 21.68/5000 | - | - | - |
| R1-147 | S.I 1,4,[5],12:i:- | 26.20/6250 | - | - | - |
| R1-148 | S.I 1,4,[5],12:i:- | 23.44/5000 | 39.83/1000 | - | - |
| R1-149 | S.I 1,4,[5],12:i:- | 28.22/3500 | - | - | - |
| R1-150 | S.I 1,4,[5],12:i:- | 22.01/5000 | - | - | - |
| R1-151 | S.I 1,4,[5],12:i:- | 23.90/6000 | 37.87/1250 | - | - |
| R1-152 | S.I 1,4,[5],12:i:- | 21.44/3000 | - | - | - |
| R1-153 | S.I 1,4,[5],12:i:- | 24.79/4000 | 36.15/1250 | - | - |
| R1-154 | S.I 1,4,[5],12:i:- | 24.70/4000 | - | - | - |
| R1-155 | S.I 1,4,[5],12:i:- | 21.31/6000 | 37.19/1000 | - | - |
| R1-156 | S.I 1,4,[5],12:i:- | 22.46/5000 | 35.45/1500 | - | - |
| T1-429 | S.I 1,4,5,12:b:- var. L(+) tartrate + | - | 38.78/1100 | - | - |
| T1-354 | S.I 4,5,12:b:- | - | - | - | - |
| T1-416 | S.I 4,5,12:r:- | - | - | *23.16/5000* | - |
| T1-259 | S.I 6,7:-:1,5 | - | 38.86/1000 | - | - |
| T1-370 | S.I 6,7:k:- | - | 39.52/1000 | - | - |
| T1-305 | S.II *salamae* | - | - | - | - |
| T1-526 | S.II *salamae* | - | - | - | - |
| T1-506 | S.IIIa *arizonae* | - | 39.26/1000 | - | - |
| T1-449 | S.IIIa 18:z4,z23:- | - | - | - | - |
| T1-401 | S.IIIb 50:k:z | - | - | - | - |
| T1-451 | S.IIIb 50:r:z | - | 36.66/1250 | - | - |
| T1-436 | S.IIIb 61:l,v:1,5,7 | - | - | - | - |
| T1-390 | S.IV 44:z4,z23:- (a4,a23) | - | - | - | - |
| T1-272 | S.IV 48:g,z51:- | - | - | - | - |
| T1-446 | S.IV 50:g,z51:- | - | - | - | - |
| T1-209 | S.V | - | - | - | - |
| 1974.09 | SaintPaul | - | *33.75/5000* | - | - |
| 4617.08 | SaintPaul | - | - | - | - |
| T1-246 | SaintPaul | - | - | - | - |
| T1-324 | SaintPaul | - | - | - | - |
| T1-270 | SaintPaul | - | 39.85/1000 | - | - |
| 3261.03 | SanDiego | - | - | - | - |
| T1-450 | Saphra | 38.64/1750 | 35.76/1250 | - | - |

FIGURE 5J

| | | | | | |
|---|---|---|---|---|---|
| 6065.08 | Schwarzengrund | - | - | - | - |
| T1-203 | Schwarzengrund | - | - | - | - |
| T1-222 | Schwarzengrund | - | - | - | - |
| T1-264 | Schwarzengrund | - | - | - | - |
| T1-226 | Schwarzengrund | - | - | - | - |
| 1385.10 | Senftenberg | - | - | - | - |
| T1-208 | Senftenberg | - | - | - | - |
| T1-240 | Senftenberg | - | - | - | - |
| T1-245 | Senftenberg | - | - | - | - |
| T1-308 | Senftenberg | - | - | - | - |
| 7073.06 | Stanley | - | - | - | - |
| T1-441 | Sundsvall | - | - | - | - |
| T1-442 | Sundsvall | - | - | - | - |
| T1-319 | Telekelbir | - | - | - | - |
| 2927.10 | Tennessee | - | - | 36.06/2750 | - |
| 2550.04 | Thompson | - | - | - | - |
| T1-221 | Thompson | - | - | - | - |
| T1-242 | Thompson | - | - | - | - |
| T1-243 | Thompson | - | - | - | - |
| T1-315 | Thompson | - | - | - | - |
| 1.7773 | Typhi | - | - | - | - |
| T1-317 | Typhi | - | - | - | - |
| T1-299 | Typhi | - | - | - | - |
| T1-300 | Typhi | - | - | - | - |
| T1-296 | Typhi | - | - | - | - |
| 1403.10 | Typhimurium | 19.64/7000 | - | - | - |
| 1433.10 | Typhimurium | 23.87/4000 | - | - | - |
| 1540.10 | Typhimurium | 23.08/4500 | - | - | - |
| R1-089 | Typhimurium | 19.46/9000 | - | - | - |
| R1-090 | Typhimurium | 21.18/6000 | - | - | - |
| R1-091 | Typhimurium | 20.44/9500 | - | - | - |
| R1-092 | Typhimurium | 20.25/8000 | - | - | - |
| R1-093 | Typhimurium | 21.34/6500 | 38.71/1000 | - | - |
| R1-094 | Typhimurium | 18.82/8000 | 34.12/1500 | - | - |
| R1-095 | Typhimurium | 20.48/8000 | - | - | - |
| R1-096 | Typhimurium | 17.45/11000 | - | - | - |
| R1-097 | Typhimurium | 21.17/8500 | - | - | - |
| R1-098 | Typhimurium | 20.60/6000 | - | - | - |
| R1-099 | Typhimurium | 20.32/10500 | 34.69/1750 | - | - |
| R1-100 | Typhimurium | 20.25/7000 | 34.14/2000 | - | - |

FIGURE 5K

| | | | | | |
|---|---|---|---|---|---|
| R1-101 | Typhimurium | 19.52/8000 | - | - | - |
| R1-102 | Typhimurium | 20.81/3500 | - | - | - |
| R1-104 | Typhimurium | 23.12/5500 | - | - | - |
| R1-105 | Typhimurium | 20.93/5000 | - | - | - |

Figure 5K (Continued)

| | | | | | |
|---|---|---|---|---|---|
| R1-106 | Typhimurium | 23.93/4700 | - | - | - |
| R1-107 | Typhimurium | 21.69/6000 | - | - | - |
| R1-108 | Typhimurium | 19.3/9900 | - | - | - |
| R1-109 | Typhimurium | 19.55/9700 | - | - | - |
| R1-110 | Typhimurium | 18.25/9700 | - | - | - |
| R1-111 | Typhimurium | 19.04/105500 | 38.79/1100 | - | - |
| 1950.10 | Uganda | - | - | - | - |
| 1842 | Uganda | - | - | - | - |
| 2711.10 | Urbana | - | - | - | - |
| 2083.10 | Virchow | - | - | - | - |
| T1-447 | Virchow | - | - | 38.85/1250 | - |
| T1-507 | Virchow | - | - | - | - |
| T1-508 | Virchow | 38.75/1500 | - | - | - |
| T1-509 | Virchow | - | - | - | - |
| T1-517 | Virchow | - | - | - | - |
| T1-523 | Virchow | - | - | - | - |
| T1-524 | Virchow | - | - | - | - |
| T1-525 | Virchow | - | - | - | *25.86/3000* |
| 2086.10 | Virchow | - | - | - | - |
| T1-212 | Wandsworth | - | - | - | - |
| T1-404 | Waycross | - | - | - | - |
| 8883.10 | Weltvreden | - | - | - | - |
| T1-302 | Worthington | - | - | - | - |
| T1-419 | Worthington | - | - | - | - |
| T1-459 | Worthington | - | - | - | - |
| T1-463 | Worthington | - | - | - | - |

FIGURE 5L

| | | | | | |
|---|---|---|---|---|---|
| T1-254 | Aeromonas hydrophila/caviae | - | - | - | - |
| T1-453 | Citrobacter freundii | - | - | - | - |
| T1-256 | Cronobacter sakazakii | - | - | - | - |
| T1-201 | Enterobacter aerogenes | - | - | - | - |
| T1-251 | Hafnia paralvei | - | - | - | - |
| T1-253 | Klebsiella oxytoca | - | - | - | - |
| T1-262 | Klebsiella pnemoniae | - | - | - | - |
| T1-250 | Pseudomonas aeruginosa | - | - | - | - |
| T1-261 | Pantoea agglomerans | - | - | - | - |
| T1-200 | Pseudomonas fluorescens | 39.92/1000 | - | - | - |
| T1-249 | Pseudomonas fragi | - | - | - | - |
| T1-252 | Proteus vulgaris | - | - | - | - |
| T1-255 | Shigella flexneri | - | - | - | - |
| T1-257 | Serratia marcesans | - | - | - | - |
| T1-465 | Shigella sonneii | - | - | - | - |
| T1-467 | Vibrio mimicus | - | - | - | - |
| T1-466 | Vibrio parahemolytics | - | - | - | - |
| T1-258 | Yersinia entercolitica | - | - | - | - |

FIGURE 6

```
SEQ ID NO: 23      ACGTCCAAAATATTTACTTAAGGATATTAAAAAATGACCAAAAAGGGGCTTTCGGTAATA  60
AHUD01000019  105716  ............................................................  105775
AHUC01000007  324160  ............................................................  324101
AHUA01000001  324460  ............................................................  324401
AHTY01000043  324502  ............................................................  324443
AHTW01000034  121595  ............................................................  121654
AHTV01000016  324507  ............................................................  324448
AHTU01000026  324977  ............................................................  324918
AHTT01000031  324977  ............................................................  324918
AHTQ01000026    5349  ............................................................    5290
AHTR01000029  121768  ............................................................  121827
ABFG01000003   78663  ............................................................   78722
AHTZ01000022  324509  ............................................................  324450
AHUF01000033  121754  ............................................................  121813
AHTP01000008  121592  ............................................................  121651
ALPP01000002  327097  ............................................................  327038
AJMN01000063  114099  ............................................................  114158
AHUE01000064  121755  ............................................................  121814
AHTS01000049  280304  ............................................................  280245
AHTO01000026  114100  ............................................................  114159
AHTN01000030  114100  ............................................................  114159
AHTL01000037  194616  ............................................................  194675
AHTJ01000054  114244  ............................................................  114303
ABEW01000005  370151  ............................................................  370092
AHUB01000013  168544  ............................................................  168603
AJMO01000041  114097  .....................................................T......  114156
AHTM01000024  281542  ............................................................  281483
AHTK01000030  113934  ............................................................  113993

Query            61   TTAGTTTTTTTGATATTTTCATATATTTTTACCGCATTAAGCTATAAATTTATCCCAAGC  120
AHUD01000019  105776  ............................................................  105835
AHUC01000007  324100  ............................................................  324041
AHUA01000001  324400  ............................................................  324341
AHTY01000043  324442  ............................................................  324383
AHTW01000034  121655  ............................................................  121714
AHTV01000016  324447  ............................................................  324388
AHTU01000026  324917  ............................................................  324858
AHTT01000031  324917  ............................................................  324858
AHTQ01000026    5289  ............................................................    5230
AHTR01000029  121828  ............................................................  121887
ABFG01000003   78723  ............................................................   78782
AHTZ01000022  324449  ............................................................  324390
AHUF01000033  121814  ............................................................  121874
                                           \
                                            |
                                            T
AHTP01000008  121652  ............................................................  121711
ALPP01000002  327037  ............................................................  326978
AJMN01000063  114159  ............................................................  114218
AHUE01000064  121815  ............................................................  121874
AHTS01000049  280244  ............................................................  280185
AHTO01000026  114160  ............................................................  114219
AHTN01000030  114160  ............................................................  114219
AHTL01000037  194676  ............................................................  194735
AHTJ01000054  114304  ............................................................  114363
ABEW01000005  370091  ............................................................  370032
AHUB01000013  168604  ............................................................  168663
AJMO01000041  114157  ............................................................  114216
AHTM01000024  281482  ............................................................  281423
AHTK01000030  113994  ............................................................  114053

Query           121   TCTGACAGCATGAGTGGTATTTTAGAGGCTGCTGACATTGCAAACGGAAACATAACACTA  180
AHUD01000019  105836  ............................................................  105895
AHUC01000007  324040  ............................................................  323981
AHUA01000001  324340  ............................................................  324281
AHTY01000043  324382  ............................................................  324323
AHTW01000034  121715  ............................................................  121774
AHTV01000016  324387  ............................................................  324328
AHTU01000026  324857  ............................................................  324798
AHTT01000031  324857  ............................................................  324798
AHTQ01000026    5229  ............................................................    5170
AHTR01000029  121888  ............................................................  121947
ABFG01000003   78783  ............................................................   78842
AHTZ01000022  324389  ............................................................  324330
AHUF01000033  121875  ............................................................  121934
AHTP01000008  121712  ............................................................  121771
ALPP01000002  326977  ............................................................  326918
```

Figure 6 (Continued)

```
AJMN01000063  114219  ..........................................................  114278
AHUE01000064  121875  ..........................................................  121934
AHTS01000049  280184  ..........................................................  280125
AHTO01000026  114220  ..........................................................  114279
AHTN01000030  114220  ..........................................................  114279
AHTL01000037  194736  ..........................................................  194795
AHTJ01000054  114364  ..........................................................  114423
ABEW01000005  370031  ..........................................................  369972
AHUB01000013  168664  ..........................................................  168723
AJMO01000041  114217  ..........................................................  114276
AHTM01000024  281422  ..........................................................  281363
AHTK01000030  114054  ..........................................................  114113

Query         181     AAAGGATGGTACTTATCTACAGTAACTTTCTATTTTACTGACTTAGTCTGGTTTGCTCTT  240
AHUD01000019  105896  ..........................................................  105955
AHUC01000007  323980  ..........................................................  323921
AHUA01000001  324280  ..........................................................  324221
AHTY01000043  324322  ..........................................................  324263
AHTW01000034  121775  ..........................................................  121834
AHTV01000016  324327  ..........................................................  324268
AHTU01000026  324797  ..........................................................  324738
AHTT01000031  324797  ..........................................................  324738
AHTQ01000026  5169    ..........................................................  5110
AHTR01000029  121948  ..........................................................  122007
ABFG01000003  78843   ..........................................................  78902
AHTZ01000022  324329  ..........................................................  324270
AHUF01000033  121935  ..........................................................  121994
AHTP01000008  121772  ..........................................................  121831
ALPP01000002  326917  ..........................................................  326858
AJMN01000063  114279  ..........................................................  114338
AHUE01000064  121935  ..........................................................  121994
AHTS01000049  280124  ..........................................................  280065
AHTO01000026  114280  ..........................................................  114339
AHTN01000030  114280  ..........................................................  114339
AHTL01000037  194796  ..........................................................  194855
AHTJ01000054  114424  ..........................................................  114483
ABEW01000005  369971  ..........................................................  369912
AHUB01000013  168724  ..........................................................  168783
AJMO01000041  114277  ..........................................................  114336
AHTM01000024  281362  ..........................................................  281303
AHTK01000030  114114  ..........................................................  114173

Query         241     GCTATAAAGCTTTTTGGTTATTCTGAATGGATAACATACGTTATACCTGGATTAATGGCT  300
AHUD01000019  105956  ..........................................................  106015
AHUC01000007  323920  ..........................................................  323861
AHUA01000001  324220  ..........................................................  324161
AHTY01000043  324262  ..........................................................  324203
AHTW01000034  121835  ..........................................................  121894
AHTV01000016  324267  ..........................................................  324208
AHTU01000026  324737  ..........................................................  324678
AHTT01000031  324737  ..........................................................  324678
AHTQ01000026  5109    ..........................................................  5050
AHTR01000029  122008  ..........................................................  122067
ABFG01000003  78903   ..........................................................  78962
AHTZ01000022  324269  ..........................................................  324210
AHUF01000033  121995  ..........................................................  122054
AHTP01000008  121832  ..........................................................  121891
ALPP01000002  326857  ..........................................................  326798
AJMN01000063  114339  ..........................................................  114398
AHUE01000064  121995  ..........................................................  122054
AHTS01000049  280064  ..........................................................  280005
AHTO01000026  114340  ..........................................................  114399
AHTN01000030  114340  ..........................................................  114399
AHTL01000037  194856  ..........................................................  194915
AHTJ01000054  114484  ..........................................................  114543
ABEW01000005  369911  ..........................................................  369852
AHUB01000013  168784  ..........................................................  168843
AJMO01000041  114337  ..........................................................  114396
AHTM01000024  281302  ..........................................................  281243
AHTK01000030  114174  ..........................................................  114233

Query         301     GGTAGCCTGTTCCCTTCATGCTATGCACTGGGAACAAATTTCTGGCTACAAAAAAGCATGG  360
AHUD01000019  106016  ..........................................................  106075
AHUC01000007  323860  ..........................................................  323801
AHUA01000001  324160  ..........................................................  324101
AHTY01000043  324202  ..........................................................  324143
AHTW01000034  121895  ..........................................................  121954
AHTV01000016  324207  ..........................................................  324148
AHTU01000026  324677  ..........................................................  324618
AHTT01000031  324677  ..........................................................  324618
AHTQ01000026  5049    ..........................................................  4990
```

Figure 6 (Continued)

```
AHTR01000029  122068  ..........................................................  122127
ABFG01000003   78963  ..........................................................   79022
AHTZ01000022  324209  .........................-................................  324151
AHUF01000033  122055  ..........................................................  122114
AHTP01000008  121892  ..........................................................  121951
ALPP01000002  326797  ..........................................................  326738
AJMN01000063  114399  ..........................................................  114458
AHUE01000064  122055  ..........................................................  122114
AHTS01000049  280004  ..........................................................  279945
AHTO01000026  114400  ..........................................................  114459
AHTN01000030  114400  ..........................................................  114459
AHTL01000037  194916  ..........................................................  194975
AHTJ01000054  114544  ..........................................................  114603
ABEW01000005  369851  ..........................................................  369792
AHUB01000013  168844  ..........................................................  168903
AJMO01000041  114397  ..........................................................  114456
AHTM01000024  281242  ..........................................................  281183
AHTK01000030  114234  ..........................................................  114293

Query            361  GCTTTG▒▒▒▒▒▒▒▒▒▒▒▒▒▒▒▒▒▒▒▒GGTGCTGCTGTCAGTTACATGCTTTCTGTAGCG  420
AHUD01000019  106076  ..........................................................  106135
AHUC01000007  323800  ..........................................................  323741
AHUA01000001  324100  ..........................................................  324041
AHTY01000043  324142  ..........................................................  324083
AHTW01000034  121955  ..........................................................  122014
AHTV01000016  324147  ..........................................................  324088
AHTU01000026  324617  ..........................................................  324558
AHTT01000031  324617  ..........................................................  324558
AHTQ01000026    4989  ..........................................................    4930
AHTR01000029  122128  ..........................................................  122187
ABFG01000003   79023  ..........................................................   79082
AHTZ01000022  324150  ..........................................................  324091
AHUF01000033  122115  ..........................................................  122174
AHTP01000008  121952  ..........................................................  122011
ALPP01000002  326737  ..........................................................  326678
AJMN01000063  114459  ..........................................................  114518
AHUE01000064  122115  ..........................................................  122174
AHTS01000049  279944  ..........................................................  279885
AHTO01000026  114460  ..........................................................  114519
AHTN01000030  114460  ..........................................................  114519
AHTL01000037  194976  ..........................................................  195035
AHTJ01000054  114604  ..........................................................  114663
ABEW01000005  369791  ..........................................................  369732
AHUB01000013  168904  ..........................................................  168963
AJMO01000041  114457  ..........................................................  114516
AHTM01000024  281182  ..........................................................  281123
AHTK01000030  114294  ..........................................................  114353

Query            421  ATAATCCATGTCCCTACATATACTTATATCGTTGTTTCATATATATTAATTGATTTTTAT  480
AHUD01000019  106136  ..........................................................  106195
AHUC01000007  323740  ..........................................................  323681
AHUA01000001  324040  ..........................................................  323981
AHTY01000043  324082  ..........................................................  324023
AHTW01000034  122015  ..........................................................  122074
AHTV01000016  324087  ..........................................................  324028
AHTU01000026  324557  ..........................................................  324498
AHTT01000031  324557  ..........................................................  324498
AHTQ01000026    4929  ..........................................................    4870
AHTR01000029  122188  ..........................................................  122247
ABFG01000003   79083  ..........................................................   79142
AHTZ01000022  324090  ..........................................................  324031
AHUF01000033  122175  ..........................................................  122234
AHTP01000008  122012  ..........................................................  122071
ALPP01000002  326677  ..........................................................  326618
AJMN01000063  114519  ..............................A...........................  114578
AHUE01000064  122175  ..............................A...........................  122234
AHTS01000049  279884  ..............................A...........................  279825
AHTO01000026  114520  ..............................A...........................  114579
AHTN01000030  114520  ..............................A...........................  114579
AHTL01000037  195036  ..............................A...........................  195095
AHTJ01000054  114664  ..............................A...........................  114723
ABEW01000005  369731  ..............................A...........................  369672
AHUB01000013  168964  ..............................A...........................  169023
AJMO01000041  114517  ..............................A...........................  114576
AHTM01000024  281122  ..............................A...........................  281063
AHTK01000030  114354  ..............................A...........................  114413

Query            481  TGTCGCAGAAGAAATAGATTATATTTATTTCTATCATCAATAATCGCATCTTTAACGATA  540
AHUD01000019  106196  ..........................................................  106255
AHUC01000007  323680  ..........................................................  323621
AHUA01000001  323980  ..........................................................  323921
```

Figure 6 (Continued)

| ID | Start | | End |
|---|---|---|---|
| AHTY01000043 | 324022 | ............................................................ | 323963 |
| AHTW01000034 | 122075 | ............................................................ | 122134 |
| AHTV01000016 | 324027 | ............................................................ | 323968 |
| AHTU01000026 | 324497 | ............................................................ | 324438 |
| AHTT01000031 | 324497 | ............................................................ | 324438 |
| AHTQ01000026 | 4869 | ............................................................ | 4810 |
| AHTR01000029 | 122248 | ............................................................ | 122307 |
| ABFG01000003 | 79143 | ............................................................ | 79202 |
| AHTZ01000022 | 324030 | ............................................................ | 323971 |
| AHUF01000033 | 122235 | ............................................................ | 122294 |
| AHTP01000008 | 122072 | ............................................................ | 122131 |
| ALPP01000002 | 326617 | ............................................................ | 326558 |
| AJMN01000063 | 114579 | ............................................................ | 114638 |
| AHUE01000064 | 122235 | ............................................................ | 122294 |
| AHTS01000049 | 279824 | ............................................................ | 279765 |
| AHTO01000026 | 114580 | ............................................................ | 114639 |
| AHTN01000030 | 114580 | ............................................................ | 114639 |
| AHTL01000037 | 195096 | ............................................................ | 195155 |
| AHTJ01000054 | 114724 | ............................................................ | 114783 |
| ABEW01000005 | 369671 | ............................................................ | 369612 |
| AHUB01000013 | 169024 | ............................................................ | 169083 |
| AJMO01000041 | 114577 | ............................................................ | 114636 |
| AHTM01000024 | 281062 | ............................................................ | 281003 |
| AHTK01000030 | 114414 | ............................................................ | 114473 |
| Query | 541 | TTTAGCGATGATATAACAATATATTTATTTTTTTGCCAATTGCATTGAGCTGTTTTATA | 600 |
| AHUD01000019 | 106256 | ............................................................ | 106315 |
| AHUC01000007 | 323620 | ............................................................ | 323561 |
| AHUA01000001 | 323920 | ............................................................ | 323861 |
| AHTY01000043 | 323962 | ............................................................ | 323903 |
| AHTW01000034 | 122135 | ............................................................ | 122194 |
| AHTV01000016 | 323967 | ............................................................ | 323908 |
| AHTU01000026 | 324437 | ............................................................ | 324378 |
| AHTT01000031 | 324437 | ............................................................ | 324378 |
| AHTQ01000026 | 4809 | ............................................................ | 4750 |
| AHTR01000029 | 122308 | ............................................................ | 122367 |
| ABFG01000003 | 79203 | ............................................................ | 79262 |
| AHTZ01000022 | 323970 | ............................................................ | 323911 |
| AHUF01000033 | 122295 | ............................................................ | 122354 |
| AHTP01000008 | 122132 | ............................................................ | 122192 |

```
                                                \
                                                 |
                                                 T
```

| ID | Start | | End |
|---|---|---|---|
| ALPP01000002 | 326557 | ............................................................ | 326498 |
| AJMN01000063 | 114639 | ............................................................ | 114698 |
| AHUE01000064 | 122295 | ............................................................ | 122354 |
| AHTS01000049 | 279764 | ............................................................ | 279705 |
| AHTO01000026 | 114640 | ............................................................ | 114699 |
| AHTN01000030 | 114640 | ............................................................ | 114699 |
| AHTL01000037 | 195156 | ............................................................ | 195215 |
| AHTJ01000054 | 114784 | ............................................................ | 114843 |
| ABEW01000005 | 369611 | ............................................................ | 369552 |
| AHUB01000013 | 169084 | ............................................................ | 169143 |
| AJMO01000041 | 114637 | ............................................................ | 114696 |
| AHTM01000024 | 281002 | ............................................................ | 280943 |
| AHTK01000030 | 114474 | ............................................................ | 114533 |
| Query | 601 | GCCAATGAAAATGCAAAAGATAAATTTGTAATATTTTCGTCTTTGGTTTTTTCGTATTTT | 660 |
| AHUD01000019 | 106316 | ............................................................ | 106375 |
| AHUC01000007 | 323560 | ............................................................ | 323501 |
| AHUA01000001 | 323860 | ............................................................ | 323801 |
| AHTY01000043 | 323902 | ............................................................ | 323843 |
| AHTW01000034 | 122195 | ............................................................ | 122254 |
| AHTV01000016 | 323907 | ............................................................ | 323848 |
| AHTU01000026 | 324377 | ............................................................ | 324318 |
| AHTT01000031 | 324377 | ............................................................ | 324318 |
| AHTQ01000026 | 4749 | ............................................................ | 4690 |
| AHTP01000029 | 122368 | ............................................................ | 122427 |
| ABFG01000003 | 79263 | ............................................................ | 79322 |
| AHTZ01000022 | 323910 | ............................................................ | 323851 |
| AHUF01000033 | 122355 | ............................................................ | 122414 |
| AHTP01000008 | 122193 | ............................................................ | 122252 |
| ALPP01000002 | 326497 | ............................................................ | 326438 |
| AJMN01000063 | 114699 | ............................................................ | 114758 |
| AHUE01000064 | 122355 | ............................................................ | 122414 |
| AHTS01000049 | 279704 | ............................................................ | 279645 |
| AHTO01000026 | 114700 | ............................................................ | 114759 |
| AHTN01000030 | 114700 | ............................................................ | 114759 |
| AHTL01000037 | 195216 | ............................................................ | 195275 |
| AHTJ01000054 | 114844 | ............................................................ | 114903 |
| ABEW01000005 | 369551 | ............................................................ | 369492 |

Figure 6 (Continued)

```
AHUB01000013   169144  A...........................................................  169203
AJMO01000041   114697  ............................................................  114756
AHTM01000024   280942  ............................................................  280883
AHTK01000030   114534  ............................................................  114594
                                                                    \
                                                                     |
                                                                     T

Query          661     TTATTCAAGTTAATCTTACATTTTACTAACTCGGCTGATTTTTTTTATTTGCCAGGGGTT  720
AHUD01000019   106376  ............................................................  106435
AHUC01000007   323500  ............................................................  323441
AHUA01000001   323800  ............................................................  323741
AHTY01000043   323842  ............................................................  323783
AHTW01000034   122255  ............................................................  122314
AHTV01000016   323847  ............................................................  323788
AHTU01000026   324317  ............................................................  324258
AHTT01000031   324317  ............................................................  324258
AHTQ01000026   4689    ............................................................  4630
AHTR01000029   122428  ............................................................  122487
ABFG01000003   79323   ............................................................  79382
AHTZ01000022   323850  ............................................................  323791
AHUF01000033   122415  ............................................................  122474
AHTP01000008   122253  ............................................................  122312
ALPP01000002   326437  ........................T...................................  326379
AJMN01000063   114759  ............................................................  114818
AHUE01000064   122415  ............................................................  122474
AHTS01000049   279644  ............................................................  279585
AHTO01000026   114760  ............................................................  114819
AHTN01000030   114760  ............................................................  114819
AHTL01000037   195276  ............................................................  195335
AHTJ01000054   114904  ............................................................  114963
ABEW01000005   369491  ............................................................  369432
AHUB01000013   169204  ............................................................  169263
AJMO01000041   114757  ........................T...................................  114816
AHTM01000024   280882  ............................................................  280823
AHTK01000030   114595  ........................-...................................  114653

Query          721     GGTTCGCCTACATTTGTTAGTTATGACAAGTTAACTTTTAACATCTCGCTACTTTTTAAA  780
AHUD01000019   106436  ............................................................  106495
AHUC01000007   323440  ............................................................  323381
AHUA01000001   323740  ............................................................  323681
AHTY01000043   323782  ............................................................  323723
AHTW01000034   122315  ............................................................  122374
AHTV01000016   323787  ............................................................  323728
AHTU01000026   324257  ............................................................  324198
AHTT01000031   324257  ............................................................  324198
AHTQ01000026   4629    ............................................................  4570
AHTR01000029   122488  ............................................................  122547
ABFG01000003   79383   ............................................................  79442
AHTZ01000022   323790  ............................................................  323731
AHUF01000033   122475  ............................................................  122534
AHTP01000008   122313  ............................................................  122372
ALPP01000002   326378  ............................................................  326319
AJMN01000063   114819  ............................................................  114878
AHUE01000064   122475  ............................................................  122534
AHTS01000049   279584  ............................................................  279525
AHTO01000026   114820  ............................................................  114879
AHTN01000030   114820  ............................................................  114879
AHTL01000037   195336  ............................................................  195395
AHTJ01000054   114964  ............................................................  115023
ABEW01000005   369431  ............................................................  369372
AHUB01000013   169264  ............................................................  169323
AJMO01000041   114817  ............................................................  114876
AHTM01000024   280822  ............................................................  280763
AHTK01000030   114654  ............................................................  114713

Query          781     GGGCTTTTGATATTATTCAACGCTGATTTTTTTAGTAAAATAATCAGTTCACCTGAAGGA  840
AHUD01000019   106496  ............................................................  106555
AHUC01000007   323380  ............................................................  323321
AHUA01000001   323680  ............................................................  323621
AHTY01000043   323722  ............................................................  323663
AHTW01000034   122375  ............................................................  122434
AHTV01000016   323727  ............................................................  323668
AHTU01000026   324197  ............................................................  324138
AHTT01000031   324197  ............................................................  324138
AHTQ01000026   4569    ............................................................  4510
AHTR01000029   122548  ............................................................  122607
ABFG01000003   79443   ............................................................  79502
AHTZ01000022   323730  ............................................................  323671
AHUF01000033   122535  ............................................................  122594
AHTP01000008   122373  ............................................................  122432
```

Figure 6 (Continued)

```
ALPP01000002   326318  ..............................................   326259
AJMN01000063   114879  ..............................................   114938
AHUE01000064   122535  ..............................................   122593
AHTS01000049   279524  ..............................................   279465
AHTO01000026   114880  ..............................................   114939
AHTN01000030   114880  ..............................................   114939
AHTL01000037   195396  ..............................................   195455
AHTJ01000054   115024  ..............................................   115083
ABEW01000005   369371  ..............................................   369312
AHUB01000013   169324  ..............................................   169383
AJMO01000041   114877  ..............................................   114936
AHTM01000024   280762  ..............................................   280704
AHTK01000030   114714  ..............................................   114773
AHTX01000051   4265    ..............................................   4205
                                         \
                                          |
                                          T

Query          841   ATATTCTCTTCTTTAAAATTCACATCATTAGTTATATTTTTTATACTTTTAATTTCTTCG   900
AHUD01000019   106556  ..............................................   106615
AHUC01000007   323320  ..............................................   323261
AHUA01000001   323620  ..............................................   323561
AHTY01000043   323662  ..............................................   323603
AHTW01000034   122435  ..............................................   122494
AHTV01000016   323667  ..............................................   323608
AHTU01000026   324137  ..............................................   324078
AHTT01000031   324137  ..............................................   324078
AHTQ01000026   4509    ..............................................   4450
AHTR01000029   122608  ..............................................   122667
ABFG01000003   79503   ..............................................   79562
AHTZ01000022   323670  ..............................................   323611
AHUF01000033   122595  ..............................................   122654
AHTP01000008   122433  ..............................................   122492
ALPP01000002   326258  ..............................................   326199
AJMN01000063   114939  ..............................................   114998
AHUE01000064   122594  ..............................................   122653
                                         \
                                          |
                                          T AHTS01000049   279464  ..............................................   279405
AHTO01000026   114940  ..............................................   114999
AHTN01000030   114940  ..............................................   114999
AHTL01000037   195456  ..............................................   195515
AHTJ01000054   115084  ..............................................   115143
ABEW01000005   369311  ..............................................   369252
AHUB01000013   169384  ..............................................   169443
AJMO01000041   114937  ..............................................   114996
AHTM01000024   280703  ..............................................   280644
AHTK01000030   114774  ..............................................   114833
AHTX01000051   4204    ..............................................   4145

Query          901   CTTATAAAAATAAGAAAGTTTAGTCTCGTTGACGCCGCGCTATTGATAGCAGCTCTTATT   960
AHUD01000019   106616  ..............................................   106675
AHUC01000007   323260  ..............................................   323201
AHUA01000001   323560  ..............................................   323501
AHTY01000043   323602  ..............................................   323543
AHTW01000034   122495  ..............................................   122554
AHTV01000016   323607  ..............................................   323548
AHTU01000026   324077  ..............................................   324018
AHTT01000031   324077  ..............................................   324018
AHTQ01000026   4449    ..............................................   4390
AHTR01000029   122668  ..............................................   122727
ABFG01000003   79563   ...........................................T....   79622
AHTZ01000022   323610  ..............................................   323551
AHUF01000033   122655  ...........................................T....   122714
AHTP01000008   122493  ...........................................T....   122552
ALPP01000002   326198  ...........................................T....   326139
AJMN01000063   114999  ...........................................T....   115058
AHUE01000064   122655  ...........................................T....   122714
AHTS01000049   279404  ...........................................T....   279345
AHTO01000026   115000  ...........................................T....   115059
AHTN01000030   115000  ...........................................T....   115059
AHTL01000037   195516  ...........................................T....   195575
AHTJ01000054   115144  ...........................................T....   115203
ABEW01000005   369251  ...........................................T....   369192
AHUB01000013   169444  ...........................................T....   169503
AJMO01000041   114997  ...........................................T....   115056
AHTM01000024   280643  ...........................................T....   280584
AHTK01000030   114834  ...........................................T....   114893
AHTX01000051   4144    ..............................................   4085
```

Figure 6 (Continued)

```
Query           961  ATGATTCCTGCATATGCCTTAAGCGATAAACCAGTGGATGAGGGTACAACAAGATATTTA 1020
AHUD01000019 106676  ............................................................ 106735
AHUC01000007 323200  ............................................................ 323141
AHUA01000001 323500  ............................................................ 323441
AHTY01000043 323542  ............................................................ 323483
AHTW01000034 122555  ............................................................ 122614
AHTV01000016 323547  ............................................................ 323488
AHTU01000026 324017  ............................................................ 323958
AHTT01000031 324017  ............................................................ 323958
AHTQ01000026   4389  ............................................................   4330
AHTR01000029 122728  ............................................................ 122787
ABFG01000003  79623  ............................................................  79682
AHTZ01000022 323550  ............................................................ 323491
AHUF01000033 122715  ............................................................ 122774
AHTP01000008 122553  ............................................................ 122612
ALPP01000002 326138  ............................................................ 326079
AJMN01000063 115059  ............................................................ 115118
AHUE01000064 122715  ............................................................ 122774
AHTS01000049 279344  ............................................................ 279285
AHTO01000026 115060  ............................................................ 115119
AHTN01000030 115060  ............................................................ 115119
AHTL01000037 195576  ............................................................ 195635
AHTJ01000054 115204  ............................................................ 115263
ABEW01000005 369191  ............................................................ 369132
AHUB01000013 169504  ............................................................ 169563
AJMO01000041 115057  ............................................................ 115116
AHTM01000024 280583  ............................................................ 280524
AHTK01000030 114894  ............................................................ 114953
AHTX01000051   4084  ............................................................   4025

Query          1021  ATTCCTGTCATTATTTTTGGTTCAATTTTCTTATGTCGAAATGCGAATGTACCAAAGATA 1080
AHUD01000019 106736  ............................................................ 106795
AHUC01000007 323140  ............................................................ 323081
AHUA01000001 323440  ............................................................ 323381
AHTY01000043 323482  ............................................................ 323423
AHTW01000034 122615  ............................................................ 122674
AHTV01000016 323487  ............................................................ 323428
AHTU01000026 323957  ............................................................ 323898
AHTT01000031 323957  ............................................................ 323898
AHTQ01000026   4329  ............................................................   4270
AHTR01000029 122788  ............................................................ 122847
ABFG01000003  79683  ............................................................  79742
AHTZ01000022 323490  ............................................................ 323431
AHUF01000033 122775  ............................................................ 122834
AHTP01000008 122613  ............................................................ 122672
ALPP01000002 326078  ............................................................ 326019
AJMN01000063 115119  ............................................................ 115178
AHUE01000064 122775  ............................................................ 122834
AHTS01000049 279284  ............................................................ 279225
AHTO01000026 115120  ............................................................ 115179
AHTN01000030 115120  ............................................................ 115179
AHTL01000037 195636  ............................................................ 195695
AHTJ01000054 115264  ............................................................ 115323
ABEW01000005 369131  ............................................................ 369072
AHUB01000013 169564  ............................................................ 169623
AJMO01000041 115117  ............................................................ 115176
AHTM01000024 280523  ............................................................ 280464
AHTK01000030 114954  ............................................................ 115013
AHTX01000051   4024  ............................................................   3965

Query          1081  TCAAATATAGTTTTATGGTTTTTTTCAATTTCAATTTCTGCTTATTCATTAATATATGTA 1140
AHUD01000019 106796  ............................................................ 106855
AHUC01000007 323080  ............................................................ 323021
AHUA01000001 323380  ............................................................ 323321
AHTY01000043 323422  ............................................................ 323363
AHTW01000034 122675  ............................................................ 122734
AHTV01000016 323427  ............................................................ 323368
AHTU01000026 323897  ............................................................ 323838
AHTT01000031 323897  ............................................................ 323838
AHTQ01000026   4269  ............................................................   4210
AHTR01000029 122848  ............................................................ 122907
ABFG01000003  79743  ............................................................  79802
AHTZ01000022 323430  ............................................................ 323371
AHUF01000033 122835  ............................................................ 122894
AHTP01000008 122673  ............................................................ 122732
ALPP01000002 326018  ............................................................ 325959
AJMN01000063 115179  ............................................................ 115238
AHUE01000064 122835  ............................................................ 122894
AHTS01000049 279224  ............................................................ 279165
AHTO01000026 115180  ............................................................ 115239
AHTN01000030 115180  ............................................................ 115239
```

Figure 6 (Continued)

```
AHTL01000037   195696   ..........................................................   195755
AHTJ01000054   115324   ..........................................................   115383
ABEW01000005   369071   ..........................................................   369012
AHUB01000013   169624   ..........................................................   169683
AJMO01000041   115177   ..........................................................   115236
AHTM01000024   280463   ...................-......................................   280405
AHTK01000030   115014   ..........................................................   115073
AHTX01000051   3964    ..........................................................   3904
                                              \
                                               |
                                               T

Query          1141    AATCAGCCTGATTTCTTATTTCGCAATGACAGAACCACATCAAAATATAGGCTTATATCT   1200
AHUD01000019   106856   ..........................................................   106915
AHUC01000007   323020   ..........................................................   322961
AHUA01000001   323320   ..........................................................   323261
AHTY01000043   323362   ..........................................................   323303
AHTW01000034   122735   ..........................................................   122794
AHTV01000016   323367   ..........................................................   323308
AHTU01000026   323837   ..........................................................   323778
AHTT01000031   323837   ..........................................................   323778
AHTQ01000026   4209    ..........................................................   4150
AHTR01000029   122908   ..........................................................   122967
ABFG01000003   79803   ..........................................................   79862
AHTZ01000022   323370   ..........................................................   323311
AHUF01000033   122895   ..........................................................   122954
AHTP01000008   122733   ..........................................................   122792
ALPP01000002   325958   ..........................................................   325899
AJMN01000063   115239   ..........................................................   115298
AHUE01000064   122895   ..........................................................   122954
AHTS01000049   279164   ..........................................................   279105
AHTO01000026   115240   ..........................................................   115299
AHTN01000030   115240   ..........................................................   115299
AHTL01000037   195756   ..........................................................   195815
AHTJ01000054   115384   ..........................................................   115443
ABEW01000005   369011   ..........................................................   368952
AHUB01000013   169684   ..........................................................   169743
AJMO01000041   115237   ..........................................................   115296
AHTM01000024   280404   ..........................................................   280345
AHTK01000030   115074   ..........................................................   115133
AHTX01000051   3903    ..........................................................   3844

Query          1201    AATTTTTTGACTCAACACAACTTATCTAATGGATATGCAACATTCTGGAATGCGGCAGCG   1260
AHUD01000019   106916   ..........................................................   106975
AHUC01000007   322960   ..........................................................   322901
AHUA01000001   323260   ..........................................................   323201
AHTY01000043   323302   ..........................................................   323243
AHTW01000034   122795   ..........................................................   122854
AHTV01000016   323307   ..........................................................   323248
AHTU01000026   323777   ..........................................................   323718
AHTT01000031   323777   ..........................................................   323718
AHTQ01000026   4149    ..........................................................   4090
AHTR01000029   122968   ..........................................................   123027
ABFG01000003   79863   ..........................................................   79922
AHTZ01000022   323310   ..........................................................   323251
AHUF01000033   122955   ..........................................................   123014
AHTP01000008   122793   ..........................................................   122852
ALPP01000002   325898   ..........................................................   325839
AJMN01000063   115299   ..........................................................   115358
AHUE01000064   122955   ..........................................................   123014
AHTS01000049   279104   ..........................................................   279045
AHTO01000026   115300   ..........................................................   115359
AHTN01000030   115300   ..........................................................   115359
AHTL01000037   195816   ..........................................................   195875
AHTJ01000054   115444   ..........................................................   115503
ABEW01000005   368951   ..........................................................   368892
AHUB01000013   169744   ..........................................................   169803
AJMO01000041   115297   ..........................................................   115356
AHTM01000024   280344   ..........................................................   280285
AHTK01000030   115134   ..........................................................   115193
AHTX01000051   3843    ..........................................................   3783
                                              \
                                               |
                                               T Query          1261    GTGAGTGTGGAAAAGAAATTCAATATAGCCCCTGTTAACATCGACATAGAAAATAAAAAA   1320
AHUD01000019   106976   ..........................................................   107035
AHUC01000007   322900   ..........................................................   322841
AHUA01000001   323200   ..........................................................   323141
AHTY01000043   323242   ..........................................................   323183
AHTW01000034   122855   ..........................................................   122914
```

Figure 6 (Continued)

```
AHTV01000016    323247    ..................................................    323188
AHTU01000026    323717    ..................................................    323658
AHTT01000031    323717    ..................................................    323658
AHTQ01000026    4089      ..................................................    4030
AHTR01000029    123028    ..................................................    123087
ABFG01000003    79923     ..................................................    79982
AHTZ01000022    323250    ..................................................    323191
AHUF01000033    123015    ..................................................    123074
AHTP01000008    122853    ..................................................    122912
ALPP01000002    325838    ..................................................    325779
AJMN01000063    115359    ..................................................    115418
AHUE01000064    123015    ..................................................    123074
AHTS01000049    279044    ..................................................    278985
AHTO01000026    115360    ..................................................    115419
AHTN01000030    115360    ..................................................    115419
AHTL01000037    195876    ..................................................    195935
AHTJ01000054    115504    ..................................................    115563
ABEW01000005    368891    ..................................................    368832
AHUB01000013    169804    ..................................................    169862
AJMO01000041    115357    ..................................................    115416
AHTM01000024    280284    ..................................................    280225
AHTK01000030    115194    ..................................................    115253
AHTX01000051    3782      ..................................................    3723

Query           1321      GTTTTGCCATCTTTTTGGTTAACAAAAATATCATATTTTAACAATGGAAATAACTTTTTC    1380
AHUD01000019    107036    ..................................................    107095
AHUC01000007    322840    ..................................................    322781
AHUA01000001    323140    ..................................................    323081
AHTY01000043    323182    ..................................................    323123
AHTW01000034    122915    ..................................................    122974
AHTV01000016    323187    ..................................................    323128
AHTU01000026    323657    ..................................................    323598
AHTT01000031    323657    ..................................................    323598
AHTQ01000026    4029      ..................................................    3970
AHTR01000029    123088    ..................................................    123147
ABFG01000003    79983     ..................................................    80042
AHTZ01000022    323190    ..................................................    323131
AHUF01000033    123075    ..................................................    123134
AHTP01000008    122913    ..................................................    122972
ALPP01000002    325778    ..................................................    325719
AJMN01000063    115419    ..................................................    115478
AHUE01000064    123075    ..................................................    123134
AHTS01000049    278984    ..................................................    278925
AHTO01000026    115420    ..................................................    115479
AHTN01000030    115420    ..................................................    115479
AHTL01000037    195936    ..................................................    195995
AHTJ01000054    115564    ..................................................    115623
ABEW01000005    368831    ..................................................    368772
AHUB01000013    169863    ..................................................    169922
AJMO01000041    115417    ..................................................    115476
AHTM01000024    280224    ..................................................    280165
AHTK01000030    115254    ..................................................    115313
AHTX01000051    3722      ..................................................    3664

Query           1381      ATTGTTGATAATGACCAACAAAAAAAAGTCATAGAAGAATTATATGGCAAACCAGAATTA    1440
AHUD01000019    107096    ..................................................    107155
AHUC01000007    322780    ..................................................    322721
AHUA01000001    323080    ..................................................    323021
AHTY01000043    323122    ..................................................    323063
AHTW01000034    122975    ..................................................    123034
AHTV01000016    323127    ..................................................    323068
AHTU01000026    323597    ..................................................    323538
AHTT01000031    323597    ..................................................    323538
AHTQ01000026    3969      ..................................................    3910
AHTR01000029    123148    ..................................................    123207
ABFG01000003    80043     ..................................................    80102
AHTZ01000022    323130    ..................................................    323071
AHUF01000033    123135    ..................................................    123194
AHTP01000008    122973    ..................................................    123032
ALPP01000002    325718    ..................................................    325659
AJMN01000063    115479    ..................................................    115538
AHUE01000064    123135    ..................................................    123194
AHTS01000049    278924    ..................................................    278865
AHTO01000026    115480    ..................................................    115539
AHTN01000030    115480    ..................................................    115539
AHTL01000037    195996    ..................................................    196055
AHTJ01000054    115624    ..................................................    115683
ABEW01000005    368771    ..................................................    368712
AHUB01000013    169923    ..................................................    169981
AJMO01000041    115477    ..................................................    115536
AHTM01000024    280164    ..................................................    280105
```

Figure 6 (Continued)

```
AHTK01000030   115314   ............................................................   115373
AHTX01000051     3663   ............................................................     3602
                               \              \
                               |              |
                               A              A

Query           1441   ACATATATGGTGTGGGATTCCCCCATCCTGGTTTACAGTCATTCTATTAATATTTATGAT   1500
AHUD01000019   107156   ............................................................   107215
AHUC01000007   322720   ............................................................   322661
AHUA01000001   323020   ............................................................   322961
AHTY01000043   323062   ............................................................   323003
AHTW01000034   123035   ............................................................   123094
AHTV01000016   323067   ............................................................   323008
AHTU01000026   323537   ............................................................   323478
AHTT01000031   323537   ............................................................   323478
AHTQ01000026     3909   ............................................................     3850
AHTR01000029   123208   ............................................................   123267
ABFG01000003    80103   ............................................................    80162
AHTZ01000022   323070   ............................................................   323011
AHUF01000033   123195   ............................................................   123254
AHTP01000008   123033   ............................................................   123092
ALPP01000002   325658   ............................................................   325599
AJMN01000063   115539   ............................................................   115598
AHUE01000064   123195   ............................................................   123254
AHTS01000049   278864   ............................................................   278805
AHTO01000026   115540   ............................................................   115599
AHTN01000030   115540   ............................................................   115599
AHTL01000037   196056   ............................................................   196115
AHTJ01000054   115684   ............................................................   115743
ABEW01000005   368711   ............................................................   368652
AHUB01000013   169982   ............................................................   170041
AJMO01000041   115537   ............................................................   115596
AHTM01000024   280104   ............................................................   280045
AHTK01000030   115374   ............................................................   115433
AHTX01000051     3601   ............................................................     3541
                                       \
                                       |
                                       C Query           1501   GGCGATATAGAAGGAAGTGCCAATGTAGTAAAAAGTGACTTCAAGGTTGGGGACAATAAT   1560
AHUD01000019   107216   ............................................................   107275
AHUC01000007   322660   ............................................................   322601
AHUA01000001   322960   ............................................................   322901
AHTY01000043   323002   ............................................................   322943
AHTW01000034   123095   ............................................................   123154
AHTV01000016   323007   ............................................................   322948
AHTU01000026   323477   ............................................................   323418
AHTT01000031   323477   ............................................................   323418
AHTQ01000026     3849   ............................................................     3790
AHTR01000029   123268   ............................................................   123327
ABFG01000003    80163   ............................................................    80222
AHTZ01000022   323010   ............................................................   322951
AHUF01000033   123255   ............................................................   123314
AHTP01000008   123093   ............................................................   123152
ALPP01000002   325598   ............................................................   325539
AJMN01000063   115599   ............................................................   115658
AHUE01000064   123255   ............................................................   123314
AHTS01000049   278804   ............................................................   278745
AHTO01000026   115600   ............................................................   115659
AHTN01000030   115600   ............................................................   115659
AHTL01000037   196116   ............................................................   196175
AHTJ01000054   115744   ............................................................   115803
ABEW01000005   368651   ............................................................   368592
AHUB01000013   170042   ............................................................   170101
AJMO01000041   115597   ............................................................   115656
AHTM01000024   280044   ............................................................   279985
AHTK01000030   115434   ............................................................   115493
AHTX01000051     3540   ............................................................     3481

Query           1561   CAAATATGCAATGCTGGCGTACAAGGCATGGTTGCATATGGGCCCTATAAGACTCTTGGT   1620
AHUD01000019   107276   ............................................................   107335
AHUC01000007   322600   ............................................................   322541
AHUA01000001   322900   ............................................................   322841
AHTY01000043   322942   ............................................................   322883
AHTW01000034   123155   ............................................................   123214
AHTV01000016   322947   ............................................................   322888
AHTU01000026   323417   ............................................................   323358
AHTT01000031   323417   ............................................................   323358
AHTQ01000026     3789   ............................................................     3730
AHTR01000029   123328   ............................................................   123387
ABFG01000003    80223   ............................................................    80282
```

Figure 6 (Continued)

```
AHTZ01000022    322950  ..........................................................  322891
AHUF01000033    123315  ..........................................................  123374
AHTP01000008    123153  ..........................................................  123212
ALPP01000002    325538  ..........................................................  325479
AJMN01000063    115659  ..........................................................  115718
AHUE01000064    123315  ..........................................................  123374
AHTS01000049    278744  ..........................................................  278685
AHTO01000026    115660  ..........................................................  115719
AHTN01000030    115660  ..........................................................  115719
AHTL01000037    196176  ..........................................................  196235
AHTJ01000054    115804  ..........................................................  115863
ABEW01000005    368591  ..........................................................  368532
AHUB01000013    170102  ..........................................................  170161
AJMO01000041    115657  ..........................................................  115716
AHTM01000024    279984  ..........................................................  279925
AHTK01000030    115494  ..........................................................  115553
AHTX01000051      3480  ..........................................................    3421

Query            1621  CGTGGGTGGTATTCTTTAAAAATTAATGCACATGGCGATCAGTATGAAGCATTAATTTTT  1680
AHUD01000019    107336  ..........................................................  107395
AHUC01000007    322540  ..........................................................  322481
AHUA01000001    322840  ..........................................................  322781
AHTY01000043    322882  ..........................................................  322823
AHTW01000034    123215  ..........................................................  123274
AHTV01000016    322887  ..........................................................  322828
AHTU01000026    323357  ..........................................................  323298
AHTT01000031    323357  ..........................................................  323298
AHTQ01000026      3729  ..........................................................    3670
AHTR01000029    123388  ..........................................................  123447
ABFG01000003     80283  ..........................................................   80342
AHTZ01000022    322890  ..........................................................  322831
AHUF01000033    123375  ..........................................................  123434
AHTP01000008    123213  ..........................................................  123272
ALPP01000002    325478  ..........................................................  325419
AJMN01000063    115719  ..........................................................  115778
AHUE01000064    123375  ..........................................................  123434
AHTS01000049    278684  ..........................................................  278625
AHTO01000026    115720  ..........................................................  115779
AHTN01000030    115720  ..........................................................  115779
AHTL01000037    196236  ..........................................................  196295
AHTJ01000054    115864  ..........................................................  115923
ABEW01000005    368531  ..........................................................  368472
AHUB01000013    170162  ..........................................................  170221
AJMO01000041    115717  ..........................................................  115776
AHTM01000024    279924  ..........................................................  279865
AHTK01000030    115554  ..........................................................- 115612
AHTX01000051      3420  ..........................................................    3361

Query            1681  TCTTATATAACAGGAAAAAAAATCAAGATGTCTGAGAATAAATATAAAAATGGTTCTTAT  1740
AHUD01000019    107396  ..........................................................  107455
AHUC01000007    322480  ..........................................................  322421
AHUA01000001    322780  ..........................................................  322721
AHTY01000043    322822  ..........................................................  322763
AHTW01000034    123275  ..........................................................  123334
AHTV01000016    322827  ..........................................................  322768
AHTU01000026    323297  ..........................................................  323238
AHTT01000031    323297  ..........................................................  323238
AHTQ01000026      3669  ..........................................................    3610
AHTR01000029    123448  ..........................................................  123507
ABFG01000003     80343  ..........................................................   80402
AHTZ01000022    322830  ..........................................................  322771
AHUF01000033    123435  ..........................................................  123494
AHTP01000008    123273  ..........................................................  123332
ALPP01000002    325418  ..........................................................  325359
AJMN01000063    115779  ..........................................................  115838
AHUE01000064    123435  ..........................................................  123494
AHTS01000049    278624  ..........................................................  278565
AHTO01000026    115780  ..........................................................  115839
AHTN01000030    115780  ..........................................................  115839
AHTL01000037    196296  ..........................................................  196355
AHTJ01000054    115924  ..........................................................  115983
ABEW01000005    368471  ..........................................................  368412
AHUB01000013    170222  ..........................................................  170281
AJMO01000041    115777  ..........................................................  115836
AHTM01000024    279864  ..........................................................  279805
AHTK01000030    115613  ..........................................................  115672
AHTX01000051      3360  .............-............................................    3301
```

```
Query            1741    ATTTTCGAAATAAACGAAGATATGCCATCTGCAGAAATACAGTTATTCGCTCAAAAAGAT    1800
AHUD01000019   107456    ............................................................   107515
AHUC01000007   322420    ............................................................   322361
AHUA01000001   322720    ............................................................   322661
AHTY01000043   322762    ............................................................   322703
AHTW01000034   123335    ............................................................   123394
AHTV01000016   322767    ............................................................   322708
AHTU01000026   323237    ............................................................   323178
AHTT01000031   323237    ............................................................   323178
AHTQ01000026     3609    ............................................................     3550
AHTR01000029   123508    ............................................................   123567
ABFG01000003    80403    ............................................................    80462
AHTZ01000022   322770    ............................................................   322711
AHUF01000033   123495    ............................................................   123554
AHTP01000008   123333    ............................................................   123392
ALPP01000002   325358    ............................................................   325299
AJMN01000063   115839    ............................................................   115898
AHUE01000064   123495    ............................................................   123554
AHTS01000049   278564    ............................................................   278505
AHTO01000026   115840    ............................................................   115899
AHTN01000030   115840    ............................................................   115899
AHTL01000037   196356    ............................................................   196415
AHTJ01000054   115984    ............................................................   116043
ABEW01000005   368411    ............................................................   368352
AHUB01000013   170282    ............................................................   170341
AJMO01000041   115837    ............................................................   115896
AHTM01000024   279804    ............................................................   279745
AHTK01000030   115673    ............................................................   115732
AHTX01000051     3300    ............................................................     3241

Query            1801    TCAAATGTATGTTTTGAGTCATACTCACTTCAGCATATAAAATAATAAAGTCATGGAAAA    1860
AHUD01000019   107516    ............................................................   107575
AHUC01000007   322360    ............................................................   322301
AHUA01000001   322660    ............................................................   322601
AHTY01000043   322702    ............................................................   322643
AHTW01000034   123395    ............................................................   123454
AHTV01000016   322707    ............................................................   322648
AHTU01000026   323177    ............................................................   323118
AHTT01000031   323177    ............................................................   323118
AHTQ01000026     3549    ............................................................     3490
AHTR01000029   123568    ............................................................   123627
ABFG01000003    80463    ............................................................    80522
AHTZ01000022   322710    ............................................................   322651
AHUF01000033   123555    ............................................................   123614
AHTP01000008   123393    ............................................................   123452
ALPP01000002   325298    ............................................................   325239
AJMN01000063   115899    ............................................................   115958
AHUE01000064   123555    ............................................................   123614
AHTS01000049   278504    ............................................................   278445
AHTO01000026   115900    ............................................................   115959
AHTN01000030   115900    ............................................................   115959
AHTL01000037   196416    ............................................................   196475
AHTJ01000054   116044    ............................................................   116103
ABEW01000005   368351    ............................................................   368292
AHUB01000013   170342    ............................................................   170401
AJMO01000041   115897    ............................................................   115956
AHTM01000024   279744    ............................................................   279685
AHTK01000030   115733    ............................................................   115792
AHTX01000051     3240    ............................................................     3181

Query            1861    GCGTCAGTAACTAATACAGGCGCTTTTTGTCTATAGAAAACTCATGCTGTTAAGCGGGTT    1920
AHUD01000019   107576    ............................................................   107635
AHUC01000007   322300    ............................................................   322241
AHUA01000001   322600    ............................................................   322541
AHTY01000043   322642    ............................................................   322583
AHTW01000034   123455    ............................................................   123514
AHTV01000016   322647    ............................................................   322588
AHTU01000026   323117    ............................................................   323058
AHTT01000031   323117    ............................................................   323058
AHTQ01000026     3489    ............................................................     3430
AHTR01000029   123628    ............................................................   123687
ABFG01000003    80523    ............................................................    80582
AHTZ01000022   322650    ............................................................   322591
AHUF01000033   123615    ............................................................   123674
AHTP01000008   123453    ............................................................   123512
ALPP01000002   325238    ............................................................   325179
AJMN01000063   115959    ............................................................   116018
AHUE01000064   123615    ............................................................   123674
AHTS01000049   278444    ............................................................   278385
AHTO01000026   115960    ............................................................   116019
AHTN01000030   115960    ............................................................   116019
```

Figure 6 (Continued)

```
AHTL01000037   196476   ..................................................   196535
AHTJ01000054   116104   ..................................................   116163
ABEW01000005   368291   ..................................................   368232
AHUB01000013   170402   ..................................................   170461
AJMO01000041   115957   ..................................................   116016
AHTM01000024   279684   ..................................................   279625
AHTK01000030   115793   ..................................................   115852
AHTX01000051   3180     ..................................................   3121

Query          1921     TTGGTTGAAATGTTCCGAAAATCGGAATAGTTATTCCACACCAGCGCTATGAATTAGATG   1980
AHUD01000019   107636   ..................................................   107695
AHUC01000007   322240   ..................................................   322181
AHUA01000001   322540   ..................................................   322481
AHTY01000043   322582   ..................................................   322523
AHTW01000034   123515   ..................................................   123574
AHTV01000016   322587   ..................................................   322528
AHTU01000026   323057   ..................................................   322998
AHTT01000031   323057   ..................................................   322998
AHTQ01000026   3429     ..................................................   3370
AHTR01000029   123688   ..................................................   123747
ABFG01000003   80583    ..................................................   80642
AHTZ01000022   322590   ..................................................   322531
AHUF01000033   123675   ..................................................   123734
AHTP01000008   123513   ..................................................   123572
ALPP01000002   325178   ..................................................   325119
AJMN01000063   116019   ..................................................   116078
AHUE01000064   123675   ..................................................   123734
AHTS01000049   278384   ..................................................   278325
AHTO01000026   116020   ..................................................   116079
AHTN01000030   116020   ..................................................   116079
AHTL01000037   196536   ..................................................   196595
AHTJ01000054   116164   ..................................................   116223
ABEW01000005   368231   ..................................................   368172
AHUB01000013   170462   ..................................................   170521
AJMO01000041   116017   ..................................................   116076
AHTM01000024   279624   ..................................................   279565
AHTK01000030   115853   ..................................................   115912
AHTX01000051   3120     ..................................................   3061

Query          1981     GCGAAGAGCATGCTGTAACCCCTACTATAGTAGCACCTTCAGATTGAACATACATGGTAC   2040
AHUD01000019   107696   ..................................................   107755
AHUC01000007   322180   ..................................................   322121
AHUA01000001   322480   ..................................................   322421
AHTY01000043   322522   ..................................................   322463
AHTW01000034   123575   ..................................................   123634
AHTV01000016   322527   ..................................................   322468
AHTU01000026   322997   ..................................................   322938
AHTT01000031   322997   ..................................................   322938
AHTQ01000026   3369     ..................................................   3310
AHTR01000029   123748   ..................................................   123807
ABFG01000003   80643    ..................................................   80702
AHTZ01000022   322530   ..................................................   322471
AHUF01000033   123735   ..................................................   123794
AHTP01000008   123573   ..................................................   123632
ALPP01000002   325118   ..................................................   325059
AJMN01000063   116079   ..................................................   116139
                                          \
                                          |
                                          C
AHUE01000064   123735   ..................................................   123794
AHTS01000049   278324   ..................................................   278264
                                          \
                                          |
                                          C
AHTO01000026   116080   ..................................................   116140
                                          \
                                          |
                                          C
AHTN01000030   116080   ..................................................   116140
                                          \
                                          |
                                          C
AHTL01000037   196596   ..................................................   196656
                                          \
                                          |
                                          C
AHTJ01000054   116224   ..................................................   116284
                                          \
                                          |
                                          C
ABEW01000005   368171   ..................................................   368111
```

Figure 6 (Continued)

```
                        \
                        |
                        C
AHUB01000013   170522   ............................................................   170581
AJM001000041   116077   ............................................................   116137
                        \
                        |
                        C
AHTM01000024   279564   ............................................................   279504
                        \
                        |
                        C
AHTK01000030   115913   ............................................................   115973
                        \
                        |
                        C
AHTX01000051   3060     ............................................................   3001

Query          2041     CAATCTTATATAATTGCCTGGCGTCGAACGCCCCGAGAAGTACCGTACCAGTAGTTGCCG   2100
AHUD01000019   107756   ............................................................   187815
AHUC01000007   322120   ............................................................   322061
AHUA01000001   322420   ............................................................   322361
AHTY01000043   322462   ............................................................   322403
AHTW01000034   123635   ............................................................   123694
AHTV01000016   322467   ............................................................   322408
AHTU01000026   322937   ............................................................   322878
AHTT01000031   322937   ............................................................   322878
AHTQ01000026   3309     ............................................................   3250
AHTR01000029   123808   ............................................................   123867
ABFG01000003   80703    ............................................................   80762
AHTZ01000022   322470   ............................................................   322411
AHUF01000033   123795   ............................................................   123854
AHTP01000008   123633   ............................................................   123692
ALPP01000002   325058   ............................................................   324999
AJMN01000063   116140   ............................................................   116199
AHUE01000064   123795   ............................................................   123854
AHTS01000049   278263   ............................................................   278204
AHTO01000026   116141   ............................................................   116200
AHTN01000030   116141   ............................................................   116200
AHTL01000037   196657   ............................................................   196716
AHTJ01000054   116285   ............................................................   116344
ABEW01000005   368110   ............................................................   368051
AHUB01000013   170582   ............................................................   170641
AJM001000041   116138   ............................................................   116197
AHTM01000024   279503   ............................................................   279444
AHTK01000030   115974   ............................................................   116033
AHTX01000051   3000     ............................................................   2941

Query          2101     TCGATTATGTCTGGCGAGCGCCGATAACTTTCATGCCGCCTACTGAACAAGATGTTACCA   2160
AHUD01000019   107816   ............................................................   107875
AHUC01000007   322060   ............................................................   322001
AHUA01000001   322360   ............................................................   322301
AHTY01000043   322402   ............................................................   322343
AHTW01000034   123695   ............................................................   123754
AHTV01000016   322407   ............................................................   322348
AHTU01000026   322877   ............................................................   322818
AHTT01000031   322877   ............................................................   322818
AHTQ01000026   3249     ............................................................   3190
AHTR01000029   123868   ............................................................   123927
ABFG01000003   80763    ............................................................   80822
AHTZ01000022   322410   ............................................................   322351
AHUF01000033   123855   ............................................................   123914
AHTP01000008   123693   ............................................................   123752
ALPP01000002   324998   ............................................................   324939
AJMN01000063   116200   ............................................................   116259
AHUE01000064   123855   ............................................................   123914
AHTS01000049   278203   ............................................................   278144
AHTO01000026   116201   ............................................................   116260
AHTN01000030   116201   ............................................................   116260
AHTL01000037   196717   ............................................................   196776
AHTJ01000054   116345   ............................................................   116404
ABEW01000005   368050   ............................................................   367991
AHUB01000013   170642   ............................................................   170701
AJM001000041   116198   ............................................................   116257
AHTM01000024   279443   ............................................................   279384
AHTK01000030   116034   ............................................................   116093
AHTX01000051   2940     ............................................................   2881

Query          2161     CATTAAGAGAGGAGACCAGCGATTACGATATTGCATCTGTTTTCGACACGTAGTCGTTCT   2220
AHUD01000019   107876   ............................................................   107935
AHUC01000007   322000   ............................................................   321941
```

Figure 6 (Continued)

```
AHUA01000001   322300   ............................................................   322241
AHTY01000043   322342   ............................................................   322283
AHTW01000034   123755   ............................................................   123814
AHTV01000016   322347   ............................................................   322288
AHTU01000026   322817   ............................................................   322758
AHTT01000031   322817   ............................................................   322758
AHTQ01000026   3189     ............................................................   3130
AHTR01000029   123928   ............................................................   123987
ABFG01000003   80823    ............................................................   80882
AHTZ01000022   322350   ............................................................   322291
AHUF01000033   123915   ............................................................   123974
AHTP01000008   123753   ............................................................   123812
ALPP01000002   324938   ............................................................   324879
AJMN01000063   116260   ............................................................   116319
AHUE01000064   123915   ............................................................   123974
AHTS01000049   278143   ............................................................   278084
AHTO01000026   116261   ............................................................   116320
AHTN01000030   116261   ............................................................   116320
AHTL01000037   196777   ............................................................   196836
AHTJ01000054   116405   ............................................................   116464
ABEW01000005   367990   ............................................................   367931
AHUB01000013   170702   ............................................................   170761
AJMO01000041   116258   ............................................................   116317
AHTM01000024   279383   ............................................................   279324
AHTK01000030   116094   ............................................................   116153
AHTX01000051   2880     ............................................................   2821

Query          2221     CAATAGAAGAGGCGAAAAAACACCAAGCCACTTGATGGCGTTTTTTATTAGAGGCAATAA   2280
AHUD01000019   107936   ............................................................   107995
AHUC01000007   321940   ............................................................   321881
AHUA01000001   322240   ............................................................   322181
AHTY01000043   322282   ............................................................   322223
AHTW01000034   123815   ............................................................   123874
AHTV01000016   322287   ............................................................   322228
AHTU01000026   322757   ............................................................   322698
AHTT01000031   322757   ............................................................   322698
AHTQ01000026   3129     ............................................................   3070
AHTR01000029   123988   ............................................................   124047
ABFG01000003   80883    ............................................................   80942
AHTZ01000022   322290   ............................................................   322231
AHUF01000033   123975   ............................................................   124034
AHTP01000008   123813   ............................................................   123872
ALPP01000002   324878   ............................................................   324819
AJMN01000063   116320   ............................................................   116379
AHUE01000064   123975   ............................................................   124034
AHTS01000049   278083   ............................................................   278024
AHTO01000026   116321   ............................................................   116380
AHTN01000030   116321   ............................................................   116380
AHTL01000037   196837   ............................................................   196896
AHTJ01000054   116465   ............................................................   116524
ABEW01000005   367930   ............................................................   367871
AHUB01000013   170762   ............................................................   170821
AJMO01000041   116318   ............................................................   116377
AHTM01000024   279323   ............................................................   279264
AHTK01000030   116154   ............................................................   116213
AHTX01000051   2820     ............................................................   2761

Query          2281     ATGTCGGCTTTGGCAATGAAGGTTTTGAAATGCTAATCGCAGGAAATGTCAGCATCACCA   2340
AHUD01000019   107996   ............................................................   108055
AHUC01000007   321880   ............................................................   321821
AHUA01000001   322180   ............................................................   322121
AHTY01000043   322222   ............................................................   322163
AHTW01000034   123875   ............................................................   123934
AHTV01000016   322227   ............................................................   322168
AHTU01000026   322697   ............................................................   322638
AHTT01000031   322697   ............................................................   322638
AHTQ01000026   3069     ............................................................   3010
AHTR01000029   124048   ............................................................   124107
ABFG01000003   80943    ............................................................   81002
AHTZ01000022   322230   ............................................................   322171
AHUF01000033   124035   ............................................................   124094
AHTP01000008   123873   ............................................................   123932
ALPP01000002   324818   ............................................................   324759
AJMN01000063   116380   ............................................................   116439
AHUE01000064   124035   ............................................................   124094
AHTS01000049   278023   ............................................................   277964
AHTO01000026   116381   ............................................................   116440
AHTN01000030   116381   ............................................................   116440
AHTL01000037   196897   ............................................................   196956
AHTJ01000054   116525   ............................................................   116584
ABEW01000005   367870   ............................................................   367811
```

Figure 6 (Continued)

```
AHUB01000013  170822  ..............................................................  170881
AJMO01000041  116378  ..............................................................  116437
AHTM01000024  279263  ..............................................................  279204
AHTK01000030  116214  ..............................................................  116273
AHTX01000051  2760    ..............................................................  2701

Query         2341    GTGCTACTCTTACTTCTATTGCGTGTGATCTGAAAAAGAATATTAATGGTGACGGCTTTG  2400
AHUD01000019  108056  ..............................................................  108115
AHUC01000007  321820  ..............................................................  321761
AHUA01000001  322120  ..............................................................  322061
AHTY01000043  322162  ..............................................................  322103
AHTW01000034  123935  ..............................................................  123994
AHTV01000016  322167  ..............................................................  322108
AHTU01000026  322637  ..............................................................  322578
AHTT01000031  322637  ..............................................................  322578
AHTQ01000026  3009    ..............................................................  2950
AHTR01000029  124108  ..............................................................  124167
ABFG01000003  81003   ..............................................................  81062
AHTZ01000022  322170  ..............................................................  322111
AHUF01000033  124095  ..............................................................  124154
AHTP01000008  123933  ..............................................................  123992
ALPP01000002  324758  ..............................................................  324699
AJMN01000063  116440  ..............................................................  116499
AHUE01000064  124095  ..............................................................  124154
AHTS01000049  277963  ..............................................................  277904
AHTO01000026  116441  ..............................................................  116500
AHTN01000030  116441  ..............................................................  116500
AHTL01000037  196957  ..............................................................  197016
AHTJ01000054  116585  ..............................................................  116644
ABEW01000005  367810  ..............................................................  367751
AHUB01000013  170882  ..............................................................  170941
AJMO01000041  116438  ..............................................................  116497
AHTM01000024  279203  ..............................................................  279144
AHTK01000030  116274  ..............................................................  116333
AHTX01000051  2700    ..............................................................  2641

Query         2401    ACACGCCATATGATCCAGCAGGCTTCCGCAGATGTGTCTGGCTTGTTCAGCAGTCTCCAG  2460
AHUD01000019  108116  ..............................................................  108175
AHUC01000007  321760  ..............................................................  321701
AHUA01000001  322060  ..............................................................  322001
AHTY01000043  322102  ..............................................................  322043
AHTW01000034  123995  ..............................................................  124054
AHTV01000016  322107  ..............................................................  322048
AHTU01000026  322577  ..............................................................  322518
AHTT01000031  322577  ..............................................................  322518
AHTQ01000026  2949    ..............................................................  2890
AHTR01000029  124168  ..............................................................  124227
ABFG01000003  81063   ..............................................................  81122
AHTZ01000022  322110  ..............................................................  322051
AHUF01000033  124155  ..............................................................  124214
AHTP01000008  123993  ..............................................................  124052
ALPP01000002  324698  ..............................................................  324639
AJMN01000063  116500  ..............................................................  116559
AHUE01000064  124155  ..............................................................  124214
AHTS01000049  277903  ..............................................................  277844
AHTO01000026  116501  ..............................................................  116560
AHTN01000030  116501  ..............................................................  116560
AHTL01000037  197017  ..............................................................  197076
AHTJ01000054  116645  ..............................................................  116704
ABEW01000005  367750  ..............................................................  367691
AHUB01000013  170942  ..............................................................  171001
AJMO01000041  116498  ..............................................................  116557
AHTM01000024  279143  ..............................................................  279084
AHTK01000030  116334  ..............................................................  116393
AHTX01000051  2640    ..............................................................  2581

Query         2461    AATCAGGGATACATCCGAAAAACGTCAAAATGAGTTCCGGAATTCAAAGATGCCCTCAGT  2520
AHUD01000019  108176  ..............................................................  108235
AHUC01000007  321700  ..............................................................  321641
AHUA01000001  322000  ..............................................................  321941
AHTY01000043  322042  ..............................................................  321983
AHTW01000034  124055  ..............................................................  124114
AHTV01000016  322047  ..............................................................  321988
AHTU01000026  322517  ..............................................................  322458
AHTT01000031  322517  ..............................................................  322458
AHTQ01000026  2889    ..............................................................  2830
AHTR01000029  124228  ...........................................T..................  124287
ABFG01000003  81123   ..............................................................  81182
AHTZ01000022  322050  ..............................................................  321991
AHUF01000033  124215  ..............................................................  124274
AHTP01000008  124053  ...........................................T..................  124112
```

Figure 6 (Continued)

```
ALPP01000002   324638   ................................................   324579
AJMN01000063   116560   ................................................   116619
AHUE01000064   124215   ................................................   124274
AHTS01000049   277843   ................................................   277784
AHTO01000026   116561   ................................................   116620
AHTN01000030   116561   ................................................   116620
AHTL01000037   197077   ................................................   197136
AHTJ01000054   116705   ................................................   116764
ABEW01000005   367690   ................................................   367631
AHUB01000013   171002   ................................................   171061
AJMO01000041   116558   ................................................   116617
AHTM01000024   279083   ................................................   279024
AHTK01000030   116394   ................................................   116453
AHTX01000051   2580     ................................................   2521

Query          2521     AAATCGGACTCCCTCGTTGCGCTGTTAAAGTCTGAAATGGAGACACGCAGGAATGTAGCA   2580
AHUD01000019   108236   ................................................   108295
AHUC01000007   321640   ................................................   321581
AHUA01000001   321940   ................................................   321881
AHTY01000043   321982   ................................................   321923
AHTW01000034   124115   ................................................   124174
AHTV01000016   321987   ................................................   321928
AHTU01000026   322457   ................................................   322398
AHTT01000031   322457   ................................................   322398
AHTQ01000026   2829     ................................................   2770
AHTR01000029   124288   ................................................   124347
ABFG01000003   81183    ................................................   81242
AHTZ01000022   321990   ................................................   321931
AHUF01000033   124275   ................................................   124334
AHTP01000008   124113   ................................................   124172
ALPP01000002   324578   ................................................   324519
AJMN01000063   116620   ................................................   116679
AHUE01000064   124275   ..........A.....................................   124334
AHTS01000049   277783   ................................................   277724
AHTO01000026   116621   ................................................   116680
AHTN01000030   116621   ................................................   116680
AHTL01000037   197137   ................................................   197196
AHTJ01000054   116765   ................................................   116824
ABEW01000005   367630   ................................................   367571
AHUB01000013   171062   ................................................   171121
AJMO01000041   116618   ................................................   116677
AHTM01000024   279023   ................................................   278964
AHTK01000030   116454   ................................................   116513
AHTX01000051   2520     ................................................   2461
ABFG01000044   1        ................................................   25

Query          2581     CCAACAACTCGCTAGAGAATCAAAAAGCTGAGCCAGATGCCCCCGGAATCACACAGCCTC   2640
AHUD01000019   108296   ................................................   108355
AHUC01000007   321580   ................................................   321521
AHUA01000001   321880   ................................................   321821
AHTY01000043   321922   ................................................   321863
AHTW01000034   124175   ................................................   124234
AHTV01000016   321927   ................................................   321868
AHTU01000026   322397   ................................................   322338
AHTT01000031   322397   ................................................   322338
AHTQ01000026   2769     ................................................   2710
AHTR01000029   124348   ................................................   124407
ABFG01000003   81243    ................................................   81302
AHTZ01000022   321930   ................................................   321871
AHUF01000033   124335   ................................................   124394
AHTP01000008   124173   ................................................   124232
ALPP01000002   324518   ................................................   324459
AJMN01000063   116680   ................................................   116739
AHUE01000064   124335   ................................................   124394
AHTS01000049   277723   ................................................   277664
AHTO01000026   116681   ................................................   116740
AHTN01000030   116681   ................................................   116740
AHTL01000037   197197   ................................................   197256
AHTJ01000054   116825   ................................................   116884
ABEW01000005   367570   ................................................   367511
AHUB01000013   171122   ................................................   171181
AJMO01000041   116678   ................................................   116737
AHTM01000024   278963   ................................................   278904
AHTK01000030   116514   ................................................   116573
AHTX01000051   2460     ................................................   2401
ABFG01000044   26       ................................................   85

Query          2641     ACACTTGATGATGCCTGTGTATTTCTTCAAGTTACCAAACCTATCGCTACTAACTGGATT   2700
AHUD01000019   108356   ................................................   108415
AHUC01000007   321520   ................................................   321461
AHUA01000001   321820   ................................................   321761
```

Figure 6 (Continued)

```
AHTY01000043    321862  ..............................................................  321803
AHTW01000034    124235  ..............................................................  124294
AHTV01000016    321867  ..............................................................  321808
AHTU01000026    322337  ..............................................................  322278
AHTT01000031    322337  ..............................................................  322278
AHTQ01000026    2709    ..............................................................  2650
AHTR01000029    124408  ..............................................................  124467
ABFG01000003    81303   ..............................................................  81362
AHTZ01000022    321870  ..............................................................  321811
AHUF01000033    124395  ..............................................................  124454
AHTP01000008    124233  ..............................................................  124292
ALPP01000002    324458  ..............................................................  324399
AJMN01000063    116740  ..............................................................  116799
AHUE01000064    124395  ..............................................................  124454
AHTS01000049    277663  ..............................................................  277604
AHTO01000026    116741  ..............................................................  116800
AHTN01000030    116741  ..............................................................  116800
AHTL01000037    197257  ..............................................................  197316
AHTJ01000054    116885  ..............................................................  116944
ABEW01000005    367510  ..............................................................  367451
AHUB01000013    171182  ..............................................................  171241
AJMO01000041    116738  ..............................................................  116797
AHTM01000024    278903  ..............................................................  278844
AHTK01000030    116574  ..............................................................  116633
AHTX01000051    2400    ..............................................................  2341
ABFG01000044    86      ..............................................................  145

Query           2701    CACACAGGCTGTCTGTAAACATCATGTAAAGATTCCGCCAAGTCAGTCAATAGGTATGCA    2760
AHUD01000019    108416  ..............................................................  108475
AHUC01000007    321460  ..............................................................  321401
AHUA01000001    321760  ..............................................................  321701
AHTY01000043    321802  ..............................................................  321743
AHTW01000034    124295  ..............................................................  124354
AHTV01000016    321807  ..............................................................  321748
AHTU01000026    322277  ..............................................................  322218
AHTT01000031    322277  ..............................................................  322218
AHTQ01000026    2649    ..............................................................  2590
AHTR01000029    124468  ..............................................................  124527
ABFG01000003    81363   ..............................................................  81422
AHTZ01000022    321810  ..............................................................  321751
AHUF01000033    124455  ..............................................................  124514
AHTP01000008    124293  ..............................................................  124352
ALPP01000002    324398  ..............................................................  324339
AJMN01000063    116800  ..............................................................  116859
AHUE01000064    124455  ..............................................................  124514
AHTS01000049    277603  ..............................................................  277544
AHTO01000026    116801  ..............................................................  116860
AHTN01000030    116801  ..............................................................  116860
AHTL01000037    197317  ..............................................................  197376
AHTJ01000054    116945  ..............................................................  117004
ABEW01000005    367450  ..............................................................  367391
AHUB01000013    171242  ..............................................................  171301
AJMO01000041    116798  ..............................................................  116857
AHTM01000024    278843  ..............................................................  278784
AHTK01000030    116634  ..............................................................  116693
AHTX01000051    2340    ..............................................................  2281
ABFG01000044    146     ..............................................................  205

Query           2761    TAAATTTAACCGAACACGCTAAGCAAATAGGCGTAATATTGAACGATTGTGTCCCAGCTT    2820
AHUD01000019    108476  ..............................................................  108535
AHUC01000007    321400  ..............................................................  321341
AHUA01000001    321700  ..............................................................  321641
AHTY01000043    321742  ..............................................................  321683
AHTW01000034    124355  ..............................................................  124414
AHTV01000016    321747  ..............................................................  321688
AHTU01000026    322217  ..............................................................  322158
AHTT01000031    322217  ..............................................................  322158
AHTQ01000026    2589    ..............................................................  2530
AHTR01000029    124528  ..............................................................  124587
ABFG01000003    81423   ..............................................................  81482
AHTZ01000022    321750  ..............................................................  321691
AHUF01000033    124515  ..............................................................  124574
AHTP01000008    124353  ..............................................................  124412
ALPP01000002    324338  ..............................................................  324279
AJMN01000063    116860  .....................A........................................  116919
AHUE01000064    124515  ..............................................................  124574
AHTS01000049    277543  .....................A........................................  277484
AHTO01000026    116861  .....................A........................................  116920
AHTN01000030    116861  .....................A........................................  116920
AHTL01000037    197377  .....................A........................................  197436
```

Figure 6 (Continued)

```
AHTJ01000054   117005   ............................A............................................   117064
ABEW01000005   367390   ............................A............................................   367331
AHUB01000013   171302   ............................A............................................   171361
AJMC01000041   116858   ............................A............................................   116917
AHTM01000024   278783   ............................A............................................   278724
AHTK01000030   116694   ............................A............................................   116753
AHTX01000051   2280     .........................................................................   2221
ABFG01000044   206      .........................................................................   265

Query          2821    CCCCACAATGAAAGAGCAG    2839
AHUD01000019   108536  ...................    108554
AHUC01000007   321340  ...................    321322
AHUA01000001   321640  ...................    321622
AHTY01000043   321682  ...................    321664
AHTW01000034   124415  ...................    124433
AHTV01000016   321687  ...................    321669
AHTU01000026   322157  ...................    322139
AHTT01000031   322157  ...................    322139
AHTQ01000026   2529    ...................    2511
AHTR01000029   124588  ...................    124606
ABFG01000003   81483   ...................    81501
AHTZ01000022   321690  ...................    321672
AHUF01000033   124575  ...................    124593
AHTP01000008   124413  ...................    124431
ALPP01000002   324278  ...................    324260
AJMN01000063   116920  ...................    116938
AHUE01000064   124575  ...................    124593
AHTS01000049   277483  ...................    277465
AHTO01000026   116921  ...................    116939
AHTN01000030   116921  ...................    116939
AHTL01000037   197437  ...................    197455
AHTJ01000054   117065  ...................    117083
ABEW01000005   367330  ...................    367312
AHUB01000013   171362  ...................    171380
AJMC01000041   116918  ...................    116936
AHTM01000024   278723  ...................    278705
AHTK01000030   116754  ...................    116772
AHTX01000051   2220    ...................    2202
ABFG01000044   266     ...................    284
```

SEQ ID NO: 24
ATGACCAAAAAGGGGCTTTCGGTAATATTAGTTTTTTTGATATTTTCATATATTTTTACCGCATTAAGCTATAAATTTAT
CCCAAGCTCTGACAGCATGAGTGGTATTTTAGAGGCTGCTGACATTGCAAACGGAAACATAACACTAAAAGGATGGTACT
TATCTACAGTAACTTTCTATTTTACTGACTTAGTCTGGTTTGCTCTTGCTATAAAGCTTTTTGGTTATTCTGAATGGATA
ACATACGTTATACCTGGATT*AATGGCTGGTAGCCTGTTCGCT***TCATGCTATGCACTGGGAACAATTTCTGGCTACAAAAA*
AGCATGGGCTTTG*CTACTGTTCCTTGCTTTCCCT*GGTGCTGCTGTCAGTTACATGCTTTCTGTAGCGATAATCCATGTCC
CTACATATACTTATATCGTTGTTTCATATATATTAATTGATTTTATTGTCGCAGAAGAAATAGATTATATTTATTTCTA
TCATCAATAATCGCATCTTTAACGATATTTAGCGATGATATAACAATATATTTATTTTTTTTGCCAATTGCATTGAGCTG
TTTTATAGCCAATGAAAATGCAAAAGATAAATTTGTAATATTTTCGTCTTTGGTTTTTTCGTATTTTTTATTCAAGTTAA
TCTTACATTTTACTAACTCGGCTGATTTTTTTTATTTGCCAGGGGTTGGTTCGCCTACATTTGTTAGTTATGACAAGTTA
ACTTTTAACATCTCGCTACTTTTTAAAGGGCTTTTGATATTATTCAACGCTGATTTTTTTAGTAAAATAATCAGTTCACC
TGAAGGAATATTCTCTTCTTTAAAATTCACATCATTAGTTATATTTTTATACTTTTAATTTCTTCGCTTATAAAAATAA
GAAAGTTTAGTCTCGTTGACGCCGCGCTATTGATAGCAGCTCTTATTATGATTCCTGCATATGCCTTAAGCGATAAACCA
GTGGATGAGGGTACAACAAGATATTTAATTCCTGTCATTATTTTTGGTTCAATTTCTTATGTCGAAATGCGAATGTACC
AAAGATATCAAATATAGTTTTATGGTTTTTTTCAATTTCAATTTCTGCTTATTCATTAATATATGTAAATCAGCCTGATT
TCTTATTTCGCAATGACAGAACCACATCAAATATAGGCTTATATCTAATTTTTTTGACTCAACACAACTTATCTAATGGA
TATGCAACATTCTGGAATGCGGCAGCGGTGAGTGTGGAAAAGAAATTCAATATAGCCCCTGTTAACATCGACATAGAAAA
TAAAAAAGTTTTGCCATCTTTTTGGTTAACAAAAATATCATATTTTAACAATGGAAATAACTTTTTCATTGTTGATAATG
ACCAACAAAAAAAGTCATAGAAGAATTATATGGCAAACCAGAATTAACATATATGGTGTGGGATTCCCCCATCCTGGTT
TACAGTCATTCTATTAATATTTATGATGGCGATATAGAAGGAAGTGCCAATGTAGTAAAAAGTGACTTCAAGGTTGGGGA
CAATAATCAAATATGCAATGCTGGCGTACAAGGCATGGTTGCATATGGGCCCTATAAGACTCTTGGTCGTGGGTGGTATT
CTTTAAAAATTAATGCACATGGCGATCAGTATGAAGCATTAATTTTTCTTATATAACAGGAAAAAAAATCAAGATGTCT
GAGAATAAATATAAAAATGGTTCTTATATTTTCGAAATAAACGAAGATATGCCATCTGCAGAAATACAGTTATTCGCTCA
AAAAGATTCAAATGTATGTTTTGAGTCATACTCACTTCAGCATATAAAATAAT

MOLECULAR DISCRIMINATION OF REGULATED AND NON-REGULATED *SALMONELLA* SEROTYPES

TECHNICAL FIELD OF THE INVENTION

The present invention relates generally to methods and compositions used for the detection of the bacteria of the genus *Salmonella* and specifically to molecular discrimination of *Salmonella* serotypes that may be targeted for regulation in raw food products.

BACKGROUND OF THE INVENTION

Without limiting the scope of the invention, its background is described in connection with methods and compositions used for the molecular discrimination of *Salmonella* serotypes. *Salmonella* is a genus of bacteria that may cause severe infections leading to bacterial enteric illness in both humans and animals, e.g., salmonellosis, which include gastro-enteritis, as well as typhoid and para-typhoid fevers. Millions of human cases are reported every year, and the diseases result in thousands of deaths worldwide. In recent years, problems related to *Salmonella* have increased significantly, both in terms of incidence and severity of cases of human salmonellosis.

U.S. Pat. No. 8,268,984, entitled, "Detection of *Salmonella* by Real-Time Multiplex PCR," discloses the detection of *Salmonella* by nucleic acid amplification and provides primer and probe oligonucleotides that can be used in multiplex to detect *Salmonella* in real-time amplification. The oligonucleotides of the invention detect all group I serotypes, and have an increased *Salmonella* detection range and cover seven *Salmonella* groups.

SUMMARY OF THE INVENTION

*Salmonella* is an important cause of human and animal morbidity and mortality. Furthermore, *Salmonella* can be divided into a variety of different serotypes yet the traditional approach to serotyping is expensive, slow, and requires considerable expertise. This is important because several serotypes are regulated as adulterants in laying hen and broiler flocks of *Gallus* chickens in Europe (e.g., *S. enteritidis, S. typhimurium, S. infantis, S. virchow,* and *S. hadar*) and some are likely to be targeted for regulation in raw foods in the United States (e.g., *S. Typhimurium, S. Newport, S. Heidelberg,* and *S. Hadar*).

The present invention provides for rapid categorization of *Salmonella* isolates. The present invention provides a set of oligonucleotides for the identification of a *Salmonella* serotype comprising: at least one oligonucleotide set selected from a first primer set having SEQ ID NOS: 1 and 3 for the amplification of one or more sequences and a first probe having SEQ ID NO: 2 of the identification a *Salmonella* serotype; a second primer set having SEQ ID NOS: 4 and 6 for the amplification of one or more sequences and a second probe having SEQ ID NO: 5 of the identification a *Salmonella* serotype; a third primer set having SEQ ID NOS: 7 and 9 for the amplification of one or more sequences and a third probe having SEQ ID NO: 8 of the identification a *Salmonella* serotype; and a fourth primer set having SEQ ID NOS: 10 and 12 for the amplification of one or more sequences and a fourth probe having SEQ ID NO: 11 of the identification a *Salmonella* serotype. At least one oligonucleotide set may include 1, 2, 3, or all 4 primer sets and the corresponding probes. However, some embodiments may include various combinations of the 4 primer sets and corresponding probes as desired. For example, the various primer sets combinations may include the individual primer sets 1, 2, 3, or 4; a combination of 2 primer sets: 1 and 2; 1 and 3; 1 and 4; 2 and 3; 2 and 4; or 3 and 4; or a combination of 3 primer sets: 1, 2 and 3; 1, 2 and 4; 1, 3 and 4, or 2, 3 and 4. The *Salmonella* serotype may be selected from *S. typhimurium, S. enteritidis, S. newport, S. heidelberg* and *S. hadar* depending on the primer set and the corresponding probe. In some embodiments the set of oligonucleotides may include one or more labels individually or attached to a nucleic acid sequence to function as a detection label.

The present invention also includes a kit for the identification of *Salmonella* serotypes. The kit includes a set of oligonucleotide primers comprising SEQ ID NOS: 1 and 3, SEQ ID NOS: 4 and 6, SEQ ID NOS: 7 and 9, or SEQ ID NOS: 10 and 12 for the amplification of one or more sequences of one or more *Salmonella* serotypes; and one or more probes selected from SEQ ID NO: 2, SEQ ID NO: 5, SEQ ID NO: 8, and SEQ ID NO: 11 for real-time detection of one or more *Salmonella* serotypes. The kit may be used to identify *Salmonella* serotypes selected from *S. typhimurium, S. enteritidis, S. newport, S. heidelberg* and *S. hadar*. The kit may also include at least one selected from a nucleic acid extraction solution; a DNA polymerase; dNTPs; a buffer having a pH adapted to a polymerase activity; a "real-time" PCR master mix; and an instruction set for performing a real-time multiplex amplification to detect a *Salmonella* serotype.

The present invention includes a method of detecting *Salmonella* in a sample by providing a nucleic acid sample suspected of having one or more *Salmonella* isolate; adding a set of primers to the nucleic acid sample, wherein the set of primers comprise at least one primer set selected from SEQ ID NOS: 1 and 3; SEQ ID NOS: 4 and 6; SEQ ID NOS: 7 and 9; and SEQ ID NOS: 10 and 12 with the appropriated probes selected from SEQ ID NO: 2, SEQ ID NO: 5, SEQ ID NO: 8, and SEQ ID NO: 11; amplifying the nucleic acid sample using the set of primers to form an amplified nucleic acid sample; and detecting the presence of one or more *Salmonella* isolate using the dual-labeled hydrolysis probes, wherein a positive detection is indicative of at least one *Salmonella* of the targeted serotype being present in the sample. The method may include the step of homogenizing a tissue sample to produce a nucleic acid sample. In addition, the method may include the step of extracting the nucleic acids from a homogenized sample. The method may be used to identify *Salmonella* selected from *S. typhimurium, S. enteritidis, S. newport, S. heidelberg, S. hadar, S. infantis* and *S. virchow*. In addition the *Salmonella* isolate identification probes may be used to identify one or more genes selected from SEN1394 (for *Enteritidis*, Accession number AM933172), SNSL254_A0607 (for *Newport* and *Hadar*, Accession number CP001113), STM4494 (for *Typhimurium*, Accession number AE006468), CFSAN002069_17050 (for *Heidelberg* and *Infantis*, Accession number CP005390) and SeV_B2621 (for *Virchow*, Accession number ABFH02000001). The process may be used in a real-time amplification process.

The present invention also provides a method of checking the safety of a foodstuff for *Salmonella* by providing a foodstuff suspected of being contaminated with *Salmonella*; homogenizing the foodstuff; extracting a nucleic acid sample from a homogenized foodstuff; adding a set of primers to the nucleic acid sample, wherein the set of primers comprise at least one primer set selected from SEQ ID NOS: 1 and 3; SEQ ID NOS: 4 and 6; SEQ ID NOS: 7 and 9; and SEQ ID NOS: 10 and 12; amplifying the nucleic acid sample using the set of primers to form an amplified nucleic acid sample; contacting the amplified nucleic acid sample with one or more *Salmonella* isolate identification probes selected from SEQ ID NO: 2, SEQ ID NO: 5, SEQ ID NO: 8, and SEQ ID NO: 11; and detecting the presence of the one or more *Salmonella* isolate identification probes, wherein a positive detection is indicative of at least one *Salmonella* being present in the sample. The foodstuff may be for human consumption, animal consumption or both and may be in the form of a food or a beverage.

The present invention includes a primer-probe set for real-time PCR assays to identify *Salmonella* isolate that includes at least one oligonucleotide set selected from SEQ ID NOS: 1 and 3, SEQ ID NOS: 4 and 6, SEQ ID NOS: 7 and 9, and SEQ ID NOS: 10 and 12 working together with the corresponding probes SEQ ID NO: 2, SEQ ID NO: 5, SEQ ID NO: 8, and SEQ ID NO: 11, respectively.

The invention also features a method of detecting *Salmonella Enteritidis* in a sample (e.g., a foodstuff) by amplifying a nucleic acid sequence including SEQ ID NO: 14, 15, 17, or 19, or a fragment of SEQ ID NO: 14, 15, 17, or 19 in a sample suspected of containing *Salmonella Enteritidis*, wherein the amplification results in the generation of an amplicon having a length between 30 and 856 nucleic acids and corresponding to SEQ ID NO: 14, 15, 17, or 19; and detecting the amplicon corresponding to SEQ ID NO: 14, 15, 17, or 19, wherein detection of the amplicon indicates the presence of the *Salmonella Enteritidis* in the sample.

The invention also features a method of generating a foodstuff packaged for shipment, the method including obtaining a sample of the foodstuff, detecting the presence or absence of *Salmonella Enteritidis* in the sample, and sealing the foodstuff in a package for shipment if it is determined that *Salmonella Enteritidis* is absent from the sample, wherein the detecting the presence or absence of *Salmonella Enteritidis* includes:
i) amplifying a nucleic acid sequence including SEQ ID NO: 14, 15, 17, or 19, or a fragment of SEQ ID NO: 14, 15, 17, or 19 in the sample, wherein the amplification results in the generation of an amplicon having a length between 30 and 856 nucleic acids and corresponding to SEQ ID NO: 14, 15, 17, or 19; and
ii) detecting the amplicon corresponding to SEQ ID NO: 14, 15, 17, or 19, wherein detection of the amplicon indicates the presence of the *Salmonella Enteritidis* in the sample.

The invention also includes a method of detecting *Salmonella Heidelberg* or *Salmonella Infantis* in a sample (e.g., a foodstuff) by amplifying a nucleic acid sequence including SEQ ID NOs: 21 or 22, or a fragment of SEQ ID NOs: 21 or 22 in a sample suspected of containing *Salmonella Heidelberg* or *Salmonella Infantis*, wherein the amplification results in the generation of an amplicon having a length between 30 and 753 nucleic acids and corresponding to SEQ ID NOs: 21 or 22; and detecting the amplicon and corresponding to SEQ ID NOs: 21 or 22, wherein detection of the amplicon corresponding to SEQ ID NOs: 21 or 22 indicates the presence of the *Salmonella Heidelberg* or *Salmonella Infantis* in the sample.

In another embodiment, the invention features a method of generating a foodstuff packaged for shipment, the method including obtaining a sample of the foodstuff, detecting the presence or absence of *Salmonella Heidelberg* or *Salmonella Infantis* in the sample, and sealing the foodstuff in a package for shipment if it is determined that *Salmonella Heidelberg* or *Salmonella Infantis* is absent from the sample, wherein the detecting the presence or absence of *Salmonella Heidelberg* or *Salmonella Infantis* includes:
i) amplifying a nucleic acid sequence including SEQ ID NOs: 21 or 22, or a fragment of SEQ ID NOs: 21 or 22 in the sample, wherein the amplification results in the generation of an amplicon having a length between 30 and 753 nucleic acids and corresponding to SEQ ID NOs: 21 or 22; and
ii) detecting the amplicon corresponding to SEQ ID NOs: 21 or 22 wherein detection of the amplicon indicates the presence of the *Salmonella Heidelberg* or *Salmonella Infantis* in the sample.

In another embodiment, the invention features a method of detecting *Salmonella Newport* or *Salmonella Hadar* in a sample (e.g., a foodstuff) by amplifying a nucleic acid sequence including SEQ ID NO: 24, or a fragment of SEQ ID NO: 24 in a sample suspected of containing *Salmonella Newport* or *Salmonella Hadar*, wherein the amplification results in the generation of an amplicon having a length between 30 and 1819 nucleic acids and corresponding to SEQ ID NO: 24; and detecting the amplicon corresponding to SEQ ID NO: 24, wherein detection of the amplicon indicates the presence of the *Salmonella Newport* or *Salmonella Hadar* in the sample.

In yet another embodiment, the invention features a method of generating a foodstuff packaged for shipment, the method including obtaining a sample of the foodstuff, detecting the presence or absence of *Salmonella Newport* or *Salmonella Hadar* in the sample, and sealing the foodstuff in a package for shipment if it is determined that *Salmonella Newport* or *Salmonella Hadar* is absent from the sample, wherein the detecting the presence or absence of *Salmonella Newport* or *Salmonella Hadar* includes:
i) amplifying a nucleic acid sequence including SEQ ID NO: 24, or a fragment of SEQ ID NO: 24 in the sample, wherein the amplification results in the generation of an amplicon having a length between 30 and 1819 nucleic acids and corresponding to SEQ ID NO: 24; and
ii) detecting the amplicon corresponding to SEQ ID NO: 24, wherein detection of the amplicon indicates the presence of the *Salmonella Newport* or *Salmonella Hadar* in the sample.

In yet another embodiment, the invention features a method of detecting *Salmonella Typhimurium* in a sample (e.g., a foodstuff) by amplifying a nucleic acid sequence including SEQ ID NO: 28, or a fragment of SEQ ID NO: 28 in a sample suspected of containing *Salmonella Typhimurium*, wherein the amplification results in the generation of an amplicon having a length between 30 and 1081 nucleic acids and corresponding to SEQ ID NO: 28; and detecting the amplicon corresponding to SEQ ID NO: 28, wherein detection of the amplicon indicates the presence of the *Salmonella Typhimurium* in the sample.

In another embodiment, the invention features a method of generating a foodstuff packaged for shipment, the method including obtaining a sample of the foodstuff, detecting the presence or absence of *Salmonella Typhimurium* in the sample, and sealing the foodstuff in a package for shipment if it is determined that *Salmonella Typhimurium* is absent from the sample, wherein the detecting the presence or absence of *Salmonella Typhimurium* includes:
i) amplifying a nucleic acid sequence including SEQ ID NO: 28, or a fragment of SEQ ID NO: 28 in the sample, wherein the amplification results in the generation of an amplicon having a length between 30 and 1081 nucleic acids and corresponding to SEQ ID NO: 28; and ii) detecting the amplicon corresponding to SEQ ID NO: 28, wherein detection of the amplicon indicates the presence of the *Salmonella Typhimurium* in the sample.

The invention also features detecting more than one serovar of *Salmonella* in a sample. For example, the invention can, in some embodiments, include the detection of combinations of any or all of *S. enteritidis, heidelberg, typhimurium, hadar, infantis, virchow* and/or *newport*.

In any of the foregoing methods, the detecting of the amplicon or amplicons corresponding to any of SEQ ID NOS: 14, 15, 17, 19, 21, 22, 24 and 28 includes contacting the amplicon or amplicons with a detectably labeled nucleic acid probe including a sequence substantially identical to a fragment of the sequence of any of SEQ ID NOS: 14, 15, 17, 19, 21, 22, 24 and 28, respectively, or the complementary strand thereof.

The foodstuff of any of the foregoing methods can be meat, poultry, pasteurized egg, and/or catfish products. The sample can be obtained by, e.g., homogenizing a portion of the foodstuff.

In another aspect, the invention features a nucleic acid including a nucleic acid having: a sequence substantially identical to a fragment of the sequence of SEQ ID NO: 14, 15, 17, or 19, or the complementary strand thereof, wherein the fragment of the sequence of SEQ ID NO: 14, 15, 17, or 19, or the complementary strand thereof, has a length of between 10 and 70 nucleic acids; a nucleic acid having a sequence substantially identical to a fragment of the sequence of SEQ ID NOs: 21 or 22, or the complementary strand thereof; and wherein the fragment of the sequence of SEQ ID NOs: 21 or 22, or the complementary strand thereof, has a length of between 10 and 70 nucleic acids; a sequence substantially identical to a fragment of the sequence of SEQ ID NO: 24, or the complementary strand thereof; and wherein the fragment of the sequence of SEQ ID NO: 24, or the complementary strand thereof, has a length of between 10 and 70 nucleic acids; and/or a sequence substantially identical to a fragment of the sequence of SEQ ID NO: 28, or the complementary strand thereof; wherein the fragment of the sequence of SEQ ID NO: 28, or the complementary strand thereof, has a length of between 10 and 70 nucleic acids. In certain embodiments, the nucleic acid will include a detectable label (e.g., a fluorophore, a radioactive moiety, and a luminescent moiety).

DESCRIPTION OF THE DRAWINGS

For a more complete understanding of the features and advantages of the present invention, reference is now made to the detailed description of the invention along with the accompanying figures and in which:

FIG. 1A is an alignment of the Ent37b1 conserved serotype-specific sequence of the *S. Enteritidis* serovar. The boldface regions are exclusive to *S. Enteritidis*. The aligned sequence is SEQ ID NO: 16. The boldface sequence has the sequence of SEQ ID NO: 17

FIG. 1B is an alignment of the Ent37b2 conserved serotype-specific sequence of the *S. Enteritidis* serovar. The boldface regions are exclusive to *S. Enteritidis*. The aligned sequence is SEQ ID NO: 13. The boldface sequences have the sequence of SEQ ID NO: 14 and SEQ ID NO: 15.

FIG. 1C is an alignment of the Ent37b3 conserved serotype-specific sequence of the *S. Enteritidis* serovar. The boldface regions are exclusive to *S. Enteritidis*. The aligned sequence is SEQ ID NO: 18. The boldface sequence has the sequence of SEQ ID NO: 19.

FIG. 2 is an alignment of a conserved serotype-specific region of *S. Heidelberg*. The aligned sequence is SEQ ID NO: 20. The boldface regions are exclusive to *S. Heidelberg* and *S. Infantis*. The boldface sequences have the sequence of SEQ ID NO: 21 and SEQ ID NO: 22.

FIGS. 3A-3D are images that show 4 alignments of *S. Newport* targeted sequence.

FIG. 4 is an image that shows the *S. Typhimurium* ORF sequence. The boldface region is exclusive to *S. Typhimurium*. The ORF sequence is SEQ ID NO: 26 and the boldface region is SEQ ID NO: 28

FIGS. 5A-5L are tables that illustrates the strain ID and the serotype results for the primers.

FIG. 6 is an alignment of a conserved serotype-specific region of *S. Newport*. The alignment shows a consensus sequence between various *Newport* strains and three *Hadar* strains (ABFG01000003, ALPP01000002, and ABFG01000044). The region is the ORF of a glycosyl transferase. The boldface region is exclusive to *S. Newport* or *S. Hadar*. The aligned consensus sequence is SEQ ID NO: 23 and the boldface region is SEQ ID NO: 24.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Various *Salmonella* strains are common foodborne microbes that cause disease in humans and animals. For example, some strains can cause intestinal infections, while others can cause typhoid fever. Because of the large variety of *Salmonella* strains present and the different pathogenic effects of these strains, it is important to develop rapid and flexible assays that have the capacity to distinguish between these strains.

Presently, *Salmonella* serotype determination takes a long period of time and can be inaccurate. This technology allows for the rapid characterization of *Salmonella*, and specifically distinguishes between those serotypes in the United States and European Union, allowing government and industry to make a determination of a serotype within hours that would have previously taken days. For the most part *Salmonella* serotyping has been used to characterize isolates from culture confirmed samples. The present invention provides screening enrichments for the presence (or absence) of regulated (and potentially regulated) *Salmonella* serotypes so that the decision can be made to accept or reject a food product. This benefit is especially important with regard to perishable food products.

The invention provides oligonucleotides that enable the detection of *Salmonella* by nucleic acid hybridization, notably by nucleic acid amplification, more particularly, by PCR, advantageously by multiplex amplification (e.g., multiplex PCR), very advantageously, by real-time multiplex amplification (e.g., real-time multiplex PCR).

The present invention features methods and compositions for identifying certain serovars of *Salmonella enterica*. These serovars include *Salmonella enteritis, heidelberg, typhimurium, hadar, infantis, virchow* and *newport*. This invention is based on the identification of certain sequences that are exclusive to these individual serovars. The invention includes methods of identifying whether a particular serovar (e.g., *enteritis, heidelberg, typhimurium, Hadar, infantis, virchow* and/or *newport*) is present in a sample. Such methods include any method known in the art for detecting a nucleic acid with a particular target sequence (e.g., a region exclusive to a particular serovar of *Salmonella*) in a sample, e.g., amplification reactions of the target sequence. The invention also features nucleic acid probes (e.g., nucleic acid sequences having a detectable label which hybridizes to the target sequence) and primers for amplification (e.g., PCR or transcription-based amplification). Such probes and primers hybridize to the target nucleic acids or nucleic acids proximate to the target nucleic acids.

The present invention also provides a primer-probe based real-time PCR (RTi PCR) assays to identify whether a *Salmonella* isolate (belongs to the regulated serotypes: 1 assay for Europe and 1 assay for the United States) or if it is outside of that group of serotypes. Specifically we have developed unique primers to detect genes SNSL254_A0607, STM4494, and CFSAN002069_17050 for detection of likely United States regulated serotypes and genes SEN1394, SNSL254_A0607, STM4494, CFSAN002069_17050, and SeV_B2621 for the 5 regulated serotypes in the European Union. With this approach, we can accurately determine the presence of a *Salmonella* isolate belonging to the regulated and/or potentially regulated serotypes is present.

The present invention includes a rapid assay to quickly categorize a *Salmonella* isolate in the United States or European Union depending on the gene targets (and identify them as regulated and/or potentially regulated). This invention allows key stakeholders (i.e., government and industry) to quickly make decision (within hours) that today take days to make which is important for perishable products. The present invention provides an assay that can quickly recognize whether or not a sample contains a regulated (or potentially regulated) *Salmonella* serotype. In addition, the assay could be used for downstream applications to characterize suspect colonies on plates.

Presently *Salmonella* serotype determination takes a long period of time and is invariably inaccurate. The present invention allows for the rapid characterization of *Salmonella* as being regulated or not. Also, if it is regulated, we can further categorize which of the regulated serotypes it is. The present invention includes primers to detect 2 batteries of sequences one specifically for the United States and one for the European Union.

In total, 447 strains were investigated. Of these, 205 were provided to us by Cornell University, 82 were supplied by the French Food Safety Agency and had been isolated from food products in France, and the remainder was available to us in the isolate bank of the Food Safety Laboratory at Texas Tech University. All isolates used had been previously serotyped using the conventional approach either in France (ANSES, Paris), or in the US (USDA, Nebraska).

Serotypes were selected to be tested against the markers in the RT PCR assay based on their prevalence in human and non-human cases of Salmonellosis, according to data collected by the CDC. In addition to the five targeted serotypes, 30 serotypes with the highest percentages of reported cases of Salmonellosis attribution were included. Also included in the exclusivity panel were serotypes that very rarely caused disease, or only caused disease in animals. To investigate the intra-serotype variability, when it was possible, we selected at least 25 strains for each targeted serotype and 5 strains for each of the 30 most prevalent serotypes. In total, the exclusivity panel includes 121 serotypes from *S. enterica* subsp. *enterica*, together with few strains of the 5 other *Salmonella* subspecies. Also included outside genus isolates from the Enterobacteriaceae family as well as similar organisms to *Salmonella enterica*. These strains belong to 13 different genera. The inclusivity panel included *S. Typhimurium* (25), *S. Enteritidis* (26), *S. Newport* (30); 4 of which were characterized as Glade A and 5 as Glade B, *S. Heidelberg* (27) and *S. Hadar* (25). The exclusivity panel included *Salmonella* strains: S.I 4,5,12:b:- (1), S.I 4,5,12:b:- var. L(+) tartrate (1), S.I 1,4,[5],12:i:- (17), S.I 4,5,12:r:- (1), S.1,4,[5],12:-:1,2 (1), S.I 6,7:-:1,5 (1), S.I 6,7:k:- (1), S.II (2), S.IIIa 18:z4,z23:- (1), S.IIIa (1), S.IIIb 50:k:z (1), S.IIIb 50:r:z (1), S.IIIb 61:1,v:1,5,7 (1), S.IV 44:z4,z23:- (1), S.IV 48:g,z51:- (1), S.IV 50:g,z51:- (1), S.V (1), Aarhus (1), Aberdeen (1), Abony (1), Adelaide (1), Agbeni (1), Agona (5), Alachua (1), Albany (1), Amager (1), Anatum (4), Anatum variant 15+ (1), Apapa (1), Arechaveleta (1), Baildon (1), Bardo (1), Bareilly (5), Barranquilla (1), Berta (1), Blockley (1), Bovismorbificans (1), Braenderup (5), Brandenburg (3), Bredeney (4), Carrau (1), Cerro (5), Chester (1), Choleraesuis (1), Colindale (1), Concord (1), Copenhagen (1), Corvallis (1), Cotham (1), Cubana (1), Derby (3), Dublin (3), Durban (1), Ealing (1), Florida (1), Gaminara (1), Give (3), Give variant 15+ (1), Glostrup (1), Grumpensis (1), Hartford (1), Havana (2), Hindmarsh (1), Holcomb (1), Hvitthingfoss (1), Ibadan (1), Indiana (1), Infantis (12), Inverness (1), Istanbul (1), Itami (1), Javiana (5), Johannesburg (1), Kentucky (12), Kiambu (1), Kintambo (1), Kottbus (1), Kuzendorf (1), Lexington (1), Lille (4), Litchfield (1), Liverpool (1), Livingstone (1), London (1), Luciana (1), Madelia (1), Manhattan (2), Mbandaka (6), Meleagridis (5), Miami (1), Mikawasima (1), Minnesota (1), Mississippi (5), Monschaui (1), Montevideo (11), Muenchen (9), Muenster (2), Napoli (1), Norwich (1), Ohio (2), Oranienburg (5), Orion (1), Panama (2), ParatyphiB (5), Pomona (1), Poona (1), Potsdam (1), Putten (1), Reading (11), Richmond (1), Rissen (1), Roodeport (1), Rubislaw (1), SaintPaul (5), SanDiego (1), Saphra (1), Schwarzengrund (5), Senftenberg (5), Stanley (1), Sundsvall (2), Telekelbir (1), Tennessee (1), Thompson (5), Typhi (5), Uganda (2), Urbana (1), *Virchow* (10), Wandsworth (1), Waycross (1), Weltevreden (1), Worthington (4). The non-*Salmonella* strains included *Aeromonas hydrophila/caviae* (1), *Citrobacter freundii* (1), *Cronobacter sakazakii* (1), *Enterobacter aerogenes* (1), *Hafnia paralvei* (1), *Klebsiella oxytoca* (1), *Klebsiella pneumoniae* (1), *Pantoea agglomerans* (1), *Pseudomonas fluorescens* (1), *Pseudomonas fragi* (1), *Pseudomonas aeruginosa* (1), *Proteus vulgaris* (1), *Serratia marcesans* (1), *Shigella flexneri* (1), *Shigella sonneii* (1), *Vibrio mimicus* (1), *Vibrio parahaemolyticus* (1), *Yersinia entercolitica* (1).

The present invention provided DNA extractions that were either provided or were performed as described herein. In brief, organisms were grown up on a BHI agar plate and one isolated colony was transferred into 50 ul of distilled water. The tubes were incubated for 10 minutes at 95-99° C. and then centrifuged for 3 minutes at maximum speed. The supernatant containing the DNA was then transferred to a fresh 1.5 ml microcentrifuge tube and stored at −20° C. until use. DNA extractions provided by ANSES were performed using the Instagene Matrix (BioRad, Berkeley, Calif., USA) following the manufacturer's recommendations. The PureLink Genomic DNA Mini Kit (Invitrogen, Carlsbad, Calif., USA) was used to extract the genomic DNA following the manufacturer's recommendations, and it was then quantified using the Nanodrop 2000c Spectrophotometer (ThermoScientific, Waltham, Mass., USA).

The present invention provided RNA extractions from an overnight culture of each of the 5 serotypes of interest. Cultures were grown in 50 mL flasks with an estimated final concentration of roughly $10^9$ CFU/ml. The cultures were pelletized and treated with RNA Protect (Qiagen, Venlo, The Netherlands) for overnight storage. Extraction was performed using a modified version of the TRI Reagent protocol (Molecular Research Center, Inc., Cincinnati, Ohio). Briefly, pelleted cells were resuspended in TRI Reagent to lyse, then bromochloropropane (BCP) was added to induce phase separation. A supernatant containing RNA was transferred to a new tube, then isopropanol was added to precipitate the RNA, the tubes were spun to pelletize the RNA, and then this supernatant was removed. The pellets were washed with an Ethanol solution, dried, treated with DNAse (Promega, Madison, Wis.), quantified using the Nanodrop 2000c Spectrophotometer (ThermoScientific, Waltham, Mass., USA), and stored in −80° C. until ready for use in quantitative reverse transcriptase (qRT) realtime (RTi) PCR.

The primer and probe sequences are shown in the table below:

FIG. 1B is an alignment of the Ent37b2 conserved serotype-specific sequence of the *S. Enteritidis* serovar. The boldface regions are ORFs located in this sequence. The aligned sequence is SEQ ID NO: 13. The sequence includes SEQ ID NO: 14 and the sequence includes SEQ ID NO: 15.

FIG. 1C is an alignment of the Ent37b3 conserved serotype-specific sequence of the *S. Enteritidis* serovar. The boldface regions are ORFs located in this sequence. The aligned sequence is SEQ ID NO: 18. The sequence includes SEQ ID NO: 19.

FIG. 2 is an alignment of a conserved serotype-specific region of *S. Heidelberg*. The alignment shows a consensus sequence between the *Heidelberg* strains: CFSAN00328 (AMBX01000015), CFSAN00325 (AMBV01000052), CFSAN00322 (AMBU01000072), 41565 (AJHA01000079), 41566 (AJGZ01000001), 41563 (AJGX01000034), 41579 (AJGW01000056), SL486 (ABEL01000005), CFSAN00326 (AMBW01000028), and 41573 (AJGY01000001). The boldface regions are ORFs located in this sequence. The aligned sequence is SEQ ID NO: 20. The first boldface sequence is SEQ ID NO: 21 (6-phospho-3-hexuloisomerase) and the second boldface sequence is SEQ ID NO: 22 (3-oxoacyl ACP reductase). The region containing the first boldface sequence SEQ ID NO: 21 to the end of the second boldface sequence is SEQ ID NO: 22 is listed as SEQ ID NO: 27.

FIGS. 3A-3D are images that show 4 alignments of *S. Newport* targeted sequence. FIG. 3A: Alignment #1 of *Newport* targeted region with localization of the primers and

| Name | Sequence (5' . . . 3') | |
|---|---|---|
| Ent6 FPrimer | TCGTACCTGCTGATGCTGGG | SEQ ID NO: 1 |
| Ent6 Probe | HEX-TATGCGCTGGTTCCGTTCCGTTTTCTGG-BHQ2 | SEQ ID NO: 2 |
| Ent6 RPrimer | AGGATGAAGACGGGTAATGTCC | SEQ ID NO: 3 |
| Newp2 FPrimer | AATGGCTGGTAGCCTGTTCG | SEQ ID NO: 4 |
| Newp2 Probe | Cy5-TCATGCTATGCACTGGGAACAATTTCTGGC-IowaBRQ | SEQ ID NO: 5 |
| Newp2 RPrimer | AGGGAAAGCAAGGAACAGTAG | SEQ ID NO: 6 |
| STM2 FPrimer | AGATATTCCGTAGCAATTGAGTTG | SEQ ID NO: 7 |
| STM2 Probe | FAM-TGTGTTCAAGCAATGGTGAACAAACATAATCCC-BHQ2 | SEQ ID NO: 8 |
| STM2 RPrimer | AATAGCTAAAAATGACTGGGACTC | SEQ ID NO: 9 |
| Heid2 FPrimer | CCTGCAGAAAGATATGTTTGGC | SEQ ID NO: 10 |
| Heid2 Probe | HEX-TTAATCTGTGCGACGAATTGGGCAGCC-BHQ2 | SEQ ID NO: 11 |
| Heid2 RPrimer | TGCGATGAAGATTGATGATGCC | SEQ ID NO: 12 |

It will be understood that the present invention includes sequences similar to the primer and probe sequences listed herein. The included sequences have a homology of between 85 and 100% homology to the sequences listed herein. For example, the homology may be 85, 86, 87, 88, 89, 90, 91, 92, 93, 94, 95, 96, 97, 98, or 99 percent to the primers and sequences listed herein.

FIG. 1A is an alignment of the Ent37b1 conserved serotype-specific sequence of the *S. Enteritidis* serovar. The boldface regions are open reading frames (ORFs). The aligned sequence is SEQ ID NO: 16. The sequence includes SEQ ID NO: 17.

probe of the marker. Primers are underlined and the probe is in bold and italic. Similar region on Accession number CP001113 from 620724 to 620144. FIG. 3B: Alignment #2 of *Newport* targeted region. Similar region on Accession number CP001113 from 619868 to 619354. FIG. 3C: Alignment #3 of *Newport* targeted region. Similar region on Accession number CP001113 from 619249 to 618599. FIG. 3D: Alignment #4 of *Newport* targeted region. Similar region on Accession number CP001113 from 618473 to 618114.

FIG. 4 is an image that shows the *S. Typhimurium* ORF sequence. FIG. 4 is an alignment of a conserved serotype-specific sequence region of *S. Typhimurium* corresponding to a part of a type II restriction enzyme. The alignment shows a consensus sequence between various *Typhimurium* strains. The ORF sequence is SEQ ID NO: 26. The boldface region is exclusive to *S. Typhimurium* and listed as SEQ ID NO: 28.

FIGS. 5A-5L are tables that illustrates the strain ID and the serotype results for the primers.

FIG. 6 is an alignment of a conserved serotype-specific region of *S. Newport*. The alignment shows a consensus sequence between various *Newport* strains and three *Hadar* strains (ABFG01000003, ALPP01000002, and ABFG01000044). The boldface region is the ORF of a glycosyl transferase. The aligned consensus sequence is SEQ ID NO: 23 and the boldface region is SEQ ID NO: 24.

Real-Time and Real-Time Reverse Transcriptase PCR conditions. Real-Time PCR reactions were performed using the following conditions: 1× Brilliant II master mix (Agilent Technologies, Santa Clara, Calif.), primers at a final concentration of 0.3 uM, probes at a final concentration of 0.6 uM, and 2.5 uL of a dilution at 1/20 of template DNA. The Real-Time PCR reactions were programmed as follows: an initial denaturation step at 95° C. for 10 minutes, then 40 cycles each of 30 seconds at 95° C. and one minute at 61° C. For Reverse-Transcriptase PCR, 62.5 ng of each RNA extraction was investigated. The Reverse-Transcriptase PCR reactions were programmed as follows: an initial reverse transcription step at 50° C. for 30 minutes and a denaturation step at 95° C. for 10 minutes, then 40 cycles each of 30 seconds at 95° C. and one minute at 61° C.

Efficiencies of the real-time primers and probes. Efficiencies of the Real-Time PCR markers were determined by performance of a standard curve using varying concentrations of gDNA from a set of positive control strains belonging to serotypes *S. newport, S. enteritidis, S. typhimurium, S. hadar,* and *S. heidelberg*. Standard curves were performed on each isolate for $10^7$, $10^5$, $10^4$, $10^3$ and $10^2$ copies of DNA per reaction using the same amplification conditions as previously described.

The tables in FIGS. 5A-5L illustrate the Strain ID, the Serotype, primer and provides a result: where (1) the underlined results are true positive results; (2) the results indicated by a "−" are true negative results; (3) the italic results are positive results expected to be negative (i.e., false positive results); (4) the results indicated by a "*" are negative results expected to be positive (i.e., false negative results); and (5) the bold results are delayed results (Ct>35). For each test, the Ct value and the final level of fluorescence are reported. For all the markers the threshold is 1000 units of fluorescence.

*S. Typhimurium* marker (STM2) detects 100% of *S. Typhimurium* and its somatic and flagellar variant (1,4,[5],12:i:-, 1,4,[5],12:-:1,2 and *S. Copenhagen*) strains tested, as well as one strain that had been serotyped as *Heidelberg*. This strain of *S. Heidelberg*, however, did not amplify with the *Heidelberg* marker (Heid2), and is presumed to have been misserotyped.

The *Heidelberg* marker (Heid2) detected all the other *S. heidelberg* isolates tested, but also amplified all 12 of the *S. Infantis* strains that were tested against this marker. This marker detects also one *S. Kintambo* strain and one S.I 4,5,12:r:- strain. Together these 3 cross-reacting serotypes represent less than 2% of human and non-human cases in the United States between 1999 and 2009 (National *Salmonella* Surveillance Annual Summary 2009).

The *Newport* marker (Newp2) detected all *S. Newport* strains tested, including isolates from both clades A and B, as well as 23 of 25 *S. Hadar* strains that were tested in the study. Furthermore, this marker also detects few strains belonging to other serotypes, such as *Bardo, Blockley, Bovismorbificans, Glostrup, Istanbul, Kottbus, Litchfield, Manhattan, Muenchen,* and *Virchow*.

The *Enteritidis* marker (Ent6) detects 24 out of the 26 *S. Enteritidis* strains tested. This marker does not strongly cross-react with non-targeted serotypes, but present several weak cross-reactions with diverse serotypes.

Furthermore, we investigated the expression of these 4 targeted regions. We were able to highlight the expression of the targeted regions for *S. Typhimurium, S. Heidelberg* and *S. Newport* markers. Only the *Enteritidis* marker seems to be located on a non-coding region.

| Marker | Targeted serotypes | Inclusivity panel | Cross-reacted serotypes | % cross-reactivity[a] | Diagnostic sensitivity[b] | Diagnostic specificity[c] |
|---|---|---|---|---|---|---|
| STM2 | *Typhimurium* and its variants | 44/44 | / | 0% | 1 | 1 |
| Ent6 | *Enteritidis* | 24/26 | / | 0% | 0.96 | 1 |
| Heid2 | Heidelberg | 26/27 | Infantis, Kintambo, S.I 4,5,12:r:— | 1.526% | 0.96 | 0.97 |
| Newp2 | Newport and Hadar | 53/55 | Bardo, Blockley, Glostrup, Bovismorbificans, Istanbul, Kottbus, Litchfield, Muenchen, Manhattan, Virchow | 3.582% | 0.96 | 0.97 |

[a] in human cases in the US between 1999 and 2009 according to the CDC report titled National *Salmonella* Surveillance Annual Summary 2009. Only the strong cross-reactions with a Ct < 32 were considered.
[b] Diagnostic sensitivity: number of true positive/number of expected positive (Saah and Hoover, 1997).
[c] Diagnostic specificity: number of true negative/number of expected positive (Saah and Hoover, 1997).

The invention also featured the identification of regions containing several open reading frames (ORFs) that were exclusive to each of *S. Enteritidis, Heidelberg, Newport,* and *Typhimurium*. FIGS. 1(A-C) contain alignments of the Ent37b1, Ent37b2, and Ent37b3 serotype-specific regions including some ORFs of *S. Enteritidis* serovar. The boldface regions of each region are the ORFs. FIG. 2 contains an alignment of a region of the *S. Heidelberg* serovar exclusive to *Heidelberg*. The boldface regions of this sequence are ORFs of *S. Heidelberg*. FIG. 6 contains an alignment of a serotype-specific region of *S. Newport*. The boldface regions of this sequence are ORFs of S. Newport. FIG. 7 is a part of an ORF from S. Typhimurium which is exclusive to S. Typhimurium.

The methods of the invention can be applied to detection of Salmonella in a variety of samples, including foodstuff samples. Such foodstuff samples can be derived from, e.g., beef (e.g., frozen or raw), chicken (e.g., cooked deli or raw), cod, cookie dough, eggs, lettuce, tomatoes, turkey (e.g., cooked deli or raw), black pepper, cheese (e.g., string cheese), chocolate (e.g., milk), cocoa, eggs (e.g., pasteurized, dried, or whole), milk (e.g., instant, nonfat, or dry), nacho cheese seasoning, pasta, pet food, peanut butter (e.g., non-organic and/or creamy), or soy flour. Other samples include environmental samples (e.g., plastic, sealed concrete, and stainless steel). The methods can be performed at the farm or processing facility prior to initial packaging, after packaging (e.g., prior to or after export from one country to another), or at the point of sale.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

---

The invention claimed is:

1. A method of checking the safety of a foodstuff for Salmonella comprising the steps of:
   providing a foodstuff suspected of being contaminated with Salmonella;
   homogenizing the foodstuff;
   extracting a nucleic acid sample from a homogenized foodstuff;
   adding a set of primers to the nucleic acid sample, wherein the set of primers comprise at least one primer set selected from SEQ ID NOS: 1 and 3; SEQ ID NOS: 4 and 6; SEQ ID NOS: 7 and 9; and SEQ ID NOS: 10 and 12;
   adding one or more Salmonella isolate identification probes to the nucleic acid sample, wherein the one or more Salmonella isolate identification probes are selected from SEQ ID NO: 2, SEQ ID NO: 5, SEQ ID NO: 8, and SEQ ID NO: 11;
   amplifying the nucleic acid sample using the set of primers to from an amplified nucleic acid sample to form a double stranded DNA;
   destroying the one or more Salmonella isolate identification probes as the double stranded DNA is formed;
   releasing a fluorophore attached to the one or more Salmonella isolate identification probes; and
   detecting the presence of the fluorophore, wherein a positive detection is indicative of at least one Salmonella being present in the sample.

2. The method of claim 1, wherein the foodstuff is for human consumption, animal consumption or both.

3. The method of claim 1, wherein the foodstuff is a food or a beverage.

4. The method of claim 1, wherein the Salmonella is selected from Typhimurium, Enteritidis, Newport, Heidelberg, Infantis, Virchow and Hadar.

5. The method of claim 1, wherein the foodstuff is selected from the group consisting of meat, poultry, pasteurized egg, and catfish products.

\* \* \* \* \*

SEQUENCE LISTING

```
<160> NUMBER OF SEQ ID NOS: 80

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tcgtacctgc tgatgctggg                                                   20

<210> SEQ ID NO 2
<211> LENGTH: 28
<212> TYPE: DNA
<213> ORGANISM: Artificial Sequence
<220> FEATURE:
<223> OTHER INFORMATION: Synthetic primer

<400> SEQUENCE: 2
tatgcgctgg ttccgttccg ttttctgg                                          28

<210> SEQ ID NO 3
<211> LENGTH: 22
<212> TYPE: DNA
<213> ORGANISM: Artificial Sequence
<220> FEATURE:
```

```
<223> OTHER INFORMATION: Synthetic primer

<400> SEQUENCE: 3
aggatgaaga cgggtaatgt cc                                              22

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
aatggctggt agcctgttcg                                                 20

<210> SEQ ID NO 5
<211> LENGTH: 30
<212> TYPE: DNA
<213> ORGANISM: Artificial Sequence
<220> FEATURE:
<223> OTHER INFORMATION: Synthetic primer

<400> SEQUENCE: 5
tcatgctatg cactgggaac aatttctggc                                      30

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
agggaaagca aggaacagta g                                               21

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
agatattccg tagcaattga gttg                                            24

<210> SEQ ID NO 8
<211> LENGTH: 33
<212> TYPE: DNA
<213> ORGANISM: Artificial Sequence
<220> FEATURE:
<223> OTHER INFORMATION: Synthetic primer

<400> SEQUENCE: 8
tgtgttcaag caatggtgaa caaacataat ccc                                  33

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9
aatagctaaa aatgactggg actc                                            24
```

```
<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
cctgcagaaa gatatgtttg gc                                          22

<210> SEQ ID NO 11
<211> LENGTH: 27
<212> TYPE: DNA
<213> ORGANISM: Artificial Sequence
<220> FEATURE:
<223> OTHER INFORMATION: Synthetic primer

<400> SEQUENCE: 11
ttaatctgtg cgacgaattg ggcagcc                                     27

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
tgcgatgaag attgatgatg cc                                          22

<210> SEQ ID NO 13
<211> LENGTH: 989
<212> TYPE: DNA
<213> ORGANISM: Artificial Sequence
<220> FEATURE:
<223> OTHER INFORMATION: Synthetic primer

<400> SEQUENCE: 13
ctggcctcgt tcctgtcccg ccttgctgac tacaacggta aaccgctgga tgcgctgtgt    60
gcagtggtga tgtcggtgct gtcagtgaaa tttctgacct tcattcatga ccaggacatt   120
tcatcgctga ccgggttttt tcacggatg cggggaggag ggagtggtca tggaaagtaa    180
tctgaccggc acactgaatg cgggcctgtg cctggtgaca gtgctggccc ttttttctcta   240 ccgccggaac ggcgccagat acaaaccggg aatagcctgg ctgtcgtacc tgctgatgct   300
gggctatgcg ctggttccgt tccgttttct ggccggacat tacccgtctt catcctggcc   360
tgtggtgctg atgaacgcgc tgttctgcgg gctggtgctg gggcgcggg gtaatgtgtc    420 gaaaatactt tcactgctga ggctgcgatg aaaccgaagg acgaaatttt tgatgaaatt   480
ctgggtaagg aaggcggcta cgtcaaccat ccggacgata aaggcgggcc gacaaaatgg   540
ggtattacgg aaaaagttgc ccgcgcccac ggataccgtg gtgatatgcg caatttaacc   600
cgtggacagg cgctggaaat tctggagacc gactactggt acggtccccg ctttgaccgg   660
gtggcgaagg cctcgccgga tgttgctgcc gaactgtgtg acacgggcgt gaacatgggg   720
ccgtcggtgg cagcgaaaat gttgcagcgc tggctgaacg tgttcaacca gggcgggagg   780
ctgtatccgg atatggatac ggacgggcgc atcgggccgc gaacccttaa cgcgttacgt   840
gtttatctgg aaaagcgcgg taaggatggc gagcgtgtac tgctggtggc gctgaactgc   900 acgcagggg agcgctatct ggagctggcg gaaaagcggg aggctgacga gtcgtttgtc   960
tatggctgga tgaaagagcg cgtattgat                                    989
```

<210> SEQ ID NO 14
<211> LENGTH: 70
<212> TYPE: DNA
<213> ORGANISM: Artificial Sequence
<220> FEATURE:
<223> OTHER INFORMATION: Synthetic primer

<400> SEQUENCE: 14

```
ctggcctcgt tcctgtcccg ccttgctgac tacaacggta aaccgctgga tgcgctgtgt      60
gcagtggtga                                                              70
```

<210> SEQ ID NO 15
<211> LENGTH: 825
<212> TYPE: DNA
<213> ORGANISM: Artificial Sequence
<220> FEATURE:
<223> OTHER INFORMATION: Synthetic primer

<400> SEQUENCE: 15

```
tggtcatgga aagtaatctg accggcacac tgaatgcggg cctgtgcctg gtgacagtgc      60
tggccctttt tctctaccgc cggaacggcg ccagatacaa accgggaata gcctggctgt     120
cgtacctgct gatgctgggc tatgcgctgg ttccgttccg ttttctggcc ggacattacc     180
cgtcttcatc ctggcctgtg gtgctgatga acgcgctgtt ctgcgggctg gtgctgtggg     240
cgcggggtaa tgtgtcgaaa atactttcac tgctgaggct gcgatgaaac cgaaggacga     300 aattttgat gaaattctgg gtaaggaagg cggctacgtc aaccatccgg acgataaagg      360
cgggccgaca aaatggggta ttacggaaaa agttgcccgc gcccacggat accgtggtga     420
tatgcgcaat ttaacccgtg acaggcgct ggaaattctg gagaccgact actggtacgg      480
tccccgcttt gaccgggtgg cgaaggcctc gccggatgtt gctgccgaac tgtgtgacac     540
gggcgtgaac atggggccgt cggtggcagc gaaaatgttg cagcgctggc tgaacgtgtt     600
caaccagggc gggaggctgt atccggatat ggatacggac gggcgcatcg gccgcgaac      660 ccttaacgcg ttacgtgttt atctggaaaa gcgcggtaag gatggcgagc gtgtactgct     720
ggtggcgctg aactgcacgc aggggagcg ctatctggag ctggcggaaa agcgggaggc     780
tgacgagtcg tttgtctatg gctggatgaa agagcgcgta ttgat                    825
```

<210> SEQ ID NO 16
<211> LENGTH: 1680
<212> TYPE: DNA
<213> ORGANISM: Artificial Sequence
<220> FEATURE:
<223> OTHER INFORMATION: Synthetic primer

<400> SEQUENCE: 16

```
tgatggataa ccttcttctg cccccgagga tcagagagcc ggttttttg tgcatcctgg      60 aaaattcacg tgaaggaacc ggctctcaac cagagaagaa gaggcgtttt tttcgataca    120
actatcgtaa ttactccgtt ggtggtgctg gcacgtaaag tgtggatagt gcgtttatga    180
tgagtgcatg atgtatatcc tgatacagca tccggtttgt gggggcggag aagccccgat    240
ggactcagtg ccacaatttt ttattgcatt cagatagcgt actgtgaatc ggataaatga    300
gaatgtcagt gtgttggtaa tgcggggttc tcagtgcgct atctgaatgc agtgaaatct    360
gctctgagca gagctaaaca gcattgtctg cgtttgatca atttgtagcg ggtcatagtg    420
gctgactaaa gactctccgg ggcatccgg cactgcattt attactaaaa atcttctat     480 cacagaggca gaacatacgg aaaattcttg tcaatacaac acctgacaca gcaatatttt    540
```

```
tcgggagtcc ccggcgcctc aggttttttta tcgccatcaa taaaactata ataataactc    600
catgttatga ttaccacctc tctctcatga ggtggttttt ttattcccgc aaattgcaga    660
aataagatgg agtcatcaga atatgccctg attgtatttt gtctttttg aattaatgca    720 aaacatttgg aataaataaa catctaatga taaatttaca tttcttgacg cgactgcttg    780
ttgaaatgaa attttatga tttattattg tcgacagttt ggcggaggtg actggcagat    840
ttctccactc cgtcgaataa gagagttgat tctttatacc tcctgagtcg tctgattaaa    900
gaatcatcac tcgatttggc attaaggtga aattaagatt ccattgatat aggtatcgtt    960
cttactcttt gtggtgcagg catatggata tggggtggtt acattaatgt tcctttaatt   1020
taacctcctg atagtgaatc aggcaccgca attttttac tgcattcaga tggcgtactg   1080 caaaaaacg gtcattgctt cgccactgt ctgatgctct gtaacacat acgggatttg   1140 tggtacgcca tctgaatgca gtgaaaccca cataaagtgg ggcataaaca ggatatgagg   1200
tgcgtttatt ttcgtctgcg ggtcatggtg actgaccaac ggccctccgg agataattcc   1260
ggcactgcat tatttattga ggtgttcccc agtgcggggg tgaccgggaa aaatgttctg   1320
ccgatggtca cagacacata ccgggctaat atgtgttttc gggaggcacc cgacacctct   1380 actgttttc cagtcgataa ctataaaaca tgcttcagat attgagcacc gcctcccgtg   1440
aggcggtttt ttttattccg ggaaaaagtt ctgcccgcca tataataaag ttaacgtttt   1500
cagaccaggg tgcgggaagt atccggggcg ggaaataatg aattaaaaaa gaagcgcggc   1560
tgtcggattt aagccgcggg acaatgtccg tgatagatag ttgaaaaatt tcaggctatc   1620
cctttcggga ggtcgccatt attttactca taacaaaata agaccggaac cccggaaaca   1680
```

<210> SEQ ID NO 17
<211> LENGTH: 249
<212> TYPE: DNA
<213> ORGANISM: Artificial Sequence
<220> FEATURE:
<223> OTHER INFORMATION: Synthetic primer

<400> SEQUENCE: 17

```
gtggggcata acaggatat gaggtgcgtt tattttcgtc tgcgggtcat ggtgactgac     60
caacggccct ccggagataa ttccggcact gcattattta ttgaggtgtt ccccagtgcg    120
ggggtgaccg gaaaaatgt tctgccgatg gtcacagaca cataccgggc taatatgtgt    180
tttcgggagg cacccgacac ctctactgtt tttccagtcg ataactataa acatgcttc    240 agatattga                                                            249
```

<210> SEQ ID NO 18
<211> LENGTH: 316
<212> TYPE: DNA
<213> ORGANISM: Artificial Sequence
<220> FEATURE:
<223> OTHER INFORMATION: Synthetic primer

<400> SEQUENCE: 18

```
gctgccgggc agagtcgtag tgaacgtctt tgggcctga aaagtaaatc cccagttgtt     60
gctgacaact ggggatttt ataacagcat ataaatcgta aggaaattg tcatatgcca    120 tattcaagaa cgtgctgagg ttgagaagtt ttggaatttt tcggtggca aaatggggc    180 aaaatgctgt aaaggggca aaatggggc aacaaaagag tggattatcg tagcttattg    240
ttgttgctga taatgcttaa cgcattgaaa aataaataaa actattatgc atcagatggt    300
```

```
tgtgattttt gccctt                                                         316
```

<210> SEQ ID NO 19
<211> LENGTH: 84
<212> TYPE: DNA
<213> ORGANISM: Artificial Sequence
<220> FEATURE:
<223> OTHER INFORMATION: Synthetic primer

<400> SEQUENCE: 19

```
gctgccgggc agagtcgtag tgaacgtctt ttgggcctga aaagtaaatc cccagttgtt    60
gctgacaact ggggattttt ataa                                           84
```

<210> SEQ ID NO 20
<211> LENGTH: 9501
<212> TYPE: DNA
<213> ORGANISM: Artificial Sequence
<220> FEATURE:
<223> OTHER INFORMATION: Synthetic primer

<400> SEQUENCE: 20

```
aaaggaaacg tccctttaag ggacgttttcc gggcgattac tcaaggtcag cgtgtctctt    60
aaacatcgtg tcgctggttt caccgagttg gccatcagc tcaagcacga tagcgtcata    120
ggtgataaag cagagttgct caaaagccga tcccataggc tgcgaaaaag caccttcttc    180
gcgatcgttg tcttctttca cagttccagg caatacaaga gtactttttgg ccagtttgcc    240 gattgtggac tccgctttca ttgtgacaag cgccacatcc acgcacagg ctacggcctt    300 ctgcgccagg ctcaccagac tgccggtctc accgctaccg gagccaataa tgaccaggtc    360
gcccggtttc gtatgaggag aagaaatttc gcccactacg cttactgaaa aaccgaggtg    420
gagaaggcgc tttgcaaagc gcggatggc gatgccgcta cgacccgcgc cctgcagaaa    480
gatatgtttg gcattcttaa tctgtgcgac gaattgggca gcctgggcat catcaatctt    540
catcgcattt gctgcaact cgctcaggat atttaaagta ttttgttgaa cgctcatgtg    600
attccctccc tttaagcgat ggtacgacca ccatccatca gaatggtttg ccctggatg    660 tacgagttgt ctttatcagc caaaagatt gcaaggtttg ctacatcgtc aatggttcca    720
aggcggcgca ctggaatttt ttccagaacg gcatcaagat cggcctgggt aggataattg    780
acgcgcatca tttcaccggt atcaatcagg cgtggagcga tagcattaac attgacaccc    840
ttaggtccca gttctttttgc cagaccacga atcaatcctt caccgccagc tttactggcc    900
gggtaactca cgccaccgcc agtaccggaa agcgccgagc cggatgagat ataaacgata    960
gatccatggt tagtagtgaa gtcgtcgtag aatgctttaa cggtgttaaa caggccagta   1020
aggttaattg caatcgtctt attccactct tcaaaagtga tgttattaac cttattagca   1080
aacgccacgc cagcgtttaa taccaaaata tcaatacgtc cgaaggtttg aaaaacctgc   1140
tcacgaacgt tttccagagc tttcggatcg gatacatcgg ttttaacgaa taaggattta   1200
acattaccga aagttaactc ttcggccgtc tttttaccat tttcttcgtt ataatcgaca   1260
atgacagtat gagccccacg gtctgcgaat tgcttagcaa ttcctttacc gattccatgt   1320
gccccaccgg ttactagcgc gactttacct tcaaatttac tcatttcact atactcctca   1380
aaatctcatg acaaagggga ggacaactcc cctttcaggt aattggtgat ttaatgaatg   1440
ccaataatag cgtccagggt tactgggttt atttggtacc gaactgctat tggatcgctg   1500
cccttaattt ctgatagctt tctctcggtg catcattaaa taacgcgcca ccaacaacaa   1560
ttaaatcagc acccgcttct tttacctttt tagcaatttc agcattaacg ccgccatcaa   1620
```

```
cctcaatctg aatattacgt ccggcaacca tcttttttagt attcctgatt ttctccagac    1680
ttttttcaat aaatgtctga ccaggctgac ctgggttgat ggtcataatc aaaacataat    1740
caatatcatc caggaggtat tcaattacat gttccggcgt ccccggattg agtaccacac    1800
cggctttgcg cccggctttc ttgatcttct ggataatata atgaacgtgc ggcgttgatt    1860
cataatgaac cgagatcatt tccgctccgg ttttaataac atcatcgata tgtctttccg    1920
ggtttgccag catcatatgc acatcaaatg tcattgaact ggcttttttc attgccgcaa    1980
tttggttagg accgaaagct atattgctta cataagtacc atccattaaa tcaacatgca    2040
gaatttctgt ttttctgtt tccagaaact gaatttcttc ctgcaaacgt aatatgtttg    2100
caccaaatac tgatggtaaa atttgtgcca ttttagtcaa ctccagaaat taatgcgtaa    2160
ctgtgctcaa ccagtaggtc agaatctccc atgggccggt taatacgaag tccgtgccct    2220
ggccattaag gccgacgcca gcaccgttca ggaactcagt tgcaccgggc gcgacatacc    2280
cccccagata cataaccact acacagaaca gtaaggttga gataatcgag cgaataacgt    2340
tgccgttact gaccatgact gtcatggtcg tcatgtagat aattgacatc agcacgccga    2400
ttgggaatat ctgaataccc ggtaaaacca gcgcacaaag cattgtcaga gggatggtaa    2460
taacggtgac agtaaccgtt gctgggtcgc caagcgcaag ggcacagtcc atcccgatat    2520
tcagctccgc atctttaccc atctgctttt gcatgatttc tttagcactc ttacctatcg    2580
ggttaagccc ttcataagg accccaacca cttttggcaa cagcaccatg acgccagcca    2640
cgcccatcgc cattggcacg atggttgtaa tgggttgttt ggttaacaat cccaggagac    2700
aaccgacaat cacgccgatg attgcgggtt caccgaatac acccagtcgt ttctgaacgc    2760
tctctaaatc cacatccagc ttgtttaaac ccggaatgaa atcgataatt ttgttaacaa    2820
cccatgcaaa tggaagtgtc catccgatgt ggatcatcgt ggtacaggtc gtcccctcga    2880
ggccgtagta ttctgccat cttggcgcaa taagatcgcc aataaacagt gcggctacgc    2940
tcagagccac ggcgacaccc aacccaagga aaaagctgtc aaagacgaaa tacgcaagag    3000
cccccggaac caggaaatgc atgtagttcc agatgtccac attaagagtt ttggtaagct    3060
tcagacgaac caggatcagg ttcaggataa tgccaatagg aataaccatt gcggcaaacg    3120
gggcaaccca cgcagctgcg ccaacggcag gccatccaat atcagccacg gtgaacccgc    3180
tgccaatttt tgagtaatac gtaattgctg gctgcagggc tgtgtttagc agcccaacaa    3240
ccagtcccag accgatgaaa ccgatatccta cagtgatgcc agatttaata gcggcaccca    3300
ctttcattcg aaaaaccaga cctaaaagga aaataacaag cggcaatatt gctgtagcgc    3360
ccatgcttgt aatagtaaac atgatgcttt ttaacatttc catttaacca tcccccgtct    3420
tttttagact ttagcctttg gaaatttcgc ttaacagttc acctaatttt ttacgcagtg    3480
cggcttcgtt aataccggta ataaaacctg cgacgctcat gtgcggctta ccaatatcac    3540
ctttataatt attcgtcgtc aggaccacat cagcgctttg catttcagag gccagctcgg    3600
acatgctgca tttattaatc ttaaagttgg caattccgta ttcagcacaa accgatttaa    3660
cttcatcagc ggctagtgtg gaggttgcga caccgcttcc gcaggctacg aggatagtaa    3720
tcatggtaaa atctccgggt aattgttatt taattatcgt gttaataaac aatgcctttg    3780
cttcttcagc aggaagctcc agcatctggt ggtaaaaatc agctaactga agatggttaa    3840 acagcgccctt caacaactgc aattgatctg caggttgggg aacaaccagg ttgacaacca    3900
ggcggaccca cagttttttca tcgccatctg cctgattaac ttctatttcc tgtggcaaac    3960
```

```
gaatgatata aatcgccggg ctgacggcgt gctggctatc gcaatggggg atggcgacag    4020
catagccgtc aagtaaaatt ccagttggat agtcggcttc acgttcacgc agcgcctgga    4080
ggtaagtctc tcttacaatc ccatcggcca gatgtttctg gtgaatatgc tccagcactt    4140
catcataatt tttgaatgcc gccccatccg cgacattgat agaaattgca cccactttct    4200
tctcctcacc taacaactcg ctcatgtgag cataaatcca atcacatgag cagttatagc    4260
acatcagtga attgctgaaa tagggagctt gcaaaagtta tatcttgatc acacaaaatc    4320
acatacgcgc aatcattaaa atgctcacat gagcaaacat gccgattgct caatgcacca    4380
caaatgctta taccattgaa ttttaattaa tttaattgaa ttggcttact ttggggattt    4440
ttacgttggt aataattcaa acgctcttat gagcatggcg ttctgatagt tgtggtttct    4500
gcaggacaac ggcacatgaa atgtaccgtt attgaattta gaatcaacag gttatcactg    4560
ttgtatgttt cgcaacttcg gcaataccgt ctttatcagc aatatcatta gtgatcagtg    4620
cggtaatctc agaccagtcg cagatcttaa ataagctgct gcgctggaac ttagtgtaat    4680
cgcccaggat atatttcttc tcggaatggg caatgatcgt tcgatccaaa aaggcatctg    4740
aggaggacgg agtggacggg cccgtcatat tgttgaaacc atcagtgccg ataaagcata    4800
gatcaacgtt aatatcatta atcattgaca cagcccaccc accaaagaca gaagagcttt    4860
ttttcctcag ttctccgccg aacaaaaaga cctggttatc tgactcgatc agcacactgg    4920
ccaccggcaa agaatcggta aaaattttaa agccagattt catgcacaac agattagcca    4980
gttcatagtt agaactcccg gtaccaataa tcattgagct attgggggggg ataaaatcca    5040 gcgcttttct ggctatagct tgtttgaaag tactgttttc ttttccctg acctggaaag    5100 gatgttcgac cgccccctgc tttaaggttg cacctccatg gcttttaacc agcagccctt    5160
ttttttcaag atgggtgaga tctttgcgga tggtttcata agtgacctca tacttttttag   5220 caagatcgct aacgtacacg gtacccgccg aaataatctc ttcaaggatc aatttttctcc   5280 tttcttcaac caggtacatc cttcccccct ataaccattc aactcaatgc catgaagcga    5340
atcatagcac acaagatgca aacaaaaaca aactcaagga gaagacaagt tgccatcggc    5400
ctgtgagcag tcattcgcga aagtaacagt cgaaaaaaaa taaatatttt ttaaatcaat    5460
acattaaatg cgttaaatcg agtttattgt ctacagccta taaatccttt ttccctgaat    5520
ggcacaacac aattggtata aattagttt tatttgtttt tattggtttt taattttaaat    5580 aaaatcaata agttatgaat tttgtgattt tgatctcagt tgacaaccaa tatttaccaa    5640
cagcatactt ggcttaagtt cttatatgaca ggttagttga gatgaaaacg aaaattgcaa    5700
tcgcatgtga tgatgtaggg tttgatcgta aggaggagat taaaaagtac cttgaagaag    5760
agaaaaatgc agatgtcgtg tacgatcccg taaaacgaaa agaagacggt ttcaacaact    5820
tcgctcgtct ggcggatgaa atggcaggtg ttattcagcg ggatgaatgc cgcctcggta    5880
tctacatctg tggaaccgga attggcttta cttgccagat aaataagcac tgggggatcc    5940
gtgcagtcgc cgtcaccaac ccctactcag ccaagcgagc aagactcagt aacaatgctc    6000
aggtgattgg tcttggctgc agagttaatg atcttgaata cacaaaaatg atcgttgatg    6060
cctggtatga caatgcgttc gactttgcca ctgcaaggga aaattccaaa aagaatctac    6120
tcgaagcaga acgcagcgac aacgcattgc tgacgaaacc tgaagatgtg cgatggaata    6180
tgggtttcag accagatgat gagaaatctg agggctaata aatggaactg atcacacagt    6240
ttatcaatga cctgggtaac tttattttta taccggtcat tttccttgta ctgatgaaac    6300
ttctggggcg tccgctgtcg gagtgtattt catcagccat taaagtcggc atcggtttta    6360
```

```
ttgcattaac catgaccatc aagctgatgc ttgaaaaaat gcagccagcg gtgacagggc    6420
ttgctgaggc caccggctcc tcactgagcg ccattgatgt tggtggcgca gccacagcag    6480
ttatgggttt tggctcaagc atgggggcga taattattcc actgtgcgtt gccgtgaata    6540
ttgccatgct ggtggcccgt tgacggact  gcgtaaacgt tgacgtattt aaccttcacc    6600
aaaatgcctc aatgggagca atcgttggag tttactccgg cagcttcctt tacggtgttc    6660
ttacggctgc attgttccat gtctgggcgc ttattgcggc tgacctgggt gcgaaaaaca    6720
acgaaaaatt cttcaacctg ccaaaaggcg ttgccatctc ccacccggtt gcaaacacct    6780
atttgctgtt cgcttatccg tttaactgga tatacgatcg catccctgga ttccgtaatc    6840
tgaacgttac ggcggaaagc attcagaaac gctttggtat ccttggcgat ccgaccatgg    6900
ttggtttcat tattggtatt cttcttggct tctgtggtta tggttgggaa tctccgtatc    6960
acaccattat cgccagcctg cagttgggta tgtaccttgc cgccgtgatg ctcctgctgc    7020
cgcgcatgac ctcaatcatg atggaaggtc tggttccgct ctccaacgtg gcacgtaaga    7080
aactggttaa acgtttcccg gatcgtgaga tcactgtcgg gatggatacc gcactgatag    7140
ttggtcatcc gtccgttatc gcgcctgcac tgctgctgat cccggtcatt gttatcctcg    7200
ccgttgtcct tcccggcaac cgagtgatgc cgctggggga cctctcacag ttcgtattct    7260
ttattgcgtg catggtaccg gttttttaatg gcaacattat tcgtacctgg gtgacttcca    7320 tcatccttt tggcggcggc ttatacatcg catcctggat ggctccagca acaaatgaag    7380
tgtttcagaa attcggcact aatcctgatg ccagcgtgat gtactcatcg cttaacccttt    7440 cagctaaccc gttcaccgga ctctttgctg gactcagcca tgttggcatc gcaggttatg    7500
ctctcgccgc tgtgtggctg ttgtccgtag gctatttact caaacagaaa gcacgccgtc    7560
agttgaaaac tgaggcagaa aaaacggctt aaaacttcat aaggtgattg aaaatgaaaa    7620 agatttagt tgtatgcgga aacggcatag cctcctcttc catcatggtt tctgtcctgc    7680
aggactacct gaaagaacag aatatcgaag cgcaggtaga taaatcctca ttgatggctt    7740
gcaccacgga cacatttaac agctatgacc tgattgtttc ttcaaccaag ctggataacc    7800
caggcatcac tactcgtgtg attgtcggag cgggcctgtt aacgggattg ggcgaagatg    7860 agattttga tgctgttaaa gaagaaatgc ttaagtaggt gaatgatgaa gcttgagatt    7920
ctggtaaatg acgttgaggg tacgatcgct gactggcatg cagcaattga gtttgccggc    7980
cagaagcttt tggagaaagg ctatatcact cccgagtata ttcaggcctg cctggagcgt    8040
gaaaagactt atccaacggg tttattgatg gcgaacggtc agggcattgc catcccgcat    8100
gcagactata cgctggtaaa aaccaacagc ataagcattg tgcgttttga taaaggagtc    8160
gtgtttggtc agatggaaga tgctgaccta acagttgaat gcagcattat gtttaatctc    8220
gcattcgcaa ccagcgacca gcatatgtct gtgctgcgtc gccttttttac gctcttccag    8280 gatatttcat tcatcgagtc gtgccgtaat ctcaaaacgc acgaagtcgg gaaatatgtt    8340
gaagagatgc ttgccgcatc ctgatagcgt gttccttct  ggaactgtct ggcggcatac    8400
ggcgtcatcc gtctgaggca gatacctccg tatctgcctc agatttctga caaagtgcat    8460
acctgttgga attgcccagg tttgtcatca gtcaccactg caggctgtgt aacgaccaat    8520
gaaaatgaaa acggctatta atccagcagt ttaatagccg tatcaaagtc agtgatcagc    8580
acattcagaa gacctgattt gagagaggca actataccttt catatttttc gtcccctcca    8640
gccacaccaa tcagtttctt tgtggcacgc aattgatctg tcgtaatgcc gaaacccagg    8700
```

| | |
|---|---|
| cggttcagcg gactatccag aatttcccct tgctatttta ccagtgttac gcatacatca | 8760 |
| gcagtaatgt cctggcttat taaagcctca cgccacgctt cagggaatat atcgcataga | 8820 |
| ctggaagagc ctgttttcca ggccccaatc cctgtaatta cgacatccat atttgagtaa | 8880 |
| aattttttgcg tatcctgaac agcctgatcg tcagcgagtt tctgggctaa actttcgtca | 8940 |
| tccacccaca tgggtacata catcgggtgc gctcttccgt gggaaattgc ggcaactttg | 9000 |
| tgtattagat caatcggtcc ctgactaaat tcaataccag gatgaacgcc agaaagctga | 9060 |
| accacatcca gaacaggtaa tgtcgtcagt tgactcaccg tacttgaaag aacccgcccc | 9120 |
| caggccagac caaacttcat accctcttta agaatctcac tcaagtaggt cgccgttatc | 9180 |
| cctcccagct tgacgtttaa ttgttcctgg gaagaccagg actcggaaac ggagagcaca | 9240 |
| actgcatcct gcaatccgta tttcttacag agatttgcg ctatttcctc gtccagagct | 9300 |
| tgctgtttag ggaaggtaaa ttttacatac tcttgcgcaa tggcttcatc aatcaggcgt | 9360 |
| gcaactttga agcgagacag accgagctcc tctgcaattt ctaccttcgt cttcatctca | 9420 |
| gagaaataac gcttaacaac aagagagtag ataaaacgag gatcgtagtt gcgcagcttc | 9480 |
| ggatttttgt tctctttggg c | 9501 |

<210> SEQ ID NO 21
<211> LENGTH: 561
<212> TYPE: DNA
<213> ORGANISM: Artificial Sequence
<220> FEATURE:
<223> OTHER INFORMATION: Synthetic primer

<400> SEQUENCE: 21

| | |
|---|---|
| ttactcaagg tcagcgtgtc tcttaaacat cgtgtcgctg gtttcaccga gttgggccat | 60 |
| cagctcaagc acgatagcgt cataggtgat aaagcagagt tgctcaaaag ccgatcccat | 120 |
| aggctgcgaa aaagcacctt cttcgcgatc gttgtcttct ttcacagttc caggcaatac | 180 |
| aagagtactt tggccagtt tgccgattgt ggactccgct ttcattgtga caagcgccac | 240 |
| atccacgcca caggctacgg ccttctgcgc caggctcacc agactgccgg tctcaccgct | 300 |
| accggagcca ataatgacca ggtcgcccgg tttcgtatga ggagaagaaa tttcgcccac | 360 |
| tacgcttact gaaaaaccga ggtggagaag gcggtttgca aagccgcgga tggcgatgcc | 420 |
| gctacgaccc gcgccctgca gaaagatatg tttggcattc ttaatctgtg cgacgaattg | 480 |
| ggcagcctgg gcatcatcaa tcttcatcgc attttgctgc aactcgctca ggatatttaa | 540 |
| agtattttgt tgaacgctca t | 561 |

<210> SEQ ID NO 22
<211> LENGTH: 753
<212> TYPE: DNA
<213> ORGANISM: Artificial Sequence
<220> FEATURE:
<223> OTHER INFORMATION: Synthetic primer

<400> SEQUENCE: 22

| | |
|---|---|
| ttaagcgatg gtacgaccac catccatcag aatggtttgc ccctggatgt acgagttgtc | 60 |
| tttatcagcc aaaagattg caaggtttgc tacatcgtca atggttccaa ggcggcgcac | 120 |
| tggaattttt tccagaacgg catcaagatc ggcctgggta ggataattga cgcgcatcat | 180 |
| ttcaccggta tcaatcaggc gtggagcgat agcattaaca ttgacaccct taggtcccag | 240 |
| ttcttttgcc agaccacgaa tcaatccttc accgccagct ttactggccg ggtaactcac | 300 |
| gccaccgcca gtaccggaaa gcgccgagcc ggatgagata taaacgatag atccatggtt | 360 |

```
agtagtgaag tcgtcgtaga atgctttaac ggtgttaaac aggccagtaa ggttaattgc    420
aatcgtctta ttccactctt caaaagtgat gttattaacc ttattagcaa acgccacgcc    480
agcgtttaat accaaaatat caatacgtcc gaaggtttga aaaacctgct cacgaacgtt    540
ttccagagct ttcggatcgg atacatcggt tttaacgaat aaggatttaa cattaccgaa    600
agttaactct tcggccgtct ttttaccatt ttcttcgtta taatcgacaa tgacagtatg    660
agccccacgg tctgcgaatt gcttagcaat tcctttaccg attccatgtg ccccaccggt    720
tactagcgcg actttacctt caaatttact cat                                 753
```

<210> SEQ ID NO 23  
<211> LENGTH: 2839  
<212> TYPE: DNA  
<213> ORGANISM: Artificial Sequence  
<220> FEATURE:  
<223> OTHER INFORMATION: Synthetic primer

<400> SEQUENCE: 23

```
acgtccaaaa tatttactta aggatattaa aaaatgacca aaaagggggct tcggtaata     60 ttagtttttt tgatattttc atatatttt accgcattaa gctataaatt tatcccaagc    120
tctgacagca tgagtggtat tttagaggct gctgacattg caaacggaaa cataacacta    180
aaaggatggt acttatctac agtaactttc tattttactg acttagtctg gtttgctctt    240
gctataaagc ttttttggtta ttctgaatgg ataacatacg ttatacctgg attaatggct    300
ggtagcctgt tcgcttcatg ctatgcactg gaacaatttt ctggctacaa aaaagcatgg    360
gctttgctac tgttccttgc tttccctggt gctgctgtca gttacatgct ttctgtagcg    420
ataatccatg tccctacata tactatatc gttgtttcat atatattaat tgattttat    480 tgtcgcagaa gaaatagatt atatttattt ctatcatcaa taatcgcatc tttaacgata    540
tttagcgatg atataacaat atatttattt ttttgccaa ttgcattgag ctgttttata    600
gccaatgaaa atgcaaaaga taaatttgta atattttcgt ctttggtttt ttcgtatttt    660
ttattcaagt taatcttaca ttttactaac tcggctgatt ttttttattt gccagggggtt    720 ggttcgccta catttgttag ttatgacaag ttaacttttta acatctcgct actttttaaa    780
gggcttttga tattattcaa cgctgatttt tttagtaaaa taatcagttc acctgaagga    840
atattctctt ctttaaaatt cacatcatta gttatatttt ttatactttt aatttcttcg    900
cttataaaaa taagaaagtt tagtctcgtt gacgccgcgc tattgatagc agctcttatt    960
atgattcctg catatgcctt aagcgataaa ccagtggatg agggtacaac aagatattta   1020
attcctgtca ttattttttgg ttcaattttc ttatgtcgaa atgcgaatgt accaaagata   1080
tcaaatatag ttttatggtt ttttttcaatt tcaatttctg cttattcatt aatatatgta   1140
aatcagcctg atttcttatt tcgcaatgac agaaccacat caaaatatag gcttatatct   1200
aattttttga ctcaacacaa cttatctaat ggatatgcaa cattctggaa tgcggcagcg   1260
gtgagtgtgg aaaagaaatt caatatagcc cctgttaaca tcgacataga aaataaaaaa   1320
gttttgccat ctttttggtt aacaaaaata tcatatttta acaatggaaa taactttttc   1380
attgttgata atgaccaaca aaaaaagtc atagaagaat tatatggcaa accagaatta   1440
acatatatgg tgtgggattc ccccatcctg gtttacagtc attctattaa tatttatgat   1500
ggcgatatag aaggaagtgc caatgtagta aaaagtgact tcaaggttgg ggacaataat   1560
caaatatgca atgctggcgt acaaggcatg gttgcatatg ggccctataa gactcttggt   1620
```

```
cgtgggtggt attcttaaaa aattaatgca catggcgatc agtatgaagc attaatttt    1680 tcttatataa caggaaaaaa aatcaagatg tctgagaata aatataaaaa tggttcttat    1740
attttcgaaa taaacgaaga tatgccatct gcagaaatac agttattcgc tcaaaaagat    1800
tcaaatgtat gttttgagtc atactcactt cagcatataa aataataaag tcatggaaaa    1860
gcgtcagtaa ctaatacagg cgcttttgt ctatagaaaa ctcatgctgt taagcgggtt    1920
ttggttgaaa tgttccgaaa atcggaatag ttattccaca ccagcgctat gaattagatg    1980
gcgaagagca tgctgtaacc cctactatag tagcaccttc agattgaaca tacatggtac    2040
caatcttata taattgcctg gcgtcgaacg ccccgagaag taccgtacca gtagttgccg    2100
tcgattatgt ctggcgagcg ccgataactt tcatgccgcc tactgaacaa gatgttacca    2160
cattaagaga ggagaccagc gattacgata ttgcatctgt tttcgacacg tagtcgttct    2220
caatagaaga ggcgaaaaaa caccaagcca cttgatggcg ttttttatta gaggcaataa    2280
atgtcggctt tggcaatgaa ggttttgaaa tgctaatcgc aggaaatgtc agcatcacca    2340
gtgctactct tacttctatt gcgtgtgatc tgaaaaagaa tattaatggt gacggctttg    2400
acacgccata tgatccagca ggcttccgca gatgtgtctg gcttgttcag cagtctccag    2460 aatcaggat acatccgaaa aacgtcaaaa tgagttccgg aattcaaaga tgccctcagt    2520
aaatcggact ccctcgttgc gctgttaaag tctgaaatgg agacacgcag gaatgtagca    2580
ccaacaactc gctagagaat caaaaagctg agccagatgc ccccggaatc acacagcctc    2640
acacttgatg atgcctgtgt atttcttcaa gttaccaaac ctatcgctac taactggatt    2700
cacacaggct gtctgtaaac atcatgtaaa gattccgcca agtcagtcaa taggtatgca    2760
taaatttaac cgaacacgct aagcaaatag gcgtaatatt gaacgattgt gtcccagctt    2820
ccccacaatg aaagagcag                                                2839

<210> SEQ ID NO 24
<211> LENGTH: 924
<212> TYPE: DNA
<213> ORGANISM: Artificial Sequence
<220> FEATURE:
<223> OTHER INFORMATION: Synthetic primer

<400> SEQUENCE: 24
atgaccaaaa aggggctttc ggtaatatta gttttttga tattttcata tatttttacc      60
gcattaagct ataaatttat cccaagctct gacagcatga gtggtatttt agaggctgct     120
gacattgcaa acggaaacat aacactaaaa ggatggtact tatctacagt aactttctat     180
tttactgact tagtctggtt tgctcttgct ataaagcttt ttggttattc tgaatggata     240
acatacgtta tacctggatt aatggctggt agcctgttcg cttcatgcta tgcactggga     300
acaatttctg gctacaaaaa agcatgggct tgctactgt tccttgcttt ccctggtgct     360
gctgtcagtt acatgctttc tgtagcgata tccatgtcc ctacatatac ttatatcgtt     420
gtttcatata tattaattga ttttattgt cgcagaagaa atatgaccaa aaagggctt     480 tcggtaatat tagtttttt gatattttca tatttttta ccgcattaag ctataaattt     540
atcccaagct ctgacagcat gagtggtatt ttagaggctg ctgacattgc aaacggaaac     600
ataacactaa aaggatggta cttatctaca gtaactttct attttactga cttagtctgg     660
tttgctcttg ctataaagct ttttggttat tctgaatgga taacatacgt tatacctgga     720
ttaatggctg gtagcctgtt cgcttcatgc tatgcactgg gaacaatttc tggctacaaa     780
aaagcatggg ctttgctact gttccttgct ttccctggtg ctgctgtcag ttacatgctt     840
```

```
tctgtagcga taatccatgt ccctacatat acttatatcg ttgtttcata tatattaatt    900
gatttttatt gtcgcagaag aaat                                            924

<210> SEQ ID NO 25
<211> LENGTH: 316
<212> TYPE: DNA
<213> ORGANISM: Artificial Sequence
<220> FEATURE:
<223> OTHER INFORMATION: Synthetic primer

<400> SEQUENCE: 25
gctgccgggc agagtcgtag tgaacgtctt ttgggcctga aaagtaaatc cccagttgtt     60
gctgacaact ggggattttt ataacagcat ataaatcgta aaggaaattg tcatatgcca    120
tattcaagaa cgtgctgagg ttgagaagtt ttggaatttt ttcggtggca aaaatggggc    180
aaaatgctgt aaaaggggca aaaatggggc aacaaaagag tggattatcg tagcttattg    240
ttgttgctga taatgcttaa cgcattgaaa aataaataaa actattatgc atcagatggt    300
tgtgattttt gccctt                                                    316

<210> SEQ ID NO 26
<211> LENGTH: 3696
<212> TYPE: DNA
<213> ORGANISM: Artificial Sequence
<220> FEATURE:
<223> OTHER INFORMATION: Synthetic primer

<400> SEQUENCE: 26
ttaaataatc tccggtgcat tgccggtaat ggctttcaca tccgccagca gatcgccaaa     60
cttaccgtag ttaaccttaa cgccgtcgtc gagatcaata ctgattctca tatcagcata    120
gtggcgcagg cgatcgtcga agctgcgcag ttcgttgaat ttttttgctca ggctatcacg    180 ctcacgtttc agacgggtgg cttcgccgcc tgaggctcca tcgacctgtt cgttcaggcg    240
atcgatattg gcctgatagc gcgccagcag cggcactaca tattcggtac gcattctcgc    300
cagcgtcgca tcgttgtagc gatgcagata gaccaggcac tcaaacgctt tctctttacc    360
ggagctgaac agccagtata tcggacgctt tttatacatc ttcatgtgat ctttccagaa    420
ctgagtggaa agatagcggc ggatggtatc cagcgcagat tcgccttttt ttggttttat    480
cgcgtataaa cagaggcttt cggcgataaa ttcgagattt cctgcaagt gttcttcgcc     540 ccaaacggtg cgaacaaact ctttgacgcg agaggtaacg tcatcgtcaa accactcgtc    600
atccatcagc ggcaggatac cgtcattgtc agccgggaag gttttgtacg cgtcttcagc    660
gaccagttcg gcaaagcctt tattgccttc atgggcatag accagtcctt cgcgatcgag    720
ggagtagcgg cccatcatgc agccgatgat gtagcttaag atatctatag tgatatcagt    780
gtaatactta ttggttagat cggtatgatc ttgaatattt ttatatcgat agtttggatt    840
acatagtaga gttatttcac tttgcaatac agctttaatt atagttttgt caagttgtaa    900
tttatctata aaaatattat ttatagtatt ttctattagg agaagtgttt cgactaactt    960
gatatttgta ttgatttttt gtttgtagat attccgtagc aattgagttg aattgtgttc   1020
aagcaatggt gaacaaacat aatcccatga ttgctcttga gagtcccagt catttttagc   1080
tatttcaata gcattggtga ctaattcgat aatttcatct tcaatttctg gatatggtac   1140
tgaggctaat tcaccactag taaagctaag tgtgggggct agtattgata aataatggtt   1200
tacaaccgga gtgcacatta atcccgcagc gtaaagcaac tcattttttgt tatttgaaaa   1260
```

```
gccgcaacgg cctgtatcat caaaaacaaa cccttttgga cgatatctca cgcaaaaatt    1320
accttggctt attttttgacc atgttatgcc ttctctaaag taatactcat catttcttac    1380
ggcagagcga gttttgccat tctcaaattt aaaatttcgt atttcgtaac cattattttc    1440
ccaatttaca actatttcgt tattaccata ccactttcga tattcacctc cactactaca    1500
aggaaaccat ttgatattat gaatgtcgat ttttgtattt gattctttat ttgtgataag    1560 ggttttttttt attgaaacct cgtaccaata tctttgaaat ttaatattgt caccggtgga    1620
catgcctgct tttaatgcta ttttttctcc aagttttta tggtggcgaa aagataatag    1680
actcggtaag tctatccaat atgctattgg cattcctggt atgttttaa atcatgctg    1740 tgtaaattta tcaaatatat ttttccttag aagtagatcg cttttctta cttcttccct    1800 accatctata agtctaaaaa atacaggttg gtaacgttcg gagtgttggt ttttaatcac    1860
ccaggcagtt gtctgtacaa cctctccaga aatttgccca aaagcccgag ctcccaaatg    1920
tgccatcgta ataaatgttt tattgtccaa taaccagtta cgtagtgctt cataacttga    1980
caaaaacatc catgattgca tattgacttg agcattaaac ccattttctt taagcaaaga    2040
aaatgcattc tgcataaaca ttgcaaacaa atcagcttta ctatccggga agttattttt    2100
ggcaaactct ttcagctcac tattcattcc cttgccaccc atatacgcg gattcgccac    2160 taccgcatca taccgctgcg ccaggatcca cgcctgctga atatacgaa taaacgcttt    2220 cgccgctgcc ttctgctgga aatcgccttc ctgctccatg cgatatagcg cttcgagaaa    2280
cgccttcagt tccgcctctt cttcctgtgg cacctggatc agcgagccca gcgttttggc    2340
gttcacaaag cgcttcagcg tgcgcatcag cagctgatat tctgcgctgt cggtatgggc    2400
taatgctgta ttttcggcaa acatatcccc catgctacca gtctggttct gctggtggaa    2460
gttcagctgc tgccacagct tagcaatatc cagatgcagg ctctcctgca gggagacaat    2520
attcagacgc acgtcgcggg tgaatatccg gcggtcatcc tgacgggcca tcattaataa    2580
ggcaaagccg gaaagctggg cagcacggtc gtcaatgtcg agaccaaaaa tattattttc    2640
cagaattagc tgtggaatat cgcgggcgcg atagccgcgc tcttcataga tattttttcag    2700 cacattatag acttcaatca gaatatgccc ggagccgcag gccgggtcga gtactttgat    2760
gctttccggt tcaatactgg caggtgtaat ggcggccagc tgcgcctgca cttctggcgt    2820
ctgttcggct ggctcaatgt agtagtccat tttgcctttc agcggcgaat ccggtaggt    2880 ctgcaaccac tggcggccga cggagttctg taccagatac tgcacaatcc agtttggggt    2940
aaacagctgg gtggcggcag gaatatcttc gctcttcacc accttaccga taaccgcatc    3000
ttttttctca gagatataga actgatacag ccagccgata acctcaactt cttgccagtc    3060
ttcttccgga ataccgtcca ccagaccgcg tagaatggag tcggtgcggg tcaggttatc    3120
cggcagcagt agttcagctt catcgtccac agcttcaaac aggaacggca tcgcgcggtg    3180
cagggcgtgg cactgggcca gcagcagttc acggtagatg gcttcgtcct ggttgccgga    3240
aagcttcatc tcgaccagct gcgccttttt ctctggtagt aatgcttccg cgacttccgg    3300
tacgtggtcc agcacttcaa agcctgtcgg gttatccggg tgcgagagca tgtggaagcc    3360
gtggtcaaga taaccgtgga tttccatata acgaatggcg cacaggcggt tgaaccaggt    3420
gtaggcacag tgctcaacca gcacgtcaaa gccctgctcg cgggcgcgtt ttaccagacg    3480
atcgcggcgg gtgaggggtgg atttggggta gtcgaactga ccatagcgca tggtttcgcc    3540
gacgagctcg gcatccgcaa tttgcagatt gcctttttta tcagcggaaa tccccagcgt    3600
ggttagcttt tggatcaccg catcgcggaa ctggttacgg gcctgtggag cgtattttt    3660
```

-continued

| | |
|---|---|
| gatgttattg gtattcatag aaaatcctgc aaaggg | 3696 |

<210> SEQ ID NO 27
<211> LENGTH: 1328
<212> TYPE: DNA
<213> ORGANISM: Artificial Sequence
<220> FEATURE:
<223> OTHER INFORMATION: Synthetic primer

<400> SEQUENCE: 27

| | |
|---|---|
| ttactcaagg tcagcgtgtc tcttaaacat cgtgtcgctg gtttcaccga gttgggccat | 60 |
| cagctcaagc acgatagcgt cataggtgat aaagcagagt tgctcaaaag ccgatcccat | 120 |
| aggctgcgaa aaagcacctt cttcgcgatc gttgtcttct ttcacagttc caggcaatac | 180 |
| aagagtactt ttggccagtt tgccgattgt ggactccgct ttcattgtga caagcgccac | 240 |
| atccacgcca caggctacgg ccttctgcgc caggctcacc agactgccgg tctcaccgct | 300 |
| accggagcca ataatgacca ggtcgcccgg tttcgtatga ggagaagaaa tttcgcccac | 360 |
| tacgcttact gaaaaaccga ggtggagaag gcggtttgca aagccgcgga tggcgatgcc | 420 |
| gctacgaccc gcgccctgca gaaagatatg tttggcattc ttaatctgtg cgacgaattg | 480 |
| ggcagcctgg gcatcatcaa tcttcatcgc attttgctgc aactcgctca ggatatttaa | 540 |
| agtattttgt tgaacgctca tgtgattccc tccctttaag cgatggtacg accaccatcc | 600 |
| atcagaatgg tttgccctg gatgtacgag ttgtctttat cagccaaaaa gattgcaagg | 660 |
| tttgctacat cgtcaatggt tccaaggcgg cgcactggaa tttttccag aacggcatca | 720 |
| agatcggcct gggtaggata attgacgcgc atcatttcac cggtatcaat caggcgtgga | 780 |
| gcgatagcat taacattgac acccttaggt cccagttctt ttgccagacc acgaatcaat | 840 |
| ccttcaccgc cagctttact ggccgggtaa ctcacgccac cgccagtacc ggaaagcgcc | 900 |
| gagccggatg agatataaac gatagatcca tggttagtag tgaagtcgtc gtagaatgct | 960 |
| ttaacggtgt taaacaggcc agtaaggtta attgcaatcg tcttattcca ctcttcaaaa | 1020 |
| gtgatgttat taaccttatt agcaaacgcc acgccagcgt ttaataccaa aatatcaata | 1080 |
| cgtccgaagg tttgaaaaac ctgctcacga acgttttcca gagctttcgg atcggataca | 1140 |
| tcggttttaa cgaataagga tttaacatta ccgaaagtta actcttcggc cgtctttta | 1200 |
| ccattttctt cgttataatc gacaatgaca gtatgagccc cacggtctgc gaattgctta | 1260 |
| gcaattcctt taccgattcc atgtgcccca ccggttacta gcgcgacttt accttcaaat | 1320 |
| ttactcat | 1328 |

<210> SEQ ID NO 28
<211> LENGTH: 1081
<212> TYPE: DNA
<213> ORGANISM: Artificial Sequence
<220> FEATURE:
<223> OTHER INFORMATION: Synthetic primer

<400> SEQUENCE: 28

| | |
|---|---|
| tatagtgata tcagtgtaat acttattggt tagatcggta tgatcttgaa tattttttata | 60 |
| tcgatagttt ggattacata gtagagttat ttcactttgc aatacagctt taattatagt | 120 |
| tttgtcaagt tgtaatttat ctataaaaat attatttata gtattttcta ttaggagaag | 180 |
| tgtttcgact aacttgatat ttgtattgat tttttgtttg tagatattcc gtagcaattg | 240 |
| agttgaattg tgttcaagca atggtgaaca aacataatcc catgattgct cttgagagtc | 300 |

```
ccagtcattt ttagctattt caatagcatt ggtgactaat tcgataattt catcttcaat    360
ttctggatat ggtactgagg ctaattcacc actagtaaag ctaagtgtgg gggctagtat    420
tgataaataa tggtttacaa ccggagtgca cattaatccc gcagcgtaaa gcaactcatt    480
tttgttattt gaaaagccgc aacggcctgt atcatcaaaa acaaacccctt ttggacgata    540 tctcacgcaa aaattacctt ggcttatttt tgaccatgtt atgccttctc taaagtaata    600
ctcatcattt cttacggcag agcgagtttt gccattctca aatttaaaat ttcgtatttc    660
gtaaccatta ttttcccaat ttacaactat ttcgttatta ccataccact ttcgatattc    720
acctccacta ctacaaggaa accatttgat attatgaatg tcgattttg tatttgattc     780 tttatttgtg ataagggttt tttttattga aacctcgtac caatatcttt gaaatttaat    840
attgtcaccg gtggacatgc ctgcttttaa tgctattttt tctccaagtt ttttatggtg    900
gcgaaaagat aatagactcg gtaagtctat ccaatatgct attggcattc ctggtatgtt    960
tttaaaatca tgctgtgtaa atttatcaaa tatattttc cttagaagta gatcgctttt     1020
ctttacttct tccctaccat ctataagtct aaaaaataca ggttggtaac gttcggagtg    1080
t                                                                    1081
```

```
<210> SEQ ID NO 29
<211> LENGTH: 1680
<212> TYPE: DNA
<213> ORGANISM: Artificial Sequence
<220> FEATURE:
<223> OTHER INFORMATION: Synthetic primer

<400> SEQUENCE: 29
tgatggataa ccttcttctg cccccgagga tcagagagcc ggttttttg tgcatcctgg      60 aaaattcacg tgaaggaacc ggctctcaac cagagaagaa gaggcgtttt tttcgataca   120
actatcgtaa ttactccgtt ggtggtgctg gcacgtaaag tgtggatagt gcgtttatga   180
tgagtgcatg atgtatatcc tgatacagca tccggtttgt gggggcggag aagccccgat   240
ggactcagtg ccacaatttt ttattgcatt cagatagcgt actgtgaatc ggataaatga   300
gaatgtcagt gtgttggtaa tgcggggttc tcagtgcgct atctgaatgc agtgaaatct   360
gctctgagca gagctaaaca gcattgtctg cgtttgatca atttgtagcg ggtcatagtg   420
gctgactaaa gactctccgg ggcatcccgg cactgcattt attactaaaa atcttcatat   480
cacagaggca gaacatacgg aaaattcttg tcaatacaac acctgacaca gcaatatttt   540
tcgggagtcc ccggcgcctc aggttttttta tcgccatcaa taaaactata ataataactc   600
catgttatga ttaccacctc tctctcatga ggtggttttt ttattcccgc aaattgcaga   660
aataagatgg agtcatcaga atatgccctg attgtatttt gtcttttttg aattaatgca   720
aaacatttgg aataaataaa catctaatga taaatttaca tttcttgacg cgactgcttg   780
ttgaaatgaa attttatga tttattattg tcgacagttt ggcggaggtg actggcagat    840
ttctccactc cgtcgaataa gagagttgat tctttatacc tcctgagtcg tctgattaaa   900
gaatcatcac tcgatttggc attaaggtga aattaagatt ccattgatat aggtatcgtt    960
cttactcttt gtggtgcagg catatggata tggggtggtt acattaatgt tcctttaatt   1020
taacctcctg atagtgaatc aggcaccgca atttttttac tgcattcaga tggcgtactg   1080
caaaaaaacg gtcattgctt gcgccactgt ctgatgctct tgtaacacat acgggatttg   1140
tggtacgcca tctgaatgca gtgaaaccca cataaagtgg ggcataaaca ggatatgagg   1200
tgcgtttatt ttcgtctgcg ggtcatggtg actgaccaac ggccctccgg agataattcc   1260
```

```
ggcactgcat tatttattga ggtgttcccc agtgcggggg tgaccgggaa aaatgttctg    1320
ccgatggtca cagacacata ccgggctaat atgtgttttc gggaggcacc cgacacctct    1380 actgttttc cagtcgataa ctataaaaca tgcttcagat attgagcacc gcctcccgtg     1440
aggcggtttt ttttattccg ggaaaaagtt ctgcccgcca tataataaag ttaacgtttt    1500
cagaccaggg tgcgggaagt atccggggcg ggaaataatg aattaaaaaa gaagcgcggc    1560
tgtcggattt aagccgcggg acaatgtccg tgatagatag ttgaaaaatt tcaggctatc    1620
cctttcggga ggtcgccatt attttactca taacaaaata agaccggaac cccggaaaca    1680
```

<210> SEQ ID NO 30
<211> LENGTH: 989
<212> TYPE: DNA
<213> ORGANISM: Artificial Sequence
<220> FEATURE:
<223> OTHER INFORMATION: Synthetic primer

<400> SEQUENCE: 30

```
ctggcctcgt tcctgtcccg ccttgctgac tacaacggta aaccgctgga tgcgctgtgt    60
gcagtggtga tgtcggtgct gtcagtgaaa tttctgacct tcattcatga ccaggacatt    120
tcatcgctga ccggggtttt ttcacggatg cggggaggag ggagtggtca tggaaagtaa    180
tctgaccggc acactgaatg cgggcctgtg cctggtgaca gtgctggccc tttttctcta    240
ccgccggaac ggcgccagat acaaaccggg aatagcctgg ctgtcgtacc tgctgatgct    300
gggctatgcg ctggttccgt tccgttttct ggccggacat tacccgtctt catcctggcc    360
tgtggtgctg atgaacgcgc tgttctgcgg gctggtgctg tgggcgcggg gtaatgtgtc    420
gaaaatactt tcactgctga ggctgcgatg aaaccgaagg acgaaatttt tgatgaaatt    480
ctgggtaagg aaggcggcta cgtcaaccat ccggacgata aaggcgggcc gacaaaatgg    540
ggtattacgg aaaagttgc ccgcgcccac ggataccgtg gtgatatgcg caatttaacc    600
cgtggacagg cgctggaaat tctggagacc gactactggt acggtccccg ctttgaccgg    660
gtggcgaagg cctcgccgga tgttgctgcc gaactgtgtg acacgggcgt gaacatgggg    720
ccgtcggtgg cagcgaaaat gttgcagcgc tggctgaacg tgttcaacca gggcgggagg    780
ctgtatccgg atatggatac ggacgggcgc atcgggccgc gaacccttaa cgcgttacgt    840
gtttatctgg aaaagcgcgg taaggatggc gagcgtgtac tgctggtggc gctgaactgc    900 acgcagggg agcgctatct ggagctggcg gaaaagcggg aggctgacga gtcgtttgtc    960
tatggctgga tgaaagagcg cgtattgat                                       989
```

<210> SEQ ID NO 31
<211> LENGTH: 340
<212> TYPE: DNA
<213> ORGANISM: Artificial Sequence
<220> FEATURE:
<223> OTHER INFORMATION: Synthetic primer

<400> SEQUENCE: 31

```
gtctggcttg ttcagcagtc tccagaatca gggatacatc cgaaaaacgt caaaatgagt    60
tccggaattc aaagatgccc tcagtaaatc ggactccctc gttgcgctgt taaagtctga    120
aatggagaca cgcaggaatg tagcaccaac aactcgctag agaatcaaaa agctgagcca    180
gatgcccccg gaatcacaca gcctcacact tgatgatgcc tgtgtatttc ttcaagttac    240
caaacctatc gctactaact ggattcacac aggctgtctg taaacatcat gtaaagattc    300
```
cgccaagtca gtcaataggt atgcataaat ttaaccgaac        340

<210> SEQ ID NO 32
<211> LENGTH: 581
<212> TYPE: DNA
<213> ORGANISM: Artificial Sequence
<220> FEATURE:
<223> OTHER INFORMATION: Synthetic primer

<400> SEQUENCE: 32
cggaaacata acactaaaag gatggtactt atctacagta actttctatt ttactgactt        60
agtctggttt gctcttgcta taaagctttt tggttattct gaatggataa catacgttat        120
acctggatta atggctggta gcctgttcgc ttcatgctat gcactgggaa caatttctgg        180
ctacaaaaaa gcatgggctt tgctactgtt ccttgctttc cctggtgctg ctgtcagtta        240
catgctttct gtagcgataa tccatgtccc tacatatact tatatcgttg tttcatatat        300
attaattgat ttttattgtc gcagaagaaa tagattatat ttatttctat catcaataat        360
cgcatcttta acgatattta gcgatgatat aacaatatat ttattttttt tgccaattgc        420
attgagctgt tttatagcca atgaaaatgc aaaagataaa tttgtaatat tttcgtcttt        480 ggtttttcg tatttttat tcaagttaat cttacatttt actaactcgg ctgatttttt        540
ttatttgcca ggggttggtt cgcctacatt tgttagttat g        581

<210> SEQ ID NO 33
<211> LENGTH: 581
<212> TYPE: DNA
<213> ORGANISM: Artificial Sequence
<220> FEATURE:
<223> OTHER INFORMATION: Synthetic primer

<400> SEQUENCE: 33
cggaaacata acactaaaag gatggtactt atctacagta actttctatt ttactgactt        60
agtctggttt gctcttgcta taaagctttt tggttattct gaatggataa catacgttat        120
acctggatta atggctggta gcctgttcgc ttcatgctat gcactgggaa caatttctgg        180
ctacaaaaaa gcatgggctt tgctactgtt ccttgctttc cctggtgctg ctgtcagtta        240
catgctttct gtagcgataa tccatgtccc tacatatact tatatcgttg tttcatatat        300
attaattgat ttttattgtc gcagaagaaa tagattatat ttatttctat catcaataat        360
cgcatcttta acgatattta gcgatgatat aacaatatat ttattttttt tgccaattgc        420
attgagctgt tttatagcca atgaaaatgc aaaagataaa tttgtaatat tttcgtcttt        480 ggtttttcg tatttttat tcaagttaat cttacatttt actaactcgg ctgatttttt        540
ttatttgcca ggggttggtt cgcctacatt tgttagttat g        581

<210> SEQ ID NO 34
<211> LENGTH: 581
<212> TYPE: DNA
<213> ORGANISM: Artificial Sequence
<220> FEATURE:
<223> OTHER INFORMATION: Synthetic primer

<400> SEQUENCE: 34
cggaaacata acactaaaag gatggtactt atctacagta actttctatt ttactgactt        60
agtctggttt gctcttgcta taaagctttt tggttattct gaatggataa catacgttat        120
acctggatta atggctggta gcctgttcgc ttcatgctat gcactgggaa caatttctgg        180
ctacaaaaaa gcatgggctt tgctactgtt ccttgctttc cctggtgctg ctgtcagtta        240

```
catgctttct gtagcgataa tccatgtccc tacatatact tatatcgttg tttcatatat      300
attaattgat ttttattgtc gcagaagaaa tagattatat ttatttctat catcaataat      360
cgcatcttta acgatattta gcgatgatat aacaatatat ttattttttt tgccaattgc      420
attgagctgt tttatagcca atgaaaatgc aaaagataaa tttgtaatat tttcgtcttt      480
ggttttttcg tatttttat  tcaagttaat cttacatttt actaactcgg ctgattttt       540 ttatttgcca ggggttggtt cgcctacatt tgttagttat g                         581
```

<210> SEQ ID NO 35
<211> LENGTH: 581
<212> TYPE: DNA
<213> ORGANISM: Artificial Sequence
<220> FEATURE:
<223> OTHER INFORMATION: Synthetic primer

<400> SEQUENCE: 35

```
cggaaacata acactaaaag gatggtactt atctacagta actttctatt ttactgactt       60
agtctggttt gctcttgcta taaagctttt tggttattct gaatggataa catacgttat      120
acctggatta atggctggta gcctgttcgc ttcatgctat gcactgggaa caatttctgg      180
ctacaaaaaa gcatgggctt tgctactgtt ccttgctttc cctggtgctg ctgtcagtta      240
catgctttct gtagcgataa tccatgtccc tacatatact tatatcgttg tttcatatat      300
attaattgat ttttattgtc gcagaagaaa tagattatat ttatttctat catcaataat      360
cgcatcttta acgatattta gcgatgatat aacaatatat ttattttttt tgccaattgc      420
attgagctgt tttatagcca atgaaaatgc aaaagataaa tttgtaatat tttcgtcttt      480
ggttttttcg tatttttat  tcaagttaat cttacatttt actaactcgg ctgattttt       540 ttatttgcca ggggttggtt cgcctacatt tgttagttat g                         581
```

<210> SEQ ID NO 36
<211> LENGTH: 581
<212> TYPE: DNA
<213> ORGANISM: Artificial Sequence
<220> FEATURE:
<223> OTHER INFORMATION: Synthetic primer

<400> SEQUENCE: 36

```
cggaaacata acactaaaag gatggtactt atctacagta actttctatt ttactgactt       60
agtctggttt gctcttgcta taaagctttt tggttattct gaatggataa catacgttat      120
acctggatta atggctggta gcctgttcgc ttcatgctat gcactgggaa caatttctgg      180
ctacaaaaaa gcatgggctt tgctactgtt ccttgctttc cctggtgctg ctgtcagtta      240
catgctttct gtagcgataa tccatgtccc tacatatact tatatcgttg tttcatatat      300
attaattgat ttttattgtc gcagaagaaa tagattatat ttatttctat catcaataat      360
cgcatcttta acgatattta gcgatgatat aacaatatat ttattttttt tgccaattgc      420
attgagctgt tttatagcca atgaaaatgc aaaagataaa tttgtaatat tttcgtcttt      480
ggttttttcg tatttttat  tcaagttaat cttacatttt actaactcgg ctgattttt       540 ttatttgcca ggggttggtt cgcctacatt tgttagttat g                         581
```

<210> SEQ ID NO 37
<211> LENGTH: 581
<212> TYPE: DNA
<213> ORGANISM: Artificial Sequence
<220> FEATURE:

<223> OTHER INFORMATION: Synthetic primer

<400> SEQUENCE: 37

| | |
|---|---|
| cggaaacata acactaaaag gatggtactt atctacagta actttctatt ttactgactt | 60 |
| agtctggttt gctcttgcta taaagctttt tggttattct gaatggataa catacgttat | 120 |
| acctggatta atggctggta gcctgttcgc ttcatgctat gcactgggaa caatttctgg | 180 |
| ctacaaaaaa gcatgggctt tgctactgtt ccttgctttc cctggtgctg ctgtcagtta | 240 |
| catgctttct gtagcgataa tccatgtccc tacatatact tatatcgttg tttcatatat | 300 |
| attaattgat ttttattgtc gcagaagaaa tagattatat ttatttctat catcaataat | 360 |
| cgcatcttta acgatattta gcgatgatat aacaatatat ttattttttt tgccaattgc | 420 |
| attgagctgt tttatagcca atgaaaatgc aaaagataaa tttgtaatat tttcgtcttt | 480 |
| ggttttttcg tattttttat tcaagttaat cttacatttt actaactcgg ctgattttt | 540 |
| ttatttgcca ggggttggtt cgcctacatt tgttagttat g | 581 |

<210> SEQ ID NO 38
<211> LENGTH: 581
<212> TYPE: DNA
<213> ORGANISM: Artificial Sequence
<220> FEATURE:
<223> OTHER INFORMATION: Synthetic primer

<400> SEQUENCE: 38

| | |
|---|---|
| cggaaacata acactaaaag gatggtactt atctacagta actttctatt ttactgactt | 60 |
| agtctggttt gctcttgcta taaagctttt tggttattct gaatggataa catacgttat | 120 |
| acctggatta atggctggta gcctgttcgc ttcatgctat gcactgggaa caatttctgg | 180 |
| ctacaaaaaa gcatgggctt tgctactgtt ccttgctttc cctggtgctg ctgtcagtta | 240 |
| catgctttct gtagcgataa tccatgtccc tacatatact tatatcgttg tttcatatat | 300 |
| attaattgat ttttattgtc gcagaagaaa tagattatat ttatttctat catcaataat | 360 |
| cgcatcttta acgatattta gcgatgatat aacaatatat ttattttttt tgccaattgc | 420 |
| attgagctgt tttatagcca atgaaaatgc aaaagataaa tttgtaatat tttcgtcttt | 480 |
| ggttttttcg tattttttat tcaagttaat cttacatttt actaactcgg ctgattttt | 540 |
| ttatttgcca ggggttggtt cgcctacatt tgttagttat g | 581 |

<210> SEQ ID NO 39
<211> LENGTH: 581
<212> TYPE: DNA
<213> ORGANISM: Artificial Sequence
<220> FEATURE:
<223> OTHER INFORMATION: Synthetic primer

<400> SEQUENCE: 39

| | |
|---|---|
| cggaaacata acactaaaag gatggtactt atctacagta actttctatt ttactgactt | 60 |
| agtctggttt gctcttgcta taaagctttt tggttattct gaatggataa catacgttat | 120 |
| acctggatta atggctggta gcctgttcgc ttcatgctat gcactgggaa caatttctgg | 180 |
| ctacaaaaaa gcatgggctt tgctactgtt ccttgctttc cctggtgctg ctgtcagtta | 240 |
| catgctttct gtagcgataa tccatgtccc tacatatact tatatcgttg tttcatatat | 300 |
| attaattgat ttttattgtc gcagaagaaa tagattatat ttatttctat catcaataat | 360 |
| cgcatcttta acgatattta gcgatgatat aacaatatat ttattttttt tgccaattgc | 420 |
| attgagctgt tttatagcca atgaaaatgc aaaagataaa tttgtaatat tttcgtcttt | 480 |

```
ggttttttcg tatttttttat tcaagttaat cttacatttt actaactcgg ctgattttttt    540 ttatttgcca ggggttggtt cgcctacatt tgttagttat g                          581

<210> SEQ ID NO 40
<211> LENGTH: 581
<212> TYPE: DNA
<213> ORGANISM: Artificial Sequence
<220> FEATURE:
<223> OTHER INFORMATION: Synthetic primer

<400> SEQUENCE: 40
cggaaacata acactaaaag gatggtactt atctacagta actttctatt ttactgactt       60
agtctggttt gctcttgcta taaagctttt tggttattct gaatggataa catacgttat      120
acctggatta atggctggta gcctgttcgc ttcatgctat gcactgggaa caatttctgg      180
ctacaaaaaa gcatgggctt tgctactgtt ccttgctttc cctggtgctg ctgtcagtta      240
catgctttct gtagcgataa tccatgtccc tacatatact tatatcgttg tttcatatat      300
attaattgat ttttattgtc gcagaagaaa tagattatat ttatttctat catcaataat      360
cgcatcttta acgatattta gcgatgatat aacaatatat ttatttttt tgccaattgc      420 attgagctgt tttatagcca atgaaaatgc aaaagataaa tttgtaatat tttcgtcttt      480
ggttttttcg tatttttttat tcaagttaat cttacatttt actaactcgg ctgattttttt    540 ttatttgcca ggggttggtt cgcctacatt tgttagttat g                          581

<210> SEQ ID NO 41
<211> LENGTH: 581
<212> TYPE: DNA
<213> ORGANISM: Artificial Sequence
<220> FEATURE:
<223> OTHER INFORMATION: Synthetic primer

<400> SEQUENCE: 41
cggaaacata acactaaaag gatggtactt atctacagta actttctatt ttactgactt       60
agtctggttt gctcttgcta taaagctttt tggttattct gaatggataa catacgttat      120
acctggatta atggctggta gcctgttcgc ttcatgctat gcactgggaa caatttctgg      180
ctacaaaaaa gcatgggctt tgctactgtt ccttgctttc cctggtgctg ctgtcagtta      240
catgctttct gtagcgataa tccatgtccc tacatatact tatatcgttg tttcatatat      300
attaattgat ttttattgtc gcagaagaaa tagattatat ttatttctat catcaataat      360
cgcatcttta acgatattta gcgatgatat aacaatatat ttatttttt tgccaattgc      420 attgagctgt tttatagcca atgaaaatgc aaaagataaa tttgtaatat tttcgtcttt      480
ggttttttcg tatttttttat tcaagttaat cttacatttt actaactcgg ctgattttttt    540 ttatttgcca ggggttggtt cgcctacatt tgttagttat g                          581

<210> SEQ ID NO 42
<211> LENGTH: 581
<212> TYPE: DNA
<213> ORGANISM: Artificial Sequence
<220> FEATURE:
<223> OTHER INFORMATION: Synthetic primer

<400> SEQUENCE: 42
cggaaacata acactaaaag gatggtactt atctacagta actttctatt ttactgactt       60
agtctggttt gctcttgcta taaagctttt tggttattct gaatggataa catacgttat      120
```

```
acctggatta atggctggta gcctgttcgc ttcatgctat gcactgggaa caatttctgg    180
ctacaaaaaa gcatgggctt tgctactgtt ccttgctttc cctggtgctg ctgtcagtta    240
catgctttct gtagcgataa tccatgtccc tacatatact tatatcgttg tttcatatat    300
attaattgat ttttattgtc gcagaagaaa tagattatat ttatttctat catcaataat    360
cgcatcttta acgatattta gcgatgatat aacaatatat ttattttttt tgccaattgc    420
attgagctgt tttatagcca atgaaaatgc aaaagataaa tttgtaatat tttcgtcttt    480
ggttttttcg tatttttat tcaagttaat cttacatttt actaactcgg ctgatttttt      540
ttatttgcca ggggttggtt cgcctacatt tgttagttat g                         581

<210> SEQ ID NO 43
<211> LENGTH: 581
<212> TYPE: DNA
<213> ORGANISM: Artificial Sequence
<220> FEATURE:
<223> OTHER INFORMATION: Synthetic primer

<400> SEQUENCE: 43
cggaaacata acactaaaag gatggtactt atctacagta actttctatt ttactgactt    60
agtctggttt gctcttgcta taaagctttt tggttattct gaatggataa catacgttat    120
acctggatta atggctggta gcctgttcgc ttcatgctat gcactgggaa caatttctgg    180
ctacaaaaaa gcatgggctt tgctactgtt ccttgctttc cctggtgctg ctgtcagtta    240
catgctttct gtagcgataa tccatgtccc tacatatact tatatcgttg tttcatatat    300
attaattgat ttttattgtc gcagaagaaa tagattatat ttatttctat catcaataat    360
cgcatcttta acgatattta gcgatgatat aacaatatat ttattttttt tgccaattgc    420
attgagctgt tttatagcca atgaaaatgc aaaagataaa tttgtaatat tttcgtcttt    480
ggttttttcg tatttttat tcaagttaat cttacatttt actaactcgg ctgatttttt      540
ttatttgcca ggggttggtt cgcctacatt tgttagttat g                         581

<210> SEQ ID NO 44
<211> LENGTH: 581
<212> TYPE: DNA
<213> ORGANISM: Artificial Sequence
<220> FEATURE:
<223> OTHER INFORMATION: Synthetic primer

<400> SEQUENCE: 44
cggaaacata acactaaaag gatggtactt atctacagta actttctatt ttactgactt    60
agtctggttt gctcttgcta taaagctttt tggttattct gaatggataa catacgttat    120
acctggatta atggctggta gcctgttcgc ttcatgctat gcactgggaa caatttctgg    180
ctacaaaaaa gcatgggctt tgctactgtt ccttgctttc cctggtgctg ctgtcagtta    240
catgctttct gtagcgataa tccatgtccc tacatatact tatatcgttg tttcatatat    300
attaattgat ttttattgtc gcagaagaaa tagattatat ttatttctat catcaataat    360
cgcatcttta acgatattta gcgatgatat aacaatatat ttattttttt tgccaattgc    420
attgagctgt tttatagcca atgaaaatgc aaaagataaa tttgtaatat tttcgtcttt    480
ggttttttcg tatttttat tcaagttaat cttacatttt actaactcgg ctgatttttt      540
ttatttgcca ggggttggtt cgcctacatt tgttagttat g                         581

<210> SEQ ID NO 45
<211> LENGTH: 581
```

<212> TYPE: DNA
<213> ORGANISM: Artificial Sequence
<220> FEATURE:
<223> OTHER INFORMATION: Synthetic primer

<400> SEQUENCE: 45

```
cggaaacata acactaaaag gatggtactt atctacagta actttctatt ttactgactt      60
agtctggttt gctcttgcta taaagctttt tggttattct gaatggataa catacgttat     120
acctggatta atggctggta gcctgttcgc ttcatgctat gcactgggaa caatttctgg     180
ctacaaaaaa gcatgggctt tgctactgtt ccttgctttc cctggtgctg ctgtcagtta     240
catgctttct gtagcgataa tccatgtccc tacatatact tatatcgttg tttcatatat     300
attaattgat ttttattgtc gcagaagaaa tagattatat ttatttctat catcaataat     360
cgcatcttta acgatattta gcgatgatat aacaatatat ttattttttt tgccaattgc     420
attgagctgt tttatagcca atgaaaatgc aaaagataaa tttgtaatat tttcgtcttt     480
ggttttttcg tatttttat tcaagttaat cttacatttt actaactcgg ctgattttt      540
ttatttgcca ggggttggtt cgcctacatt tgttagttat g                        581
```

<210> SEQ ID NO 46
<211> LENGTH: 581
<212> TYPE: DNA
<213> ORGANISM: Artificial Sequence
<220> FEATURE:
<223> OTHER INFORMATION: Synthetic primer

<400> SEQUENCE: 46

```
cggaaacata acactaaaag gatggtactt atctacagta actttctatt ttactgactt      60
agtctggttt gctcttgcta taaagctttt tggttattct gaatggataa catacgttat     120
acctggatta atggctggta gcctgttcgc ttcatgctat gcactgggaa caatttctgg     180
ctacaaaaaa gcatgggctt tgctactgtt ccttgctttc cctggtgctg ctgtcagtta     240
catgctttct gtagcgataa tccatgtccc tacatatact tatatcgttg tttcatatat     300
attaattgat ttttattgtc gcagaagaaa tagattatat ttatttctat catcaataat     360
cgcatcttta acgatattta gcgatgatat aacaatatat ttattttttt tgccaattgc     420
attgagctgt tttatagcca atgaaaatgc aaaagataaa tttgtaatat tttcgtcttt     480
ggttttttcg tatttttat tcaagttaat cttacatttt actaactcgg ctgattttt      540
ttatttgcca ggggttggtt cgcctacatt tgttagttat g                        581
```

<210> SEQ ID NO 47
<211> LENGTH: 581
<212> TYPE: DNA
<213> ORGANISM: Artificial Sequence
<220> FEATURE:
<223> OTHER INFORMATION: Synthetic primer

<400> SEQUENCE: 47

```
cggaaacata acactaaaag gatggtactt atctacagta actttctatt ttactgactt      60
agtctggttt gctcttgcta taaagctttt tggttattct gaatggataa catacgttat     120
acctggatta atggctggta gcctgttcgc ttcatgctat gcactgggaa caatttctgg     180
ctacaaaaaa gcatgggctt tgctactgtt ccttgctttc cctggtgctg ctgtcagtta     240
catgctttct gtagcgataa tccatgtccc tacatatact tatatcgttg tttcatatat     300
attaattgat ttttattgtc gcagaagaaa tagattatat ttatttctat catcaataat     360
```

```
cgcatcttta acgatattta gcgatgatat aacaatatat ttattttttt tgccaattgc    420
attgagctgt tttatagcca atgaaaatgc aaaagataaa tttgtaatat tttcgtcttt    480
ggttttttcg tatttttat tcaagttaat cttacatttt actaactcgg ctgattttt    540 ttatttgcca ggggttggtt cgcctacatt tgttagttat g                        581
```

<210> SEQ ID NO 48
<211> LENGTH: 581
<212> TYPE: DNA
<213> ORGANISM: Artificial Sequence
<220> FEATURE:
<223> OTHER INFORMATION: Synthetic primer

<400> SEQUENCE: 48

```
cggaaacata acactaaaag gatggtactt atctacagta actttctatt ttactgactt     60
agtctggttt gctcttgcta taaagctttt tggttattct gaatggataa catacgttat    120
acctggatta atggctggta gcctgttcgc ttcatgctat gcactgggaa caatttctgg    180
ctacaaaaaa gcatgggctt tgctactgtt ccttgctttc cctggtgctg ctgtcagtta    240
catgctttct gtagcgataa tccatgtccc tacatatact tatatcgttg tttcatatat    300
attaattgat ttttattgtc gcagaagaaa tagattatat ttatttctat catcaataat    360
cgcatcttta acgatattta gcgatgatat aacaatatat ttattttttt tgccaattgc    420
attgagctgt tttatagcca atgaaaatgc aaaagataaa tttgtaatat tttcgtcttt    480
ggttttttcg tatttttat tcaagttaat cttacatttt actaactcgg ctgattttt    540 ttatttgcca ggggttggtt cgcctacatt tgttagttat g                        581
```

<210> SEQ ID NO 49
<211> LENGTH: 581
<212> TYPE: DNA
<213> ORGANISM: Artificial Sequence
<220> FEATURE:
<223> OTHER INFORMATION: Synthetic primer

<400> SEQUENCE: 49

```
cggaaacata acactaaaag gatggtactt atctacagta actttctatt ttactgactt     60
agtctggttt gctcttgcta taaagctttt tggttattct gaatggataa catacgttat    120
acctggatta atggctggta gcctgttcgc ttcatgctat gcactgggaa caatttctgg    180
ctacaaaaaa gcatgggctt tgctactgtt ccttgctttc cctggtgctg ctgtcagtta    240
catgctttct gtagcgataa tccatgtccc tacatatact tatatcgttg tttcatatat    300
attaattgat ttttattgtc gcagaagaaa tagattatat ttatttctat catcaataat    360
cgcatcttta acgatattta gcgatgatat aacaatatat ttattttttt tgccaattgc    420
attgagctgt tttatagcca atgaaaatgc aaaagataaa tttgtaatat tttcgtcttt    480
ggttttttcg tatttttat tcaagttaat cttacatttt actaactcgg ctgattttt    540 ttatttgcca ggggttggtt cgcctacatt tgttagttat g                        581
```

<210> SEQ ID NO 50
<211> LENGTH: 515
<212> TYPE: DNA
<213> ORGANISM: Artificial Sequence
<220> FEATURE:
<223> OTHER INFORMATION: Synthetic primer

<400> SEQUENCE: 50

```
attcctgtca ttatttttgg ttcaattttc ttatgtcgaa atgcgaatgt accaaagata     60
```

```
tcaaatatag ttttatggtt tttttcaatt tcaatttctg cttattcatt aatatatgta    120
aatcagcctg atttcttatt tcgcaatgac agaaccacat caaaatatag gcttatatct    180
aattttttga ctcaacacaa cttatctaat ggatatgcaa cattctggaa tgcggcagcg    240
gtgagtgtgg aaaagaaatt caatatagcc cctgttaaca tcgacataga aaataaaaaa    300
gttttgccat cttttggtt aacaaaaata tcatatttta acaatggaaa taacttttc    360 attgttgata atgaccaaca aaaaaaagtc atagaagaat tatatggcaa accagaatta    420
acatatatgg tgtgggattc ccccatcctg gtttacagtc attctattaa tatttatgat    480
ggcgatatag aaggaagtgc caatgtagta aaaag                               515
```

<210> SEQ ID NO 51
<211> LENGTH: 515
<212> TYPE: DNA
<213> ORGANISM: Artificial Sequence
<220> FEATURE:
<223> OTHER INFORMATION: Synthetic primer

<400> SEQUENCE: 51

```
attcctgtca ttattttgg ttcaattttc ttatgtcgaa atgcgaatgt accaaagata     60
tcaaatatag ttttatggtt tttttcaatt tcaatttctg cttattcatt aatatatgta   120
aatcagcctg atttcttatt tcgcaatgac agaaccacat caaaatatag gcttatatct   180
aattttttga ctcaacacaa cttatctaat ggatatgcaa cattctggaa tgcggcagcg   240
gtgagtgtgg aaaagaaatt caatatagcc cctgttaaca tcgacataga aaataaaaaa   300
gttttgccat cttttggtt aacaaaaata tcatatttta acaatggaaa taacttttc    360 attgttgata atgaccaaca aaaaaaagtc atagaagaat tatatggcaa accagaatta   420
acatatatgg tgtgggattc ccccatcctg gtttacagtc attctattaa tatttatgat   480
ggcgatatag aaggaagtgc caatgtagta aaaag                              515
```

<210> SEQ ID NO 52
<211> LENGTH: 515
<212> TYPE: DNA
<213> ORGANISM: Artificial Sequence
<220> FEATURE:
<223> OTHER INFORMATION: Synthetic primer

<400> SEQUENCE: 52

```
attcctgtca ttattttgg ttcaattttc ttatgtcgaa atgcgaatgt accaaagata     60
tcaaatatag ttttatggtt tttttcaatt tcaatttctg cttattcatt aatatatgta   120
aatcagcctg atttcttatt tcgcaatgac agaaccacat caaaatatag gcttatatct   180
aattttttga ctcaacacaa cttatctaat ggatatgcaa cattctggaa tgcggcagcg   240
gtgagtgtgg aaaagaaatt caatatagcc cctgttaaca tcgacataga aaataaaaaa   300
gttttgccat cttttggtt aacaaaaata tcatatttta acaatggaaa taacttttc    360 attgttgata atgaccaaca aaaaaaagtc atagaagaat tatatggcaa accagaatta   420
acatatatgg tgtgggattc ccccatcctg gtttacagtc attctattaa tatttatgat   480
ggcgatatag aaggaagtgc caatgtagta aaaag                              515
```

<210> SEQ ID NO 53
<211> LENGTH: 515
<212> TYPE: DNA
<213> ORGANISM: Artificial Sequence
<220> FEATURE:

<223> OTHER INFORMATION: Synthetic primer

<400> SEQUENCE: 53

```
attcctgtca ttattttggg ttcaattttc ttatgtcgaa atgcgaatgt accaaagata      60
tcaaatatag ttttatggtt tttttcaatt tcaatttctg cttattcatt aatatatgta     120
aatcagcctg atttcttatt tcgcaatgac agaaccacat caaaatatag gcttatatct     180
aattttttga ctcaacacaa cttatctaat ggatatgcaa cattctggaa tgcggcagcg     240
gtgagtgtgg aaagaaatt caatatagcc cctgttaaca tcgacataga aaataaaaaa      300
gttttgccat cttttttggtt aacaaaaata tcatatttta acaatggaaa taacttttc     360
attgttgata atgaccaaca aaaaaagtc atagaagaat tatatggcaa accagaatta     420
acatatatgg tgtgggattc ccccatcctg gtttacagtc attctattaa tatttatgat    480
ggcgatatag aaggaagtgc caatgtagta aaaag                                 515
```

<210> SEQ ID NO 54
<211> LENGTH: 515
<212> TYPE: DNA
<213> ORGANISM: Artificial Sequence
<220> FEATURE:
<223> OTHER INFORMATION: Synthetic primer

<400> SEQUENCE: 54

```
attcctgtca ttattttggg ttcaattttc ttatgtcgaa atgcgaatgt accaaagata      60
tcaaatatag ttttatggtt tttttcaatt tcaatttctg cttattcatt aatatatgta     120
aatcagcctg atttcttatt tcgcaatgac agaaccacat caaaatatag gcttatatct     180
aattttttga ctcaacacaa cttatctaat ggatatgcaa cattctggaa tgcggcagcg     240
gtgagtgtgg aaagaaatt caatatagcc cctgttaaca tcgacataga aaataaaaaa      300
gttttgccat cttttttggtt aacaaaaata tcatatttta acaatggaaa taacttttc     360
attgttgata atgaccaaca aaaaaagtc atagaagaat tatatggcaa accagaatta     420
acatatatgg tgtgggattc ccccatcctg gtttacagtc attctattaa tatttatgat    480
ggcgatatag aaggaagtgc caatgtagta aaaag                                 515
```

<210> SEQ ID NO 55
<211> LENGTH: 515
<212> TYPE: DNA
<213> ORGANISM: Artificial Sequence
<220> FEATURE:
<223> OTHER INFORMATION: Synthetic primer

<400> SEQUENCE: 55

```
attcctgtca ttattttggg ttcaattttc ttatgtcgaa atgcgaatgt accaaagata      60
tcaaatatag ttttatggtt tttttcaatt tcaatttctg cttattcatt aatatatgta     120
aatcagcctg atttcttatt tcgcaatgac agaaccacat caaaatatag gcttatatct     180
aattttttga ctcaacacaa cttatctaat ggatatgcaa cattctggaa tgcggcagcg     240
gtgagtgtgg aaagaaatt caatatagcc cctgttaaca tcgacataga aaataaaaaa      300
gttttgccat cttttttggtt aacaaaaata tcatatttta acaatggaaa taacttttc     360
attgttgata atgaccaaca aaaaaagtc atagaagaat tatatggcaa accagaatta     420
acatatatgg tgtgggattc ccccatcctg gtttacagtc attctattaa tatttatgat    480
ggcgatatag aaggaagtgc caatgtagta aaaag                                 515
```

<210> SEQ ID NO 56
<211> LENGTH: 515
<212> TYPE: DNA
<213> ORGANISM: Artificial Sequence
<220> FEATURE:
<223> OTHER INFORMATION: Synthetic primer

<400> SEQUENCE: 56

```
attcctgtca ttatttttgg ttcaattttc ttatgtcgaa atgcgaatgt accaaagata    60
tcaaatatag ttttatggtt tttttcaatt tcaatttctg cttattcatt aatatatgta   120
aatcagcctg atttcttatt tcgcaatgac agaaccacat caaaatatag gcttatatct   180
aattttttga ctcaacacaa cttatctaat ggatatgcaa cattctggaa tgcggcagcg   240
gtgagtgtgg aaaagaaatt caatatagcc cctgttaaca tcgacataga aaataaaaaa   300
gttttgccat cttttttggtt aacaaaaata tcatatttta acaatggaaa taacttttttc  360 attgttgata atgaccaaca aaaaaagtc atagaagaat tatatggcaa accagaatta   420
acatatatgg tgtgggattc ccccatcctg gtttacagtc attctattaa tatttatgat   480
ggcgatatag aaggaagtgc caatgtagta aaaag                              515
```

<210> SEQ ID NO 57
<211> LENGTH: 515
<212> TYPE: DNA
<213> ORGANISM: Artificial Sequence
<220> FEATURE:
<223> OTHER INFORMATION: Synthetic primer

<400> SEQUENCE: 57

```
attcctgtca ttatttttgg ttcaattttc ttatgtcgaa atgcgaatgt accaaagata    60
tcaaatatag ttttatggtt tttttcaatt tcaatttctg cttattcatt aatatatgta   120
aatcagcctg atttcttatt tcgcaatgac agaaccacat caaaatatag gcttatatct   180
aattttttga ctcaacacaa cttatctaat ggatatgcaa cattctggaa tgcggcagcg   240
gtgagtgtgg aaaagaaatt caatatagcc cctgttaaca tcgacataga aaataaaaaa   300
gttttgccat cttttttggtt aacaaaaata tcatatttta acaatggaaa taacttttttc  360 attgttgata atgaccaaca aaaaaagtc atagaagaat tatatggcaa accagaatta   420
acatatatgg tgtgggattc ccccatcctg gtttacagtc attctattaa tatttatgat   480
ggcgatatag aaggaagtgc caatgtagta aaaag                              515
```

<210> SEQ ID NO 58
<211> LENGTH: 515
<212> TYPE: DNA
<213> ORGANISM: Artificial Sequence
<220> FEATURE:
<223> OTHER INFORMATION: Synthetic primer

<400> SEQUENCE: 58

```
attcctgtca ttatttttgg ttcaattttc ttatgtcgaa atgcgaatgt accaaagata    60
tcaaatatag ttttatggtt tttttcaatt tcaatttctg cttattcatt aatatatgta   120
aatcagcctg atttcttatt tcgcaatgac agaaccacat caaaatatag gcttatatct   180
aattttttga ctcaacacaa cttatctaat ggatatgcaa cattctggaa tgcggcagcg   240
gtgagtgtgg aaaagaaatt caatatagcc cctgttaaca tcgacataga aaataaaaaa   300
gttttgccat cttttttggtt aacaaaaata tcatatttta acaatggaaa taacttttttc  360 attgttgata atgaccaaca aaaaaagtc atagaagaat tatatggcaa accagaatta   420
```
acatatatgg tgtgggattc ccccatcctg gtttacagtc attctattaa tatttatgat    480
ggcgatatag aaggaagtgc caatgtagta aaaag    515

<210> SEQ ID NO 59
<211> LENGTH: 515
<212> TYPE: DNA
<213> ORGANISM: Artificial Sequence
<220> FEATURE:
<223> OTHER INFORMATION: Synthetic primer

<400> SEQUENCE: 59
attcctgtca ttattttgg ttcaattttc ttatgtcgaa atgcgaatgt accaaagata    60
tcaaatatag ttttatggtt tttttcaatt tcaatttctg cttattcatt aatatatgta    120
aatcagcctg atttcttatt tcgcaatgac agaaccacat caaaatatag gcttatatct    180 aatttttga ctcaacacaa cttatctaat ggatatgcaa cattctggaa tgcggcagcg    240
gtgagtgtgg aaaagaaatt caatatagcc cctgttaaca tcgacataga aaataaaaaa    300
gttttgccat cttttggtt aacaaaaata tcatatttta acaatggaaa taactttttc    360
attgttgata atgaccaaca aaaaaagtc atagaagaat tatatggcaa accagaatta    420
acatatatgg tgtgggattc ccccatcctg gtttacagtc attctattaa tatttatgat    480
ggcgatatag aaggaagtgc caatgtagta aaaag    515

<210> SEQ ID NO 60
<211> LENGTH: 515
<212> TYPE: DNA
<213> ORGANISM: Artificial Sequence
<220> FEATURE:
<223> OTHER INFORMATION: Synthetic primer

<400> SEQUENCE: 60
attcctgtca ttattttgg ttcaattttc ttatgtcgaa atgcgaatgt accaaagata    60
tcaaatatag ttttatggtt tttttcaatt tcaatttctg cttattcatt aatatatgta    120
aatcagcctg atttcttatt tcgcaatgac agaaccacat caaaatatag gcttatatct    180 aatttttga ctcaacacaa cttatctaat ggatatgcaa cattctggaa tgcggcagcg    240
gtgagtgtgg aaaagaaatt caatatagcc cctgttaaca tcgacataga aaataaaaaa    300
gttttgccat cttttggtt aacaaaaata tcatatttta acaatggaaa taactttttc    360
attgttgata atgaccaaca aaaaaagtc atagaagaat tatatggcaa accagaatta    420
acatatatgg tgtgggattc ccccatcctg gtttacagtc attctattaa tatttatgat    480
ggcgatatag aaggaagtgc caatgtagta aaaag    515

<210> SEQ ID NO 61
<211> LENGTH: 515
<212> TYPE: DNA
<213> ORGANISM: Artificial Sequence
<220> FEATURE:
<223> OTHER INFORMATION: Synthetic primer

<400> SEQUENCE: 61
attcctgtca ttattttgg ttcaattttc ttatgtcgaa atgcgaatgt accaaagata    60
tcaaatatag ttttatggtt tttttcaatt tcaatttctg cttattcatt aatatatgta    120
aatcagcctg atttcttatt tcgcaatgac agaaccacat caaaatatag gcttatatct    180 aatttttga ctcaacacaa cttatctaat ggatatgcaa cattctggaa tgcggcagcg    240
gtgagtgtgg aaaagaaatt caatatagcc cctgttaaca tcgacataga aaataaaaaa    300

```
gttttgccat cttttttggtt aacaaaaata tcatatttta acaatggaaa taacttttc      360 attgttgata atgaccaaca aaaaaaagtc atagaagaat tatatggcaa accagaatta      420
acatatatgg tgtgggattc ccccatcctg gtttacagtc attctattaa tatttatgat     480
ggcgatatag aaggaagtgc caatgtagta aaaag                                 515

<210> SEQ ID NO 62
<211> LENGTH: 515
<212> TYPE: DNA
<213> ORGANISM: Artificial Sequence
<220> FEATURE:
<223> OTHER INFORMATION: Synthetic primer

<400> SEQUENCE: 62
attcctgtca ttattttggg ttcaattttc ttatgtcgaa atgcgaatgt accaaagata      60
tcaaatatag ttttatggtt ttttcaatt tcaatttctg cttattcatt aatatatgta     120
aatcagcctg atttcttatt tcgcaatgac agaaccacat caaaatatag gcttatatct    180 aatttttga ctcaacacaa cttatctaat ggatatgcaa cattctggaa tgcggcagcg    240
gtgagtgtgg aaagaaatt caatatagcc cctgttaaca tcgacataga aaataaaaaa    300
gttttgccat cttttttggtt aacaaaaata tcatatttta acaatggaaa taacttttc    360 attgttgata atgaccaaca aaaaaaagtc atagaagaat tatatggcaa accagaatta    420
acatatatgg tgtgggattc ccccatcctg gtttacagtc attctattaa tatttatgat   480
ggcgatatag aaggaagtgc caatgtagta aaaag                                515

<210> SEQ ID NO 63
<211> LENGTH: 515
<212> TYPE: DNA
<213> ORGANISM: Artificial Sequence
<220> FEATURE:
<223> OTHER INFORMATION: Synthetic primer

<400> SEQUENCE: 63
attcctgtca ttattttggg ttcaattttc ttatgtcgaa atgcgaatgt accaaagata      60
tcaaatatag ttttatggtt ttttcaatt tcaatttctg cttattcatt aatatatgta     120
aatcagcctg atttcttatt tcgcaatgac agaaccacat caaaatatag gcttatatct    180 aatttttga ctcaacacaa cttatctaat ggatatgcaa cattctggaa tgcggcagcg    240
gtgagtgtgg aaagaaatt caatatagcc cctgttaaca tcgacataga aaataaaaaa    300
gttttgccat cttttttggtt aacaaaaata tcatatttta acaatggaaa taacttttc    360 attgttgata atgaccaaca aaaaaaagtc atagaagaat tatatggcaa accagaatta    420
acatatatgg tgtgggattc ccccatcctg gtttacagtc attctattaa tatttatgat   480
ggcgatatag aaggaagtgc caatgtagta aaaag                                515

<210> SEQ ID NO 64
<211> LENGTH: 651
<212> TYPE: DNA
<213> ORGANISM: Artificial Sequence
<220> FEATURE:
<223> OTHER INFORMATION: Synthetic primer

<400> SEQUENCE: 64
aaattaatgc acatggcgat cagtatgaag cattaatttt ttcttatata acaggaaaaa      60
aaatcaagat gtctgagaat aaatataaaa atggttctta tattttcgaa ataaacgaag    120
```

```
atatgccatc tgcagaaata cagttattcg ctcaaaaaga ttcaaatgta tgttttgagt      180
catactcact tcagcatata aaataataaa gtcatggaaa agcgtcagta actaatacag      240 gcgcttttg  tctatagaaa actcatgctg ttaagcgggt tttggttgaa atgttccgaa      300
aatcggaata gttattccac accagcgcta tgaattagat ggcgaagagc atgctgtaac      360
ccctactata gtagcacctt cagattgaac atacatggta ccaatcttat ataattgcct      420
ggcgtcgaac gccccgagaa gtaccgtacc agtagttgcc gtcgattatg tctggcgagc      480
gccgataact ttcatgccgc ctactgaaca agatgttacc acattaagag aggagaccag      540
cgattacgat attgcatctg ttttcgacac gtagtcgttc tcaatagaag aggcgaaaaa      600
acaccaagcc acttgatggc gttttttatt agaggcaata aatgtcggct t               651
```

<210> SEQ ID NO 65
<211> LENGTH: 651
<212> TYPE: DNA
<213> ORGANISM: Artificial Sequence
<220> FEATURE:
<223> OTHER INFORMATION: Synthetic primer

<400> SEQUENCE: 65

```
aaattaatgc acatggcgat cagtatgaag cattaatttt ttcttatata acaggaaaaa       60
aaatcaagat gtctgagaat aaatataaaa atggttctta tattttcgaa ataaacgaag      120
atatgccatc tgcagaaata cagttattcg ctcaaaaaga ttcaaatgta tgttttgagt      180
catactcact tcagcatata aaataataaa gtcatggaaa agcgtcagta actaatacag      240 gcgcttttg  tctatagaaa actcatgctg ttaagcgggt tttggttgaa atgttccgaa      300
aatcggaata gttattccac accagcgcta tgaattagat ggcgaagagc atgctgtaac      360
ccctactata gtagcacctt cagattgaac atacatggta ccaatcttat ataattgcct      420
ggcgtcgaac gccccgagaa gtaccgtacc agtagttgcc gtcgattatg tctggcgagc      480
gccgataact ttcatgccgc ctactgaaca agatgttacc acattaagag aggagaccag      540
cgattacgat attgcatctg ttttcgacac gtagtcgttc tcaatagaag aggcgaaaaa      600
acaccaagcc acttgatggc gttttttatt agaggcaata aatgtcggct t               651
```

<210> SEQ ID NO 66
<211> LENGTH: 651
<212> TYPE: DNA
<213> ORGANISM: Artificial Sequence
<220> FEATURE:
<223> OTHER INFORMATION: Synthetic primer

<400> SEQUENCE: 66

```
aaattaatgc acatggcgat cagtatgaag cattaatttt ttcttatata acaggaaaaa       60
aaatcaagat gtctgagaat aaatataaaa atggttctta tattttcgaa ataaacgaag      120
atatgccatc tgcagaaata cagttattcg ctcaaaaaga ttcaaatgta tgttttgagt      180
catactcact tcagcatata aaataataaa gtcatggaaa agcgtcagta actaatacag      240 gcgcttttg  tctatagaaa actcatgctg ttaagcgggt tttggttgaa atgttccgaa      300
aatcggaata gttattccac accagcgcta tgaattagat ggcgaagagc atgctgtaac      360
ccctactata gtagcacctt cagattgaac atacatggta ccaatcttat ataattgcct      420
ggcgtcgaac gccccgagaa gtaccgtacc agtagttgcc gtcgattatg tctggcgagc      480
gccgataact ttcatgccgc ctactgaaca agatgttacc acattaagag aggagaccag      540
cgattacgat attgcatctg ttttcgacac gtagtcgttc tcaatagaag aggcgaaaaa      600
```

```
acaccaagcc acttgatggc gttttttatt agaggcaata aatgtcggct t          651
```

<210> SEQ ID NO 67
<211> LENGTH: 651
<212> TYPE: DNA
<213> ORGANISM: Artificial Sequence
<220> FEATURE:
<223> OTHER INFORMATION: Synthetic primer

<400> SEQUENCE: 67

```
aaattaatgc acatggcgat cagtatgaag cattaatttt ttcttatata acaggaaaaa   60
aaatcaagat gtctgagaat aaatataaaa atggttctta tattttcgaa ataaacgaag  120
atatgccatc tgcagaaata cagttattcg ctcaaaaaga ttcaaatgta tgttttgagt  180
catactcact tcagcatata aaataataaa gtcatggaaa agcgtcagta actaatacag  240
gcgcttttg tctatagaaa actcatgctg ttaagcgggt tttggttgaa atgttccgaa   300
aatcggaata gttattccac accagcgcta tgaattagat ggcgaagagc atgctgtaac  360
ccctactata gtagcaccct cagattgaac atacatggta ccaatcttat ataattgcct  420
ggcgtcgaac gccccgagaa gtaccgtacc agtagttgcc gtcgattatg tctggcgagc  480
gccgataact ttcatgccgc ctactgaaca agatgttacc acattaagag aggagaccag  540
cgattacgat attgcatctg ttttcgacac gtagtcgttc tcaatagaag aggcgaaaaa  600
acaccaagcc acttgatggc gttttttatt agaggcaata aatgtcggct t           651
```

<210> SEQ ID NO 68
<211> LENGTH: 645
<212> TYPE: DNA
<213> ORGANISM: Artificial Sequence
<220> FEATURE:
<223> OTHER INFORMATION: Synthetic primer

<400> SEQUENCE: 68

```
atgcacatgg cgatcagtat gaagcattaa tttttcttta taacagga aaaaaatca     60
agatgtctga gaataaatat aaaaatggtt cttatatttt cgaaataaac gaagatatgc  120
catctgcaga aatacagtta ttcgctcaaa aagattcaaa tgtatgtttt gagtcatact  180
cacttcagca tataaaataa aaagtcatg gaaaagcgtc agtaactaat acaggcgctt   240
tttgtctata gaaaactcat gctgttaagc gggttttggt tgaaatgttc cgaaaatcgg  300
aatagttatt ccacaccagc gctatgaatt agatggcgaa gagcatgctg taacccctac  360
tatagtagca ccttcagatt gaacatacat ggtaccaatc ttatataatt gcctggcgtc  420
gaacgccccg agaagtaccg taccagtagt tgccgtcgat tatgtctggc gagcgccgat  480
aactttcatg ccgcctactg aacaagatgt taccacatta agaggagga ccagcgatta   540
cgatattgca tctgttttcg acacgtagtc gttctcaata agaggcga aaaaacacca    600
agccacttga tggcgttttt tattagaggc aataaatgtc ggctt                 645
```

<210> SEQ ID NO 69
<211> LENGTH: 637
<212> TYPE: DNA
<213> ORGANISM: Artificial Sequence
<220> FEATURE:
<223> OTHER INFORMATION: Synthetic primer

<400> SEQUENCE: 69

```
ggcgatcagt atgaagcatt aatttttct tatataacag gaaaaaaat caagatgtct    60
```
gagaataaat ataaaaatgg ttcttatatt ttcgaaataa acgaagatat gccatctgca    120
gaaatacagt tattcgctca aaaagattca aatgtatgtt ttgagtcata ctcacttcag    180
catataaaat aataaagtca tggaaaagcg tcagtaacta atacaggcgc ttttttgtcta    240 tagaaaactc atgctgttaa gcgggttttg gttgaaatgt tccgaaaatc ggaatagtta    300
ttccacacca gcgctatgaa ttagatggcg aagagcatgc tgtaaccoct actatagtag    360 caccttcaga ttgaacatac atggtaccaa tcttatataa ttgcctggcg tcgaacgccc    420
cgagaagtac cgtaccagta gttgccgtcg attatgtctg gcgagcgccg ataactttca    480
tgccgcctac tgaacaagat gttaccacat taagagagga gaccagcgat tacgatattg    540
catctgtttt cgacacgtag tcgttctcaa tagaagaggc gaaaaaacac caagccactt    600
gatggcgttt tttattagag gcaataaatg tcggctt                             637

<210> SEQ ID NO 70
<211> LENGTH: 645
<212> TYPE: DNA
<213> ORGANISM: Artificial Sequence
<220> FEATURE:
<223> OTHER INFORMATION: Synthetic primer

<400> SEQUENCE: 70
atgcacatgg cgatcagtat gaagcattaa ttttttctta tataacagga aaaaaaatca     60
agatgtctga aataaatat aaaaatggtt cttatatttt cgaaataaac gaagatatgc    120
catctgcaga aatacagtta ttcgctcaaa aagattcaaa tgtatgtttt gagtcatact    180
cacttcagca tataaaataa taaagtcatg gaaaagcgtc agtaactaat acaggcgctt    240
tttgtctata gaaaactcat gctgttaagc gggttttggt tgaaatgttc cgaaaatcgg    300
aatagttatt ccacaccagc gctatgaatt agatggcgaa gagcatgctg taaccctac     360 tatagtagca ccttcagatt gaacatacat ggtaccaatc ttatataatt gcctggcgtc    420
gaacgccccg agaagtaccg taccagtagt tgccgtcgat tatgtctggc gagcgccgat    480
aactttcatg ccgcctactg aacaagatgt taccacatta agagaggaga ccagcgatta    540
cgatattgca tctgttttcg acacgtagtc gttctcaata agagaggcga aaaacacca     600 agccacttga tggcgttttt tattagaggc aataaatgtc ggctt                    645

<210> SEQ ID NO 71
<211> LENGTH: 637
<212> TYPE: DNA
<213> ORGANISM: Artificial Sequence
<220> FEATURE:
<223> OTHER INFORMATION: Synthetic primer

<400> SEQUENCE: 71
ggcgatcagt atgaagcatt aatttttct tatataacag gaaaaaaaat caagatgtct     60
gagaataaat ataaaaatgg ttcttatatt ttcgaaataa acgaagatat gccatctgca    120
gaaatacagt tattcgctca aaaagattca aatgtatgtt ttgagtcata ctcacttcag    180
catataaaat aataaagtca tggaaaagcg tcagtaacta atacaggcgc ttttttgtcta   240 tagaaaactc atgctgttaa gcgggttttg gttgaaatgt tccgaaaatc ggaatagtta    300
ttccacacca gcgctatgaa ttagatggcg aagagcatgc tgtaaccoct actatagtag    360 caccttcaga ttgaacatac atggtaccaa tcttatataa ttgcctggcg tcgaacgccc    420
cgagaagtac cgtaccagta gttgccgtcg attatgtctg gcgagcgccg ataactttca    480
tgccgcctac tgaacaagat gttaccacat taagagagga gaccagcgat tacgatattg    540

```
catctgtttt cgacacgtag tcgttctcaa tagaagaggc gaaaaaacac caagccactt    600
gatggcgttt tttattagag gcaataaatg tcggctt                            637
```

<210> SEQ ID NO 72
<211> LENGTH: 645
<212> TYPE: DNA
<213> ORGANISM: Artificial Sequence
<220> FEATURE:
<223> OTHER INFORMATION: Synthetic primer

<400> SEQUENCE: 72

```
atgcacatgg cgatcagtat gaagcattaa ttttttctta tataacagga aaaaaaatca    60
agatgtctga gaataaatat aaaaatggtt cttatatttt cgaaataaac gaagatatgc   120
catctgcaga aatacagtta ttcgctcaaa aagattcaaa tgtatgtttt gagtcatact   180
cacttcagca tataaaataa ttaagtcatg gaaaagcgtc agtaactaat acaggcgctt   240
tttgtctata gaaaactcat gctgttaagc gggttttggt tgaaatgttc cgaaaatcgg   300
aatagttatt ccacaccagc gctatgaatt agatggcgaa gagcatgctg taaccctac    360 tatagtagca ccttcagatt gaacatacat ggtaccaatc ttatataatt gcctggcgtc    420
gaacgccccg agaagtaccg taccagtagt tgccgtcgat tatgtctggc gagcgccgat    480
aactttcatg ccgcctactg aacaagatgt taccacatta agagaggaga ccagcgatta    540
cgatattgca tctgttttcg acacgtagtc gttctcaata gaagaggcga aaaaacacca    600
agccacttga tggcgttttt tattagaggc aataaatgtc ggctt                    645
```

<210> SEQ ID NO 73
<211> LENGTH: 360
<212> TYPE: DNA
<213> ORGANISM: Artificial Sequence
<220> FEATURE:
<223> OTHER INFORMATION: Synthetic primer

<400> SEQUENCE: 73

```
cagcaggctt ccgcagatgt gtctggcttg ttcagcagtc tccagaatca gggatacatc    60
cgaaaaacgt caaaatgagt tccggaattc aaagatgccc tcagtaaatc ggactccctc   120
gttgcgctgt taaagtctga aatggagaca cgcaggaatg tagcaccaac aactcgctag   180
agaatcaaaa agctgagcca gatgcccccg gaatcacaca gcctcacact tgatgatgcc   240
tgtgtatttc ttcaagttac caaacctatc gctactaact ggattcacac aggctgtctg   300
taaacatcat gtaaagattc cgccaagtca gtcataggt atgcataaat ttaaccgaac    360
```

<210> SEQ ID NO 74
<211> LENGTH: 353
<212> TYPE: DNA
<213> ORGANISM: Artificial Sequence
<220> FEATURE:
<223> OTHER INFORMATION: Synthetic primer

<400> SEQUENCE: 74

```
cttccgcaga tgtgtctggc ttgttcagca gtctccagaa tcagggatac atccgaaaaa    60
cgtcaaaatg agttccggaa ttcaaagatg ccctcagtaa atcggactcc ctcgttgcgc   120
tgttaaagtc tgaaatggag acacgcagga atgtagcacc aacaactcgc tagagaatca   180
aaaagctgag ccagatgccc ccggaatcac acagcctcac acttgatgat gcctgtgtat   240
ttcttcaagt taccaaacct atcgctacta actggattca cacaggctgt ctgtaaacat    300
```
catgtaaaga ttccgccaag tcagtcaata ggtatgcata aatttaaccg aac       353

<210> SEQ ID NO 75
<211> LENGTH: 331
<212> TYPE: DNA
<213> ORGANISM: Artificial Sequence
<220> FEATURE:
<223> OTHER INFORMATION: Synthetic primer

<400> SEQUENCE: 75
gttcagcagt ctccagaatc agggatacat ccgaaaaacg tcaaaatgag ttccggaatt    60
caaagatgcc ctcagtaaat cggactccct cgttgcgctg ttaaagtctg aaatggagac   120
acgcaggaat gtagcaccaa caactcgcta gagaatcaaa aagctgagcc agatgccccc   180
ggaatcacac agcctcacac ttgatgatgc ctgtgtattt cttcaagtta ccaaacctat   240
cgctactaac tggattcaca caggctgtct gtaaacatca tgtaaagatt ccgccaagtc   300
agtcaatagg tatgcataaa tttaaccgaa c                                 331

<210> SEQ ID NO 76
<211> LENGTH: 340
<212> TYPE: DNA
<213> ORGANISM: Artificial Sequence
<220> FEATURE:
<223> OTHER INFORMATION: Synthetic primer

<400> SEQUENCE: 76
gtctggcttg ttcagcagtc tccagaatca gggatacatc cgaaaaacgt caaatgagt    60 tccggaattc aaagatgccc tcagtaaatc ggactccctc gttgcgctgt taaagtctga   120
aatggagaca cgcaggaatg tagcaccaac aactcgctag agaatcaaaa agctgagcca   180 gatgccccg gaatcacaca gcctcacact tgatgatgcc tgtgtatttc ttcaagttac   240
caaacctatc gctactaact ggattcacac aggctgtctg taaacatcat gtaaagattc   300
cgccaagtca gtcaataggt atgcataaat ttaaccgaac                        340

<210> SEQ ID NO 77
<211> LENGTH: 340
<212> TYPE: DNA
<213> ORGANISM: Artificial Sequence
<220> FEATURE:
<223> OTHER INFORMATION: Synthetic primer

<400> SEQUENCE: 77
gtctggcttg ttcagcagtc tccagaatca gggatacatc cgaaaaacgt caaatgagt    60 tccggaattc aaagatgccc tcagtaaatc ggactccctc gttgcgctgt taaagtctga   120
aatggagaca cgcaggaatg tagcaccaac aactcgctag agaatcaaaa agctgagcca   180 gatgccccg gaatcacaca gcctcacact tgatgatgcc tgtgtatttc ttcaagttac   240
caaacctatc gctactaact ggattcacac aggctgtctg taaacatcat gtaaagattc   300
cgccaagtca gtcaataggt atgcataaat ttaaccgaac                        340

<210> SEQ ID NO 78
<211> LENGTH: 360
<212> TYPE: DNA
<213> ORGANISM: Artificial Sequence
<220> FEATURE:
<223> OTHER INFORMATION: Synthetic primer

<400> SEQUENCE: 78
cagcaggctt ccgcagatgt gtctggcttg ttcagcagtc tccagaatca gggatacatc    60

```
cgaaaaacgt caaaatgagt tccggaattc aaagatgccc tcagtaaatc ggactccctc    120
gttgcgctgt taaagtctga aatggagaca cgcaggaatg tagcaccaac aactcgctag    180
agaatcaaaa agctgagcca gatgcccccg aatcacaca gcctcacact tgatgatgcc    240
tgtgtatttc ttcaagttac caaacctatc gctactaact ggattcacac aggctgtctg    300
taaacatcat gtaaagattc cgccaagtca gtcaataggt atgcataaat ttaaccgaac    360

<210> SEQ ID NO 79
<211> LENGTH: 342
<212> TYPE: DNA
<213> ORGANISM: Artificial Sequence
<220> FEATURE:
<223> OTHER INFORMATION: Synthetic primer

<400> SEQUENCE: 79
gtgtctggct tgttcagcag tctccagaat cagggataca tccgaaaaac gtcaaaatga     60
gttccggaat tcaaagatgc cctcagtaaa tcggactccc tcgttgcgct gttaaagtct    120
gaaatggaga cacgcaggaa tgtagcacca acaactcgct agagaatcaa aaagctgagc    180
cagatgcccc cggaatcaca cagcctcaca cttgatgatg cctgtgtatt tcttcaagtt    240
accaaaccta tcgctactaa ctggattcac acaggctgtc tgtaaacatc atgtaaagat    300
tccgccaagt cagtcaatag gtatgcataa atttaaccga ac                      342

<210> SEQ ID NO 80
<211> LENGTH: 360
<212> TYPE: DNA
<213> ORGANISM: Artificial Sequence
<220> FEATURE:
<223> OTHER INFORMATION: Synthetic primer

<400> SEQUENCE: 80
cagcaggctt ccgcagatgt gtctggcttg ttcagcagtc tccagaatca gggatacatc     60
cgaaaaacgt caaaatgagt tccggaattc aaagatgccc tcagtaaatc ggactccctc    120
gttgcgctgt taaagtctga aatggagaca cgcaggaatg tagcaccaac aactcgctag    180
agaatcaaaa agctgagcca gatgcccccg aatcacaca gcctcacact tgatgatgcc    240
tgtgtatttc ttcaagttac caaacctatc gctactaact ggattcacac aggctgtctg    300
taaacatcat gtaaagattc cgccaagtca gtcaataggt atgcataaat ttaaccgaac    360
```